United States Patent
Xue et al.

(10) Patent No.: US 6,858,626 B2
(45) Date of Patent: Feb. 22, 2005

(54) CYCLIC HYDROXAMIC ACID AS METALLOPROTEINASE INHIBITORS

(75) Inventors: Chu-Biao Xue, Hockessin, DE (US); Carl P. Decicco, Kennett Square, PA (US); Xiaohua He, Hockessin, DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 233 days.

(21) Appl. No.: 10/177,235

(22) Filed: Jun. 20, 2002

(65) Prior Publication Data

US 2003/0139597 A1 Jul. 24, 2003

Related U.S. Application Data

(62) Division of application No. 09/335,086, filed on Jun. 17, 1999, now Pat. No. 6,429,213.
(60) Provisional application No. 60/089,557, filed on Jun. 17, 1998, and provisional application No. 60/127,599, filed on Apr. 2, 1999.

(51) Int. Cl.[7] ........................ A61K 31/47; A61K 31/16; C07C 233/00; C07D 211/72; C07D 215/36
(52) U.S. Cl. ........................ 514/312; 514/330; 514/346; 514/613; 546/153; 546/225; 546/298; 564/163
(58) Field of Search ................................ 514/330, 346, 514/312, 613; 546/225, 298, 153; 564/163

(56) References Cited

U.S. PATENT DOCUMENTS

| | | | |
|---|---|---|---|
| 4,207,091 A | 6/1980 | Fischer | 71/113 |
| 6,211,154 B1 * | 4/2001 | Scarborough et al. | 514/18 |

FOREIGN PATENT DOCUMENTS

| | | |
|---|---|---|
| DE | 2705034 | 8/1977 |
| EP | 0780306 | 6/1997 |
| EP | 0780386 | 6/1997 |
| EP | 0818442 | 1/1998 |
| WO | 9209282 | 6/1992 |
| WO | 9633172 | 10/1996 |
| WO | 9720824 | 6/1997 |
| WO | 9816506 | 4/1998 |
| WO | 9932451 | 7/1999 |
| WO | WO 99/65867 | * 12/1999 |

OTHER PUBLICATIONS

Hanessian et al, "Synthesis of conformationally constrained potential inhibitors of mammalian metalloproteinases", Bioorg. Med. Chem. Lett., vol. 7, No. 24, (1997), pp. 3119–3124.

Bade, Maria L., "Aminoacylhydroxamates. A case of slow proton transfer between electronegative atoms in solution", J. Amer. Chem. Soc., vol. 93, No. 4, (1971) pp. 949–953.

Wahl, Robert C., "Biochemistry and Inhibition of Collagenase and Stromelysin", Ann. Rep. Med. Chem., 25, 177–184, AP, San Diego, 1990.

Sharma, CA 112:98439, 1989.

Fushimi, CA 113:123796, 1989.

* cited by examiner

*Primary Examiner*—D. Margaret Seaman
(74) *Attorney, Agent, or Firm*—David H. Vance; Jing S. Belfield

(57) ABSTRACT

The present application describes novel cyclic hydroxamic acids of formula I:

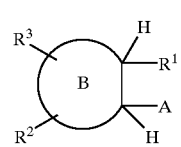

or pharmaceutically acceptable salt forms thereof, wherein ring B is a 5–7 membered cyclic system containing from 0–2 heteroatoms selected from O, N, $NR^a$, and $S(O)_p$, and 0–1 carbonyl groups and the other variables are defined in the present specification, which are useful as metalloprotease inhibitors.

20 Claims, No Drawings

CYCLIC HYDROXAMIC ACID AS METALLOPROTEINASE INHIBITORS

CROSS-REFERENCE TO RELATED APPLICATIONS

This application is a divisional application of U.S. application Ser. No. 09/335,086 filed on Jun. 17, 1999 and issued as U.S. Pat. No. 6,429,213 on Aug. 6, 2002, which claims the priority benefits of U.S. Provisional Application No. 60/089,557, filed Jun. 17, 1998 and U.S. Provisional Application No. 60/127,599, filed Apr. 2, 1999, all which are expressly incorporated fully herein by reference.

FIELD OF THE INVENTION

This invention relates generally to novel cyclic hydroxamic acids as metalloproteinase inhibitors, pharmaceutical compositions containing the same, and methods of using the same.

BACKGROUND OF THE INVENTION

There is now a body of evidence that metalloproteinases (MP) are important in the uncontrolled breakdown of connective tissue, including proteoglycan and collagen, leading to resorption of the extracellular matrix. This is a feature of many pathological conditions, such as rheumatoid and osteoarthritis, corneal, epidermal or gastric ulceration; tumor metastasis or invasion; periodontal disease and bone disease. Normally these catabolic enzymes are tightly regulated at the level of their synthesis as well as at their level of extracellular activity through the action of specific inhibitors, such as alpha-2-macroglobulins and TIMP (tissue inhibitor of metalloproteinase), which form inactive complexes with the MP's.

Osteo- and Rheumatoid Arthritis (OA and RA respectively) are destructive diseases of articular cartilage characterized by localized erosion of the cartilage surface. Findings have shown that articular cartilage from the femoral heads of patients with OA, for example, had a reduced incorporation of radiolabeled sulfate over controls, suggesting that there must be an enhanced rate of cartilage degradation in OA (Mankin et al. J. Bone Joint Surg. 52A, 1970, 424–434). There are four classes of protein degradative enzymes in mammalian cells: serine, cysteine, aspartic and metalloproteinases. The available evidence supports that it is the metalloproteinases which are responsible for the degradation of the extracellular matrix of articular cartilage in OA and RA. Increased activities of collagenases and stromelysin have been found in OA cartilage and the activity correlates with severity of the lesion (Mankin et al. Arthritis Rheum. 21, 1978, 761–766, Woessner et al. Arthritis Rheum. 26, 1983, 63–68 and Ibid. 27, 1984, 305–312). In addition, aggrecanase (a newly identified metalloproteinase enzymatic activity) has been identified that provides the specific cleavage product of proteoglycan, found in RA and OA patients (Lohmander L. S. et al. Arthritis Rheum. 36, 1993, 1214–22).

Therefore metalloproteinases (MP) have been implicated as the key enzymes in the destruction of mammalian cartilage and bone. It can be expected that the pathogenesis of such diseases can be modified in a beneficial manner by the administration of MP inhibitors, and many compounds have been suggested for this purpose (see Wahl et al. Ann. Rep. Med. Chem. 25, 175–184, AP, San Diego, 1990).

Tumor necrosis factor (TNF) is a cell associated cytokine that is processed from a 26 kd precursor form to a 17 kd active form. TNF has been shown to be a primary mediator in humans and in animals, of inflammation, fever, and acute phase responses, similar to those observed during acute infection and shock. Excess TNF has been shown to be lethal. There is now considerable evidence that blocking the effects of TNF with specific antibodies can be beneficial in a variety of circumstances including autoimmune diseases such as rheumatoid arthritis (Feldman et al, Lancet, 1994, 344, 1105) and non-insulin dependent diabetes melitus. (Lohmander L. S. et al. Arthritis Rheum. 36, 1993, 1214–22) and Crohn's disease (MacDonald T. et al. Clin. Exp. Immunol. 81, 1990, 301).

Compounds which inhibit the production of TNF are therefore of therapeutic importance for the treatment of inflammatory disorders. Recently it has been shown that a matrix metalloproteinase or family of metalloproteinases, hereafter known as TNF-convertases (TNF-C), as well as other MP's are capable of cleaving TNF from its inactive to active form (Gearing et al Nature, 1994, 370, 555). This invention describes molecules that inhibit this conversion and hence the secretion of active TNF-a from cells. These novel molecules provide a means of mechanism based therapeutic intervention for diseases including but not restricted to septic shock, haemodynamic shock, sepsis syndrom, post ischaemic reperfusion injury, malaria, Crohn's disease, inflammatory bowel diseases, mycobacterial infection, meningitis, psoriasis, congestive heart failure, fibrotic diseases, cachexia, graft rejection, cancer, diseases involving angiogenesis, autoimmune diseases, skin inflammatory diseases, OA, RA, multiple sclerosis, radiation damage, hyperoxic alveolar injury, periodontal disease, HIV and non-insulin dependent diabetes melitus.

Since excessive TNF production has been noted in several disease conditions also charactarized by MMP-mediated tissue degradation, compounds which inhibit both MMPs and TNF production may also have a particular advantage in diseases where both mechansisms are involved.

EP 0,780,286 describes MMP inhibitors of formula A:

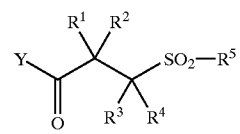

A wherein Y can be NHOH, $R^1$ and $R^2$ can combine to form a cycloalkyl or heterocyclo alkyl group, $R^3$ and $R^4$ can be a variety of groups including H, and $R^5$ can be substituted aryl.

WO 97/20824 depicts MMP inhibitors of formula B:

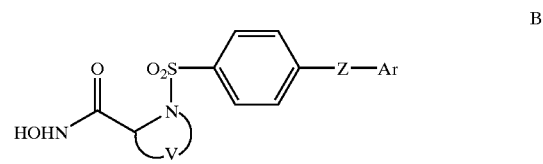

B wherein ring V contains six atoms, Z is O or S, and Ar is an aryl or heteroaryl group. Ar is preferably a monocyclic aryl group with an optional para substituent or an unsubstituted monocyclic heteroaryl group.

EP 0,818,442 illustrates MMP inhibitors of formula C:

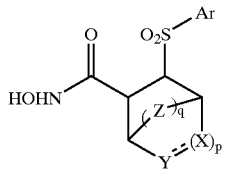

wherein Ar is optionally substituted phenyl or naphthyl, Z can be absent and X and Y can be a variety of substituents. Compounds of this sort are not considered to be part of the present invention.

The compounds of the present invention act as inhibitors of MMPs, in particular aggrecanase and TNF. These novel molecules are provided as anti-inflammatory compounds and cartilage protecting therapeutics. The inhibiton of aggrecanase, TNF-C, and other metalloproteinases by molecules of the present invention indicates they are anti-inflammatory and should prevent the degradation of cartilage by these enzymes, thereby alleviating the pathological conditions of OA and RA,.

SUMMARY OF THE INVENTION

Accordingly, one object of the present invention is to provide novel cyclic hydroxamic acids which are useful as metalloprotease inhibitors or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating inflammatory disorders comprising administering to a host in need of such treatment a therapeutically effective amount of at least one of the compounds of the present invention or a pharmaceutically acceptable salt or prodrug form thereof.

It is another object of the present invention to provide novel compounds of formula (I) for use in therapy.

It is another object of the present invention to provide the use of novel compounds of formula (I) for the manufacture of a medicament for the treatment of a condition or disease mediated by MMPs, TNF, aggrecanase, or a combination thereof.

These and other objects, which will become apparent during the following detailed description, have been achieved by the inventors' discovery that compounds of formula (I):

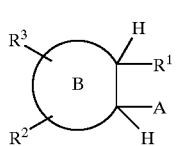

or pharmaceutically acceptable salt or prodrug forms thereof, wherein A, B, $R^1$, $R^2$, and $R^3$ are defined below, are effective metalloprotease inhibitors.

DETAILED DESCRIPTION OF PREFERRED EMBODIMENTS

[1] Thus, in an embodiment, the present invention provides a novel compound of formula I:

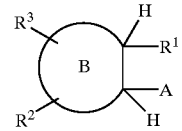

or a stereoisomer or pharmaceutically acceptable salt form thereof, wherein;

A is selected from, —$COR^5$, —$CO_2H$, $CH_2CO_2H$, —$CO_2R^6$, —CONHOH, —$CONHOR^5$, —$CONHOR^6$, —$NHR^a$, —$N(OH)COR^5$, —SH, —$CH_2SH$, —$SONHR^a$, —$SN_2H_2R^a$, —$PO(OH)_2$, and —$PO(OH)NHR^a$;

ring B is a 3–8 membered non-aromatic ring with 0–1 carbonyl groups and from 0–2 ring heteroatoms selected from O, N, $NR^2$, and $S(O)_p$, provided that ring B contains a total of 0–1 ring S and O atoms;

$R^1$ is —U—X—Y—Z—$U^a$—$X^a$—$Y^a$—$Z^a$;

U is absent or is selected from: O, $NR^{a'}$, C(O), C(O)O, OC(O), C(O)$NR^{a'}$, $NR^{a'}$C(O), OC(O)O, OC(O)$NR^{a'}$, $NR^{a'}$C(O)O, $NR^{a'}$C(O)$NR^{a'}$, $S(O)_p$, $S(O)_pNR^{a'}$, $NR^{a'}S(O)_p$, and $NR^{a'}SO_2NR^{a'}$;

X is absent or selected from $C_{1-10}$ alkylene, $C_{2-10}$ alkenylene, and $C_{2-10}$ alkynylene;

Y is absent or selected from O, $NR^{a'}$, $S(O)_p$, and C(O);

Z is absent or selected from a $C_{3-13}$ carbocyclic residue substituted with 0–5 $R^b$ and a 5–14 membered heterocyclic system containing from 1–4 heteroatoms selected from the group consisting of N, O, and S and substituted with 0–5 $R^b$;

$U^a$ is absent or is selected from: O, $NR^{a'}$, C(O), C(O)O, OC(O), C(O)$NR^{a'}$, $NR^{a'}$C(O), OC(O)O, OC(O)$NR^{a'}$, $NR^{a'}$C(O)O, $NR^{a'}$C(O)$NR^{a'}$, $S(O)_p$, $S(O)_pNR^{a'}$, $NR^{a'}S(O)_p$, and $NR^{a'}SO_2NR^{a'}$;

$X^a$ is absent or selected from $C_{1-10}$ alkylene, $C_{2-10}$ alkenylene, and $C_{2-10}$ alkynylene;

$Y^a$ is absent or selected from O, $NR^{a'}$, $S(O)_p$, and C(O);

$Z^a$ is selected from H, a $C_{3-13}$ carbocyclic residue substituted with 0–5 $R^c$ and a 5–14 membered heterocyclic system containing from 1–4 heteroatoms selected from the group consisting of N, O, and S and substituted with 0–5 $R^c$;

provided that U, Y, Z, $U^a$, $Y^a$, and $Z^a$ do not combine to form a N—N, N—O, O—N, O—O, $S(O)_p$—O, O—$S(O)_p$ or $S(O)_p$—$S(O)_p$ group;

$R^2$ is selected from H, $C_{1-6}$ alkylene-Q, $C_{2-6}$ alkenylene-Q, $C_{2-6}$ alkynylene-Q, $(CR^aR^{a'})_rO(CR^aR^{a'})_r$—Q, $(CR^aR^{a'})_r$-$NR^a(CR^aR^{a'})_r$—Q, $(CR^aR^{a'})_rC(O)$ $(CR^aR^{a'})_r$—Q, $(CR^aR^{a'})_rC(O)O(CR^aR^{a'})_r$—Q, $(CR^aR^{a'})_r$OC(O) $(CR^aR^{a'})_r$—Q, $(CR^aR^{a'})_rC(O)NR^a(CR^aR^{a'})_r$—Q, $(CR^aR^{a'})_rNR^aC(O)$ $(CR^aR^{a'})_r$—Q, $(CR^aR^{a'})_r$OC(O)O $(CR^aR^{a'})_r$—Q, $(CR^aR^{a'})_rOC(O)NR^a(CR^aR^{a'})_r$—Q, $(CR^aR^{a'})_rNR^aC(O)O(CR^aR^{a'})_r$—Q, $(CR^aR^{a'})_rNR^aC(O)NR^a(CR^aR^{a'})_r$—Q, $(CR^aR^{a'})_rS(O)_p(CR^aR^{a'})_r$—Q, $(CR^aR^{a'})_rSO_2NR^a(CR^aR^{a'})_r$—Q, $(CR^aR^{a'})_rNR^aSO_2$ $(CR^aR^{a'})_r$—Q, and $(CR^aR^{a'})_rNR^aSO_2NR^a(CR^aR^{a'})_r$—Q;

Q is selected from H, a $C_{3-13}$ carbocyclic residue substituted with 0–5 $R^d$ and a 5–14 membered heteroaryl system containing from 1–4 heteroatoms selected from the group consisting of N, O, and S and substituted with 0–5 $R^d$;

$R^3$ is selected from H, $C_{1-16}$ alkylene-Q', $C_{2-6}$ alkenylene-Q', $C_{2-6}$ alkynylene-Q', $(CR^aR^{a'})_rO(CH_2)_r$—Q', $(CR^aR^{a'})_r$-$NR^a(CR^aR^{a'})_r$—Q', $(CR^aR^{a'})_rNR^aC(O)$ $(CR^aR^{a'})_r$—Q', $(CR^aR^{a'})_r\cdot C(O)NR^a(CR^aR^{a'})_r$—Q', $(CR^aR^{a'})_rC(O)$
$(CR^aR^{a'})_r$—Q', $(CR^aR^{a'})_rC(O)O(CR^aR^{a'})_r$—Q',
$(CR^aR^{a'}_2)_rS(O)_p(CR^aR^{a'})_r$—Q', and $(CR^aR^{a'})_rSO_2NR^a$
$(CR^aR^{a'})_r$—Q';

Q' is selected from H, phenyl substituted with 0–3 $R^d$, naphthyl substituted with 0–3 $R^d$ and a 5–10 membered heteroaryl system containing from 1–4 heteroatoms selected from the group consisting of N, O, and S and substituted with 0–3 $R^d$;

alternatively, $R^2$ and $R^3$ combine to form a fused benzo ring substituted with $R^{3'}$;

$R^{3'}$ is selected from H, $(CR^aR^{a'})_r$—Q', $C_{2-6}$ alkenylene-Q', $C_{2-6}$ alkynylene-Q', $(CR^aR^{a'})_rO(CH_2)_r$—Q', $(CR^aR^{a'})_r$ $NR^a(CR^aR^{a'})_r$—Q', $(CR^aR^{a'})_rNR^aC(O)$ $(CR^aR^{a'})_r$—Q', $(CR^aR^{a'})_r\cdot C(O)NR^a(CR^aR^{a'})_r$—Q', $(CR^aR^{a'})_rC(O)$ $(CR^aR^{a'})_r$—Q', $(CR^aR^{a'})_rC(O)O(CR^aR^{a'})_r$—Q', $(CR^aR^{a'})_r$ $S(O)_p(CR^aR^{a'})_r$—Q', and $(CR^aR^{a'})_rSO_2NR^a$ $(CR^aR^{a'})_r$—Q';

$R^a$, at each occurrence, is independently selected from H, $C_{1-4}$ alkyl, phenyl and benzyl;

$R^{a'}$, at each occurrence, is independently selected from H and $C_{1-4}$ alkyl;

alternatively, $R^a$ and $R^{a'}$ taken together with the nitrogen to which they are attached form a 5 or 6 membered ring containing from 0–1 additional heteroatoms selected from the group consisting of N, O, and S;

$R^{a''}$, at each occurrence, is independently selected from $C_{1-4}$ alkyl, phenyl and benzyl;

$R^b$, at each occurrence, is independently selected from $C_{1-6}$ alkyl, $OR^a$, Cl, F, Br, I, =O, —CN, $NO_2$, $NR^aR^{a'}$, $C(O)R^a$, $C(O)OR^a$, $C(O)NR^aR^{a'}$, $R^aNC(O)NR^aR^{a'}$, $OC(O)NR^aR^{a'}$, $R^aNC(O)O$, $S(O)_2NR^aR^{a'}$, $NR^aS(O)_2R^{a''}$, $NR^aS(O)_2NR^aR^{a'}$, $OS(O)_2NR^aR^{a'}$, $NR^aS(O)_2R^{a''}$, $S(O)_p$ $R^{a''}$, $CF_3$, and $CF_2CF_3$;

$R^c$, at each occurrence, is independently selected from $C_{1-6}$ alkyl, $OR^a$, Cl, F, Br, I, =O, —CN, $NO_2$, $NR^aR^{a'}$, $C(O)R^a$, $C(O)OR^a$, $C(O)NR^aR^{a'}$, $R^aNC(O)NR^aR^{a'}$, $OC(O)NR^aR^{a'}$, $R^aNC(O)O$, $S(O)_2NR^aR^{a'}$, $NR^aS(O)_2R^{a''}$, $NR^aS(O)_2NR^aR^{a'}$, $OS(O)_2NR^aR^{a'}$, $NR^aS(O)_2R^{a''}$, $S(O)_p$ $R^{a''}$, $CF_3$, $CF_2CF_3$, $C_{3-10}$ carbocyclic residue and a 5–14 membered heterocyclic system containing from 1–4 heteroatoms selected from the group consisting of N, O, and S;

$R^d$, at each occurrence, is independently selected from $C_{1-6}$ alkyl, $OR^a$, Cl, F, Br, I, =O, —CN, $NO_2$, $NR^aR^{a'}$, $C(O)R^a$, $C(O)OR^a$, $C(O)NR^aR^{a'}$, $R^aNC(O)NR^aR^{a'}$, $OC(O)NR^aR^{a'}$, $R^aNC(O)O$, $S(O)_2NR^aR^{a'}$, $NR^aS(O)_2R^{a''}$, $NR^aS(O)_2NR^aR^{a'}$, $OS(O)_2NR^aR^{a'}$, $NR^aS(O)_2R^{a''}$, $S(O)_p$ $R^{a''}$, $CF_3$, $CF_2CF_3$, $C_{3-10}$ carbocyclic residue and a 5–14 membered heterocyclic system containing from 1–4 heteroatoms selected from the group consisting of N, O, and S;

$R^5$, at each occurrence, is selected from $C_{1-10}$ alkyl substituted with 0–2 $R^b$, and $C_{1-8}$ alkyl substituted with 0–2 $R^e$;

$R^e$, at each occurrence, is selected from phenyl substituted with 0–2 $R^b$ and biphenyl substituted with 0–2 $R^b$;

$R^6$, at each occurrence, is selected from phenyl, naphthyl, $C_{1-10}$ alkyl-phenyl-$C_{1-6}$ alkyl-, $C_{3-11}$ cycloalkyl, $C_{1-6}$ alkylcarbonyloxy-$C_{1-3}$ alkyl-, $C_{1-6}$ alkoxycarbonyloxy-$C_{1-3}$ alkyl-, $C_{2-10}$ alkoxycarbonyl, $C_{3-6}$ cycloalkylcarbonyloxy-$C_{1-3}$ alkyl-, $C_{3-6}$ cycloalkoxycarbonyloxy-$C_{1-3}$ alkyl-, $C_{3-6}$ cycloalkoxycarbonyl, phenoxycarbonyl, phenyloxycarbonyloxy-$C_{1-3}$ alkyl-, phenylcarbonyloxy-$C_{1-3}$ alkyl-, $C_{1-6}$ alkoxy-$C_{1-6}$ alkylcarbonyloxy-$C_{1-3}$ alkyl-, $[5-(C_1-C_5\ \text{alkyl})\text{-1,3-dioxa-cyclopenten-2-one-yl}]$ methyl, $[5-(R'')\text{-1,3-dioxa-cyclopenten-2-one-yl}]$methyl, (5-aryl-1,3-dioxa-cyclopenten-2-one-yl)methyl, —$C_{1-10}$ alkyl-$NR^7R^{7a}$, —$CH(R^8)OC(=O)R^9$, and —$CH(R^8)OC$ $(=O)OR^9$;

$R^7$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^{7a}$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^8$ is selected from H and $C_{1-4}$ linear alkyl;

$R^9$ is selected from H, $C_{1-8}$ alkyl substituted with 1–2 $R^f$, $C_{3-8}$ cycloalkyl substituted with 1–2 $R^f$, and phenyl substituted with 0–2 $R^b$;

$R^f$, at each occurrence, is selected from $C_{1-4}$ alkyl, $C_{3-8}$ cycloalkyl, $C_{1-5}$ alkoxy, phenyl substituted with 0–2 $R^b$;

p, at each occurrence, is selected from 0, 1, and 2;

r, at each occurrence, is selected from 0, 1, 2, 3, and 4; and, r', at each occurrence, is selected from 1, 2, 3, and 4;

provided that the moiety in ring B adjacent to CH—A is other than substituted or unsubstituted N—$SO_2$-phenyl-O—Ar and N—$SO_2$-phenyl-S—Ar, wherein Ar is aryl or heteroaryl; and, provided that when ring B is cyclopentyl or cyclohexyl, then $R^1$ is other than a substituted or unsubstituted phenyl-S $(O)_p$— group.

[2] In a preferred embodiment, the present invention provides a novel compound of formula II, wherein;

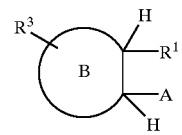

II or a stereoisomer or pharmaceutically acceptable salt form thereof, wherein;

A is selected from $COR^5$, —$CO_2H$, $CH_2CO_2H$, —CONHOH, —$CONHOR^5$, —$CONHOR^6$, —N(OH) $COR^5$, —SH, and —$CH_2SH$;

ring B is a 5–7 membered non-aromatic ring with 0–1 carbonyl groups and 0–2 ring heteroatoms selected from O and $NR^2$, provided that ring B contains a total of 0–1 ring O atoms;

$R^1$ is —U—X—Y—Z—$U^a$—$X^a$—$Y^a$—$Z^a$;

U is absent or is selected from: O, $NR^{a'}$, C(O), C(O)O, $C(O)NR^{a'}$, $NR^{a'}C(O)$, $S(O)_p$, and $S(O)_pNR^{a'}$;

X is absent;

Y is absent;

Z is absent or selected from a $C_{3-6}$ carbocyclic residue substituted with 0–5 $R^b$ and a 5–6 membered heterocyclic system containing from 1–4 heteroatoms selected from the group consisting of N, O, and S and substituted with 0–5 $R^b$;

$U^a$ is absent or is selected from: O, $NR^{a'}$, C(O), C(O)O, $C(O)NR^{a'}$, $NR^{a'}C(O)$, $S(O)_p$, and $S(O)_pNR^{a'}$;

$X^a$ is absent or selected from $C_{1-4}$ alkylene;

$Y^a$ is absent or selected from O and $NR^{a'}$;

$Z^a$ is selected from H, a $C_{3-6}$ carbocyclic residue substituted with 0–5 $R^c$ and a 5–10 membered heterocyclic system containing from 1–4 heteroatoms selected from the group consisting of N, O, and S and substituted with 0–5 $R^c$;

provided that U, Z, $U^a$, $Y^a$, and $Z^a$ do not combine to form a N—N, N—O, O—N, O—O, $S(O)_p$—O, O—$S(O)_p$ or $S(O)_p$—$S(O)_p$ group;

$R^2$ is selected from H, $C_{1-6}$ alkylene-Q, $(CR^aR^{a'})_rO$ $(CR^aR^{a'})_r$—Q, $(CR^aR^{a'})_rNR^a(CR^aR^{a'})_r$—Q, $(CR^aR^{a'})_rC$ (O) $(CR^aR^{a'})_r$—Q, $(CR^aR^{a'})_rC(O)O(CR^aR^{a'})_r$—Q, $(CR^aR^{a'})_r\cdot C(O)NR^a(CR^aR^{a'})_r$—Q, $(CR^aR^{a'})_rS(O)_p$ $(CR^aR^{a'})_r$—Q, and $(CR^aR^{a'})_rSO_2NR^a(CR^aR^{a'})_r$—Q;

Q is selected from H, a $C_{3-6}$ carbocyclic residue substituted with 0–5 $R^d$, and a 5–10 membered heteroaryl system containing from 1–4 heteroatoms selected from the group consisting of N, O, and S and substituted with 0–5 $R^d$;

$R^3$ is selected from H, $C_{1-6}$ alkylene-Q', $(CR^aR^{a'})_rO(CR^aR^{a'})_r$—Q', $(CR^aR^{a'})_rNR^a(CR^aR^{a'})_r$—Q', $(CR^aR^{a'})_rC(O)NR^a(CR^aR^{a'})_r$—Q', $(CR^aR^{a'})_rC(O)(CR^aR^{a'})_r$—Q', $(CR^aR^{a'})_rC(O)O(CR^aR^{a'})_r$—Q', $(CR^aR^{a'})_rS(O)_p(CR^aR^{a'})_r$—Q', and $(CR^aR^{a'})_rSO_2NR^a(CR^aR^{a'})_r$—Q';

Q' is selected from H, phenyl substituted with 0–3 $R^d$, naphthyl substituted with 0–3 $R^d$ and a 5–6 membered heteroaryl system containing from 1–4 heteroatoms selected from the group consisting of N, O, and S and substituted with 0–3 $R^d$;

$R^a$, at each occurrence, is independently selected from H, $C_{1-4}$ alkyl, phenyl and benzyl;

$R^{a'}$, at each occurrence, is independently selected from H and $C_{1-4}$ alkyl;

alternatively, $R^a$ and $R^{a'}$ taken together with the nitrogen to which they are attached form a 5 or 6 membered ring containing from 0–1 additional heteroatoms selected from the group consisting of N, O, and S;

$R^{a''}$, at each occurrence, is independently selected from $C_{1-4}$ alkyl, phenyl and benzyl;

$R^b$, at each occurrence, is independently selected from $C_{1-6}$ alkyl, $OR^a$, Cl, F, Br, =O, —CN, $NR^aR^{a'}$, $C(O)R^a$, $C(O)OR^a$, $C(O)NR^aR^{a'}$, $S(O)_2NR^aR^{a'}$, $S(O)_pR^{a''}$, and $CF_3$;

$R^c$, at each occurrence, is independently selected from $C_{1-6}$ alkyl, $OR^a$, Cl, F, Br, =O, —CN, $NR^aR^{a'}$, $C(O)R^a$, $C(O)OR^a$, $C(O)NR^aR^{a'}$, $S(O)_2NR^aR^{a'}$, $S(O)_pR^{a''}$, $CF_3$, $C_{3-6}$ carbocyclic residue and a 5–6 membered heterocyclic system containing from 1–4 heteroatoms selected from the group consisting of N, O, and S;

$R^d$, at each occurrence, is independently selected from $C_{1-6}$ alkyl, $OR^a$, Cl, F, Br, =O, —CN, $NR^aR^{a'}$, $C(O)R^a$, $C(O)OR^a$, $C(O)NR^aR^{a'}$, $S(O)_2NR^aR^{a'}$, $S(O)_pR^{a''}$, $CF_3$, $C_{3-6}$ carbocyclic residue and a 5–6 membered heterocyclic system containing from 1–4 heteroatoms selected from the group consisting of N, O, and S;

$R^5$, at each occurrence, is selected from $C_{1-6}$ alkyl substituted with 0–2 $R^b$, and $C_{1-4}$ alkyl substituted with 0–2 $R^e$;

$R^e$, at each occurrence, is selected from phenyl substituted with 0–2 $R^b$ and biphenyl substituted with 0–2 $R^b$;

$R^6$, at each occurrence, is selected from phenyl, naphthyl, $C_{1-10}$ alkyl-phenyl-$C_{1-6}$ alkyl-, $C_{3-11}$ cycloalkyl, $C_{1-6}$ alkylcarbonyloxy-$C_{1-3}$ alkyl-, $C_{1-6}$ alkoxycarbonyloxy-$C_{1-3}$ alkyl-, $C_{2-10}$ alkoxycarbonyl, $C_{3-6}$ cycloalkylcarbonyloxy-$C_{1-3}$ alkyl-, $C_{3-6}$ cycloalkoxycarbonyloxy-$C_{1-3}$ alkyl-, $C_{3-6}$ cycloalkoxycarbonyl, phenoxycarbonyl, phenyloxycarbonyloxy-$C_{1-3}$ alkyl-, phenylcarbonyloxy-$C_{1-3}$ alkyl-, $C_{1-6}$ alkoxy-$C_{1-6}$ alkylcarbonyloxy-$C_{1-3}$ alkyl-, [5-($C_1$–$C_5$ alkyl)-1,3-dioxa-cyclopenten-2-one-yl]methyl, [5-($R^a$)-1,3-dioxa-cyclopenten-2-one-yl]methyl, (5-aryl-1,3-dioxa-cyclopenten-2-one-yl)methyl, —$C_{1-10}$ alkyl-$NR^7R^{7a}$, —$CH(R^8)OC(=O)R^9$, and —$CH(R^8)OC(=O)OR^9$;

$R^7$ is selected from H and $C_{1-6}$ alkyl, $C_{2-6}$ alkenyl, $C_{3-6}$ cycloalkyl-$C_{1-3}$ alkyl-, and phenyl-$C_{1-6}$ alkyl-;

$R^{7a}$ is selected from H and $C_{1-6}$ alkyl, $C_{2-6}$ alkenyl, $C_{3-6}$ cycloalkyl-$C_{1-3}$ alkyl-, and phenyl-$C_{1-6}$ alkyl-;

$R^8$ is selected from H and $C_{1-4}$ linear alkyl;

$R^9$ is selected from H, $C_{1-6}$ alkyl substituted with 1–2 $R^f$, $C_{3-6}$ cycloalkyl substituted with 1–2 $R^f$, and phenyl substituted with 0–2 $R^b$;

$R^f$, at each occurrence, is selected from $C_{1-4}$ alkyl, $C_{3-6}$ cycloalkyl, $C_{1-5}$ alkoxy, phenyl substituted with 0–2 $R^b$;

p, at each occurrence, is selected from 0, 1, and 2;

r, at each occurrence, is selected from 0, 1, 2, 3, and 4; and, r', at each occurrence, is selected from 1, 2, 3, and 4;

provided that the moiety in ring B adjacent to CH—A is other than substituted or unsubstituted N—$SO_2$-phenyl-O—Ar and N—$SO_2$-phenyl-S—Ar, wherein Ar is aryl or heteroaryl; and, provided that when ring B is cyclopentyl or cyclohexyl, then $R^1$ is other than a substituted or unsubstituted phenyl-S$(O)_p$— group.

[3] In a more preferred embodiment, the present invention provides a novel compound of formula II, wherein;

A is selected from —$CO_2H$, $CH_2CO_2H$, —CONHOH, —$CONHOR^5$, and —N(OH)$COR^5$;

ring B is a 5–7 membered non-aromatic ring with 0–1 carbonyl groups and 0–2 ring heteroatoms selected from O and $NR^2$, provided that ring B contains a total of 0–1 ring O atoms;

$R^1$ is —U—X—Y—Z—$U^a$—$X^a$—$Y^a$—$Z^a$;

U is absent or is selected from: O, $NR^{a'}$, C(O), $C(O)NR^{a'}$, $S(O)_p$, and $S(O)_pNR^{a'}$;

X is absent;

Y is absent;

Z is absent or selected from a $C_{5-6}$ carbocyclic residue substituted with 0–3 $R^b$ and a 5–6 membered heteroaryl containing from 1–4 heteroatoms selected from the group consisting of N, O, and S and substituted with 0–3 $R^b$;

$U^a$ is absent or is selected from: O, $NR^{a'}$, C(O), $C(O)NR^{a'}$, $S(O)_p$, and $S(O)_pNR^{a'}$;

$X^a$ is absent or selected from $C_{1-2}$ alkylene;

$Y^a$ is absent or selected from O and $NR^{a'}$;

$Z^a$ is selected from H, a $C_{5-6}$ carbocyclic residue substituted with 0–3 $R^c$ and a 5–10 membered heteroaryl containing from 1–4 heteroatoms selected from the group consisting of N, O, and S and substituted with 0–3 $R^c$;

provided that U, Z, $U^a$, $Y^a$, and $Z^a$ do not combine to form a N—N, N—O, O—N, O—O, $S(O)_p$—O, O—$S(O)_p$ or $S(O)_p$—$S(O)_p$ group;

$R^2$ is selected from H, $C_{1-6}$ alkylene-Q, $(CR^aR^{a'})_rC(O)(CR^aR^{a'})_r$—Q, $(CR^aR^{a'})_rC(O)O(CR^aR^{a'})_r$—Q, $(CR^aR^{a''})_rC(O)NR^a(CR^aR^{a'})_r$—Q, and $(CR^aR^{a'})_rS(O)_p(CR^aR^{a'})_r$—Q;

Q is selected from H, a $C_{3-6}$ carbocyclic residue substituted with 0–3 $R^d$ and a 5–10 membered heteroaryl system containing from 1–4 heteroatoms selected from the group consisting of N, O, and S and substituted with 0–3 $R^d$;

$R^3$ is selected from H, $C_{1-6}$ alkylene-Q', $(CHR^a)_rO(CHR^a)_r$—Q', $(CHR^a)_rNR^a(CHR^a)_r$—Q', $(CHR^a)_rC(O)NR^a(CHR^a)_r$—Q', $(CHR^a)_rC(O)(CHR^a)_r$—Q', and $(CHR^a)_rS(O)_p(CHR^a)_r$—Q';

Q' is selected from H, phenyl substituted with 0–3 $R^d$, and a 5–6 membered heteroaryl system containing from 1–4 heteroatoms selected from the group consisting of N, O, and S and substituted with 0–3 $R^d$;

$R^a$, at each occurrence, is independently selected from H, $C_{1-4}$ alkyl, phenyl and benzyl;

$R^{a'}$, at each occurrence, is independently selected from H and $C_{1-4}$ alkyl;

$R^{a''}$, at each occurrence, is independently selected from $C_{1-4}$ alkyl, phenyl and benzyl;

$R^b$, at each occurrence, is independently selected from $C_{1-4}$ alkyl, $OR^a$, Cl, F, =O, $NR^aR^{a'}$, $C(O)R^a$, $C(O)OR^a$, $C(O)NR^aR^{a'}$, $S(O)_2NR^aR^{a'}$, $S(O)_pR^{a''}$, and $CF_3$;

$R^c$, at each occurrence, is independently selected from $C_{1-6}$ alkyl, $OR^a$, Cl, F, Br, =O, $NR^aR^{a'}$, $C(O)R^a$, $C(O)NR^aR^{a'}$, $S(O)_2NR^aR^{a'}$, $S(O)_pR^{a''}$, and $CF_3$;

$R^d$, at each occurrence, is independently selected from $C_{1-6}$ alkyl, $OR^a$, Cl, F, Br, =O, $NR^aR^{a'}$, $C(O)R^a$, $C(O)NR^aR^{a'}$, $S(O)_2NR^aR^{a'}$, $S(O)_pR^{a''}$, $CF_3$ and phenyl;

$R^5$, at each occurrence, is selected from $C_{1-4}$ alkyl substituted with 0–2 $R^b$, and $C_{1-4}$ alkyl substituted with 0–2 $R^e$;

$R^e$, at each occurrence, is selected from phenyl substituted with 0–2 $R^b$ and biphenyl substituted with 0–2 $R^b$;

p, at each occurrence, is selected from 0, 1, and 2;

r, at each occurrence, is selected from 0, 1, 2, 3, and 4; and, r', at each occurrence, is selected from 1, 2, 3, and 4;

provided that the moiety in ring B adjacent to CH—A is other than substituted or unsubstituted N—SO$_2$-phenyl-O—Ar and N—SO$_2$-phenyl-S—Ar, wherein Ar is aryl or heteroaryl; and, provided that when ring B is cyclopentyl or cyclohexyl, then $R^1$ is other than a substituted or unsubstituted phenyl-S(O)$_p$— group.

[4] In a further preferred embodiment, the present invention provides a novel compound of formula III, wherein;

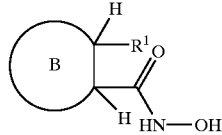

III ring B is a 5–7 membered non-aromatic ring with 0–1 carbonyl groups and 0–2 ring heteroatoms selected from O and $NR^2$, provided that ring B contains a total of 0–1 ring O atoms;

$R^1$ is —U—Z—$U^a$—$X^a$—$Y^a$—$Z^a$;

U is absent or is selected from C(O) and C(O)$NR^{a'}$;

Z is absent or selected from phenyl substituted with 0–3 $R^b$ and pyridyl substituted with 0–3 $R^b$;

$U^a$ is absent or is O;

$X^a$ is absent or is CH$_2$ or CH$_2$CH$_2$;

$Y^a$ is absent or is O;

$Z^a$ is selected from H, phenyl substituted with 0–3 $R^c$, pyridyl substituted with 0–3 $R^c$, and quinolinyl substituted with 0–3 $R^c$;

provided that U, Z, $U^a$, $Y^a$, and $Z^a$ do not combine to form a N—N, N—O, O—N, or O—O group;

$R^2$ is selected from H, $C_{1-6}$ alkylene-Q, C(O) (CR$^a$R$^{a'}$)$_r$—Q, C(O)O(CR$^a$R$^{a'}$)$_r$—Q, C(O)NR$^a$(CR$^a$R$^{a'}$)$_r$—Q, and S(O)$_p$(CR$^a$R$^{a'}$)$_r$—Q;

Q is selected from H, cyclopropyl substituted with 0–1 $R^d$, cyclopentyl substituted with 0–1 $R^d$, cyclohexyl substituted with 0–1 $R^d$, phenyl substituted with 0–2 $R^d$ and a heteroaryl substituted with 0–3 $R^d$, wherein the heteroaryl is selected from pyridyl, quinolinyl, thiazolyl, furanyl, imidazolyl, and isoxazolyl;

$R^a$, at each occurrence, is independently selected from H and CH$_3$, and CH$_2$CH$_3$;

$R^{a'}$, at each occurrence, is independently selected from H and CH$_3$, and CH$_2$CH$_3$;

$R^{a''}$, at each occurrence, is independently selected from H and CH$_3$, and CH$_2$CH$_3$;

$R^b$, at each occurrence, is independently selected from $C_{1-4}$ alkyl, OR$^a$, Cl, F, =O, NR$^a$R$^{a'}$, C(O)R$^a$, C(O)OR$^a$, (O)NR$^a$R$^{a'}$, S(O)$_2$NR$^a$R$^{a'}$, S(O)$_p$R$^{a''}$, and CF$_3$;

$R^c$, at each occurrence, is independently selected from $C_{1-6}$ alkyl, OR$^a$, Cl, F, Br, =O, NR$^a$R$^{a'}$, C(O)R$^a$, C(O)NR$^a$R$^{a'}$, S(O)$_2$NR$^a$R$^{a'}$, S(O)$_p$R$^{a''}$, and CF$_3$;

$R^d$, at each occurrence, is independently selected from $C_{1-6}$ alkyl, OR$^a$, Cl, F, Br, =O, NR$^a$R$^{a'}$, C(O)R$^a$, C(O)NR$^a$R$^{a'}$, S(O)$_2$NR$^a$R$^{a'}$, S(O)$_p$R$^{a''}$, CF$_3$ and phenyl;

p, at each occurrence, is selected from 0, 1, and 2;

r, at each occurrence, is selected from 0, 1, 2, and 3; and, r', at each occurrence, is selected from 1, 2, and 3;

provided that the moiety in ring B adjacent to CH—A is other than substituted or unsubstituted N—SO$_2$-phenyl-O—Ar and N—SO$_2$-phenyl-S—Ar, wherein Ar is aryl or heteroaryl; and, provided that when ring B is cyclopentyl or cyclohexyl, then $R^1$ is other than a substituted or unsubstituted phenyl-S(O)$_p$— group.

[5] In a still further preferred embodiment, the present invention provides a novel compound of formula IV:

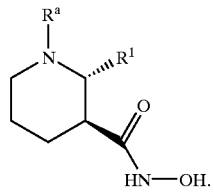

IV

[6] In an even further preferred embodiment, the present invention provides a compound selected from the group:

trans-N-Hydroxy-2-[(4-phenyl-1-piperidinyl)carbonyl]cyclopentanecarboxamide;

trans-N-Hydroxy-2-{[4-[(4-methylphenoxy) methyl]-1-piperidinyl]carbonyl}cyclopentanecarboxamide;

trans-N-Hydroxy-2-[[4-(2-phenoxyethyl)-1-piperidinyl]carbonyl]cyclopentanecarboxamide;

trans-N-Hydroxy-N'-[4-(phenylmethoxy)phenyl]-1,2-cyclopentanedicarboxamide;

trans-N-Hydroxy-N'-[4-(4-pyridinylmethoxy)phenyl]-1,2-cyclopentanedicarboxamide;

trans-N-[4-[(3,5-Dichlorophenyl)methoxy]phenyl]-N'-hydroxy-1,2-cyclopentanedicarboxamide;

trans-N-Hydroxy-N'-[4-[4-quinolinyloxy)methyl]phenyl]-1,2-cyclopentanedicarboxamide;

trans-N-Hydroxy-N'-[4-(4-pyridinylmethyl) phenyl]-1,2-cyclopentanedicarboxamide;

trans-N-Hydroxy-N'-[4-(phenylmethoxy)phenyl]-1,2-cyclohexanedicarboxamide;

trans-N-Hydroxy-N'-[4-[(4-quinolinyloxy)methyl]phenyl]-1,2-cyclohexanedicarboxamide;

trans-N-Hydroxy-N'[4-[(5-quinolinyloxy)methyl]phenyl]-1,2-cyclohexanedicarboxamide;

trans-N-Hydroxy-N'-[4-[(6-quinolinyloxy)methyl]phenyl]-1,2-cyclohexanedicarboxamide;

(3R-trans)-2-methylpropyl4-[(hydroxyamino)carbonyl]-3-[[[4-[(4-quinolinyloxy)methyl]phenyl]amino]carbonyl]-1-piperidinecarboxylate;

(3R-trans)-2-Methylpropyl3-[(hydroxyamino)carbonyl]-4-[[[4-[(4-quinolinyloxy)methyl]phenyl]amino]carbonyl]-1-piperidinecarboxylate;

(3R-trans)-1-(3,3-Dimethyl-1-oxobutyl)-N3-hydroxy-N4-[4-[(4-quinolinyloxy)methyl]phenyl]-3,4-piperidinedicarboxamide;

(3R-trans)-N3-Hydroxy-1-[(1-phenylcyclopropyl)carbonyl]-N4-[4-[(4-quinolinyloxy)methyl]phenyl]-3,4-piperidinedicarboxamide;

17(3R-trans)-N3-Hydroxy-1-(phenylsulfonyl)-N4-[4-[(4-quinolinyloxy)methyl]phenyl]-3,4-piperidinedicarboxamide;

(3R-trans)-2-Methylpropyl3-[(hydroxyamino)carbonyl]-4-[[[4-(2-phenylethoxy)phenyl]amino]carbonyl]-1-piperidinecarboxylate;

(3R-trans)-2-Methylpropyl4-[[[2-fluoro-4-(2-phenylethoxy)phenyl]amino]carbonyl]-3-[(hydroxyamino)carbonyl]-1-piperidinecarboxylate;

(3R-trans)-2-Methylpropyl3-[(hydroxyamino)carbonyl]-4-[[[4-(4-pyridinyloxy)phenyl]amino]carbonyl]-1-piperidinecarboxylate;

(3R-trans)-1-(3,3-Dimethyl-1-oxobutyl)-N3-hydroxy-N4-[4-(4-quinolinyloxy)phenyl]-3,4-piperidinedicarboxamidemono(;

(3R-trans)-N4-[4-[3,5-bis(Trifluoromethyl)phenoxyy]phenyl]-1-(2,2-dimethylpropyl)-N3-hydroxy-3,4-piperidinedicarboxamide;

(3R-trans)-N4-[4-(3,5-dichlorophenoxy)phenyl]-1-(2,2-dimethylpropyl)-N3-hydroxy-3,4-piperidinedicarboxamide;

(3R-trans)-N4-[4-(3-chlorophenoxy)phenyl]-1-(2,2-dimethylpropyl)-N3-hydroxy-3,4-piperidinedicarboxamide;

(3R-trans)-1-(2,2-dimethylpropyl)-N3-hydroxy-N4-(4-phenoxyphenyl)-3,4-piperidinedicarboxamide;

(3R-trans)-tert-Butyl4-[[[4-[(2-methyl-4-quinolinyl)methoxy]phenyl]amino]carbonyl]-3-[(hydroxyamino)carbonyl]-1-piperidinecarboxylate;

(3R-trans)-N3-Hydroxy-N4-[4-[(2-methyl-4-quinolinyl)methoxy]phenyl]-3,4-piperidinedicarboxamide;

(3R-trans)-Methyl4-[[[4-[(2-methyl-4-quinolinyl)methoxy]phenyl]amino]carbonyl]-3-[(hydroxyamino)carbonyl]-1-piperidinecarboxylate;

(3R-trans)-2-propyl4-[[[4-[(2-methyl-4-quinolinyl)methoxy]phenyl]amino]carbonyl]-3-[(hydroxyamino)carbonyl]-1-piperidinecarboxylate;

(3R-trans)-Cyclopropylmethyl4-[[[4-[(2-methyl-4-quinolinyl)methoxy]phenyl]amino]carbonyl]-3-[(hydroxyamino)carbonyl]-1-piperidinecarboxylate;

(3R-trans)-Cyclopentylmethyl4-[[[4-[(2-methyl-4-quinolinyl)methoxy]phenyl]amino]carbonyl]-3-[(hydroxyamino)carbonyl]-1-piperidinecarboxylate;

(3R-trans)-Allyl4-[[[4-[(2-methyl-4-quinolinyl)methoxy]phenyl]amino]carbonyl]-3-[(hydroxyamino)carbonyl]-1-piperidinecarboxylate;

(3R-trans)-Propargyl4-[[[4-[(2-methyl-4-quinolinyl)methoxy]phenyl]amino]carbonyl]-3-[(hydroxyamino)carbonyl]-1-piperidinecarboxylate;

Tetrahydro-4H-pyran-4-yl(3R-trans)-4-[[[4-[(2-methyl-4-quinolinyl)methoxy]phenyl]amino]carbonyl]-3-[(hydroxyamino)carbonyl]-1-piperidinecarboxylate;

(S)-Tetrahydrofuran-3-yl(3R-trans)-4-[[[4-[(2-methyl-4-quinolinyl)methoxy]phenyl]amino]carbonyl]-3-[(hydroxyamino)carbonyl]-1-piperidinecarboxylate;

2-Methyl-4-thiazolemethyl(3R-trans)-4-[[[4-[(2-methyl-4-quinolinyl)methoxy]phenyl]amino]carbonyl]-3-[(hydroxyamino)carbonyl]-1-piperidinecarboxylate;

2-Thiazolemethyl(3R-trans)-4-[[[4-[(2-methyl-4-quinolinyl)methoxy]phenyl]amino]carbonyl]-3-[(hydroxyamino)carbonyl]-1-piperidinecarboxylate;

4-Thiazolemethyl (3R-trans)-4-[[[4-[(2-methyl-4-quinolinyl)methoxy]phenyl]amino]carbonyl]-3-[(hydroxyamino)carbonyl]-1-piperidinecarboxylate;

4-Quinolinylmethyl (3R-trans)-4-[[[4-[(2-methyl-4-quinolinyl)methoxy]phenyl]amino]carbonyl]-3-[(hydroxyamino)carbonyl]-1-piperidinecarboxylate;

(3R-trans)-1-Acetyl-N3-hydroxy-N4-[4-[(2-methyl-4-quinolinyl)methoxy]phenyl]-3,4-piperidinedicarboxamide;

(3R-trans)-1-(2-Furoyl)-N3-hydroxy-N4-[4-[(2-methyl-4-quinolinyl)methoxy]phenyl]-3,4-piperidinedicarboxamide;

(3R-trans)-1-[(2-amino-4-thiazole)acetyl]-N3-hydroxy-N4-[4-[(2-methyl-4-quinolinyl)methoxy]phenyl]-3,4-piperidinedicarboxamide;

(3R-trans)-1-[(2-pyridinyl)carbonyl]-N3-hydroxy-N4-[4-[(2-methyl-4-quinolinyl)methoxy]phenyl]-3,4-piperidinedicarboxamide;

(3R-trans)-1-[(2-Chloro-6-methyl-4-pyridinyl)carbonyl]-N3-hydroxy-N4-[4-[(2-methyl-4-quinolinyl)methoxy]phenyl]-3,4-piperidinedicarboxamide;

(3R-trans)-1-[(4-pyridinyl)carbonyl]-N3-hydroxy-N4-[4-[(2-methyl-4-quinolinyl)methoxy]phenyl]-3,4-piperidinedicarboxamide;

(3R-trans)-1-[(4-quinolinyl)carbonyl]-N3-hydroxy-N4-[4-[(2-methyl-4-quinolinyl)methoxy]phenyl]-3,4-piperidinedicarboxamide;

(3R-trans)-1-[(2-quinolinyl)carbonyl]-N3-hydroxy-N4-[4-[(2-methyl-4-quinolinyl)methoxy]phenyl]-3,4-piperidinedicarboxamide;

(3R-trans)-1-Benzoyl-N3-hydroxy-N4-[4-[(2-methyl-4-quinolinyl)methoxy]phenyl]-3,4-piperidinedicarboxamide;

(3R-trans)-1-[(4-Methylsulfonyl)benzoyl]-N3-hydroxy-N4-[4-[(2-methyl-4-quinolinyl)methoxy]phenyl]-3,4-piperidinedicarboxamide;

(3R-trans)-1-(4-Chlorobenzoyl)-N3-hydroxy-N4-[4-[(2-methyl-4-quinolinyl)methoxy]phenyl]-3,4-piperidinedicarboxamide;

(3R-trans)-1-(4-Cyanobenzoyl)-N3-hydroxy-N4-[4-[(2-methyl-4-quinolinyl)methoxy]phenyl]-3,4-piperidinedicarboxamide;

(3R-trans)-1-(4-Methoxybenzoyl)-N3-hydroxy-N4-[4-[(2-methyl-4-quinolinyl)methoxy]phenyl]-3,4-piperidinedicarboxamide;

(3R-trans)-1-(3-Methoxybenzoyl)-N3-hydroxy-N4-[4-[(2-methyl-4-quinolinyl)methoxy]phenyl]-3,4-piperidinedicarboxamide;

(3R-trans)-1-(5-Nitro-2-pyridinyl)-N3-hydroxy-N4-[4-[(2-methyl-4-quinolinyl)methoxy]phenyl]-3,4-piperidinedicarboxamide;

(3R-trans)-1-Methylsulfonyl-N3-hydroxy-N4-[4-[(2-methyl-4-quinolinyl)methoxy]phenyl]-3,4-piperidinedicarboxamide;

(3R-trans)-1-[(1-Methyl-4-imidazole)sulfonyl]-N3-hydroxy-N4-[4-[(2-methyl-4-quinolinyl)methoxy]phenyl]-3,4-piperidinedicarboxamide;

(3R-trans)-1-(2-Thiophenesulfonyl)-N3-hydroxy-N4-[4-[(2-methyl-4-quinolinyl)methoxy]phenyl]-3,4-piperidinedicarboxamide;

(3R-trans)-1-(tert-Butylaminocarbonyl)-N3-hydroxy-N4-[4-[(2-methyl-4-quinolinyl)methoxy]phenyl]-3,4-piperidinedicarboxamide;

trans-1,1-Dimethylethyl3-[(hydroxyamino)carbonyl]-4-[[[4-[(4-quinolinyloxy)methyl]phenyl]amino]carbonyl]-1-pyrrolidinecarboxylate;

trans-N3-Hydroxy-N4-[4-[(4-quinolinyloxy)methyl]phenyl]-3,4-pyrrolidinedicarboxamidebis-;

trans-1,1-Dimethylethyl3-[[[4-[(2,6-dichloro-4-pyridinyl)methoxy]phenyl]amino]carbonyl]-4-[(hydroxyamino)carbonyl]-1-pyrrolidinecarboxylate;

trans-N3-[4-[(2,6-Dichloro-4-pyridinyl)methoxy]phenyl]-N4-hydroxy-3,4-pyrrolidinedicarboxamidebis-;

(2R-trans)-N2-[4-(4-quinolinyloxymethyl)phenyl]-N3-hydroxy-2,3-piperidinedicarboxamide;

(2R-trans)-1-methyl-N2-[4-(4-quinolinyloxymethyl)phenyl]-N3-hydroxy-2,3-piperidinedicarboxamide;

(2R-trans)-N2-[4-(2-methyl-4-quinolinylmethoxy)phenyl]-N3-hydroxy-2,3-piperidinedicarboxamide;

(2R-trans)-1-methyl-N2-[4-(2-methyl-4-quinolinylmethyloxy)phenyl]-N3-hydroxy-2,3-piperidinedicarboxamide;

(2R-trans)-1-ethyl-N2-[4-(2-methyl-4-quinolinylmethyloxy)phenyl]-N3-hydroxy-2,3-piperidinedicarboxamide;

(2R-trans)-1-cyclopropylmethyl-N2-[4-(2-methyl-4-quinolinylmethyloxy)phenyl]-N3-hydroxy-2,3-piperidinedicarboxamide;

(2R-trans)-1-(2-thiazolemethyl)-N2-[4-(2-methyl-4-quinolinylmethyloxy)phenyl]-N3-hydroxy-2,3-piperidinedicarboxamide;

(2R-trans)-1-Methyl-2-[[4-(2-methyl-4-quinolinylmethyloxy)piperidinyl]carbonyl]-3-(N-hydroxy)piperidinecarboxamide;

(2R-trans)-1-Methyl-2-[[4-(4-quinolinyloxymethyl)piperidinyl]carbonyl]-3-(N-hydroxy)piperidinecarboxamide;

(2R-trans)-1-Methyl-2-[[4-(2-methyl-4-quinolinyloxymethyl)piperidinyl]carbonyl]-3-(N-hydroxy)piperidinecarboxamide;

(2R-trans)-1-Methyl-2-[[4-(2-trifluoromethyl-4-quinolinyloxymethyl)piperidinyl]carbonyl]-3-(N-hydroxy)piperidinecarboxamide;

(2R-trans)-2-[(4-phenylpiperidinyl) carbonyl]-3-(N-hydroxy)piperidinecarboxamide;

(2R-trans)-1-Ethyl-2-[(4-phenylpiperidinyl)carbonyl]-3-(N-hydroxy)piperidinecarboxamide;

(2R-trans)-1-Methyl-2-[[4-(2-methoxyphenyl)piperidinyl]carbonyl]-3-(N-hydroxy)piperidinecarboxamide;

(2R-trans)-1-Methyl-2-[[4-(2-trifluoromethylphenyl)piperidinyl]carbonyl]-3-(N-hydroxy)piperidinecarboxamide;

(2R-trans)-1-Methyl-2-[[4-(2-methylphenyl)piperidinyl]carbonyl]-3-(N-hydroxy)piperidinecarboxamide;

(2R-trans)-1-Methyl-2-[[4-(3-methoxyphenyl)piperidinyl]carbonyl]-3-(N-hydroxy)piperidinecarboxamide; and, (2R-trans)-1-Methyl-2-[[4-(3-trifluoromethylphenyl)piperidinyl]carbonyl]-3-(N-hydroxy)piperidinecarboxamide;

or a pharmaceutically acceptable salt form thereof.

In another embodiment, the present invention provides a novel pharmaceutical composition, comprising: a pharmaceutically acceptable carrier and a therapeutically effective amount of a compound of formula (I) or a pharmaceutically acceptable salt form thereof.

In another embodiment, the present invention provides a novel method for treating or preventing an inflammatory disorder, comprising: administering to a patient in need thereof a therapeutically effective amount of a compound of formula (I) or a pharmaceutically acceptable salt form thereof.

In another embodiment, the present invention provides a novel method of treating a condition or disease mediated by MMPs, TNF, aggrecanase, or a combination thereof in a mammal, comprising: administering to the mammal in need of such treatment a therapeutically effective amount of a compound of formula (I) or a pharmaceutically acceptable salt form thereof.

In another embodiment, the present invention provides a novel method of treating a condition or disease wherein the disease or condition is referred to as rheumatoid arthritis, osteoarthritis, periodontitis, gingivitis, corneal ulceration, solid tumor growth and tumor invasion by secondary metastases, neovascular glaucoma, multiple sclerosis, or psoriasis in a mammal, comprising: administering to the mammal in need of such treatment a therapeutically effective amount of a compound of formula (I) or a pharmaceutically acceptable salt form thereof.

In another embodiment, the present invention provides a novel method of treating a condition or disease wherein the disease or condition is referred to as fever, cardiovascular effects, hemorrhage, coagulation, cachexia, anorexia, alcoholism, acute phase response, acute infection, shock, graft versus host reaction, autoimmune disease or HIV infection in a mammal comprising administering to the mammal in need of such treatment a therapeutically effective amount of a compound of formula (I) or a pharmaceutically acceptable salt form thereof.

In another embodiment, the present invention provides novel compounds of formula (I) for use in therapy.

In another embodiment, the present invention provides the use of novel compounds of formula (I) for the manufacture of a medicament for the treatment of a condition or disease mediated by MMPs, TNF, aggrecanase, or a combination thereof.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Geometric isomers of double bonds such as olefins and C=N double bonds can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^b$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms. $C_{1-10}$ alkyl (or alkylene), is intended to include $C_1$, $C_2$, $C_3$, $C_4$, $C_5$, $C_6$, $C_7$, $C_8$, $C_9$, and $C_{10}$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$, and $C_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl, is intended to include $C_3$, $C_4$, $C_5$, $C_6$, and $C_7$ cycloalkyl groups. "Alkenyl" or "alkenylene" is intended to include hydrocarbon chains of either a straight or branched configuration and one or more unsaturated carbon-carbon bonds which may occur in any stable point along the chain, such as ethenyl and propenyl. $C_{2-10}$ alkenyl (or alkenylene), is intended to include $C_2$, $C_3$, $C_4$, $C_5$, $C_6$, $C_7$, $C_8$, $C_9$, and $C_{10}$ alkenyl groups. "Alkynyl" or "alkynylene" is intended to include hydrocarbon chains of either a straight or branched configuration and one or more triple carbon-carbon bonds which may occur in any stable point along the chain, such as ethynyl and propynyl. $C_{2-10}$ alkynyl (or alkynylene), is intended to include $C_2$, $C_3$, $C_4$, $C_5$, $C_6$, $C_7$, $C_8$, $C_9$, and $C_{10}$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl.

As used herein, the term "heterocycle" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heterotams independently selected from the group consisting of N, NH, O and S. It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc. . . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

"Therapeutically effective amount" is intended to include an amount of a compound of the present invention or an amount of the combination of compounds claimed effective to inhibit a desired metalloprotease in a host. The combination of compounds is preferably a synergistic combination. Synergy, as described for example by Chou and Talalay, Adv. Enzyme Regul. 22:27–55 (1984), occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

A series of five, six and seven membered ring heterocycles (B ring in formula I) can be constructed using the methods outlined in Schemes 1–10. (2S)-trans-2,3-Pyrrolidinedicarboxylate of formula 5 can be prepared using the procedures described in scheme 1. Alkylation of Cbz-protected L-aspartic acid 1 with allyl bromide using LDA followed by a chromatography to separate the two produced diastereomers yields the desired syn-diastereomer 2. An ozonolysis converts the vinyl 2 to an aldehyde 3. Hydrogenation leads to a ring closure to give a pyrrolidine 4. Derivatization at the nitrogen using an acid chloride, a chloroformate, a sulfonyl chloride or an aldehyde in the presence of NaBH$_3$CN affords the pyrrolidine derivative 5.

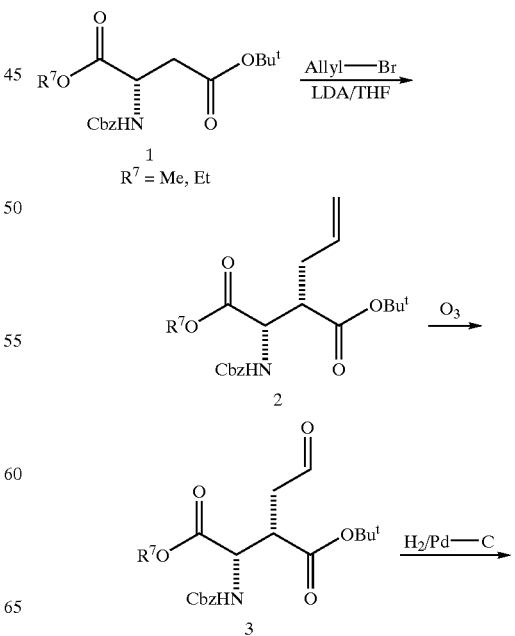

Scheme 1

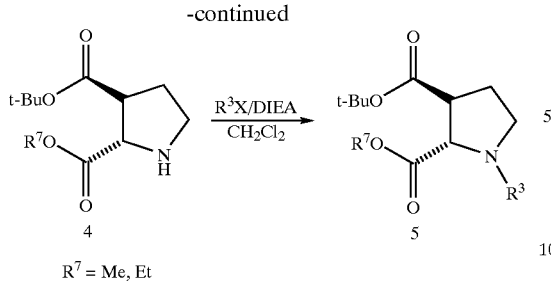

A series of (4S)-trans-2-oxo-4,5-pyrrolidinediccarboxylate of formula 9 can be prepared using the method shown in Scheme 2. Alkylation of Cbz-protected L-aspartic acid 1 with benzyl bromoacetate using LDA followed by a chromatography to separate the two produced diastereomers yields the desired syn-diastereomer 6. Hydrogenation removes the Cbz and benzyl groups. Cyclization using a coupling agent such as BOP produces a γ-lactam 8. Alkylation using an alkyl halide or an alkyl sulfonate gives the 2-oxopyrrolidine derivative 9.

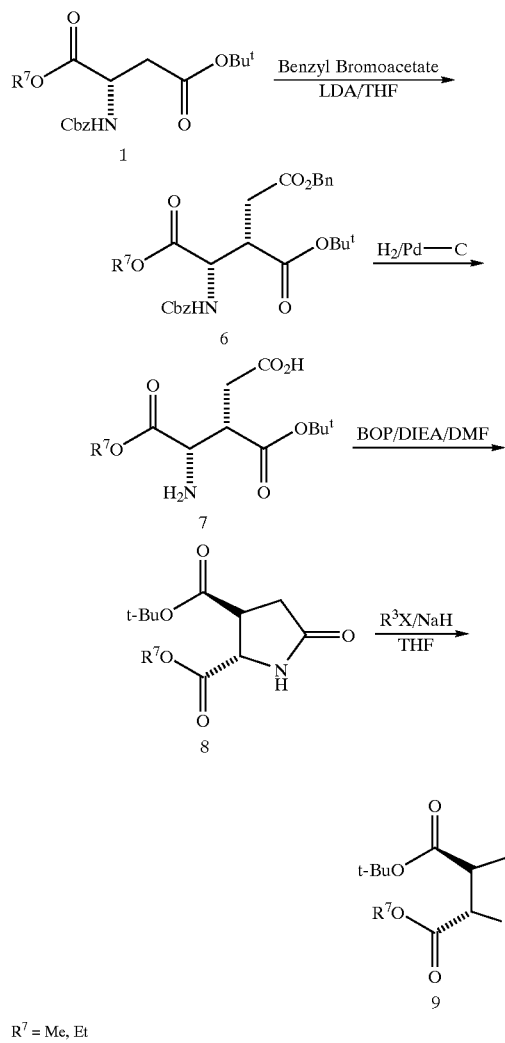

trans-3,4-Pyrrolidinedicarboxylate of formula 12 can be synthesized from a cycloaddition of fumarate 10 with an intermediate generated from reaction of paraformaldehyde and glycine followed by a derivatization at the nitrogen using an acid chloride, a chloroformate, a sulfonyl chloride or an aldehyde in the presence of $NaBH_3CN$ (Scheme 3).

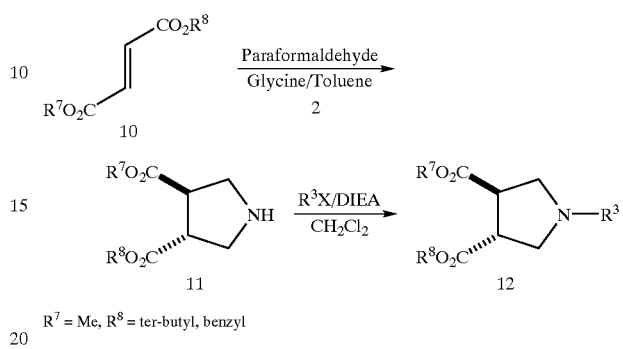

(2S)-trans-2,3-Piperidinedicarboxylate of formula 16 can be prepared starting with the intermediate 2 (Scheme 4). A hydroboration using 9-BBN converts the vinyl group to an alcohol 13 which is oxidized to give an aldehyde 14. Upon removal of the Cbz by hydrogenation, reductive amination between the released amine and the aldelhyde took place, resulting in a ring closure to give the piperidine 15. Derivatization at the nitrogen using an acid chloride, a chloroformate, a sulfonyl chloride or an aldehyde in the presence of $NaBH_3CN$ affords the piperidine derivative 16.

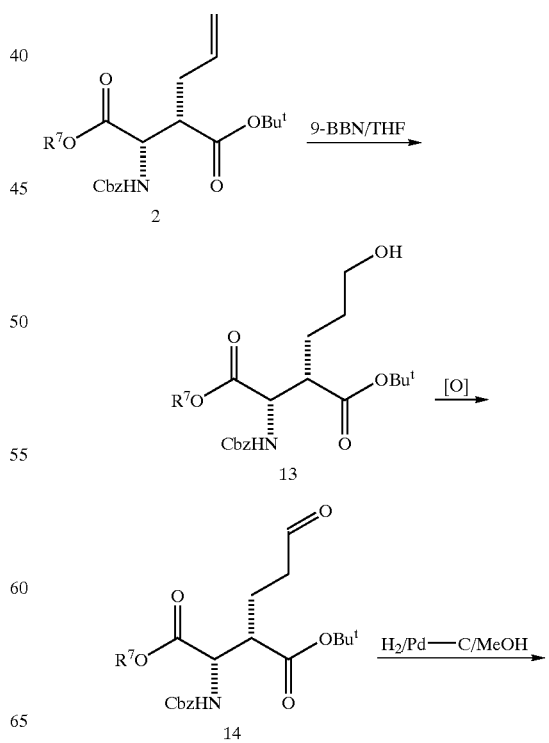

-continued

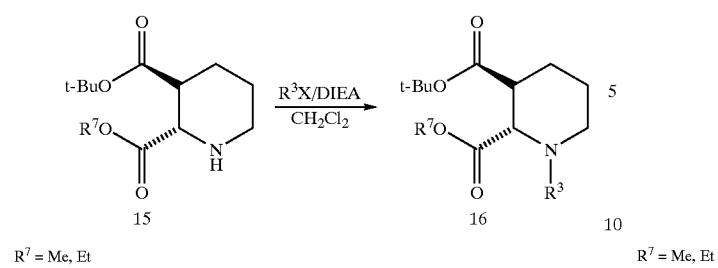

R⁷ = Me, Et

-continued

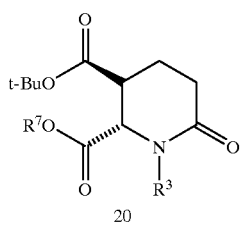

R⁷ = Me, Et

The synthesis of (5S)-trans-2-oxo-5,6-piperidinecarboxylate of formula 20 can be prepared using the method depicted in Scheme 5. The alcohol intermediate 13 is oxidized to give a carboxylic acid 17. Hydrogenation to remove the Cbz followed by coupling using BOP yields the δ-lactam 19. Alkylation at the nitrogen with an alkyl halide or an alkyl sulfonate using NaH gives the δ-lactam derivative 20.

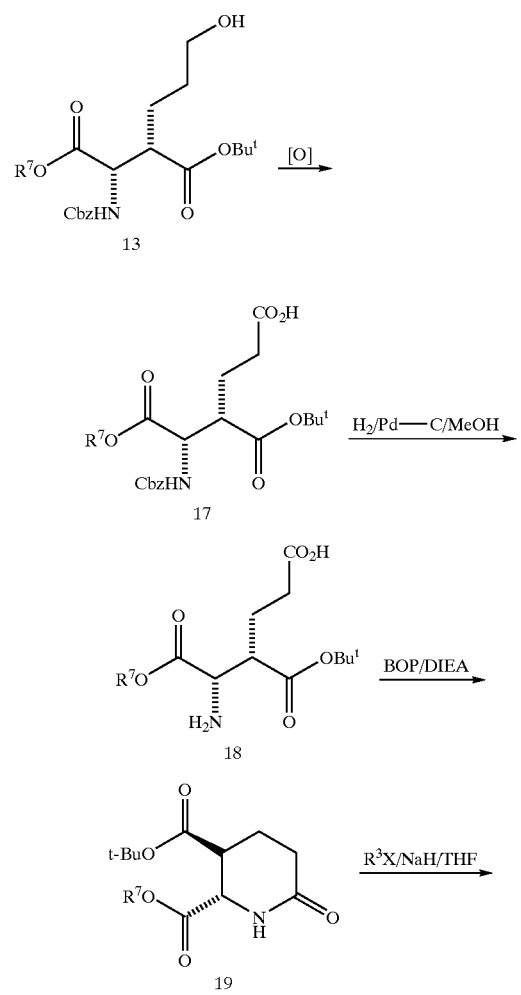

The synthesis of (3S)-trans-3,4-piperidinedicarboxylate of formula 30 starts with a Cbz-protected β-alanine 21 as shown in Scheme 6. Regioselective N-benzylation with benzyl bromide can be accomplished using NaH/THF. The acid 22 is coupled with the chiral auxiliary group (R)-4-phenylmethyl-2-oxazolidinone (HX) using pivaloyl chloride as the activating agent. Alkylation of 23 with tert-butyl bromoacetate using LDA produces the mono-substituted succinate 24. The chiral auxiliary group is removed using LiOH/H₂O₂ and the resulting acid is alkylated with allyl bromide using 2 equivalents of LDA to give the double-substituted succinate 26. The carboxylic acid is converted to a methyl ester 27 using iodomethane/DBU and the vinyl is converted to an aldehyde 28 by an ozonolysis. Hydrogenation results in a ring closure to give the piperidine 29 which is derived with an acid chloride, a chloroformate, a sulfonyl chloride or an aldehyde in the presence of NaBH₃CN to give 30.

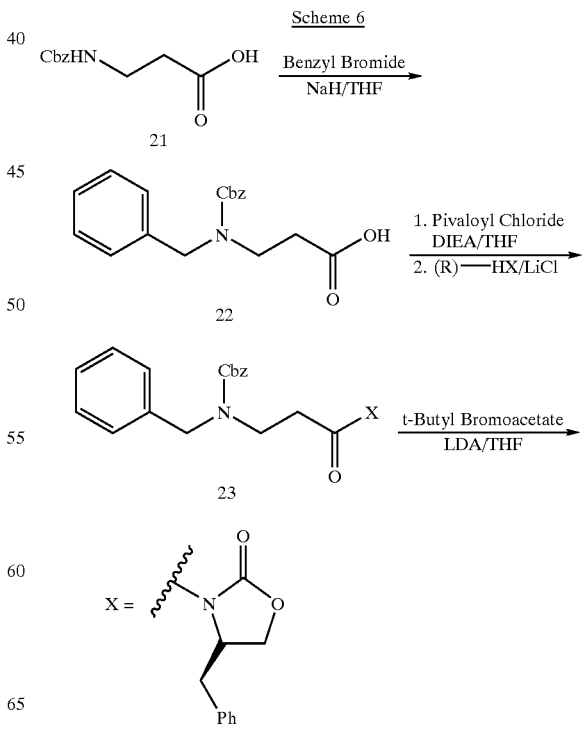

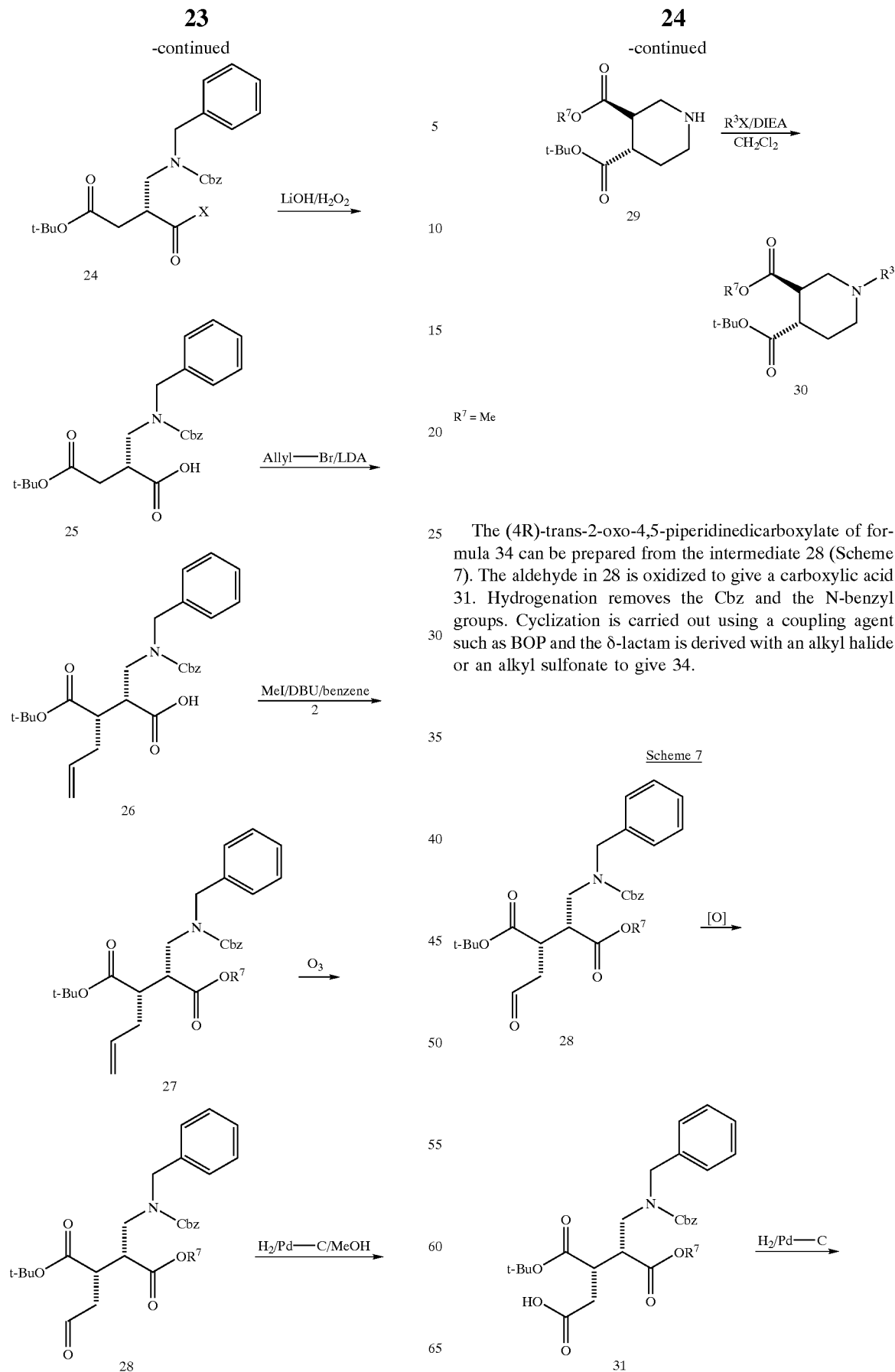
The (4R)-trans-2-oxo-4,5-piperidinedicarboxylate of formula 34 can be prepared from the intermediate 28 (Scheme 7). The aldehyde in 28 is oxidized to give a carboxylic acid 31. Hydrogenation removes the Cbz and the N-benzyl groups. Cyclization is carried out using a coupling agent such as BOP and the δ-lactam is derived with an alkyl halide or an alkyl sulfonate to give 34.
Scheme 7

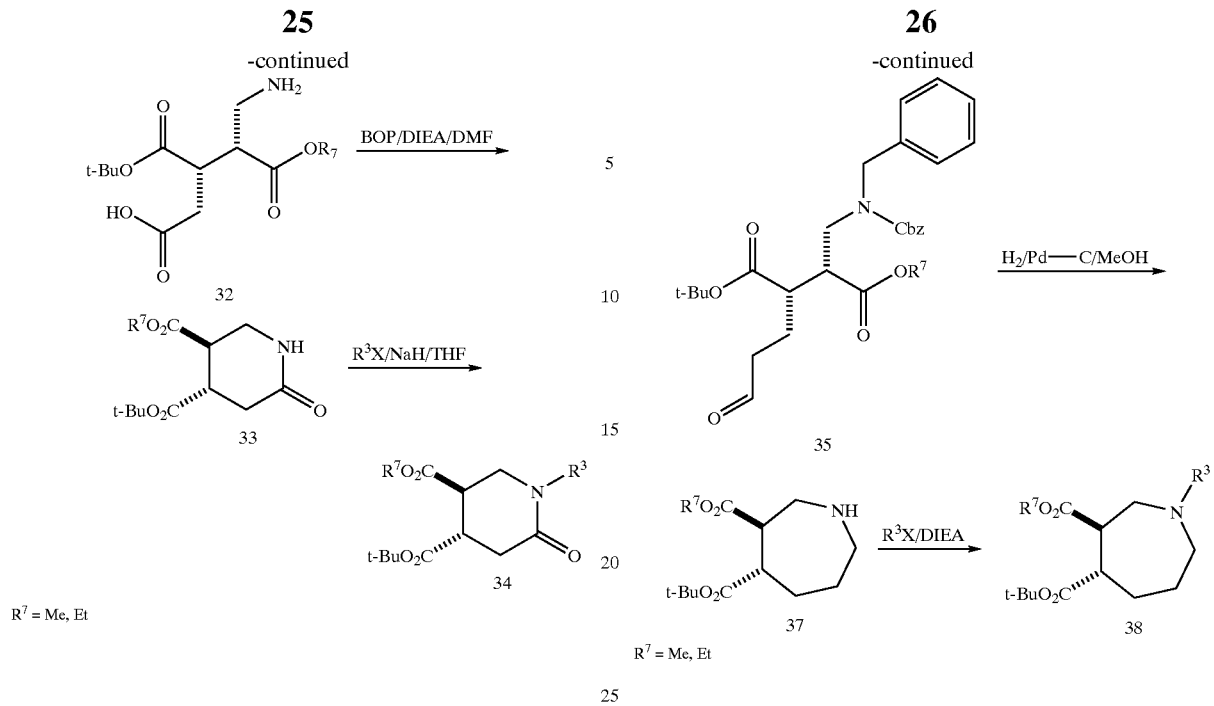

The (3S)- trans-3,4-homopiperidinedicarboxylate of formula 38 can be prepared starting from the intermediate 27. A hydroboration using 9-BBN converts the vinyl to an alcohol 35 which is oxidized to give an aldehyde 36. Hydrogenation produces the homopiperidine 37 which is derived with an acid chloride, a chloroformate, a sulfonyl chloride or an aldehyde in the presence of $NaBH_3CN$ to give 38.

The synthesis of (5R)-trans-2-oxo-5,6-homopiperidinedicarboxylate of formula 42 starts with the alcohol intermediate 35 which is oxidized to give a carboxylic acid 39. Hydrogenation followed by cyclization using a coupling agent such as BOP yields the ε-caprolactam 41 which is derived with an alkyl halide or an alkyl sulfonate to give 42.

Scheme 8

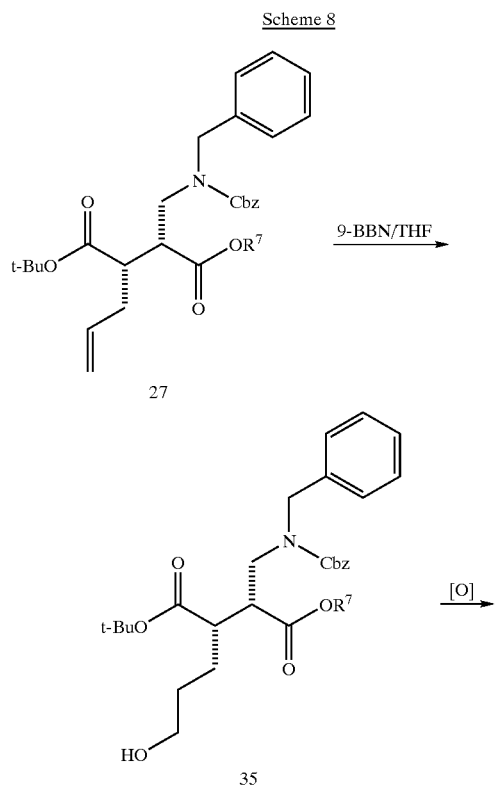

Scheme 9

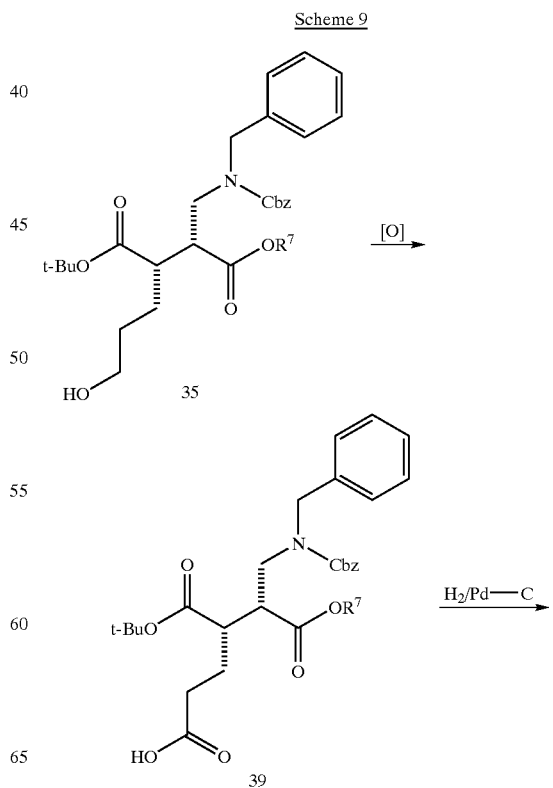

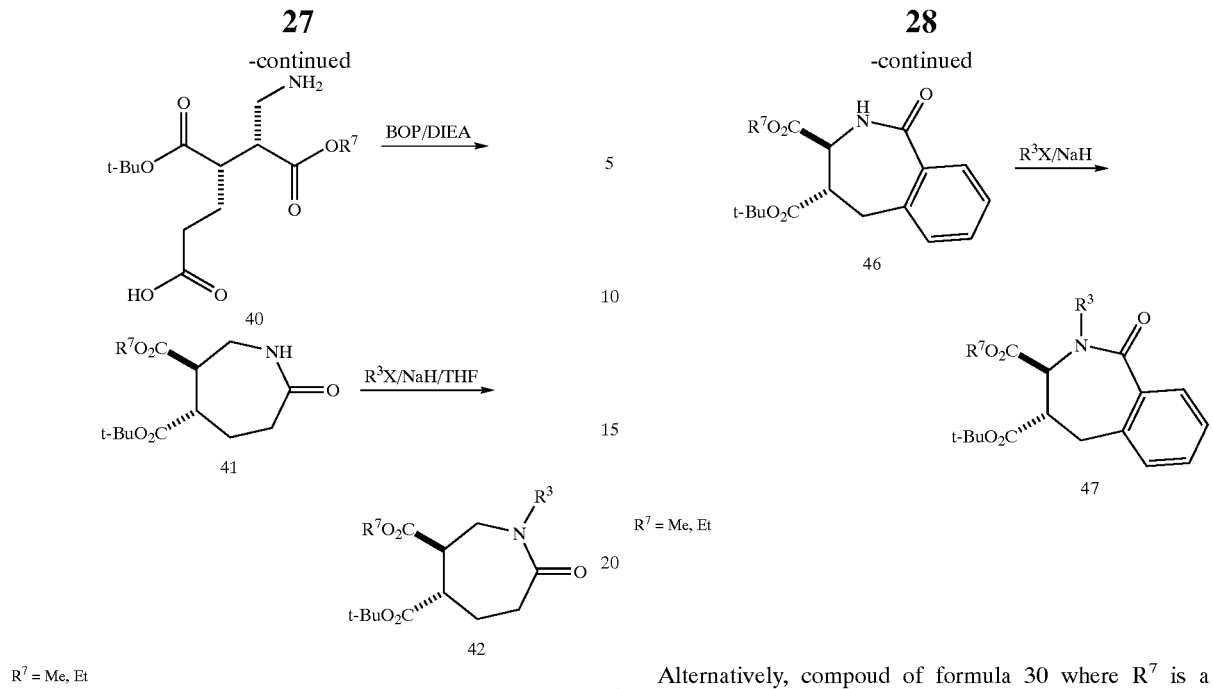

The synthesis of (6R)-trans-2-oxo-3,4-benzo-6,7-homopiperidinedicarboxylate of formula 47 is prepared as outlined in Scheme 10. Alkylation of 1 with benzyl 2-bromomethylbenzoate 43 using LDA followed by chromatography to separate the produced two diastereomers yields the aspartic acid derivative 44. Hydrogenation followed by cyclization using a coupling agent such as BOP produces the lactam 46 which is derived with an alkyl halide or an alkyl sulfonate to give 47.

Alternatively, compoud of formula 30 where $R^7$ is a benzyl and $R^3$ is a benzyloxycarbonyl (Cbz) can be prepared using the method outlined in Scheme 11. The carboxylic acid 26 is converted to a benzyl ester 48 using benzyl bromide/$K_2CO_3$/DMF at an elevated temperature. An ozonolysis converts the vinyl to an aldehyde 49. Hydrogenation produces the piperidine ring 50. The amino is protected with a Cbz using N-benzyloxycarbonyloxysuccinimide (CbzOSu) and the carboxylic acid is converted to a benzyl ester using benzyl bromide/$K_2CO_3$/DMF at an elevated temperature to give 30

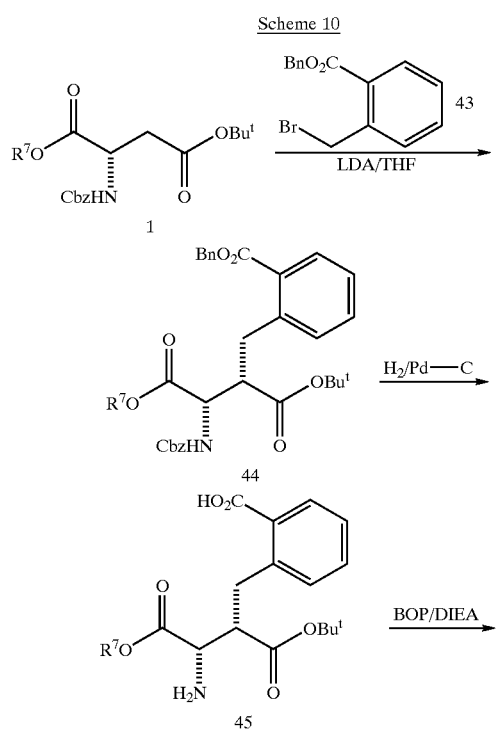

Scheme 10

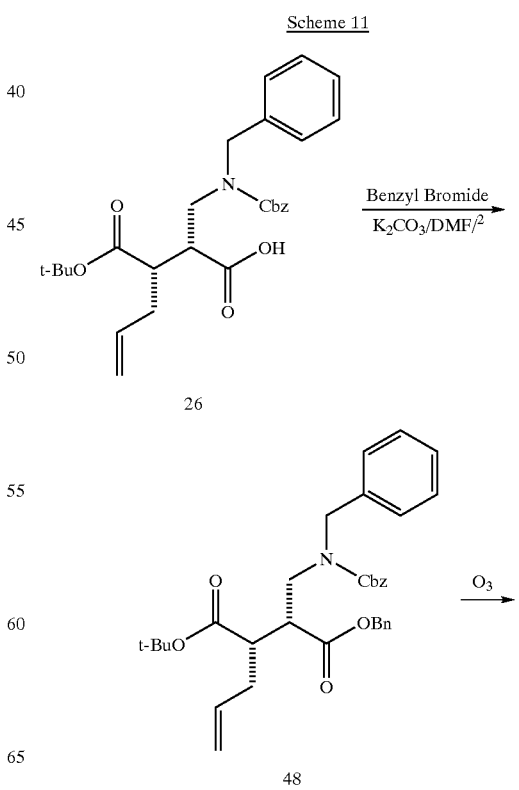

Scheme 11

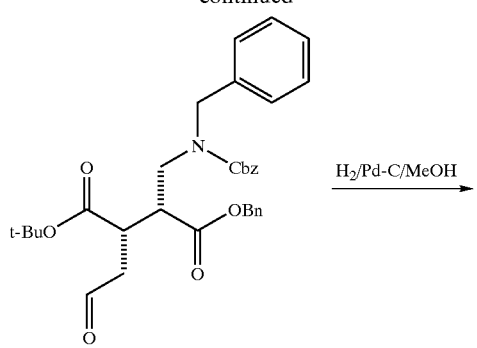

49

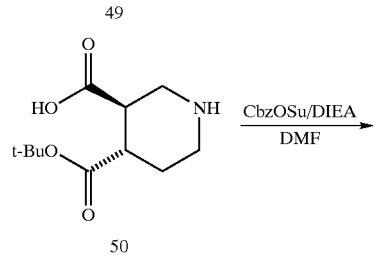

50

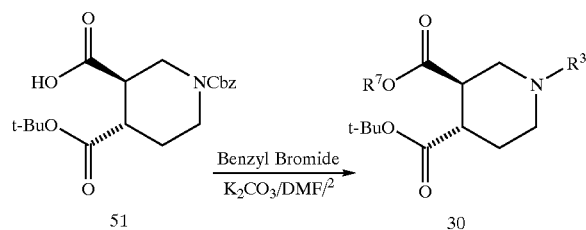

51 → 30

R⁷ = Benzyl, R³ = Cbz

Alternatively, compound of formula 30 where R⁷ is 9-fluorenylmethyl and R³ is 9-fluorenylmethoxycarbonyl (Fmoc) can be prepared using the method shown in Scheme 12. The piperidine 50 is reacted with FmocOSu to give Fmoc-protected intermediate 52. Coupling of the carboxylic acid 52 with 9-fluorenylmethanol using DCC in the presence of 4-dimethylaminopyridine yields compound 30.

Scheme 12

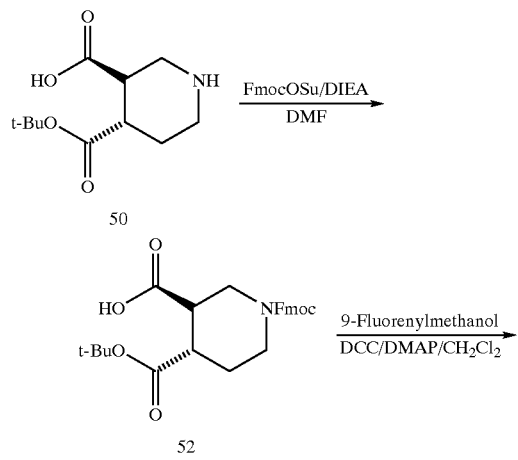

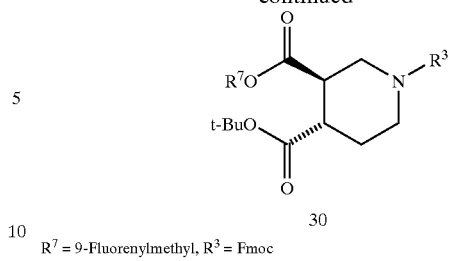

30

$R^7$ = 9-Fluorenylmethyl, $R^3$ = Fmoc

A series of $R^1$ groups in formula I can be prepared using the methods outlined in Schemes 13–15. The 4-(aryloxyalkyl)aniline derivative of formula 58 is prepared starting from 4-(hydroxyalkyl)aniline 53 (Scheme 13). The amino is protected with a Boc to give 54. The alcohol of 54 is converted to a sulfonate 55. Displacement of 55 with an aryl or a heteroaryl alcohol 56 yields the ether intermediate 57 which is treated with 4 N HCl/dioxane to give 58.

Scheme 13

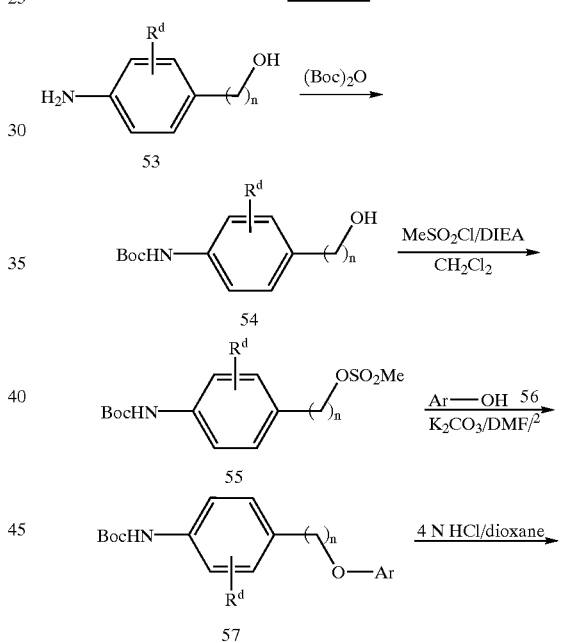

n = 1–2

The 4-(aralkyloxy)aniline of formula 62 can be prepared using the method described in Scheme 14. Reaction of 4-tert-butoxycarbonylaminophenol 59, which was prepared from reaction of 4-aminophenol with di-tert-butyl-dicarbonate, with an aralkyl halide or sulfonate 60 yields the ether 61. Reduction of the nitro group using zinc or iron in acetic acid/water gives the aniline derivative 62.

Scheme 14

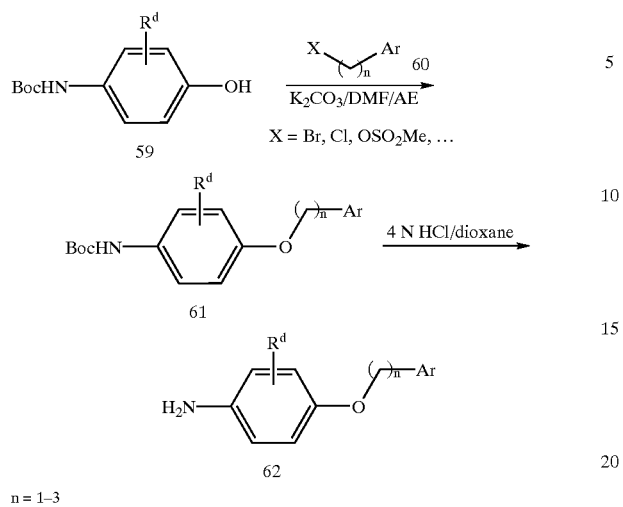

n = 1–3

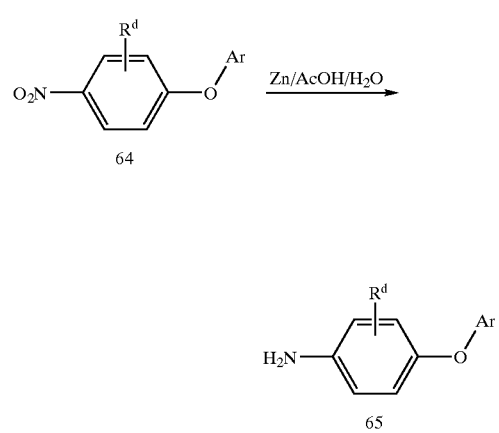

The diphenyl ether of formula 65 can be prepared using the method shown in Scheme 15. Reaction of 1-fluoro-4-nitrobenzene or its derivative 63 with an aryl or a heteroaryl alcohol 56 using cesium carbonate as base yields the diphenyl ether 64. Treatment with zinc in acetic acid/water reduces the nitro to an amine 65.

Scheme 15

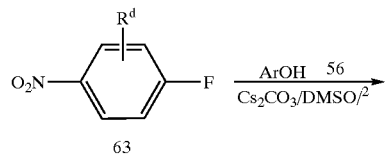

A series of hydroxamate compounds of formulas 68, 72 and 76 can be prepared by assembling the B ring of formula 5, 9, 12, 16, 20, 30, 34, 38, 42, 47, or 66 with the $R^1$ group of formula 58, 62, or 65 followed by conversion of a carboxylic acid to a hydroxamic acid using the methods outlined in Scheme 16–19. The hydroxamate of formula 68 can be prepared by condensation of a trans-1,2-cyclopentanedicarboxylic acid or trans-1,2-cyclohexanedicarboxylic acid with an aniline derivative 58, 62 or 65 followed by coupling of the carboxylic acid with a hydroxylamine hydrochloride using a coupling agent such as BOP (Scheme 16).

Scheme 16

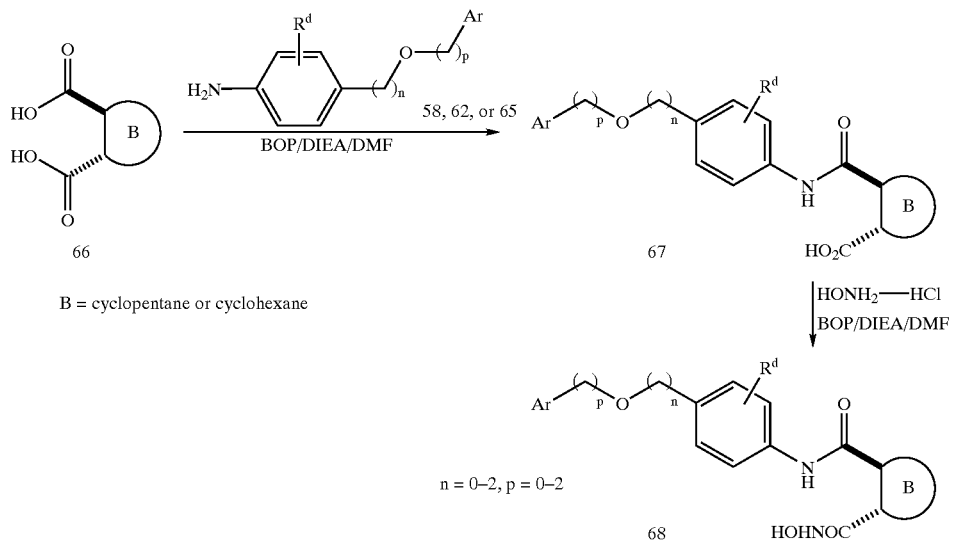

B = cyclopentane or cyclohexane n = 0–2, p = 0–2

The synthesis of the hydroxamate of formula 72 is shown in Scheme 17. The B ring of formula 5, 9, 12, 16, 20, 30, 34, 38, 42 or 47 where $R^7$ is methyl, ethyl, benzyl or 9-fluorenylmethyl and $R^8$ is tert-butyl is treated with TFA/ $CH_2Cl_2$ to remove the tert-butyl. The resulting carboxylic acid is condensed with an aniline derivative of formula 58, 62 or 65 using a coupling agent such as BOP to give the amide 70. The methyl ester is saponified using sodium hydroxide and the resulting carboxylic acid 71 is converted to a hydroxamic acid 72.

The hydroxamate of formula 76 is prepared using the method shown in Scheme 18. The B ring of formula 5, 9, 12, 16, 20, 30, 34, 38, 42 or 47 where $R^7$ is methyl or ethyl and $R^8$ is tert-butyl or benzyl is saponified to give a carboxylic acid 73. Coupling of 73 with an aniline derivative of formula 58, 62 or 65 using a coupling agent such as BOP yields the amide 74. Removal of the tert-butyl group using TFA or the benzyl group using hydrogenation followed by coupling with hydroxylamine hydrochloride using BOP affords the final product 76.

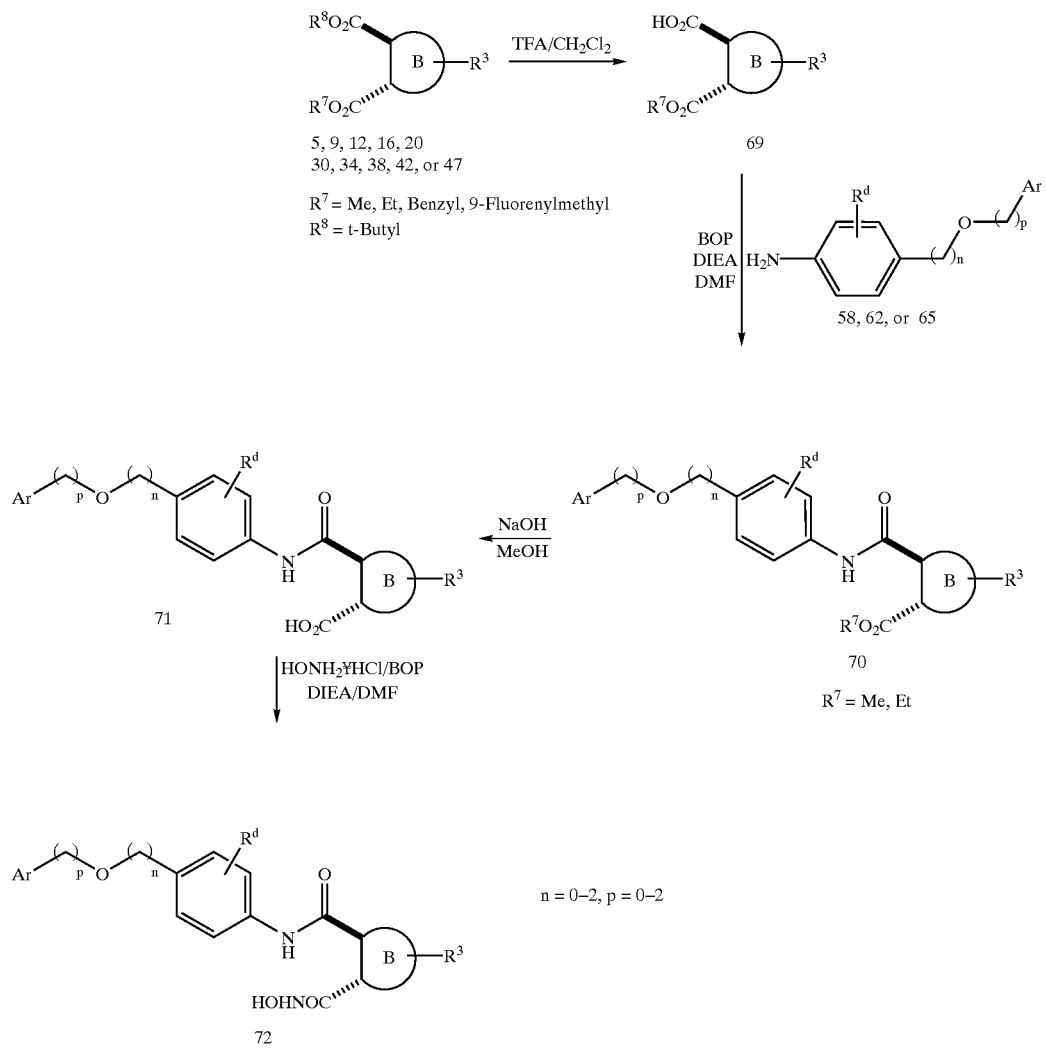

Scheme 17

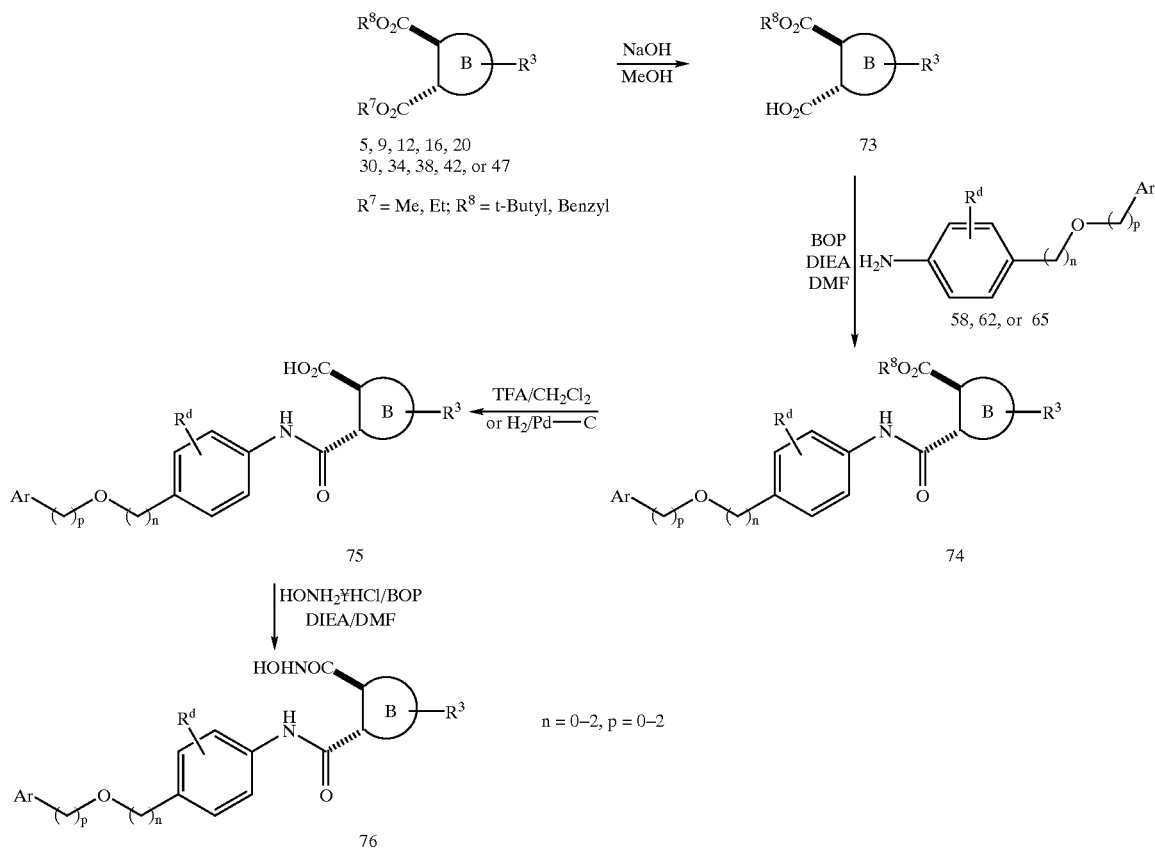

Alternatively, compound 72 can be prepared using the procedures described in Scheme 19. The amide intermediate 70 where $R^7$ is a benzyl or 9-fluorenylmethyl and $R^3$ is benzyloxycarbonyl or 9-fluorenylmethoxycarbonyl is subjected to a hydrogenation or treatment with piperidine in DMF to give 77. Reaction of 77 with an acid chloride, a chloroformate or an aldehyde in the presence of NaBH$_3$CN produces 78 which is converted to a hydroxamic acid 72 by coupling with hydroxylamine hydrochloride using BOP.

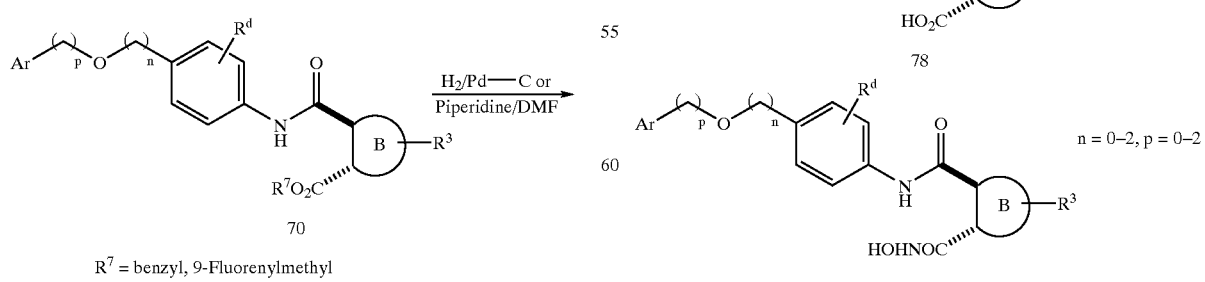

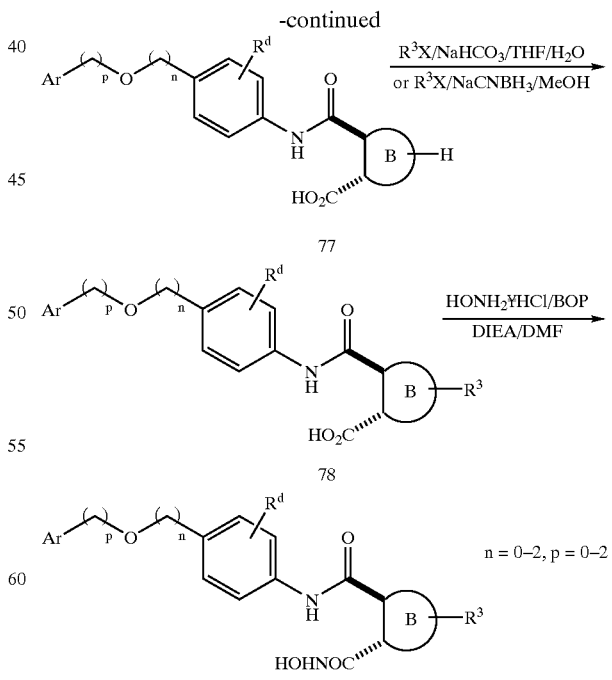

Alternatively, the B ring of formulas 83 and 86 where the ring structure is a 2,3-disubstituted pyrrolidine or piperidine can be prepared using the methods described in Schemes 20–21. L-Aspartic acid β-tert-butyl ester 79 was alkylated with benzyl bromide to give the tris-benzylated aspartic acid derivative 80. Allylation of 80 with allyl bromide using LiHMDS provided the allylated derivative 81 as a mixture of 2 diastereomers which was subjected to an ozonolysis. Chromatography on a silica gel column of the aldehyde separated the two diastereomers. Hydrogenation of the syn-diastereomer 82 produced the pyrrolidine derivative 83.

diastereomer 84 was oxidized using an oxidizing agent such as pyridinium dichromate to give the aldehyde 85 which was subjected to hydrogenation to afford the piperidine derivative 86.

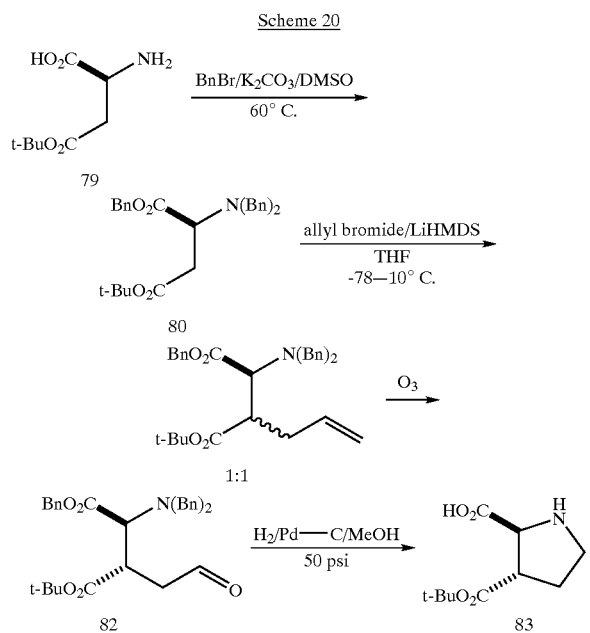

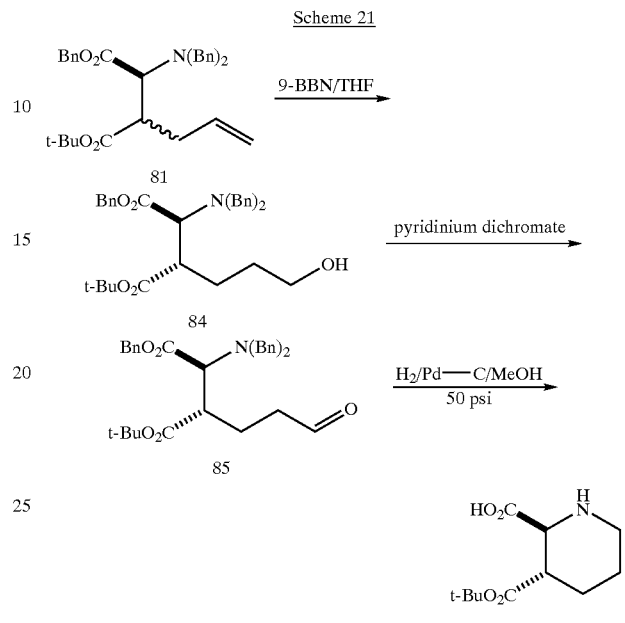

The olefin functionality of 81 was converted to an alcohol using 9-BBN. The two diastereomers of the alcohol were then separated using flash chromatography. The syn- The B ring of formula 83 or 86 was assembled with the R1 residue of formula 58, 62 or 65 using a coupling agent such as BOP. Reductive amination of 87 with an aldehyde using sodium cyanoborohydride produced N-alkylated derivative 88. Removal of the tert-butyl using acid followed by coupling with hydroxylamine hydrochloride using a coupling agent such as propyl chloroformate afforded the hydroxamic acid 90.

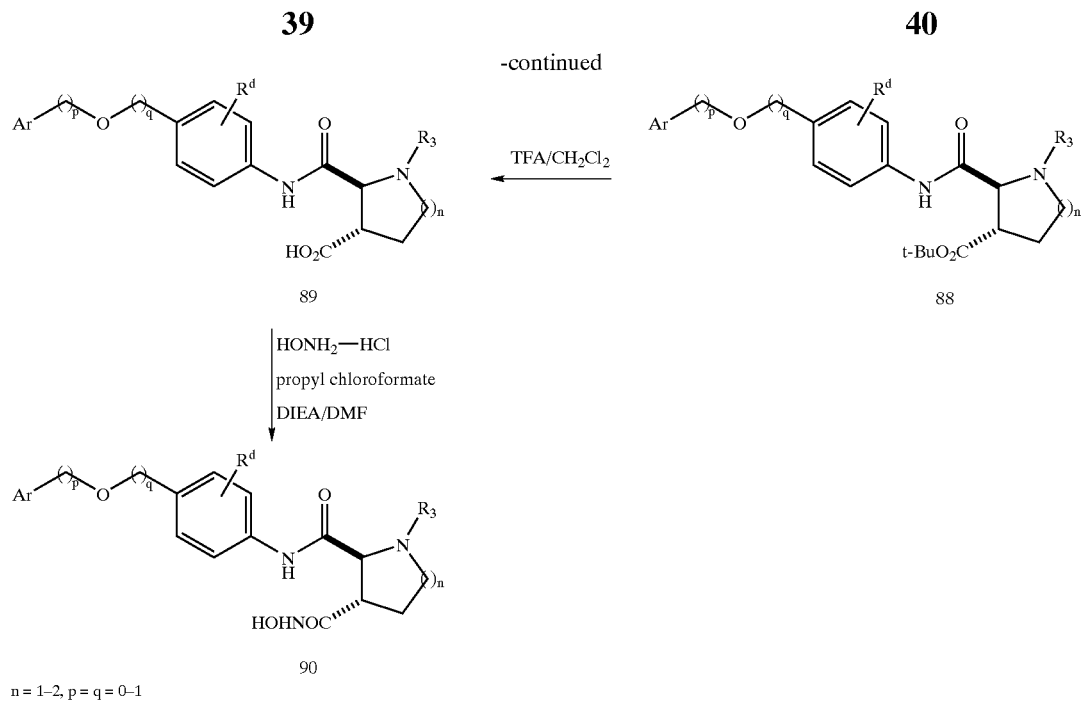

n = 1–2, p = q = 0–1

Another type of R1 in formula I can be prepared using the methods described in Schemes 23–25. The N-Boc protected 4-hydroxypiperidine 91, which was prepared from reaction of 4-hydroxypiperidine with di-tert-butyl-dicarbonate, was alkylated with arylmethylhalide or arylmethyl sulfonate 92 to give the ether derivative 93. Deprotection of the Boc group using acid produced the unprotected piperidine derivative 94.

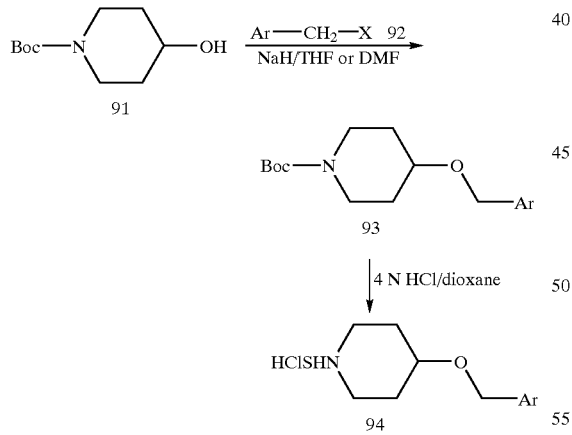

N-Boc protected 4-hydroxymethylpiperidine 95, which was prepared from reaction of 4-hydroxymethylpiperidine with di-tert-butyl-di-carbonate, was converted to a sulfonate or halide 96. Displacement of the sulfonate or halide with phenol or its derivative, or quinolinol or its derivative produced the ether derivative 97 which was treated with acid to give the unprotected piperidine derivative 98.

Another type of piperidine derivative 101 was prepared by coupling of 4-bromopyridine with a boronic acid 99 using $Pd(PPh_3)_4$ as catalyst followed by hydrogenation as shown in Scheme 25.

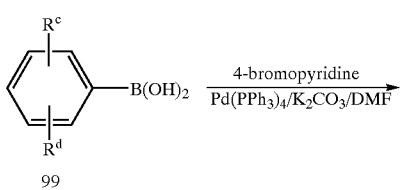

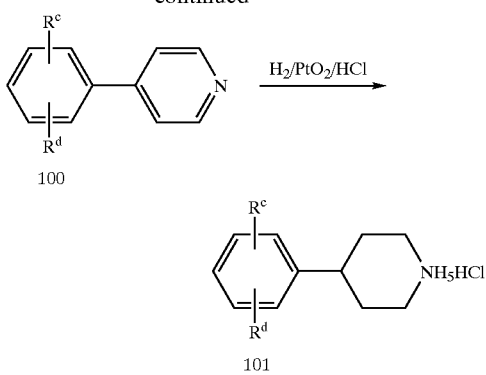

A series of hydroxamic acids of formulas 104 and 107 can be prepared using the methods described in Schemes 26–27. Coupling of the B ring of formula 69 with the R1 residue of formula 94, 98 or 101 using a coupling agent such as BOP produced the carboxamide derivative 102. Saponification of the ester produced the the acid 103 which was converted to the hydroxamic acid 103 by coupling with hydroxylamine hydrochloride using a coupling agent such as n-propyl chloroformate.

Coupling of the B ring of formula 73 with the R1 residue of formula 94, 98 or 101 using a coupling agent such as BOP produced the carboxamide 105 which was subjected to treatment using an acid such as TFA or hydrogenation to remove the R8 group. Coupling of carboxylic acid 106 with hydroxylamine hydrochloride using coupling agent such as isobutyl chloroformate produced the hydroxamic acid 107.

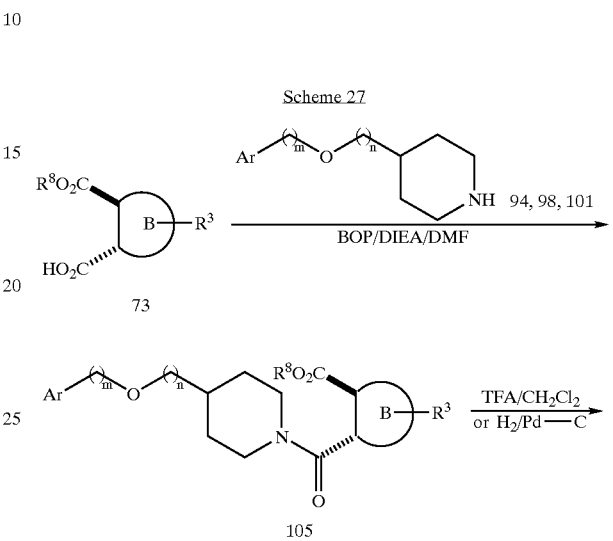

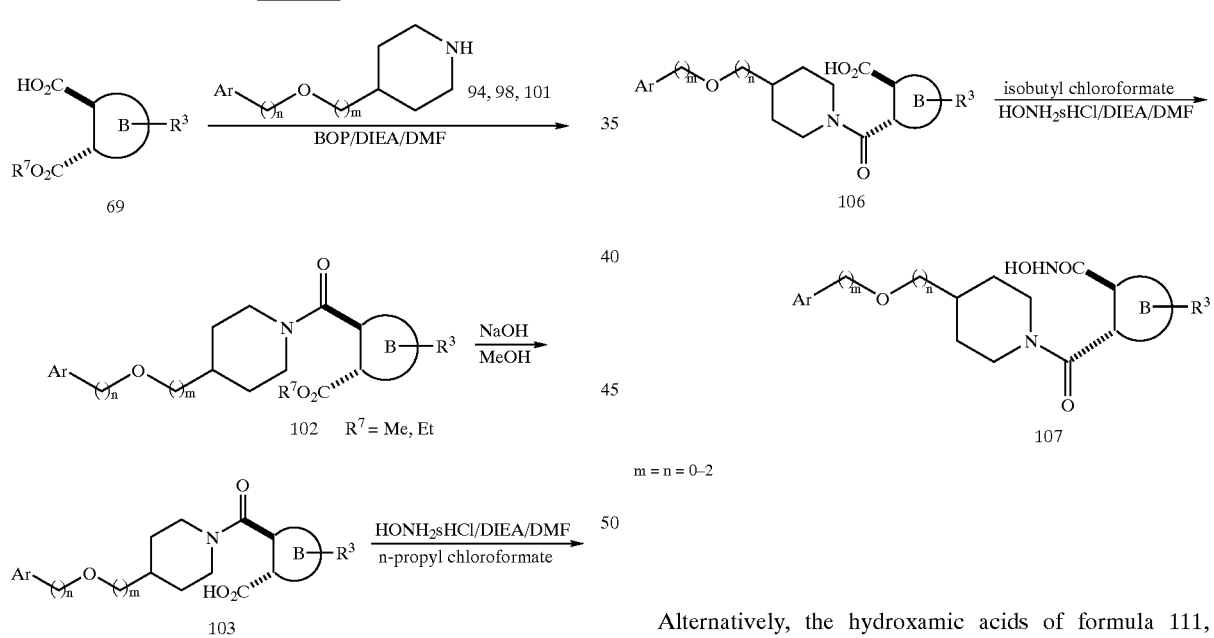

Alternatively, the hydroxamic acids of formula 111, where the B ring is a 2,3-disubstituted pyrrolidine or piperidine, can be prepared using the method described in Scheme 28. Coupling of the B ring of the formula 83 or 86 with the R1 residue of the formula 94, 98 or 101 produced the carboxamide derivative 108. Reductive amination at the pyrrolidine or piperidine nitrogen using an aldehyde in the presence of sodium cyanoborohydride produced the N-alkyl derivative 109 which was treated with an acid to remove the tert-butyl group. The carboxylic acid 110 was converted to the hydroxamic acid 111 in a manner as described previously.

Scheme 28

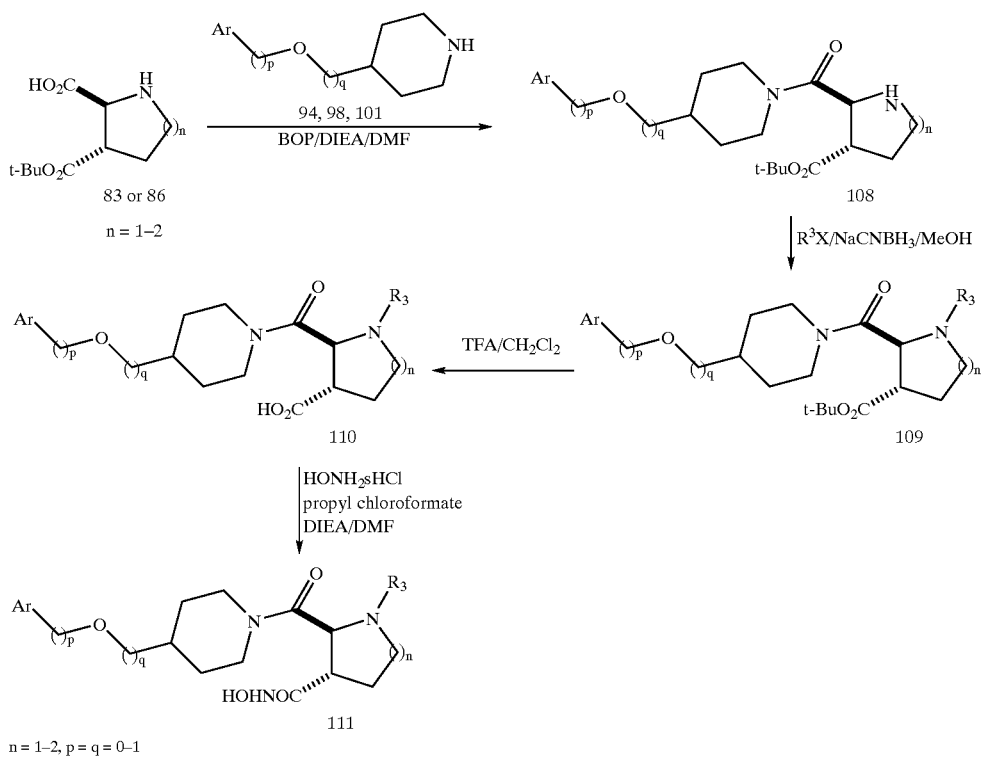

n = 1-2, p = q = 0-1

One diastereomer of a compound of Formula I may display superior activity compared with the others. Thus, the following stereochemistries are considered to be a part of the present invention.

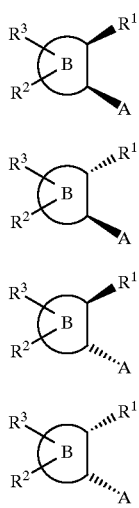

Ia

Ib

Ic

Id

When required, separation of the racemic material can be achieved by HPLC using a chiral column or by a resolution using a resolving agent such as camphonic chloride as in Steven D. Young, et al, *Antimicrobial Agents and Chemotheraphy*, 1995, 2602–2605. A chiral compound of Formula I may also be directly synthesized using a chiral catalyst or a chiral ligand, e.g., Andrew S. Thompson, et al, *Tet. lett.* 1995, 36, 8937–8940).

Other features of the invention will become apparent in the course of the following descriptions of exemplary embodiments which are given for illustration of the invention and are not intended to be limiting thereof.

EXAMPLES

Abbreviations used in the Examples are defined as follows: "1×" for once, "2×" for twice, "3×" for thrice, "° C." for degrees Celsius, "eq" for equivalent or equivalents, "g" for gram or grams, "mg" for milligram or milligrams, "mL" for milliliter or milliliters, "$^1$H" for proton, "h" for hour or hours, "M" for molar, "min" for minute or minutes, "MHz" for megahertz, "MS" for mass spectroscopy, "NMR" for nuclear magnetic resonance spectroscopy, "rt" for room temperature, "tlc" for thin layer chromatography, "v/v" for volume to volume ratio and BOP for benzotriazol-1-yloxy-tris(dimethylamino)phosphonium hexafluorophosphate. "α", "β", "R" and "S" are stereochemical designations familiar to those skilled in the art.

Example 1 trans-N-Hydroxy-2-[(4-phenyl-1-piperidinyl)carbonyl]cyclopentanecarboxamide (1a) To a solution of trans-1,2-cyclopentanedicarboxylic acid (950 mg, 6 mmol) and 4-phenylpiperidine (322 mg, 2 mmol) in DMF (5 mL) cooled in an ice bath was added BOP (930 mg, 2.1 mmol) followed by diisopropylethylamine (2.1 mL, 12 mmol). The mixture was stirred for 3.5 hours at room temperature. Ethyl acetate was added and the solution was washed with citric acid and brine, dried (MgSO$_4$), and concentrated. Silica gel column chromatography eluting with 10% methanol/methylene chloride gave the desired carboxylic acid (410 mg, 68%). MS(NH$_3$-CI): (M+H)$^+$=302.

(1b) BOP (221 mg 0.5 mmol) was added to a solution of the carboxylic acid 1a (150 mg, 0.5 mmol), hydroxylamine hydrochloride (70 mg, 1 mmol) and diisopropylethylamine (0.35 mL, 2 mmol) in DMF (5 mL) cooled in an ice bath. The mixture was stirred at room temperature for 1 hour and concentrated. The residue was taken up in ethyl acetate, and the solution was washed with brine and concentrated. Purification on a reversed phase HPLC gave the desired hydroxamic acid (107 mg, 70%). MS(ESI): $(M+H)^+=317$.

Example 2 trans-N-Hydroxy-2-{[4-[(4-methylphenoxy)methyl]-1-piperidinyl]carbonyl}cyclopentanecarboxamide (2a) A solution of ethyl isonipecotate (15.72 g, 100 mmol), di-tert-butyl dicarbonate (21.82 g, 100 mmol) and diisopropylethylamine (17.4 mL, 100 mmol) in THF (100 mL) was stirred at room temperature overnight and the solution was concentrated. The residue was taken up in ethyl acetate, and the solution was washed with brine, dried ($MgSO_4$), and concentrated. Purification on a silica gel column eluting with 20% ethyl acetate/hexane produced the desired Boc-protected product (22.43 g, 87%). MS ($NH_3$—Cl): $(M+H)^+=258$.

(2b) To a solution of the ethyl ester 2a (22.43 g, 87.27 mmol) in ethanol (100 mL) was added $NaBH_4$ (5.94 g, 157 mmol) and the mixture was heated at 50° C. overnight. The solvent was removed by concentration and the residue was taken up in ethyl acetate. The solution was washed with 10% citric acid and brine, dried ($MgSO_4$), and concentrated. Purification on a silica gel column eluting with 40% ethyl acetate/hexane gave the desired alcohol (14.12 g, 75%). MS($NH_3$—Cl): $(M+H)^+=216$.

(2c) To absolution of the alcohol 2b (4.3 g, 20 mmol) and N-methylmorpholine (3.3 mL, 30 mmol) in methylene chloride (20 mL) cooled in an ice bath was slowly added toluenesulfonyl chloride (4.2 g, 22 mmol) and the mixture was stirred for 8 hours. The solvent was removed by concentration. After addition of ethyl acetate, the solution was washed with brine, dried ($MgSO_4$), and concentrated. Silica gel chromatography eluting with 40% ethyl acetate/hexane produced the desired sulfonate (4.3 g, 58%). MS(ESI): $(M+H)^+=369.8$.

(2d) A suspension of the sulfonate 2c (0.8 g, 2.16 mmol), p-cresol (0.28 g, 2.6 mmol) and potassium carbonate (0.6 g, 4.3 mmol) in DMF (10 mL) was heated at 100° C. for 2.5 hours. After cooling to room temperature, ethyl acetate was added and the solution was washed with brine, dried (MgSO4), and concentrated. Silica gel chromatography eluting with 60% ethyl acetate/hexane yielded the desired piperidine derivative (0.54 g, 82%). MS(ESI): $(M+H)^+=306.1$.

(2e) The piperidine derivative 2d (0.53 g, 1.65 mmol) was dissolved in 4 N HCl/dioxane (10 mL) and after stirring for 90 minutes, the solution was concentrated to give a solid. The solid was washed with ether three times and dried (0.33 g, 78%). MS(ESI): $(M+H)^+=206.1$.

(2f) Coupling of the deprotected piperidine derivative 2e with trans-1,2-cyclopentanedicarboxylic acid using a procedure analogous to that in (1a) gave the desired carboxylic acid. MS(ESI): $(M+H)^+=346$.

(2g). The carboxylic acid 2f was converted to a hydroxamic acid using a procedure analogous to that in (1b). MS(ESI): $(M+H)^+=361$.

Example 3 trans-N-Hydroxy-2-[[4-(2-phenoxyethyl)-1-piperidinyl]carbonyl]cyclopentanecarboxamide (3a) To a solution of 4-(2-hydroxyethyl)piperridine (5 g, 38.7 mmol) and diisopropylethylamine (6.74 mL, 38.7 mmol) in THF (40 mL) cooled in an ice bath was added di-tert-butyl-dicarbonate (8.44 g, 38.7 mmol). The mixture was stirred at room temperature for 2 hours and concentrated. The residue was taken up in ethyl acetate, and the solution was washed with brine, dried ($MgSO_4$), and concentrated to give the desired Boc-protected alcohol (8.2 g, 92.55%). MS ($NH_3$—Cl): $(M+H)^+=230$.

(3b) A mixture of the alcohol 3a (1 g, 4.37 mmol), phenol (0.41 g, 4.37 mmol), triphenylphosphine (1.26 g, 4.8 mmol) and DEAD (0.84 mL, 4.8 mmol) in THF (8 mL) was stirred at room temperature overnight and concentrated. Silica gel chromatography eluting with 20% ethyl acetate/hexane yielded the desired phenylether (1 g, 75%). MS(ESI): $(M+Na)^+=328$.

(3c) The phenylether 3b (800 mg, 2.62 mmol) was dissolved in 4 N HCl dioxane (10 mL) and after stirring for 30 minutes, the solution was concentrated to yield the desired piperidine derivative as a salt (660 mg, 100%). MS($NH_3$—Cl): $(M+H)^+=206$.

(3d) Coupling of the piperidine derivative 3c with trans-1,2-cyclopentanedicarboxylic acid using a procedure analogous to that in (1a) produced the desired carboxylic acid. MS($NH_3$—Cl): $(M+H)^+=346$.

(3e) The carboxylic acid 3d was converted to a hydroxamic acid using a procedure analogous to that in (1b). MS(ESI): $(M+H)^+=361.1$.

Example 4 trans-N-Hydroxy-N'-[4-(Phenylmethoxy)phenyl]-1,2-cyclopentanedicarboxamide (4a) Coupling of 4-benzyloxyaniline hydrochloride with trans-1,2-cyclopentanedicarboxylic acid using a procedure analogous to that in (1a) afforded the desired monocarboxylate product. MS(ESI): $(M-H)^-=338$.

(4b) The monocarboxylate 4a was converted to a hydroxamic acid using a procedure analogous to that in (1b). MS(ESI): $(M+TFA-1)^-=466.9$.

Example 5 trans-N-Hydroxy-N'-[4-(4-pyridinylmethoxy)phenyl]-1,2-cyclopentanedicarboxamide Trifluoroacetate Salt (5a) A mixture of 4-picolyl chloride hydrochloride (1.64 g, 10 mmol), 4-nitrophenol (1.39 g, 10 mmol) and potassium carbonate (5.5 g, 40 mmol) in DMF (20 mL) was heated at 100° C. for 2 hours. After cooling to room temperature and addition of ethyl acetate, the solution was washed with brine, dried (MgSO4), and concentrated. Purification on a silica gel column eluting with 5% methanol/methylene chloride gave the desired nitrophenylether (2.1 g, 91%). MS(ESI): $(M+H)^+=231$.

(5b) The nitrophenylether 5a (0.42 g, 0.826 mmol) was dissolved in a mixed solvent of acetic acid and water (5:1) and the solution was cooled in an ice bath. To it was added zinc (1 g) and the mixture was stirred for 1.5 hours at room temperature. After addition of ethyl acetate, the solution was adjusted to pH>8 using sodium carbonate solution. The organic layer was separated, washed with brine, dried ($MgSO_4$), and concentrated to give the desired amine (0.32 g, 88%). MS(ESI): $(M+H)^+=201$.

(5c) Coupling of 4-picolyloxyaniline 5b with trans-1,2-cyclopentanedicarboxylic acid using a procedure analogous to that in (1a) afforded the desired monocarboxylic acid. MS(ESI): $(M+H)^+=341$.

(5d) The monocarboxylic acid 5c was converted to a hydroxamic acid using a procedure analogous to that in (1b). MS(ESI): $(M+H)^+=356$.

Example 6 trans-N-[4-[(3,5-Dichlorophenyl)methoxy]phenyl]-N'-hydroxy-1,2-cyclopentanedicarboxamide

(6a) The monocarboxylic acid 4a (2.39 g, 6.73 mmol) was dissolved in 4 N HCl/dioxane (30 mL) and methanol (3 mL). After stirring at room temperature for 3 hours, the solution was concentrated to give the methyl ester (2.4 g, 100%). (ESI): (M+H)$^+$=354.

(6b) The ester 6a (2.37 g, 6.7 mmol) was hydrogenated for 2 hours in methanol (20 mL) at atmospheric pressure using palladium on carbon as catalyst. The catalyst was filtered off and the solution was concentrated to give the desired phenol product (1.93 g, 100%). MS(NH$_3$—CI): (M+H)$^+$=264.

(6c) A mixture of the phenol 6b (0.3 g, 1.14 mmol), 3,5-dichlorobenzylchloride (0.22 g, 1.14 mmol) and potassium carbonate (0.31 g, 2.28 mmol) in DMF (10 mL) was heated at 100° C. for 1 hour. After cooling to room temperature and addition of ethyl acetate, the solution was washed with brine, dried (MgSO4), and concentrated. Purification on a silica gel column eluting with 35% ethyl acetate/hexane gave the desired ester (0.27 g, 56%). MS(ESI): (M−H)$^-$=419.9.

(6d) The ester 6c (0.24 g, 0.57 mmol) was hydrolyzed in methanol (20 mL) using 1 N LiOH (1.7 mL) for 2.5 hours. The solution was concentrated. After addition of ethyl acetate, the solution was acidified with 1 N HCl to pH 3 The organic layer was separated and washed with brine, dried (MgSO$_4$), and concentrated to give the acid product (0.23 g, 100%). MS(ESI): (M−H)$^-$=405.7.

(6e) The acid 6d was converted to a hydroxamic acid using a procedure analogous to that in (1b). MS(ESI): (M−H)$^-$=422.8.

Example 7 trans-N-Hydroxy-N'-[4-[4-quinolinyloxy)methyl]phenyl]-1,2-cyclopentanedicarboxamide trifluoroacetate salt

(7a) To a solution of 4-aminobenzylalcohol (12.3 g, 100 mmol) and diisopropylethylamine (5.23 mL, 300 mmol) in THF (100 mL) cooled in an ice bath was added di-tert-butyl dicarbonate (21.8 g, 100 mmol). The solution was stirred at room temperature overnight and concentrated. The residue was taken up in ethyl acetate and the solution was washed with brine, dried (MgSO$_4$), and concentrated. Purification on a silica gel column eluting with 40% ethyl acetate/hexane gave the desired Boc-protected product (21.64 g, 97%). MS(NH$_3$—CI): (M+NH3+H)$^+$=241.

(7b) To a solution of the alcohol 7a (1.1 g, 5 mmol) and diisopropylethylamine (1.74 mL, 10 mmol) in methylene chloride (20 mL) cooled in an ice bath was slowly added methanesulfonyl chloride (0.464 mL, 6 mmol). The mixture was stirred at 0° C. for 2 hours and at room temperature for 30 minutes, and concentrated. The residue was taken up in ethyl acetate and the solution was washed with brine, NaHCO3 and brine, dried (MgSO$_4$), and concentrated. Silica gel chromatography gave the desired sulfonate (0.8 g, 53%). MS(NH$_3$—CI): (M+H)$^+$=302.

(7c) A solution of the sulfonate 7b (9.37 g, 31.13 mmol), 4-hydroxyquinoline (4.52 g, 31.13 mmol) and potassium carbonate (17.2 g, 124 mmol) in DMF (30 mL) was heated with stirring at 50° C. for 5 hours. The insoluble material was filtered off and the solution was concentrated. The residue was taken up in ethyl acetate and the solution was washed with brine, dried (MgSO$_4$), and concentrated. Purification on a silica gel column eluting with 5% methanol/methylene chloride gave the desired aniline derivative (8.4 g, 77%). MS(NH$_3$—CI): (M+H)$^+$=351.

(7d) The Boc-protected aniline 7c (8.43 g, 24 mmol) was dissolved in methanol (15 mL) and to it was added 4 N HCl in dioxane (15 mL). The solution was stirred at room temperature for 2 hours and concentrated. The resulting solid was washed with ether to give the aniline as a salt (7.5 g, 96%). MS(ESI): (M+H)$^+$=251.1.

(7e) Coupling of the aniline salt 7d with trans-1,2-cyclopentanedicarboxylic acid using a procedure analogous to that in (1a) gave the monocarboxylic acid product. MS(ESI): (M+H)$^+$=391.

(7f) The monocarboxylic acid was converted to a hydroxamic acid using a procedure analogous to that in (1b). MS(ESI): (M+H)$^+$=406.

Example 8 trans-N-Hydroxy-N'-[4-(4-pyridinylmethyl)phenyl]-1,2-cyclopentanedicarboxamide trifluoroacetate salt

This compound was produced using procedures analogous to those for example 4 starting from 4-picolylaniline and trans-1,2-cyclopentanedicarboxylic acid. MS(ESI): (M+H)$^+$=340.

Example 9 trans-N-Hydroxy-N'-[4-(phenylmethoxy)phenyl]-1,2-cyclohexanedicarboxamide

This compound was produced using procedures analogous to those for example 4 starting from 4-benzyloxyaniline hydrochloride and trans-1,2-cyclohexanedicarboxylic acid. MS(ESI): (M+TFA−H)$^-$=480.9.

Example 10 trans-N-Hydroxy-N'-[4-[(4-quinolinyloxy)methyl]phenyl]-1,2cyclohexanedicarboxamide trifluoroacetate salt

This compound was produced using procedures analogous to those for example 7. MS(ESI): (M+H)$^+$=420.0.

Example 11 trans-N-Hydroxy-N'[4-[(5-quinolinyloxy)methyl]phenyl]-1,2-cyclohexanedicarboxamide trifluoroacetate salt

This compound was produced using procedures analogous to those for example 7. MS(ESI): (M+H)$^+$=420.0

Example 12 trans-N-Hydroxy-N'-[4-[(6-quinolinyloxy)methyl]phenyl]-1,2-cyclohexanedicarboxamide trifluoroacetate salt

This compound was produced using procedures analogous to those for example 7. MS(ESI): (M+H)$^+$=420.0.

Example 13

(3R-trans)-2-methylpropyl 4-[(hydroxyamino)carbonyl]-3-[[[4-[(4-qinolinyloxy)methyl]phenyl]amino]carbonyl]-1-piperidinecarboxylate trifluoroacetate salt

(13a) To a solution of benzyloxycarbonyl-b-alanine (25 g, 112 mmol) in THF (400 mL) cooled in an ice bath was slowly added NaH (21.5 g, 448 mmol). After stirring at 0° C. for 30 minutes, a solution of benzylbromide (53.6 mL, 448 mmol) in THF (50 mL) was added. The mixture was stirred at room temperature over the weekend and concentrated. Water was added and the solution was extracted with ether twice. The water layer was acidified with 1 N HCl to pH 3 and extracted with ethyl acetate twice. The extracts were combined and washed with brine, dried (MgSO$_4$), and concentrated. Purification on a silica gel column eluting with 40% ethyl acetate/hexane followed by crystallization from ethyl acetate/hexane gave the N-benzyl product as a crystal (25 g, 71%).

(13b) To a solution of the carboxylic acid 13a (28.5 g, 91 mmol) and diisopropylethylamine (63.44 mL, 364 mmol) in THF (300 mL) cooled to −30° C. was slowly added pivaloyl chloride (11 mL, 91 mmol). The mixture was stirred at −30° C. for 1 hour. LiCl (3.85 g, 91 mmol) was added followed by (R)-(+)-4-benzyl-2-oxazolidinone (16.12 g, 91 mmol). The mixture was stirred at room temperature overnight and concentrated. Water and ethyl acetate were added and the organic layer was separated, washed with brine, dried (MgSO$_4$), and concentrated. Purification on a silica gel column eluting with 40% ethyl acetate/hexane followed by crystallization from ethyl acetate/hexane gave the oxazolidinone derivative (25 g, 57%). MS (NH$_3$—CI): (M+H)$^+$=473.

(13c) To a solution of diisopropylamine (1.95 mL, 13.9 mmol) in THF (7 mL) cooled to −78° C. was added 2.5 M n-butyl lithium (5.8 mL, 14.6 mmol). The solution was stirred at 0° C. for 30 minutes and after cooling back to −78° C., added to a solution of the oxazolidinone derivative 13b (6.0 g, 12.7 mmol) in THF (20 mL) at −78° C. The mixture was stirred at −78° C. for 1 hour. To it was added a solution of t-butyl bromoacetate (2.72 g, 12.7 mmol) in THF (10 mL) at −78° C. Stirring continued at 0° C. for 3 hours. The solution was concentrated at room temperature and the residue was took up in ethyl acetate. The soution was washed with 10% citric acid and brine, dried (MgSO$_4$), and concentrated. Silica gel chromatography eluting with 25% ethyl aceate/hexane gave the alkylated product (4.16 g, 56%). MS(ESI): (M+Na)$^+$=609.5, (13d) To a solution of the alkylated material 13c (16.44 g, 28 mmol) in THF (125 mL)/water (72 mL) cooled in an ice bath was added hydrogen peroxide (12.6 mL, 112 mmol). After stirring for 5 minutes, a solution of lithium hydroxide (1.76 g, 42 mmol) in water (20 mL) was added. The mixture was allowed to stir at 0° C. for 90minutes and sodium sulfite was added. THF was removed by concentration. The solution was diluted with water (150 mL) and extracted with ether. The water layer was acidified with 10% citric acid and extracted with ethyl acetate. The extracts were combined and washed with brine, dried (MgSO$_4$), and concentrated. Purification on a silica gel column eluting with 3% methanol/methylene chloride gave the carboxylic acid (7.78 g, 65%). MS(ESI): (M−H)$^-$=426.3.

(13e) To a solution of diisopropylamine (4.6 mL, 32.9 mmol) in THF (18 mL) cooled to −78° C. was added 2.5 M n-butyl lithium (12.8 mL, 32.2 mmol). The solution was stirred at 0° C. for 30 minutes and after cooling back to −78° C., added to a solution of the carboxylic acid 13d (5.98 g, 14 mmol) in THF (30 mL) at −78° C. The mixture was allowed to stir at −78° C. for 90 minutes and allyl bromide (1.45 mL, 16.8 mmol) was added. The solution was stirred at 0° C. for 5 hours, poured into a cold 0.5 N HCl solution containing ethyl acetate with vigorous stirring. The organic layer was separated and the water layer was extracted with ethyl acetate twice. The combined organic layers were washed with brine, dried (MgSO$_4$), and concentrated. The crude product was used for the next reaction without purification. MS(ESI): (M+Na)$^+$=490.3.

(13f) A mixture of the acid 13e (6 g, 12.9 mmol), iodomethane (4 mL, 64.6 mmol) and potassium carbonate (3.93 g, 28.4 mmol) in DMF (40 mL) was heated at 60° C. for 5 hours with stirring. DMF was removed by concentration under high vacuum. The residue was taken up in ethyl acetate and the solution was washed with brine, dried (MgSO$_4$) and concentrated. Purification on a silica gel column eluting with 15% ethyl acetate/hexane gave the methyl ester (2.69 g, 40%). MS(ESI): (M+Na)$^+$=504.3.

(13g) The ester 13f (1.69 g, 3.5 mmol) was dissolved in methylene chloride (30 mL) and the solution was cooled to −78° C. Into it was bubbled O$_2$ for 10 minutes, followed by O$_3$. The solution turned blue in 10 minutes and bubbling continued for an additional 15 minutes. Nitrogen was bubbled into the mixture until the blue color disappeared. Triphenylphosphine (1.1 g, 4.2 mmol) was added and the solution was allowed to stir at room temperature overnight. The reaction was quenched with 1 N HCl. The organic layer was separated, washed with brine, dried (MgSO$_4$), and concentrated. Chromatography on a silica gel column eluting with 60% ethyl acetate gave the aldehyde (1.41 g, 83%). MS(ESI): (M+Na)$^+$=506.4.

(13h) The aldehyde 13 g (1.4 g, 2.9 mmol) was hydrogenated at atmospheric pressure in methanol for 1 hour using palladium on carbon as catalyst. Hydrogenation continued at 50 psi overnight in the presence of 5 mL 1 N HCl. The catalyst was removed by filtration and the solution was concentrated to give the piperidine derivative (0.72 g, 100%). MS(ESI): (M+H)$^+$=244.

(13i) To a solution of the piperidine derivative 13 h (0.7 g, 2.5 mmol) in chloroform (20 mL) was added diisopropylethylamine (1.3 mL, 7.5 mmol) and the solution was cooled in an ice bath. To it was added isobutylchloroformate (0.52 g, 3.75 mmol) and the mixture was stirred for 1 hour. Chloroform was removed by concentration and the residue was taken up in ethyl acetate. The solution was washed with sodium bicarbonate and brine, dried (MgSO$_4$), and concentrated to give the carbamate (0.83 g, 97%). MS(ESI): (M+H)$^+$=344.

(13j) To a solution of the carbamate 13i (34 mg, 0.1 mmol) in methanol (2 mL) was added 1 N NaOH (0.6 mL). The mixture was stirred at room temperature overnight. Ethyl acetate was added and the solution was washed with citric acid, brine, dried (MgSO$_4$), and concentrated to give the acid (32 mg, 100%). MS(ESI): (M−H)$^-$=328.2.

(13k) To a solution of the acid 13j (32 mg, 0.1 mmol) and the aniline derivative (57 mg, 0.12 mmol) prepared in (7d) in DMF (2 mL) cooled in an ice bath was added BOP (53 mg, 0.12 mmol) followed by diisopropylethylamine (88 μL, 0.5 mmol). The mixture was stirred at room temperature for 2 hours, and concentrated. Purification on a reversed phase HPLC gave the amide (16 mg, 28%). MS(ESI): (M+H)$^+$=562.3.

(13l) The amide 13k (16 mg, 28.4 μmol) was dissolved in a mixed solvent of methylene chloride (2 mL) and TFA (2 mL). After stirring at room temperature for 1 hour, the solution was concentrated to give the acid (15 mg, 100%). MS(ESI): (M+H)$^+$=506.3.

(13m) To a solution of the acid 13l (15 mg, 28.4 μmol) and hydroxylamine hydrochloride (10 mg, 120 μmol) in DMF (2 mL) cooled in an ice bath was added BOP (16 mg, 36 μmol) followed by diisopropylethylamine (0.1 mL, 500 μmol). The mixture was stirred at room temperature for 4 hours. Purification on reversed phase HPLC gave the hydroxamic acid (5 mg, 33%). MS(ESI): (M+H)$^+$=521.3.

Example 14

(3R-trans)-2-Methylpropyl 3-[(hydroxyamino)carbonyl]-4-[[[4-[(4-quinolinyloxy)methyl]phenyl]amino]carbonyl]-1-piperidinecarboxylate trifluoroacetate salt (14a) The carbamate 13i (350 mg, 1.02 mmol) was dissolved in a mixed solvent of 50% TFA/methylene chloride (8 mL).

After stirring at room temperature for 2 hours, the solution was concentrated to give the acid. MS(ESI): (M+H)+=288.1.
(14b) To a solution of the acid 14a (301 mg, 1.02 mmol) and the aniline derivative (388 mg, 1.2 mmol) prepared in (7d) in DMF (5 mL) cooled in an ice bath was added BOP (486 mg, 1.1 mmol) followed by diisopropylethylamine (0.7 mL, 4 mmol). The mixture was stirred at room temperature overnight. Ethyl acetate was added and the solution was washed with brine, NaHCO3, citric acid and brine, dried (MgSO$_4$), and concentrated. Purification on a silica gel column eluting with 5% methanol/methylene chloride gave the amide (170 mg, 32%). MS(ESI): (M−H)−=518.2.
(14c) The amide 14b (170 mg, 0.32 mmol) was dissolved in methanol (10 mL) and 1 N NaOH (2 mL) was added. The mixture was stirred at room temperature for 2 hours and concentrated. Ethyl acetate was added followed by 1 N HCl (1 mL). The solution was washed with brine, dried (MgSO$_4$) and concentrated. Purification on a silica gel column eluting with 10% methanol in methylene chloride gave the acid (70 mg, 42%). MS(ESI): (M+H)+=506.3.
(14d) To a solution of the acid 14c (70 mg, 0.138 mmol) and hydroxylamine hydrochloride (34 mg, 0.5 mmol) in DMF (2 mL) cooled in an ice bath was added BOP (88 mg, 0.2 mmol) followed by diisopropylethylamine (0.17 mL, 1 mmol). The mixture was stirred at room temperature for 4 hours. Purification on reversed phase HPLC gave the hydroxamic acid (41 mg, 56%). MS(ESI): (M+H)+=521.3.

Example 15

(3R-trans)-1-(3,3-Dimethyl-1-oxobutyl)-N3-hydroxy-N4-[4-[(4-quinolinyloxy)methyl]phenyl]-3,4-piperidinedicarboxamide trifluoroacetate salt
This compound was prepared using procedures analogous to those for example 14. MS(ESI): (M+H)+=519.3.

Example 16

(3R-trans)-N3-Hydroxy-1-[(1-phenylcyclopropyl)carbonyl]-N4-[4-[(4-quinolinyloxy)methyl]phenyl]-3,4-piperidinedicarboxamide trifluoroacetate salt
This compound was prepared using procedures analogous to those for example 14. MS(ESI): (M+H)+=565.3.

Example 17

(3R-trans)-N3-Hydroxy-1-(phenylsulfonyl)-N4-[4-[(4-quinolinyloxy)methyl]phenyl]-3,4-piperidinedicarboxamide trifluoroacetate salt
This compound was prepared using procedures analogous to those for example 14. MS(ESI): (M+H)+=561.4.

Example 18

(3R-trans)-2-Methylpropyl 3-[(hydroxyamino)carbonyl]-4-[[[4-(2-phenylethoxy)phenyl]amino]carbonyl]-1-piperidinecarboxylate
(18a) A mixture of 4-nitrobenzene (2.78 g, 20 mmol), (2-bromoethyl)benzene (3.7 g, 20 mmol) and potassium carbonate (5.53 g, 40 mmol) in DMF (10 mL) was heated with stirring for 1 hour at 80° C. Ethyl acetate was added and the solution was washed with brine, dried (MgSO$_4$) and concentrated. Chromatography eluting with 20% ethyl acetate/hexane gave the ether product (2.05 g, 47%). MS(NH$_3$—Cl): (M+NH$_3$+H)+=261.
(18b) The ether compound 18a (2.03 g, 8.42 mmol) was dissolved in methanol (20 mL). Hydrogenation under atmospheric pressure for 1 hour using Pd/C as catalyst gave the aniline product (1.8 g, 100%). MS(ESI): (M+H)+=214.2.
(18c) The title compound was obtained by coupling the aniline compound 18b with the carboxylic acid 14a followed by conversion of the ester to a hydroxamic acid using procedures analogous to those in (14b), (14c) and (14d). MS(ESI): (M+H)+=484.3.

Example 19

(3R-trans)-2-Methylpropyl 4-[[[2-fluoro-4-(2-phenylethoxy)phenyl]amino]carbonyl]-3-[(hydroxyamino)carbonyl]-1-piperidinecarboxylate
This compound was prepared using procedures analogous to those for example 18. MS(ESI): (M+H)+=502.3.

Example 20

(3R-trans)-2-Methylpropyl 3-[(hydroxyamino)carbonyl]-4-[[[4-(4-pyridinyloxy)phenyl]amino]carbonyl]-1-piperidinecarboxylate trifluoroacetate salt
(20a) A mixture of 1-fluoro-4-nitrobenzene (2.82 g, 20 mmol), 4-hydroxypyridine (1.9 g, 20 mmol) and cesium carbonate (13 g, 40 mmol) in DMSO (30 mL) was heated at 110° C. with stirring for 2 hours. After cooling to room temperature, insoluble material was filtered off and the solution was poured into water. The precipitate was filtered and rinsed with water and ether to give the desired ether (2.2 g, 51%). MS(NH$_3$—Cl): (M+H)+=217.
(20b) The ether compound 20a (1.2 g, 5.5 mmol) was dissolved in methanol (20 mL) and 1 N HCl (20 mL) was added followed by zinc (1.2 g, 22 mmol). The mixture was stirred at room temperature for 3 hours and then heated at 60° C. for 2 hours. Insoluble material was filtered off and the solution was concentrated. Purification on a silica gel column eluting with 5% methanol/methylene chloride gave the aniline derivative as a dichloride (0.76 g, 54%). MS(NH$_3$—Cl): (M+H)+=187.
(20c) The title compound was obtained by coupling the aniline derivative 20b with the carboxylic acid 14a followed by conversion of the ester to a hydroxamic acid using procedures analogous to those in (14b), (14c) and (14d). MS(ESI): (M+H)+=457.3.

Example 21

(3R-trans)-1-(3,3-Dimethyl-1-oxobutyl)-N3-hydroxy-N4-[4-(4-quinolinyloxy)phenyl]-3,4-piperidinedicarboxamide mono(trifluoroacetate salt
This compound was prepared using procedures analogous to those for example 20. MS(ESI): (M+H)+=505.3.

Example 22

(3R-trans)-N4-[4-[3,5-bis(Trifluoromethyl)phenoxyy]phenyl]-1-(2,2-dimethylpropyl)-N3-hydroxy-3,4-piperidinedicarboxamide trifluoroacetate salt
(22a) A mixture of 1-fluoro-4-nitrobenzene (1.4 g, 10 mmol), 3,5-bis(trifluoromethyl)phenol (2.3 g, 10 mmol) and cesium carbonate (9.7 g, 30 mmol) in DMSO (20 mL) was heated at 110° C. with stirring for 2 hours. Insoluble material was filtered off and ethyl acetate was added. The solution was washed with brine, dried (MgSO$_4$), and concentrated. The solid was triturated with hexane to give the desired ether product (2.27 g, 65%). MS(ESI): (M+H)+=352.
(22b) The ether compound 22a (2.2 g, 6.56 mmol) was dissolved in methanol (20 mL) and the solution was hydrogenated at atmospheric pressure for 2 hours using Pd/C (400 mg) as catalyst. The catalyst was filtered off and the solution was concentrated to give the aniline derivative (2.19 g, 100%). MS(ESI): (M+H)$^+$=336.2.

(22c) A mixture of the carboxylic acid 13e (7.0 g, 14.9 mmol), benzyl bromide (6.4 g, 37.4 mmol) and potassium carbonate (4.5 g, 32.9 mmol) in DMF (20 mL) was heated at 80° C. with stirring for 2 hours. Insoluble material was filtered off and DMF was removed under high vacuum. The residue was taken up in ethyl acetate, washed with brine, dried (MgSO$_4$) and concentrated. Purification on a silica gel column eluting with 15% ethyl acetate/hexane gave the benzyl ester (6 g, 72%). MS(ESI): (M+H)$^+$=558.4.

(22d) The ester 22c (4.0 g, 7.18 mmol) was dissolved in methylene chloride (75 mL) and the solution was cooled to −78° C. Into it was bubbled O$_2$ for 10 minutes, followed by O$_3$. The solution turned blue in 10 minutes and bubbling continued for an additional 15 minutes. Nitrogen was bubbled into the mixture until the blue color disappeared. Triphenylphosphine (2.2 g, 8.6 mmol) was added and the solution was allowed to stir at room temperature overnight. The reaction was quenched with 1 N HCl. The organic layer was separated, washed with brine, dried (MgSO$_4$), and concentrated. Chromatography on a silica gel column eluting with 20% ethyl acetate gave the aldehyde (3.0 g, 75%). MS(ESI): (M+H)$^+$=560.

(22e) The aldehyde 22d (3.0 g, 5.36 mmol) was hydrogenated at atmospheric pressure in methanol (50 mL) for 1 hour using palladium on carbon as catalyst. Hydrogenation continued at 50 psi overnight in the presence of 5 mL acetic acid. The catalyst was removed by filtration and the solution was concentrated to give the piperidine derivative (1.6 g, 100%). MS(ESI): (M+H)$^+$=230.

(22f) To a solution of the piperidine derivative 22e (1.54 g, 5.36 mmol) and N-(benzyloxycarbonyloxy)succinimide (1.6 g, 6.4 mmol) in DMF (10 mL) was added diisopropylethylamine (3.25 mL, 18.7 mmol). The mixture was stirred for 2 hours and concentrated. The residue was taken up in ethyl acetate and the solution was washed with citric acid and brine, dried (MgSO$_4$), and concentrated. Chromatography eluting with 7% methanol/chloroform gave the Cbz-protected product (1.9 g, 100%). MS(ESI): (M+Na)$^+$=386.2.

(22g) A mixture of the Cbz-protected compound 22f (1.94 g, 5.34 mmol), benzyl bromide (2.28 g, 13.3 mmol) and potassium carbonate (1.6 g, 11.7 mmol) was heated at 80° C. with stirring for 2 hours. Insoluble material was filtered off and the solution was concentrated under high vacuum. The residue was taken up in ethyl acetate and the solution was washed with brine, dried (MgSO$_4$), and concentrated. Flash chromatography on a silica gel column eluting with 15% ethyl acetate/hexane gave the benzyl ester (1.25 g, 52%). MS(ESI): (M+H)$^+$=454.3.

(22h) The benzyl ester 22 g (1.25 g, 2.76 mmol) was dissolved in methylene chloride (7 mL) and TFA (7 mL) was added. The solution was stirred for 1 hour and concentrated to give the carboxylic acid (1.1 g, 100%). MS(ESI): (M+H)$^+$=398.3.

(22i) To a solution of the carboxylic acid 22 h (200 mg, 0.5 mmol) and the aniline derivative 22b (184 mg, 0.6 mmol) in DMF (3 mL) cooled in an ice bath was added BOP (267 mg, 0.6 mmol) followed by diisopropylethylamine (0.35 mL, 2 mmol). The mixture was stirred at room temperature overnight. Ethyl acetate was added and the solution was washed with brine, citric acid and brine, dried (MgSO$_4$), and concentrated to give the amide (340 mg, 98%). MS(ESI): (M+H)$^+$=690.3.

(22j) The amide 22i (320 mg, 0.46 mmol) was dissolved in methanol (10 mL) and the solution was hydrogenated at atmospheric pressure for 1 hour using Pd/C (30 mg) as catalyst. The catalyst was filtered off and the solution was concentrated to give the piperidinecarboxylic acid (152 mg, 69%). MS(ESI): (M+H)$^+$=477.2.

(22k) To a solution of the piperidinecarboxylic acid 22j (139 mg, 0.29 mmol), trimethylacetaldehyde (30 mg, 0.35 mmol) and diisopropylethylamine (38 mg, 0.29 mmol) in methanol (5 mL) was added NaCNBH$_3$ (18 mg, 0.29 mmol) followed by titanium (IV) isopropoxide (100 mg, 0.35 mmol). The mixture was stirred at room temperature overnight and concentrated. The residue was taken up in ethyl acetate and 1 N HCl (2 mL) was added. The solution was washed with brine, dried (MgSO$_4$) and concentrated. Purification on a silica gel column eluting with 10% methanol/methylene chloride gave the tertiary amine (55 mg, 34%). MS(ESI): (M+H)$^+$=547.2.

(22l) To a solution of the tertiary amine 22k (55 mg, 0.1 mmol), hydroxylamine hydrochloride (35 mg, 0.5 mmol) in DMF (2 mL) cooled in an ice bath was added BOP (53 mg, 0.12 mmol) followed by diisopropylethylamine (0.175 mL, 1 mmol). The mixture was stirred for 1 hour and concentrated. Purification on a reversed phase HPLC gave the hydroxamic acid (18 mg, 32%). MS(ESI): (M+H)$^+$=562.3.

Example 23

(3R-trans)-N4-[4-(3,5-dichlorophenoxy)phenyl]-1-(2,2-dimethylpropyl)-N3-hydroxy-3,4-piperidinedicarboxamide trifluoroacetate salt This compound was prepared using procedures analogous to those for example 22. MS(ESI): (M+H)$^+$=495.1.

Example 24

(3R-trans)-N4-[4-(3-chlorophenoxy)phenyl]-1-(2,2-dimethylpropyl)-N3-hydroxy-3,4-piperidinedicarboxamide trifluoroacetate salt This compound was prepared using procedures analogous to those for example 22. MS(ESI): (M+H)$^+$=460.6.

Example 25

(3R-trans)-1-(2,2-dimethylpropyl)-N3-hydroxy-N4-(4-phenoxyphenyl)-3,4-piperidinedicarboxamide trifluoroacetate salt This compound was prepared using procedures analogous to those for example 22. MS(ESI): (M+H)$^+$=426.3

Example 26

(3R-trans)-tert-Butyl 4-[[[4-[(2-methyl-4-quinolinyl)methoxy]phenyl]amino]carbonyl]-3-[(hydroxyamino)carbonyl]-1-piperidinecarboxylate trifluoroacetate salt (26a) To a solution of quinaldine (75 g, 0.523 mol) in methanol (1100 mL) and water (550 mL) at room temperature was added sulfuric acid (28 mL, 0.523 mol) followed by iron(II) sulfate heptahydrate. Nitrogen was bubbled into the solution for 20 min and ammonium sulfate (177 g, 1.56 mol) was added. The resultant mixture was stirred in a water bath (20° C.) under nitrogen for 4 hours and quenched with 10% sodium hydroxide (pH=9–10). Methanol was removed by concentration in vacuo and the resulting aqueous solution was extracted with ethyl acetate three times. The combined organic phase was filtered through silica gel and washed with water and brine, dried (MgSO$_4$) and concentrated. Crystallization from ethyl acetate gave 2-methyl-4-hydroxymethylquinoline (24.6 g, 27%) as a solid. MS(NH$_3$—CI): (M+H)$^+$=174.

(26b) To a solution of 26a (24.6 g, 0.142 mol) in chloroform (300 mL) cooled in an ice bath was added thionyl chloride (41.4 mL, 0.56 mol). The mixture was stirred at room temperature for 2 hours and concentrated to give 2-methyl-4-chloromethylquinoline as a HCl salt (32.4 g, 100%). MS(NH$_3$—CI): (M+H)$^+$=192.

(26c) To a solution of 4-aminophenol (10.9 g, 100 mmol) in THF (150 mL) cooled in an ice bath was added di-tert-butyl-dicarbonate (21.8 g, 100 mmol) followed by diisopropyl-ethylamine (17.4 mL, 100 mmol). The mixture was stirred at room temperature overnight and concentrated. The residue was taken up in ethyl acetate and the solution was washed with brine, dried (MgSO$_4$), and concentrated. Purification on a silica gel column eluting with 5% methanol/40% ethyl acetate hexane gave 4Boc-aminophenol (20.1 g, 96%). MS(NH$_3$—CI): (M+NH$_3$+H)=227.

(26d) A mixture of 26b (11.4 g, 50 mmol), 26c (10.4 g, 50 mmol), Cs$_2$CO$_3$ (32.5 g, 100 mmol) and tetrabutylammonium iodide (18.5 g, 50 mmol) in DMSO was heated at 60° C. with stirring for 3 hours. After cooling to room temperature, ethyl acetate was added and the solution was washed with brine three times, dried (MgSO4) and concentrated. Chromatography on a silica gel column eluting with 3% methanol/methylene chloride gave 4-(2-methyl-4-quinolylmethyloxy)aniline (10 g, 56%). MS(ESI): (M+H)$^+$=365.3.

(26e) The aniline derivative 26d was dissolved in methanol (40 mL) and 4 N HCl in dioxane (50 mL) was added. The mixture was stirried mechanically for 6 hours. The product, which precipitated out of the solution during the reaction as a bis-HCl salt, was collected by filtration and washing with ether (10 g, 100%). MS(ESI): (M+H)$^+$=338.2.

(26f) To a solution of 22e (2.2 g, 7.6 mmol) in water (50 mL) and THF (50 mL) cooled in an ice bath was added diallyl pyrocarbonate (1.4 g, 7.6 mmol) followed by sodium bicarbonate (1.6 g, 15 mmol). After stirring for 3 hours, at 0° C., the solution was concentrated to remove THF. Ethyl acetate was added followed by 5% citric acid. The two layers were separated and the organic layer was washed with brine, dried (MgSO$_4$) and concentrated. Chromatography on a silica gel column using 5% MeOH/EtOAc provided the carboxylic acid (1.42 g, 59%). ESI(M+H)$^+$=312.2.

(26g) A mixture of 26f 1.42 g, 4.5 mmol), allyl bromide (0.55 g, 4.5 mmol) and DBU (1.38 g, 9 mmol) in benzene (10 mL) was heated with stirring at 60° C. overnight. The insoluble material was filtered off and the solution was concentrated. Chromatography on a silica gel column afforded the allyl ester (1.1 g, 68%). MS(ESI): (M+H)$^+$=354.2.

(26h) The allyl ester 26 g (1.1 g, 3.1 mmol) was dissolved in methylene chloride (6 mL) and TFA (9 mL) and the mixture was stirred for 3 hours and concentrated to give the carboxylic acid. MS(ESI): (M+H)$^+$=298.2.

(26i) To a solution of 26 h (0.99 g, 3.1 mmol) and 26e (0.81 g, 3.1 mmol) in DMF (8 mL) cooled in an ice bath was added BOP (1.37 g, 3.1 mmol) followed by DIEA (2.1 mL, 12 mmol). The mixture was stirred overnight and concentrated. The residue was taken up in EtOAc and the solution was washed with sodium bicarbonate and brine, dried (MgSO$_4$) and concentrated. Chromatography on a silica gel column using 5% MeOH/CH$_2$Cl$_2$ provided the desired product (1.6 g, 90%). MS(ESI): (M+H)$^+$=544.3.

(26j) A mixture of 26i (1.6 g, 3.2 mol), morpholine (2.37 g, 27.2 mmol) and Pd(PPh$_3$)$_4$ (92 mg, 0.08 mmol) in THF (30 mL) was heated at 60° C. with stirring for 2 hours. After cooling the product which precipitated out during the reaction was filtered and rinsed with THF (1.2 g, 90%). MS(ESI): (M+H)$^+$=420.3.

(26k) A mixture of 26j (40 mg, 0.095 mmol), di-tert-butyl-dicarbonate (44 mg, 0.2 mmol) and sodium bicarbonate (24 mg, 0.3 mmol) in DMF (1 mL), THF (0.5 mL) and water (0.5 mL) was stirred at room temperature for 2 hours. Purification on HPLC afforded the Boc derivative as a TFA salt. MS(ESI): (M+H)$^+$=520.4.

(26l) To a solution of 26k (40 mg, 0.063 mmol), hydroxy-lamine hydrochloride (35 mg, 0.5 mol) and DIEA (78 mg, 0.6 mmol) in DMF (1 mL) cooled in an ice bath was added BOP (44 mg, 0.1 mmol). The mixture was stirred at 0° C. for 2 hours and purified on HPLC. MS(ESI): (M+H)$^+$=535.3.

Example 27

(3R-trans)-N3-Hydroxy-N4-[4-[(2-methyl-4-quinolinyl)methoxy]phenyl]-3,4-piperidinedicarboxamide trifluoroacetate salt Compound 26 was treated with 50% TFA/CH$_2$Cl$_2$ (1 mL) for 30 min to give the title compound. MS(ESI): (M+H)$^+$=435.3.

Example 28

(3R-trans)-Methyl 4-[[[4-[(2-methyl-4-quinolinyl)methoxy]phenyl]amino]carbonyl]-3-[(hydroxyamino)carbonyl]-1-piperidinecarboxylate trifluoroacetate salt This compound was prepared in a manner analogous to that for example 26. MS(ESI): (M+H)$^+$=493.3.

Example 29

(3R-trans)-2-propyl 4-[[[4-[(2-methyl-4-quinolinyl)methoxy]phenyl]amino]carbonyl]-3-[(hydroxyamino)carbonyl]-1-piperidinecarboxylate trifluoroacetate salt This compound was prepared in a manner analogous to that for example 26. MS(ESI): (M+H)$^+$=521.4.

Example 30

(3R-trans)-Cyclopropylmethyl 4-[[[4-[(2-methyl-4-quinolinyl)methoxy]phenyl]amino]carbonyl]-3-[(hydroxyamino)carbonyl]-1-piperidinecarboxylate trifluoroacetate salt This compound was prepared in a manner analogous to that for example 26. MS(ESI): (M+H)$^+$=533.4.

Example 31

(3R-trans)-Cyclopentylmethyl 4-[[[4-[(2-methyl-4-quinolinyl)methoxy]phenyl]amino]carbonyl]-3-[(hydroxyamino)carbonyl]-1-piperidinecarboxylate trifluoroacetate salt This compound was prepared in a manner analogous to that for example 26. MS(ESI): (M+H)$^+$=547.4.

Example 32

(3R-trans)-Allyl 4-[[[4-[(2-methyl-4-quinolinyl)methoxy]phenyl]amino]carbonyl]-3-[(hydroxyamino)carbonyl]-1-piperidinecarboxylate trifluoroacetate salt This compound was prepared in a manner analogous to that for example 26. MS(ESI): (M+H)$^+$=519.3.

Example 33

(3R-trans)-Propargyl 4-[[[4-[(2-methyl-4-quinolinyl)methoxy]phenyl]amino]carbonyl]-3-[(hydroxyamino) carbonyl]-1-piperidinecarboxylate trifluoroacetate salt This compound was prepared in a manner analogous to that for example 26. MS(ESI): (M+H)$^+$=517.3.

Example 34

Tetrahydro-4H-pyran-4-yl (3R-trans)-4-[[[4-[(2-methyl-4-quinolinyl)methoxy]phenyl]amino]carbonyl]-3-[(hydroxyamino)carbonyl]-1-piperidinecarboxylate trifluoroacetate salt This compound was prepared in a manner analogous to that for example 26. MS(ESI): $(M+H)^+=563.4$.

Example 35

(S)-Tetrahydrofuran-3-yl (3R-trans)-4-[[[4-[(2-methyl-4-quinolinyl)methoxy]phenyl]amino]carbonyl]-3-[(hydroxyamino)carbonyl]-1-piperidinecarboxylate trifluoroacetate salt This compound was prepared in a manner analogous to that for example 26. MS(ESI): $(M+H)^+=549.4$.

Example 36

2-Methyl-4-thiazolemethyl (3R-trans)-4-[[[4-[(2-methyl-4-quinolinyl)methoxy]phenyl]amino]carbonyl]-3-[(hydroxyamino)carbonyl]-1-piperidinecarboxylate trifluoroacetate salt This compound was prepared in a manner analogous to that for example 26. MS(ESI): $(M+H)^+=590.5$.

Example 37

2-Thiazolemethyl (3R-trans)-4-[[[4-[(2-methyl-4-quinolinyl)methoxy]phenyl]amino]carbonyl]-3-[(hydroxyamino)carbonyl]-1-piperidinecarboxylate trifluoroacetate salt This compound was prepared in a manner analogous to that for example 26. MS(ESI): $(M+H)^+=576.5$.

Example 38

4-Thiazolemethyl (3R-trans)-4-[[[4-[(2-methyl-4-quinolinyl)methoxy]phenyl]amino]carbonyl]-3-[(hydroxyamino) carbonyl]-1-piperidinecarboxylate trifluoroacetate salt This compound was prepared in a manner analogous to that for example 26. MS(ESI): $(M+H)^+=576.5$.

Example 39

4-Quinolinylmethyl (3R-trans)-4-[[[4-[(2-methyl-4-quinolinyl)methoxy]phenyl]amino]carbonyl]-3-[(hydroxyamino)carbonyl]-1-piperidinecarboxylate trifluoroacetate salt This compound was prepared in a manner analogous to that for example 26. MS(ESI): $(M+H)^+=620.5$.

Example 40

(3R-trans)-1-Acetyl-N3-hydroxy-N4-[4-[(2-methyl-4-quinolinyl)methoxy]phenyl]-3,4-piperidinedicarboxamide trifluoroacetate salt This compound was prepared in a manner analogous to that for example 26. MS(ESI): $(M+H)^+=477.3$.

Example 41

(3R-trans)-1-(2-Furoyl)-N3-hydroxy-N4-[4-[(2-methyl-4-quinolinyl)methoxy]phenyl]-3,4-piperidinedicarboxamide trifluoroacetate salt This compound was prepared in a manner analogous to that for example 26. MS(ESI): $(M+H)^+=529.4$.

Example 42

(3R-trans)-1-[(2-amino-4-thiazole)acetyl]-N3-hydroxy-N4-[4-[(2-methyl-4-quinolinyl)methoxy]phenyl]-3,4-piperidinedicarboxamide trifluoroacetate salt This compound was prepared in a manner analogous to that for example 26. MS(ESI): $(M+H)^+=575.5$.

Example 43

(3R-trans)-1-[(2-pyridinyl)carbonyl]-N3-hydroxy-N4-[4-[(2-methyl-4-quinolinyl)methoxy]phenyl]-3,4-piperidinedicarboxamide trifluoroacetate salt This compound was prepared in a manner analogous to that for example 26. MS(ESI): $(M+H)^+=540.4$.

Example 44

(3R-trans)-1-[(2-Chloro-6-methyl-4-pyridinyl)carbonyl]-N3-hydroxy-N4-[4-[(2-methyl-4-quinolinyl)methoxy]phenyl]-3,4-piperidinedicarboxamide trifluoroacetate salt This compound was prepared in a manner analogous to that for example 26. MS(ESI): $(M+H)^+=588.9$.

Example 45

(3R-trans)-1-[(4-pyridinyl)carbonyl]-N3-hydroxy-N4-[4-[(2-methyl-4-quinolinyl)methoxy]phenyl]-3,4-piperidinedicarboxamide trifluoroacetate salt This compound was prepared in a manner analogous to that for example 26. MS(ESI): $(M+H)^+=540.4$.

Example 46

(3R-trans)-1-[(4-quinolinyl)carbonyl]-N3-hydroxy-N4-[4-[(2-methyl-4-quinolinyl)methoxy]phenyl]-3,4-piperidinedicarboxamide trifluoroacetate salt This compound was prepared in a manner analogous to that for example 26. MS(ESI): $(M+H)^+=590.5$.

Example 47

(3R-trans)-1-[(2-quinolinyl)carbonyl]-N3-hydroxy-N4-[4-[(2-methyl-4-quinolinyl)methoxy]phenyl]-3,4-piperidinedicarboxamide trifluoroacetate salt This compound was prepared in a manner analogous to that for example 26. MS(ESI): $(M+H)^+=590.5$.

Example 48

(3R-trans)-1-Benzoyl-N3-hydroxy-N4-[4-[(2-methyl-4-quinolinyl)methoxy]phenyl]-3,4-piperidinedicarboxamide trifluoroacetate salt This compound was prepared in a manner analogous to that for example 26. MS(ESI): $(M+H)^+=539.4$.

Example 49

(3R-trans)-1-[(4-Methylsulfonyl)benzoyl]-N3-hydroxy-N4-[4-[(2-methyl-4-quinolinyl)methoxy]phenyl]-3,4-piperidinedicarboxamide trifluoroacetate salt This compound was prepared in a manner analogous to that for example 26. MS(ESI): $(M+H)^+=617.5$.

Example 50

(3R-trans)-1-(4-Chlorobenzoyl)-N3-hydroxy-N4-[4-[(2-methyl-4-quinolinyl)methoxy]phenyl]-3,4-piperidinedicarboxamide trifluoroacetate salt This compound was prepared in a manner analogous to that for example 26. MS(ESI): $(M+H)^+=573.9$.

Example 51

(3R-trans)-1-(4-Cyanobenzoyl)-N3-hydroxy-N4-[4-[(2-methyl-4-quinolinyl)methoxy]phenyl]-3,4-piperidinedicarboxamide trifluoroacetate salt This compound was prepared in a manner analogous to that for example 26. MS(ESI): (M+H)$^+$=564.4.

Example 52

(3R-trans)-1-(4-Methoxybenzoyl)-N3-hydroxy-N4-[4-[(2-methyl-4-quinolinyl)methoxy]phenyl]-3,4-piperidinedicarboxamide trifluoroacetate salt This compound was prepared in a manner analogous to that for example 26. MS(ESI): (M+H)$^+$=569.4.

Example 53

(3R-trans)-1-(3-Methoxybenzoyl)-N3-hydroxy-N4-[4-[(2-methyl-4-quinolinyl)methoxy]phenyl]-3,4-piperidinedicarboxamide trifluoroacetate salt This compound was prepared in a manner analogous to that for example 26. MS(ESI): (M+H)$^+$=569.4.

Example 54

(3R-trans)-1-(5-Nitro-2-pyridinyl)-N3-hydroxy-N4-[4-[(2-methyl-4-quinolinyl)methoxy]phenyl]-3,4-piperidinedicarboxamide trifluoroacetate salt This compound was prepared in a manner analogous to that for example 26. MS(ESI): (M+H)$^+$=557.4.

Example 55

(3R-trans)-1-Methylsulfonyl-N3-hydroxy-N4-[4-[(2-methyl-4-quinolinyl)methoxy]phenyl]-3,4-piperidinedicarboxamide trifluoroacetate salt This compound was prepared in a manner analogous to that for example 26. MS(ESI): (M+H)$^+$=513.3.

Example 56

(3R-trans)-1-[(1-Methyl-4-imidazole) sulfonyl]-N3-hydroxy-N4-[4-[(2-methyl-4-quinolinyl)methoxy]phenyl]-3,4-piperidinedicarboxamide trifluoroacetate salt This compound was prepared in a manner analogous to that for example 26. MS(ESI): (M+H)$^+$=579.4.

Example 57

(3R-trans)-1-(2-Thiophenesulfonyl)-N3-hydroxy-N4-[4-[(2-methyl-4-quinolinyl)methoxy]phenyl]-3,4-piperidinedicarboxamide trifluoroacetate salt This compound was prepared in a manner analogous to that for example 26. MS(ESI): (M+H)$^+$=581.4.

Example 58

(3R-trans)-1-(tert-Butylaminocarbonyl)-N3-hydroxy-N4-[4-[(2-methyl-4-quinolinyl)methoxy]phenyl]-3,4-piperidinedicarboxamide trifluoroacetate salt This compound was prepared in a manner analogous to that for example 26. MS(ESI): (M+H)$^+$=534.4.

Example 59 trans-1,1-Dimethylethyl 3-[(hydroxyamino)carbonyl]-4-[[[4-[(4-quinolinyloxy)methyl]phenyl]amino]carbonyl]-1-pryrrolidinecarboxylate trifluoroacetate salt (59a) 1,8-Diazabicyclo[5.4.0]undec-7-ene (5.55 g, 36.4 mmol) was added dropwise to fumaric acid mono ethyl ester (5.0 g, 34.7 mmol) and benzyl bromide (7.71 g, 45.1 mmol) in benzene (75 mL) at room temperature. The reaction mixture was stirred overnight then diluted to 200 mL with ethyl acetate and washed with water (2×), 10% citric acid, saturated NaHCO$_3$(2×), and brine. After drying over MgSO$_4$ the solvent was removed in vacuo and the residue chromatographed to provide the diester (6.31 g, 78%) as a clear liquid. $^1$HNMR, (CDCl$_3$, 300 MHz), d: 7.38 (m, 5H), 6.89 (s, 2H), 5.24 (s, 2H), 4.25 (q, J=6.9 Hz, 2H), 1.31 (t, J=6.9 Hz, 3H).

(59b) Glycine (1.5 g, 20 mmol) and paraformaldehyde (1.2 g, 40 mmol) were mixed together then added portionwise to the diester 59a (2.34 g, 100 mmol) in refluxing toluene (150 mL) over a 2 h period. The reaction mixture was cooled to room temperature, filtered through celite, then the solvent was evaporated in vacuo to give the pyrrolidine (2.64 g, 95%) as a brown viscous oil which was taken forward without further purification. MS(ESI): (M+H)$^+$=278.

(59c) Di-tert-butyl dicarbonate (2.46 g, 11.3 mmol) was added in one portion to a solution of the pyrrolidine 59b (2.60 g, 9.38 mmol) in DMF (20 mL) at room temperature. The mixture was stirred overnight at room temperature, diluted to 200 mL with ether then washed with water (2×), 10% citric acid, saturated NaHCO$_3$ (2×), and brine. The solution was dried over MgSO$_4$ and the solvent removed in vacuo. The residue was purified by flash chromatography eluting with ethyl acetate/hexane to provide the Boc-protected pyrrolidine (1.83 g, 52%) as a clear viscous oil. MS(ESI): (M+Na)$^+$=400.

(59d) Ethanol (40 mL) was added carefully under nitrogen to the Boc-protected pyrrolidine 59c (1.83 g, 4.85 mmol) and 10% palladium on carbon (0.5 g). A hydrogen balloon was attached via a 3-way stopcock and the atmosphere over the reaction was removed and replaced with hydrogen (3×). After 1 h the reaction mixture was filtered through celite washing with ethanol. The solvent was removed in vacuo to provide the carboxylic acid (1.40 g, 100%) as a clear viscous oil. MS(ESI): (M−H)$^-$=286.

(59e) Diisopropylethylamine (111 mg, 0.86 mmol) was added dropwise to a solution of the carboxylic acid 59d (82 mg, 0.29 mmol), BOP reagent (139 mg, 0.31 mmol) and 7d (90 mg, 0.31 mmol) in DMF (2 mL) at room temperature. The mixture was stirred overnight and the solvent was evaporated in vacuo. The residue was taken up in ethyl acetate (20 mL) then washed with water, saturated NaHCO$_3$ (2×), and brine, dried over MgSO$_4$, then purified by flash chromatography (75% ethyl acetate/hexane to 10% methanol/ethyl acetate) to provide 59e (111 mg, 75%) as a waxy solid.

(59f) Lithium hydroxide (45 mg, 1.07 mmol) in water (1 mL) was added to a solution of 59e (111 mg, 0.21 mmol) in THF (3 mL) at room temperature. The mixture was stirred 1 h then the solvent was removed in vacuo. The residue was taken up in water (10 mL), washed with ethyl acetate (2×, discard), then the aqueous solution was acidified with 10% citric acid until pH=3. The solution was extracted with ethyl acetate (3×), then the combined organic extracts were washed with brine, dried over MgSO$_4$. The solvent was removed in vacuo to provide 59f (51 mg, 49%) which was taken forward without further purification. MS(ESI): (M+H)$^+$=492.

(59g) Diisopropylethylamine (134 mg, 0.1.04 mmol) was added dropwise to a solution of 59f (51 mg, 0.10 mmol), BOP reagent (51 mg, 0.11 mmol) and hydroxylamine hydrochloride (22 mg, 0.31 mmol) in DMF (1.5 mL) at room temperature. The mixture was stirred overnight and the solvent was evaporated in vacuo. The residue was purified by reverse phase HPLC to provide example 59 (27 mg, 51%) as a white powder. MS(ESI): (M−H)$^-$=505.

Example 60 trans-N3-Hydroxy-N4-[4-[(4-quinolinyloxy)methyl]phenyl]-3,4-pyrrolidinedicarboxamide bis-trifluoroacetate salt Trifluoroacetic acid (1.5 mL) was added to example 59 (16 mg, 0.031 mmol) suspended in dichloromethane (1.5 mL) at room temperature under nitrogen. The mixture was stirred for 1 h, then the solvent was removed in vacuo. The residual TFA was removed by evaporation in vacuo with chloroform (5 mL, 4×), the residue dissolved in water (3 mL) then freeze dried to provide example 60 (100%) as a white powder. MS(ESI): (M+H)$^+$=407.

Example 61 trans-1,1-Dimethylethyl 3-[[[4-[(2,6-dichloro-4-pyridinyl)methoxy]phenyl]amino]carbonyl]-4-[(hydroxyamino)carbonyl]-1-pyrrolidinecarboxylate trifluoroacetate salt (61a) Diisopropylethylamine (1.88 g, 14.5 mmol) was added dropwise to a solution of 59d (1.39 g, 4.83 mmol), BOP reagent (2.35 g, 5.32 mmol) and 4-aminophenol (0.79 g, 7.26 mmol) in DMF (15 mL) at 0° C. The mixture was allowed to warm to room temperature then stirred overnight and the solvent was evaporated in vacuo. The residue was taken up in ethyl acetate (100 mL) then washed with water, saturated NaHCO$_3$ (2×), and brine then dried over MgSO$_4$. The solvent was removed in vacuo and the residue purified by flash chromatography (SiO$_2$, 50–80% ethyl acetate/hexane) to provide 61a (1.29 g, 70%) as a viscous oil. MS(ESI): (M+H)$^+$=401.

(61b) Cesium carbonate (145 mg, 0.44 mmol) was added in one portion to a solution of 61a (112 mg, 0.30 mmol) and 2,6-dicholoro-4-bromomethylpyridine (71 mg, 0.30 mmol) in DMF (5 mL) at room temperature. The mixture was stirred 3 h then quenched with saturated NH$_4$Cl (5 mL). Water (5 mL) was added and the solution was extracted with ethyl acetate (3×). The combined extracts were washed with water (2×), saturated NaHCO$_3$, and brine, dried over MgSO$_4$, then the solvent was removed in vacuo. The residue was purified by flash chromatography (25–50% ethyl acetate/hexane) to provide 61b (62 mg, 39%) as a waxy solid. MS(ESI): (M+Na)$^+$=560.

(61c) Following the procedure for 59f, intermediate 61c was obtained (44 mg, 75%) and taken forward without further purification.

(61d) Following the procedure for 59 g, example 61 was prepared (30 mg 66%) as a white solid. MS(ESI): (M−H)$^−$=525.

Example 62 trans-N3-[4-[(2,6-Dichloro-4-pyridinyl)methoxy]phenyl]-N4-hydroxy-3,4-pyrrolidinedicarboxamide bis-trifluoroacetate salt This compound was synthesized following the procedures given for example 60. MS(ESI): (M+H)$^+$=427.

Example 63

(2R-trans)-N2-[4-(4-quinolinyloxymethyl)phenyl]-N3-hydroxy-2,3-piperidinedicarboxamide trifluoroacetate salt (63a) To a suspension of L-aspartic acid β-tert-butyl ester (25 g, 132 mmol) in DMF (250 mL) and DMSO (50 mL) was added benzyl bromide (79 mL, 462 mmol) followed by potassium carbonate (55 g, 396 mmol). The mixture was mechanically stirred at 50° C. overnight, cooled to room temperature and diluted with water (200 mL). The solution was extracted with ethyl acetate three times. The combined extracts were washed with brine, dried (MgSO$_4$) and concentrated. Purification on a silica gel column eluting with ethyl acetate (10%)/hexane gave the tri-benzylated product (60 g, 99%) as a viscous oil. MS(ESI): (M+H)$^+$=460.

(63b) To a solution of the tri-benzylated compound 63a (30 g, 65.35 mmol) in THF (500 mL) cooled at −78° C. was added a 1 M solution of lithium bis(trimethylsilyl)amide in THF (72 mL). The mixture was stirred at −78° C. for 1 hour and allyl bromide (6.78 mL, 78.4 mmol) was added. The temperature was raised to −10° C. and stirring was continued at −10° C. for 3 hours. The reaction was quenched with 10% citric acid solution followed by dilution with brine. The mixture was extracted with ethyl acetate three times. The combined extracts were washed with brine, dried (MgSO$_4$), and concentrated. Chromatography on a silica gel column eluting with ethyl acetate (20%)/hexane produced the allylated product (22 g, 67%) as a viscous oil. MS(ESI): (M+H)$^+$=500.1.

(63c) To a solution of the allylated product 63b (21 g, 42 mmol) in THF (50 mL) cooled in an ice bath was added a 0.5 M solution of 9-BBN (168 mL, 84 mmol). The mixture was stirred at room temperature overnight and cooled in an ice bath. To it was added a solution of sodium acetate (69 g) in water followed by a solution of 33% H$_2$O$_2$ (68.5 mL). The mixture was stirred at room temperature for 3 hours and extracted with ethyl acetate three times. The combined extracts were washed with brine, dried (MgSO$_4$), and concentrated. The crude product was a mixture of two isomers (syn and anti, 1:1 ratio) which were separated by chromatography on a silica gel column eluting with ethyl acetate (30%)/hexane. The fast moving isomer was characterized as the desired syn isomer (9.7 g, 44%). MS(ESI): (M+H)$^+$=518.1.

(63d) To a solution of the alcohol 63c (9.3 g, 18 mmol) in methylene chloride (100 mL) cooled in an ice bath was added Dess-Martin reagent (10.6 g, 25 mmol). The mixture was stirred at room temperature for 5 hours and filtered through silica gel and concentrated. The residue was taken up in ethyl acetate and the solution was washed with brine, dried (MgSO$_4$) and concentrated. Purification on a silica gel column eluting with ethyl acetate (40%)/hexane produced the aldehyde (5.6 g, 60%) as a viscous oil. MS(ESI): (M+H)$^+$=516.3.

(63e) A solution of the aldehyde 63d (5.15 g, 10 mmol) in methanol (100 mL) in a Parr bottle was hydrogenated under a pressure of 40 psi for 5 hours using 10% palladium on carbon (1.0 g) as catalyst. The catalyst was filtered off and the solution was concentrated to give the crude cyclized product (2.3 g) which was used for the next reaction without purification. MS(ESI): (M+H)$^+$=230.1.

(63f) To a solution of 63e (112 mg, 0.49 mmol) and 7d (150 mg, 0.49 mmol) in DMF (2 mL) cooled in an ice bath was added BOP (221 mg, 0.5 mmol) followed by diisopropylethylamine (0.35 mL, 2 mmol). The mixture was stirred at room temperature overnight and concentrated. Purification using reversed phase HPLC gave the desired product (100 mg, 47%) as a TFA salt. MS(ESI): (M+H)$^+$=462.4.

(63g) A solution of 63f (25 mg, 0.054 mmol) in methylene chloride (1 mL) and TFA (1 mL) was stirred at room temperature for 4 hours and concentrated to give the carboxylic acid. MS(ESI): (M+H)$^+$=406.2.

(63h) To a solution of 63 g (25 mg, 0.038 mmol) in DMF (1 mL) cooled to −30° C. was added DIEA (65 mg, 0.5 mmol) followed by propyl chloroformate (12 mg, 0.1 mmol). After stirring at between −20° C. and −30° C. for 20 min, hydroxylamine hydrochloride (21 mg, 0.3 mmol) was added. Stirring was continued at between −20° C. and −5° C. for 30 min and the solution was concentrated. Purification using reversed phase HPLC afforded the desired hydroxainate 63 (12 mg) as a TFA salt. MS(ESI):(M+H)$^+$=421.2.

Example 64

(2R-trans)-1-methyl-N2-[4-(4-quinolinyloxymethyl) phenyl]-N3-hydroxy-2,3-piperidinedicarboxamide trifluoroacetate salt (64a) To a solution of 63f (19 mg, 0.027 mmol), paraformaldehyde (12 mg, 0.4 mmol) and diisopropylethylamine (26 mg, 0.2 mmol) in DMF (1 mL) was added titanium isopropoxide (28 mg, 0.1 mmol). After stirring at room temperature for 10 min, sodium triacetoxyborohydride (21 mg, 0.1 mmol) was added. The mixture was stirred at room temperature overnight. Insoluble material was filtered off and the filtrate was concentrated. Purification using reversed phase HPLC gave the N-methyl derivative (16 mg) as a TFA salt. MS(ESI): (M+H)$^+$=476.3.

(64b) The title compound was obtained by deprotection of the tert-butyl ester 64a followed by coupling with hydroxylamine hydrochloride using procedures given for 63 g and 63 h. MS(ESI): (M+H)$^+$=435.2.

Example 65

(2R-trans)-N2-[4-(2-methyl-4-quinolinylmethoxy) phenyl]1-N3-hydroxy-2,3-piperidinedicarboxamide trifluoroacetate salt (65a) Coupling of 63e with 26e using a procedure given for 63f provided the anilide product 65a. MS(ESI): (M+H)$^+$=476.3.

(65b). The title compound was obtained by converting the tert-butyl ester 65a to a hydroxamate 65 using procedures given for 63 g and 63 h. MS(ESI): (M+H)$^+$=435.3.

Example 66

(2 R-trans)-1-methyl-N2-[4-(2-methyl-4-quinolinylmethyloxy)phenyl]-N3-hydroxy-2,3-piperidinedicarboxamide trifluoroacetate salt (66a) The intermediate 65a was N-methylated using a procedure given for 64a to give the 1-methylpiperidine derivative 66a. MS(ESI): (M+H)$^+$=433.3.

(66b) The title compound was obtained by conversion of the tert-butyl ester 66a to a hydroxamate 66 using procedures given for 63 g and 63 h. MS(ESI): (M+H)$^+$=449.4.

Example 67

(2R-trans)-1-ethyl-N2-[4-(2-methyl-4-quinolinylmethyloxy)phenyl]-N3-hydroxy-2,3-piperidinedicarboxamide trifluoroacetate salt This compound was prepared in a manner analogous to that for example 66. MS(ESI): (M+H)$^+$=463.3.

Example 68

(2R-trans)-1-cyclopropylmethyl-N2-[4-(2-methyl-4-quinolinylmethyloxy)phenyl]-N3-hydroxy-2,3-piperidinedicarboxamide trifluoroacetate salt This compound was prepared in a manner analogous to that for example 66. MS(ESI): (M+H)$^+$=489.3.

Example 69

(2R-trans)-1-(2-thiazolemethyl)-N2-[4-(2-methyl-4-quinolinylmethyloxy)phenyl]-N3-hydroxy-2,3-piperidinedicarboxamide trifluoroacetate salt This compound was prepared in a manner analogous to that for example 66. MS(ESI): (M+H)$^+$=532.2.

Example 70

(2R-trans)-1-Methyl-2-[[4-(2-methyl-4-quinolinylmethyloxy)piperidinyl]carbonyl]-3-(N-hydroxy)piperidinecarboxamide trifluoroacetate salt (70a) To a solution of 26a (5 g, 28.9 mmol) in methylene chloride (50 mL) cooled in an ice bath was added DIEA (7.5 mL, 43.3 mmol) followed by methanesulfonyl chloride (3.6 g, 31.8 mmol). After stirring for 1 hour, the solvent was removed in vacuo. The residue was taken up in EtOAc and the solution was washed with brine, dried (MgSO$_4$) and concentrated. Chromatography on a silica gel column using 5% methanol/methylene chloride as eluent provided the mesylate 70a (5.1 g, 71%) as a powder. MS(ESI): (M+H)$^+$=252.2.

(70b) A mixture of 4-hydroxypiperidine (10.1 g, 100 mmol), di-tert-butyl-dicarbonate (21.8 g, 100 mmol) and DIEA (17.4 mL, 100 mmol) in THF (100 mL) was stirred in an ice bath for 2 hours and the solvent removed in vacuo. The residue was taken up in EtOAc and the solution was washed with brine, dried (MgSO$_4$) and concentrated. Chromatography on a silica gel column using 60% EtOAc/hexane provided the Boc-protected piperidine derivative 70b (14.9 g, 74%) as a viscous oil. MS(CI): (M+H)$^+$=202.1.

(70c) To a solution of 70b (2.01 g, 10 mmol) in DMF (20 mL) cooled in an ice bath was added NaH (0.35 g, 14.9 mmol) followed by 70a (2.5 g, 9.96 mmol). After stirring for 5 hours, the solvent was removed in vacuo. The residue was taken up in EtOAc and the solution was washed with brine, dried (MgSO$_4$) and concentrated. The residue was triturated with ether to provide the product (1.4 g, 40%) as a solid. MS(ESI): (M+H)$^+$=357.2.

(70d) The intermediate 70c (0.33 g, 0.926 mmol) was dissolved in 4 N HCl in dioxane (20 mL). After stirring for 1 hour, the solution was concentrated to give the deprotected product as a solid. MS(ESI): (M+H)$^+$=257.3.

(70e) The title compound was obtained by coupling of 70c with 63e followed by N-methylation and conversion of the tert-butyl ester to hydroxamate using procedures given for 64. MS(ESI): (M+H)$^+$=441.4.

Example 71

(2R-trans)-1-Methyl-2-[[4-(4-quinolinyloxymethyl) piperidinyl]carbonyl]-3-(N-hydroxy) piperidinecarboxamide trifluoroacetate salt (71a) A mixture of ethyl 4-piperidinecarboxylate (15.7 g, 100 mmol), di-tert-butyl-dicarbonate (21.8 g, 100 mmol) and DIEA (17.4 mL, 100 mmol) in THF (100 mL) was stirred overnight and the solvent was removed in vacuo. The residue was taken up in EtOAc and the solution was washed with brine, dried (MgSO$_4$) and concentrated. Chromatography on a silica gel column eluting with 20% EtOAc/hexane provided the Boc protected product (22.4 g, 87%) as a viscous oil. MS(NH$_3$—CI): (M+H)$^+$=258.

(71b) A mixture of 71a (22.4 g, 87 mmol) and sodium borohydride (5.94 g, 156 mmol) in THF (80 mL) and ethanol (100 mL) was refluxed for 5 hours and then stirred at room temperature overnight. The solvent was removed in vacuo and the residue was washed with citric acid and brine, dried (MgSO$_4$) and concentrated. Chromatography on a silica gel column eluting with 40% EtOAc/hexane provided the alcohol product (14.1 g, 75%) as an oil. MS(NH$_3$—CI): (M+H)$^+$=216.

(71c) To a solution of 71b (6.2 g, 37 mmol) in methylene chloride (20 mL) cooled in an ice bath was added N-methylmorpholine (5.5 mL, 50.5 mmol) followed by toluenesulfonyl chloride (7.08 g, 37 mmol). After stirring overnight, the solvent was removed in vacuo. The residue was taken up in EtOAc and the solution was washed with brine, dried (MgSO$_4$) and concentrated. Chromatography on a silica gel column eluting with 60% EtOAc/hexane provided the sulfonate (10.8 g, 91%) as a viscous oil. MS(ESI): (M+H)$^+$=376.2.

(71d) A mixture of 71c (369 mg, 1 mmol), 4-quinolinol (145 mg, 1 mmol) and potassium carbonate (414 mg, 3 mmol) in DMF (2 mL) was heated at 100° C. for 4 hours. Purification on HPLC afforded the product (260 mg) as a TFA salt. MS(ESI): (M+H)$^+$=343.2.

(71e) The intermediate 71d (260 mg, 0.57 mmol) was dissolved in methanol (2 mL) and 4 N HCl/dioxane (5 mL) was added. After stirring for 2 hours, the solution was concentrated to give the product as a HCl salt. MS(ESI): (M+H)$^+$=243.3.

(71f) The title compound was obtained by coupling of 71e with 63e followed by N-methylation and conversion of the tert-butyl ester to hydroxamate using procedures given for 64. MS(ESI): (M+H)$^+$=427.2.

Example 72

(2R-trans)-1-Methyl-2-[[4-(2-methyl-4-quinolinyloxymethyl)piperidinyl]carbonyl]-3-(N-hydroxy)piperidinecarboxamide trifluoroacetate salt This compound was prepared in a manner analogous to that for example 71. MS(ESI): (M+H)$^+$=441.4.

Example 73

(2R-trans)-1-Methyl-2-[[4-(2-trifluoromethyl-4-quinolinyloxymethyl)piperidinyl]carbonyl]-3-(N-hydroxy)piperidinecarboxamide trifluoroacetate salt This compound was prepared in a manner analogous to that for example 71. MS(ESI): (M+H)$^+$=495.4

Example 74

(2R-trans)-2-[(4-phenylpiperidinyl)carbonyl]-3-(N-hydroxy)piperidinecarboxamide trifluoroacetate salt Example 74 was obtained by coupling 4-phenylpiperidine with 63e followed by conversion of the tert-butyl ester to hydroxamate using procedures given for example 63. MS(ESI): (M+H)$^+$=332.2.

Example 75

(2R-trans)-1-Ethyl-2-[(4-phenylpiperidinyl)carbonyl]-3-(N-hydroxy)piperidinecarboxamide trifluoroacetate salt Example 75 was obtained by coupling 4-phenylpiperidine with 63e followed by N-ethylation and conversion of the tert-butyl ester to hydroxamate using procedures given for example 64. MS(ESI): (M+H)$^+$=360.2.

Example 76

(2R-trans)-1-Methyl-2-[[4-(2-methoxyphenyl)piperidinyl]carbonyl]-3-(N-hydroxy)piperidinecarboxamide trifluoroacetate salt (76a) A mixture of 2-methoxybenzeneboronic acid (1 g, 6.58 mmol), 4-bromopyridine hydrochloride (1.4 g, 7.23 mmol), potassium carbonate (2.73 g, 17.8 mmol) and Pd(PPh$_3$)$_4$ (1.52 g, 1.2 mmol) in DMF (15 mL) and water (3 mL) was heated at 100° C. with stirring for 2 hours. After cooling to room temperature, insoluble material was filtered off. The filtrate was diluted with EtOAc and washed with brine, dried (MgSO$_4$) and concentrated. Purification on a silica gel column eluting with 40% EtOAc/hexane provided 76a (1 g, 82%) as a viscous oil. MS(ESI): (M+H)$^+$=186.4.

(76b) The intermediate 76a (1 g, 5.3 mmol) was dissolved in methanol (10 mL) and TFA (1 mL) was added followed by PtO$_2$ (0.2 g). The mixture was hydrogenated at 50 psi overnight. The catalyst was filtered off and the solution was concentrated to give 76b (1.07, 99%) as a TFA salt. MS(ESI): (M+H)$^+$=192.4.

(76c) The title compound was obtained by coupling of 76b with 63e followed by N-methylation and conversion of the tert-butyl ester to a hydroxamate using procedures given for example 64. MS(ESI): (M+H)$^+$=376.2.

Example 77

(2R-trans)-1-Methyl-2-[[4-(2-trifluoromethylphenyl)piperidinyl]carbonyl]-3-(N-hydroxy)piperidinecarboxamide trifluoroacetate salt Example 77 was prepared in a manner analogous to that for example 76. MS(ESI): (M+H)$^+$=414.4.

Example 78

(2R-trans)-1-Methyl-2-[[4-(2-methylphenyl)piperidinyl]carbonyl]-3-(N-hydroxy)piperidinecarboxamide trifluoroacetate salt Example 78 was prepared in a manner analogous to that for example 76. MS(ESI): (M+H)$^+$=360.2.

Example 79

(2R-trans)-1-Methyl-2-[[4-(3-methoxyphenyl)piperidinyl]carbonyl]-3-(N-hydroxy)piperidinecarboxamide trifluoroacetate salt Example 79 was prepared in a manner analogous to that for example 76. MS(ESI): (M+H)$^+$=376.2.

Example 80

(2R-trans)-1-Methyl-2-[[4-(3-trifluoromethylphenyl)piperidinyl]carbonyl]-3-(N-hydroxy)piperidinecarboxamide trifluoroacetate salt Example 80 was prepared in a manner analogous to that for example 76. MS(ESI): (M+H)$^+$=414.4.

TABLE 1
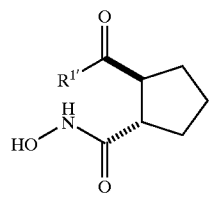
Examples 1–8
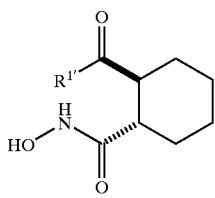
Examples 9–12
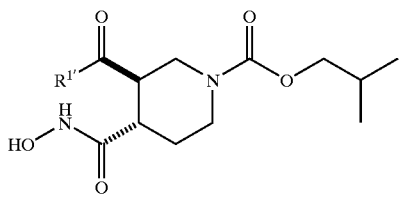
Examples 13
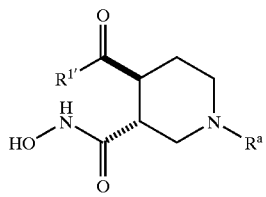
Examples 14–58
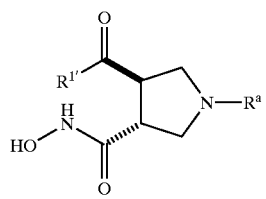
Examples 59–62
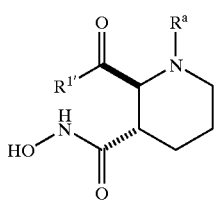
Examples 63–80
| Ex | $R^{1'}$ | $R^a$ | MS |
|---|---|---|---|
| 1 | 4-phenyl-1-piperidinyl | | 317 (M + H)+ |
| 2 | 4-(4-methylphenoxymeth-yl)-1-piperidinyl | | 361 (M + H)+ |

TABLE 1-continued

| | | | |
|---|---|---|---|
| 3 | 4-(2-phenoxyethyl)-1-piperidinyl | | 361.1 (M + H)+ |
| 4 | [4-(phenylmethoxy)phenyl]amino | | 466.9 (M + TFA − H)− |
| 5 | [4-(4-pyridinyl-methoxy)phenyl]amino | | 356 (M + H)+ |
| 6 | [4-[(3,5-dichlorophenyl)methoxy]phenyl]amino | | 422.8 (M − H)− |
| 7 | [4-[(4-quinolinyloxy)methyl]phenyl]amino | | 406 (M + H)+ |
| 8 | [4-(4-pyridinyl-methyl)phenyl]amino | | 340 (M + H)+ |
| 9 | [4-(phenylmethoxy)phenyl]amino | | 480.9 (M + TFA − H)− |
| 10 | [4-[(4-quinolinyl-oxy)methyl]phenyl]amino | | 420.0 (M + H)+ |
| 11 | [4-[(5-quinolinyl-oxy)methyl]phenyl]amino | | 420.0 (M + H)+ |
| 12 | [4-[(6-quinolinyl-oxy)methyl]phenyl]amino | | 420.0 (M + H)+ |
| 13 | [4-[(4-quinolinyl-oxy)methyl]phenyl]amino | | 521.3 (M + H)+ |
| 14 | [4-[(4-quinolinyl-oxy)methyl]phenyl]amino | isobutoxycarbonyl | 521.3 (M + H)+ |
| 15 | [4-[(4-quinolinyl-oxy)methyl]phenyl]amino | 3,3-dimethylbutyryl | 519.3 (M + H)+ |
| 16 | [4-[(4-quinolinyl-oxy)methyl]phenyl]amino | 1-phenyl-1-cyclopropylcarbonyl | 565.3 (M + H)+ |
| 17 | [4-[(4-quinolinyl-oxy)methyl]phenyl]amino | benzenesulfonyl | 561.4 (M + H)+ |
| 18 | [4-(2-phenylethoxy)phenyl]amino | isobutoxycarbonyl | 484.3 (M + H)+ |
| 19 | [2-fluoro-4-(2-phenylethoxy)phenyl]amino | isobutoxycarbonyl | 502.3 (M + H)+ |
| 20 | [4-(pyridinyloxy)phenyl]amino | isobutoxycarbonyl | 457.3 (M + H)+ |
| 21 | [4-(4-quinolinyloxy)phenyl]amino | 3,3-dimethylbutyryl | 505.3 (M + H)+ |
| 22 | [4-[3,5-bis(trifluoromethyl)phenoxy]phenyl]amino | 2,2-dimethylpropyl | 562.3 (M + H)+ |
| 23 | [4-(3,5-dichlorophenoxy)phenyl]amino | 2,,2-dimethylpropyl | 495.1 (M + H)+ |
| 24 | [4-(3-chlorophenoxy)phenyl]amino | 2,2-dimethylpropyl | 460.6 (M + H)+ |
| 25 | (4-phenoxyphenyl)amino | 2,2-dimethylpropyl | 426.3 (M + H)+ |
| 26 | [4-[(2-methylquinolinyl-oxy)methyl]phenyl]amino | tert-butoxycarbonyl | 535.4 (M + H)+ |
| 27 | [4-[(2-methylquinolinyl-oxy)methyl]phenyl]amino | H | 435.3 (M + H)+ |
| 28 | [4-[(2-methylquinolinyl-oxy)methyl]phenyl]amino | Methoxycarbonyl | 493.3 (M + H)+ |
| 29 | [4-[(2-methylquinolinyl-oxy)methyl]phenyl]amino | 2-propoxycarbonyl | 521.4 (M + H)+ |
| 30 | [4-[(2-methylquinolinyl-oxy)methyl]phenyl]amino | Cyclopropyl Methoxycarbonyl | 533.4 (M + H)+ |
| 31 | [4-[(2-methylquinolinyl-oxy)methyl]phenyl]amino | Cyclopentyl Methoxycarbonyl | 547.4 (M + H)+ |
| 32 | [4-[(2-methylquinolinyl-oxy)methyl]phenyl]amino | Allyloxycarbonyl | 519.3 (M + H)+ |
| 33 | [4-[(2-methylquinolinyl-oxy)methyl]phenyl]amino | Propargyloxycarbonyl | 517.3 (M + H)+ |
| 34 | [4-[(2-methylquinolinyl-oxy)methyl]phenyl]amino | Tetrahydro-4H-pyran-4-yloxycarbonyl | 563.4 (M + H)+ |
| 35 | [4-[(2-methylquinolinyl-oxy)methyl]phenyl]amino | (S)-tetrahydro-3-furanyloxycarbonyl | 549.4 (M + H)+ |
| 36 | [4-[(2-methylquinolinyl-oxy)methyl]phenyl]amino | (2-methyl-4-thiazolyl)methoxycarbonyl | 590.5 (M + H)+ |
| 37 | [4-[(2-methylquinolinyl-oxy)methyl]phenyl]amino | 2-thiazole methoxycarbonyl | 576.5 (M + H)+ |
| 38 | [4-[(2-methylquinolinyl-oxy)methyl]phenyl]amino | 4-thiazole methoxycarbonyl | 576.5 (M + H)+ |
| 39 | [4-[(2-methylquinolinyl-oxy)methyl]phenyl]amino | 4-quinolinyl methoxycarbonyl | 620.5 (M + H)+ |

TABLE 1-continued

| | | | |
|---|---|---|---|
| 40 | [4-[(2-methylquinolinyl-oxy)methyl]phenyl]amino | acetyl | 477.3 (M + H)+ |
| 41 | [4-[(2-methylquinolinyl-oxy)methyl]phenyl]amino | 2-furoyl | 529.4 (M + H)+ |
| 42 | [4-[(2-methylquinolinyl-oxy)methyl]phenyl]amino | (2-amino-4-thiazolyl) acetyl | 575.4 (M + H)+ |
| 43 | [4-[(2-methylquinolinyl-oxy)methyl]phenyl]amino | 2-pyridinyl carbonyl | 540.4 (M + H)+ |
| 44 | [4-[(2-methylquinolinyl-oxy)methyl]phenyl]amino | (2-chloro-6-methyl-4-pyridinyl) carbonyl | 588.9 (M + H)+ |
| 45 | [4-[(2-methylquinolinyl-oxy)methyl]phenyl]amino | 4-pyridinyl carbonyl | 540.4 (M + H)+ |
| 46 | [4-[(2-methylquinolinyl-oxy)methyl]phenyl]amino | 4-quinolinyl carbonyl | 590.5 (M + H)+ |
| 47 | [4-[(2-methylquinolinyl-oxy)methyl]phenyl]amino | 2-quinolinyl carbonyl | 590.5 (M + H)+ |
| 48 | [4-[(2-methylquinolinyl-oxy)methyl]phenyl]amino | benzoyl | 539.4 (M + H)+ |
| 49 | [4-[(2-methylquinolinyl-oxy)methyl]phenyl]amino | 4-methylsulfonyl benzoyl | 617.5 (M + H)+ |
| 50 | [4-[(2-methylquinolinyl-oxy)methyl]phenyl]amino | 4-chlorobenzoyl | 573.9 (M + H)+ |
| 51 | [4-[(2-methylquinolinyl-oxy)methyl]phenyl]amino | 4-cyanobenzoyl | 564.4 (M + H)+ |
| 52 | [4-[(2-methylquinolinyl-oxy)methyl]phenyl]amino | 4-methoxybenzoyl | 569.4 (M + H)+ |
| 53 | [4-[(2-methylquinolinyl-oxy)methyl]phenyl]amino | 3-methoxybenzoyl | 569.4 (M + H)+ |
| 54 | [4-[(2-methylquinolinyl-oxy)methyl]phenyl]amino | 5-nitro-2-pyridinyl | 557.4 (M + H)+ |
| 55 | [4-[(2-methylquinolinyl-oxy)methyl]phenyl]amino | methylsulfonyl | 513.3 (M + H)+ |
| 56 | [4-[(2-methylquinolinyl-oxy)methyl]phenyl]amino | (1-methyl-4-imidazolyl) sulfonyl | 579.4 (M + H)+ |
| 57 | [4-[(2-methylquinolinyl-oxy)methyl]phenyl]amino | 2-thiophene sulfonyl | 581.5 (M + H)+ |
| 58 | [4-[(2-methylquinolinyl-oxy)methyl]phenyl]amino | Tert-butylamino carbonyl | 534.4 (M + H)+ |
| 59 | [4-[(4-quinolinyl-oxy)methyl]phenyl]amino | Tert-butoxycarbonyl | 505 (M − H)− |
| 60 | [4-[(4-quinolinyl-oxy)methyl]phenyl]amino | H | 407 (M + H)+ |
| 61 | [4-[(2,6-dichloro-4-pyridinyl)methoxy]phenyl]amino | Tert-butoxycarbonyl | 525 (M − H)− |
| 62 | [4-[(2,6-dichloro-4-pyridinyl)methoxy]phenyl]amino | H | 427 (M + H)+ |
| 63 | [4-[(4-quinolinyl-oxy)methyl]phenyl]amino | H | 421.2 (M + H)+ |
| 64 | [4-[(4-quinolinyl-oxy)methyl]phenyl]amino | methyl | 435.2 (M + H)+ |
| 65 | [4-[(2-methyl-4-quinolinyl-methyl)oxy]phenyl]amino | H | 435.2 (M + H)+ |
| 66 | [4-[(2-methyl-4-quinolinyl-methyl)oxy]phenyl]amino | methyl | 449.3 (M + H)+ |
| 67 | [4-[(2-methyl-4-quinolinyl-methyl)oxy]phenyl]amino | ethyl | 463.3 (M + H)+ |
| 68 | [4-[(2-methyl-4-quinolinyl-methyl)oxy]phenyl]amino | cyclopropylmethyl | 489.3 (M + H)+ |
| 69 | [4-[(2-methyl-4-quinolinyl-methyl)oxy]phenyl]amino | 2-thiazolemethyl | 532.2 (M + H)+ |
| 70 | 4-[(2-methyl-4-quinolinyl-methyl)oxy]piperidinyl | methyl | 441.4 (M + H)+ |
| 71 | 4-[(4-quinolinyl-oxy)methyl]piperidinyl | methyl | 427.2 (M + H)+ |
| 72 | 4-[(2-methyl-4-quinolinyl-oxy)methyl]piperidinyl | methyl | 441.4 (M + H)+ |
| 73 | 4-[(2-trifluoromethyl-4-quinolinyloxy)methyl]piperidinyl | methyl | 495.4 (M + H)+ |
| 74 | 4-phenylpiperidinyl | H | 332.2 (M + H)+ |
| 75 | 4-phenylpiperidinyl | ethyl | 360.2 (M + H)+ |
| 76 | 4-(2-methoxyphenyl)piperidinyl | methyl | 376.2 (M + H)+ |
| 77 | 4-(2-trifluoromethylphenyl) piperidinyl | methyl | 414.4 (M + H)+ |

TABLE 1-continued

| 78 | 4-(2-methylphenyl)piperidinyl | methyl | 360.2 (M + H)+ |
|---|---|---|---|
| 79 | 4-(3-methoxyphenyl)piperidinyl | methyl | 376.2 (M + H)+ |
| 80 | 4-(3-trifluoromethyl-phenyl)piperidinyl | methyl | 414.4 (M + H)+ |

The following tables contain representative examples of the present invention. Each entry in each table is intended to be paired with each formula at the start of the table. For example, in Table 2, example 1 is intended to be paired with each of formulae A1–X7.

TABLE 2

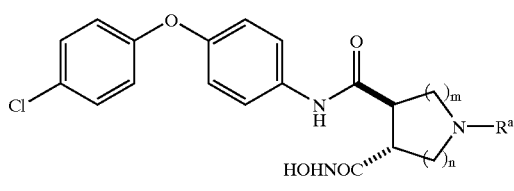

A1 (m = 0, n = 2)
A2 (m = 0, n = 3)
A3 (m = 1, n = 2)
A4 (m = 1, n = 1)
A5 (m = 2, n = 0)
A6 (m = 2, n = 1)
A7 (m = 3, n = 0)

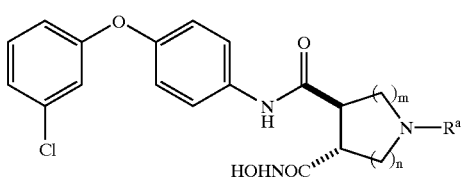

B1 (m = 0, n = 2)
B2 (m = 0, n = 3)
B3 (m = 1, n = 2)
B4 (m = 1, n = 1)
B5 (m = 2, n = 0)
B6 (m = 2, n = 1)
B7 (m = 3, n = 0)

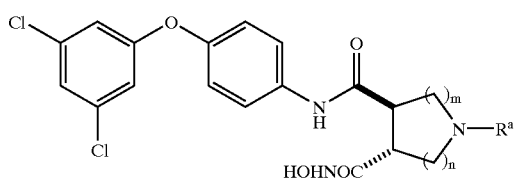

C1 (m = 0, n = 2)
C2 (m = 0, n = 3)
C3 (m = 1, n = 2)
C4 (m = 1, n = 1)
C5 (m = 2, n = 0)
C6 (m = 2, n = 1)
C7 (m = 3, n = 0)

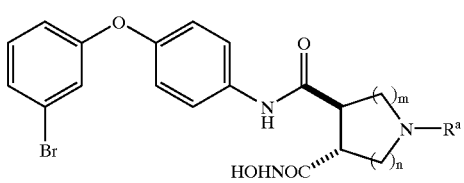

D1 (m = 0, n = 2)
D2 (m = 0, n = 3)
D3 (m = 1, n = 2)
D4 (m = 1, n = 1)
D5 (m = 2, n = 0)
D6 (m = 2, n = 1)
D7 (m = 3, n = 0)

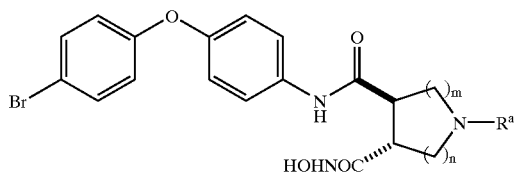

E1 (m = 0, n = 2)
E2 (m = 0, n = 3)
E3 (m = 1, n = 2)
E4 (m = 1, n = 1)
E5 (m = 2, n = 0)
E6 (m = 2, n = 1)
E7 (m = 3, n = 0)

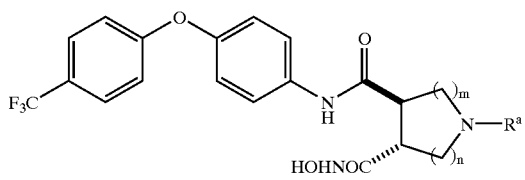

F1 (m = 0, n = 2)
F2 (m = 0, n = 3)
F3 (m = 1, n = 2)
F4 (m = 1, n = 1)
F5 (m = 2, n = 0)
F6 (m = 2, n = 1)
F7 (m = 3, n = 0)

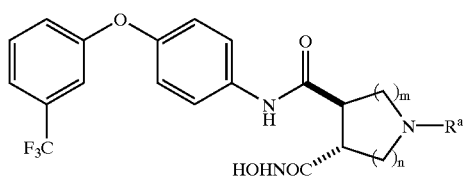

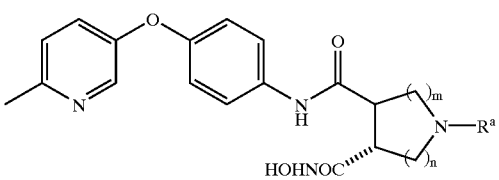

TABLE 2-continued

| G1 (m = 0, n = 2) | H1 (m = 0, n = 2) |
| G2 (m = 0, n = 3) | H2 (m = 0, n = 3) |
| G3 (m = 1, n = 2) | H3 (m = 1, n = 2) |
| G4 (m = 1, n = 1) | H4 (m = 1, n = 1) |
| G5 (m = 2, n = 0) | H5 (m = 2, n = 0) |
| G6 (m = 2, n = 1) | H6 (m = 2, n = 1) |
| G7 (m = 3, n = 0) | H7 (m = 3, n = 0) |

| I1 (m = 0, n = 2) | J1 (m = 0, n = 2) |
| I2 (m = 0, n = 3) | J2 (m = 0, n = 3) |
| I3 (m = 1, n = 2) | J3 (m = 1, n = 2) |
| I4 (m = 1, n = 1) | J4 (m = 1, n = 1) |
| I5 (m = 2, n = 0) | J5 (m = 2, n = 0) |
| I6 (m = 2, n = 1) | J6 (m = 2, n = 1) |
| I7 (m = 3, n = 0) | J7 (m = 3, n = 0) |

| K1 (m = 0, n = 2) | L1 (m = 0, n = 2) |
| K2 (m = 0, n = 3) | L2 (m = 0, n = 3) |
| K3 (m = 1, n = 2) | L3 (m = 1, n = 2) |
| K4 (m = 1, n = 1) | L4 (m = 1, n = 1) |
| K5 (m = 2, n = 0) | L5 (m = 2, n = 0) |
| K6 (m = 2, n = 1) | L6 (m = 2, n = 1) |
| K7 (m = 3, n = 0) | L7 (m = 3, n = 0) |

| M1 (m = 0, n = 2) | N1 (m = 0, n = 2) |
| M2 (m = 0, n = 3) | N2 (m = 0, n = 3) |
| M3 (m = 1, n = 2) | N3 (m = 1, n = 2) |
| M4 (m = 1, n = 1) | N4 (m = 1, n = 1) |
| M5 (m = 2, n = 0) | N5 (m = 2, n = 0) |
| M6 (m = 2, n = 1) | N6 (m = 2, n = 1) |
| M7 (m = 3, n = 0) | N7 (m = 3, n = 0) |

TABLE 2-continued
O1 (m = 0, n = 2)
O2 (m = 0, n = 3)
O3 (m = 1, n = 2)
O4 (m = 1, n = 1)
O5 (m = 2, n = 0)
O6 (m = 2, n = 1)
O7 (m = 3, n = 0)
P1 (m = 0, n = 2)
P2 (m = 0, n = 3)
P3 (m = 1, n = 2)
P4 (m = 1, n = 1)
P5 (m = 2, n = 0)
P6 (m = 2, n = 1)
P7 (m = 3, n = 0)
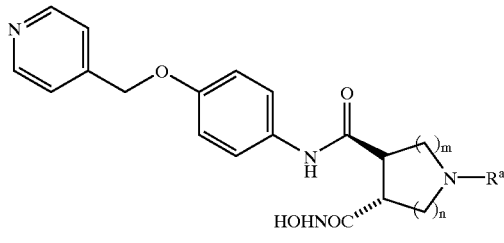
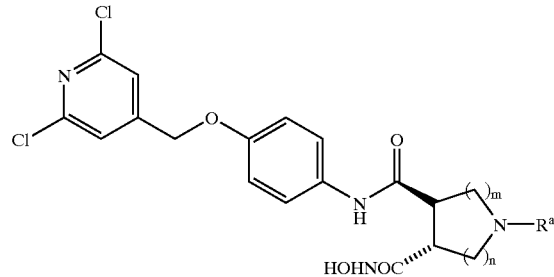
Q1 (m = 0, n = 2)
Q2 (m = 0, n = 3)
Q3 (m = 1, n = 2)
Q4 (m = 1, n = 1)
Q5 (m = 2, n = 0)
Q6 (m = 2, n = 1)
Q7 (m = 3, n = 0)
R1 (m = 0, n = 2)
R2 (m = 0, n = 3)
R3 (m = 1, n = 2)
R4 (m = 1, n = 1)
R5 (m = 2, n = 0)
R6 (m = 2, n = 1)
R7 (m = 3, n = 0)
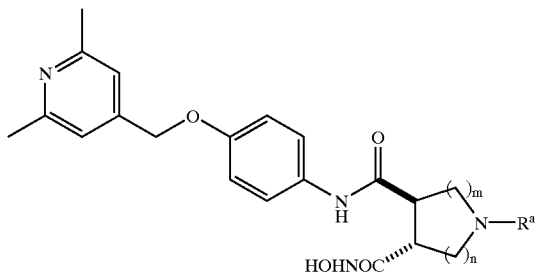
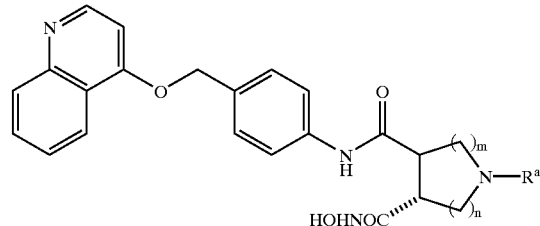
S1 (m = 0, n = 2)
S2 (m = 0, n = 3)
S3 (m = 1, n = 2)
S4 (m = 1, n = 1)
S5 (m = 2, n = 0)
S6 (m = 2, n = 1)
S7 (m = 3, n = 0)
T1 (m = 0, n = 2)
T2 (m = 0, n = 3)
T3 (m = 1, n = 2)
T4 (m = 1, n = 1)
T5 (m = 2, n = 0)
T6 (m = 2, n = 1)
T7 (m = 3, n = 0)
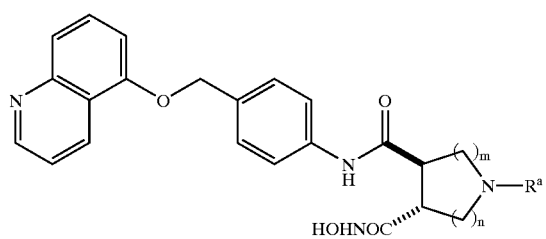
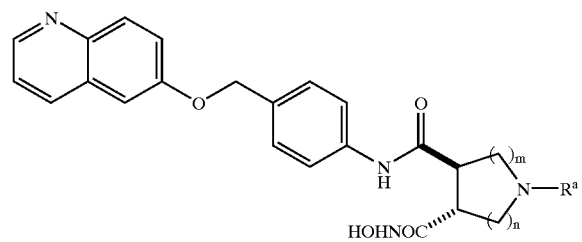
U1 (m = 0, n = 2)
U2 (m = 0, n = 3)
U3 (m = 1, n = 2)
U4 (m = 1, n = 1)
U5 (m = 2, n = 0)
U6 (m = 2, n = 1)
U7 (m = 3, n = 0)
V1 (m = 0, n = 2)
V2 (m = 0, n = 3)
V3 (m = 1, n = 2)
V4 (m = 1, n = 1)
V5 (m = 2, n = 0)
V6 (m = 2, n = 1)
V7 (m = 3, n = 0)

TABLE 2-continued

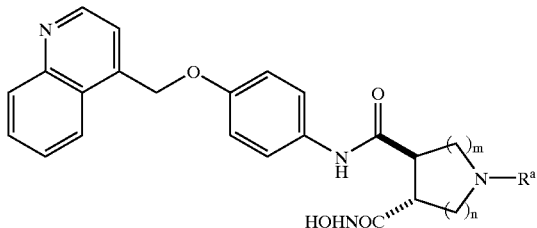

W1 (m = 0, n = 2)
W2 (m = 0, n = 3)
W3 (m = 1, n = 2)
W4 (m = 1, n = 1)
W5 (m = 2, n = 0)
W6 (m = 2, n = 1)
W7 (m = 3, n = 0)

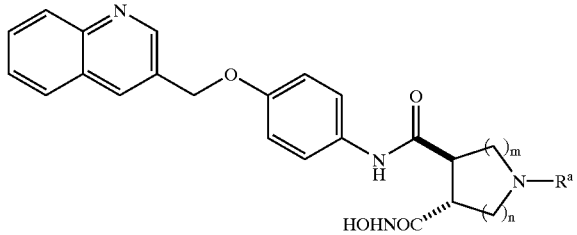

X1 (m = 0, n = 2)
X2 (m = 0, n = 3)
X3 (m = 1, n = 2)
X4 (m = 1, n = 1)
X5 (m = 2, n = 0)
X6 (m = 2, n = 1)
X7 (m = 3, n = 0)

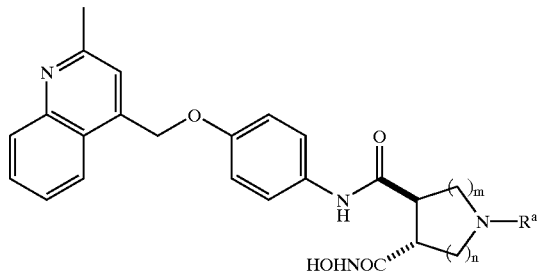

Y1 (m = 0, n = 2)
Y2 (m = 0, n = 3)
Y3 (m = 1, n = 2)
Y4 (m = 1, n = 1)
Y5 (m = 2, n = 0)
Y6 (m = 2, n = 1)
Y7 (m = 3, n = 0)

| Ex # | $R^a$ |
| --- | --- |
| 1 | methyl |
| 2 | ethyl |
| 3 | propyl |
| 4 | butyl |
| 5 | pentyl |
| 6 | hexyl |
| 7 | isopropyl |
| 8 | isobutyl |
| 9 | 3-methylbutyl |
| 10 | 4-methylpentyl |
| 11 | neopentyl |
| 12 | cyclopropanemethyl |
| 13 | cyclopentanemethyl |
| 14 | cyclohexanemethyl |
| 15 | cyclopropyl |
| 16 | cyclopentyl |
| 17 | cyclohexyl |
| 18 | benzyl |
| 19 | 4-fluorobenzyl |
| 20 | 4-chlorobenzyl |
| 21 | 2-picolyl |
| 22 | 3-picolyl |
| 23 | 4-picolyl |
| 24 | 2-pyridinyl |
| 25 | 4-pyridinyl |
| 26 | methyloxycarbonyl |
| 27 | ethyloxycarbonyl |
| 28 | propyloxycarbonyl |
| 29 | butyloxycarbonyl |
| 30 | pentyloxycarbonyl |
| 31 | hexyloxycarbonyl |
| 32 | isopropyloxycarbonyl |
| 33 | isobutyloxycarbonyl |
| 34 | 3-methylbutyloxycarbonyl |
| 35 | cyclopropanemethyloxycarbonyl |

TABLE 2-continued

| | |
|---|---|
| 36 | cyclopentanemethyloxycarbonyl |
| 37 | cyclohexanemethyloxycarbonyl |
| 38 | benzyloxycarbonyl |
| 39 | 2-picolyloxycarbonyl |
| 40 | 3-picolyloxycarbonyl |
| 41 | 4-picolyloxycarbonyl |
| 42 | 2-thiazolylmethyloxycarbonyl |
| 43 | methanesulfonyl |
| 44 | ethanesulfonyl |
| 45 | propanesulfonyl |
| 46 | butanesulfonyl |
| 47 | benzenesulfonyl |
| 48 | p-toluenesulfonyl |
| 49 | o-toluenesulfonyl |
| 50 | m-toluenesulfonyl |
| 51 | p-methoxybenzenesulfonyl |
| 52 | 2-thiophenesulfonyl |
| 53 | 3,5-dimethyl-4-isoxazolesulfonyl |
| 54 | 2,5-dimethyl-4-thiazolesulfonyl |
| 55 | acetyl |
| 56 | propionyl |
| 57 | butyryl |
| 58 | valeryl |
| 59 | t-butylacetyl |
| 60 | cyclopropylacetyl |
| 61 | cyclopentylacetyl |
| 62 | cyclohexylacetyl |
| 63 | phenylacetyl |
| 64 | 2-pyridylacetyl |
| 65 | 3-pyridylacetyl |
| 66 | 4-pyridylacetyl |
| 67 | α,α-dimethylphenylacetyl |
| 68 | 1-phenyl-1-cyclopropanecarbonyl |
| 69 | benzoyl |
| 70 | 2-pyridinecarbonyl |
| 71 | 2-quinolinecarbonyl |
| 72 | 3-quinolinecarbonyl |
| 73 | 4-quinolinecarbonyl |
| 74 | 2-thiazolecarbonyl |
| 75 | 2-furoyl |
| 76 | 2-imidazolecarbonyl |

TABLE 3

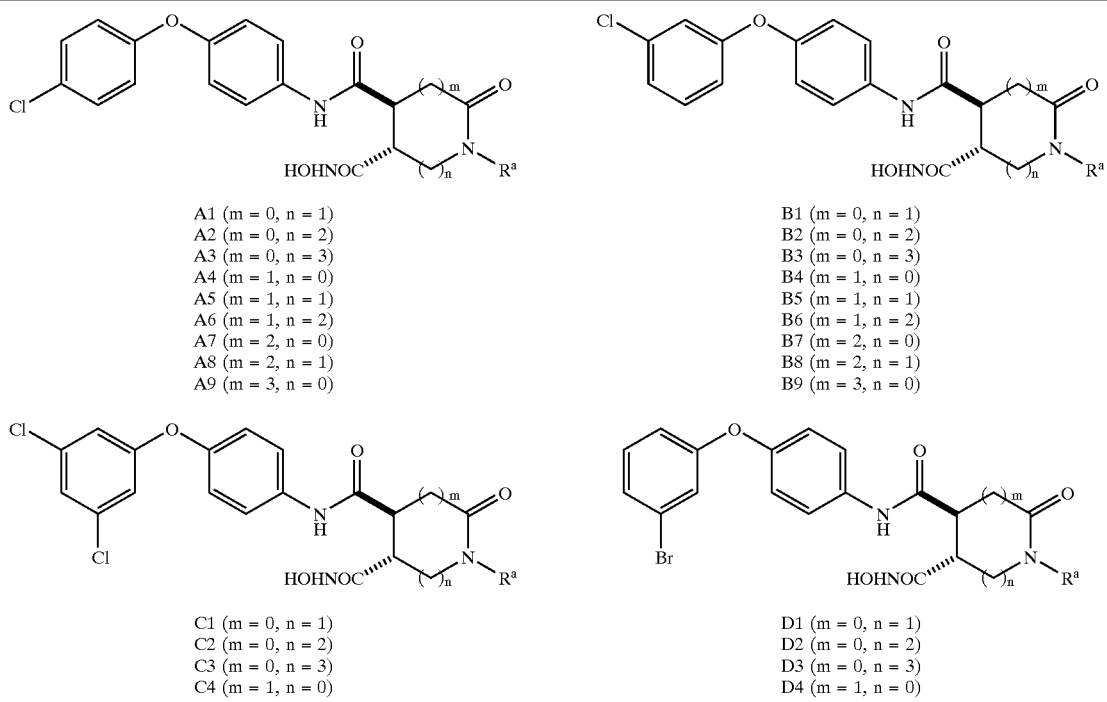

A1 (m = 0, n = 1)
A2 (m = 0, n = 2)
A3 (m = 0, n = 3)
A4 (m = 1, n = 0)
A5 (m = 1, n = 1)
A6 (m = 1, n = 2)
A7 (m = 2, n = 0)
A8 (m = 2, n = 1)
A9 (m = 3, n = 0)

B1 (m = 0, n = 1)
B2 (m = 0, n = 2)
B3 (m = 0, n = 3)
B4 (m = 1, n = 0)
B5 (m = 1, n = 1)
B6 (m = 1, n = 2)
B7 (m = 2, n = 0)
B8 (m = 2, n = 1)
B9 (m = 3, n = 0)

C1 (m = 0, n = 1)
C2 (m = 0, n = 2)
C3 (m = 0, n = 3)
C4 (m = 1, n = 0)

D1 (m = 0, n = 1)
D2 (m = 0, n = 2)
D3 (m = 0, n = 3)
D4 (m = 1, n = 0)

TABLE 3-continued

C5 (m = 1, n = 1)
C6 (m = 1, n = 2)
C7 (m = 2, n = 0)
C8 (m = 2, n = 1)
C9 (m = 3, n = 0)

D5 (m = 1, n = 1)
D6 (m = 1, n = 2)
D7 (m = 2, n = 0)
D8 (m = 2, n = 1)
D9 (m = 3, n = 0)

E1 (m = 0, n = 1)
E2 (m = 0, n = 2)
E3 (m = 0, n = 3)
E4 (m = 1, n = 0)
E5 (m = 1, n = 1)
E6 (m = 1, n = 2)
E7 (m = 2, n = 0)
E8 (m = 2, n = 1)
E9 (m = 3, n = 0)

F1 (m = 0, n = 1)
F2 (m = 0, n = 2)
F3 (m = 0, n = 3)
F4 (m = 1, n = 0)
F5 (m = 1, n = 1)
F6 (m = 1, n = 2)
F7 (m = 2, n = 0)
F8 (m = 2, n = 1)
F9 (m = 3, n = 0)

G1 (m = 0, n = 1)
G2 (m = 0, n = 2)
G3 (m = 0, n = 3)
G4 (m = 1, n = 0)
G5 (m = 1, n = 1)
G6 (m = 1, n = 2)
G7 (m = 2, n = 0)
G8 (m = 2, n = 1)
G9 (m = 3, n = 0)

H1 (m = 0, n = 1)
H2 (m = 0, n = 2)
H3 (m = 0, n = 3)
H4 (m = 1, n = 0)
H5 (m = 1, n = 1)
H6 (m = 1, n = 2)
H7 (m = 2, n = 0)
H8 (m = 2, n = 1)
H9 (m = 3, n = 0)

I1 (m = 0, n = 1)
I2 (m = 0, n = 2)
I3 (m = 0, n = 3)
I4 (m = 1, n = 0)
I5 (m = 1, n = 1)
I6 (m = 1, n = 2)
I7 (m = 2, n = 0)
I8 (m = 2, n = 1)
I9 (m = 3, n = 0)

J1 (m = 0, n = 1)
J2 (m = 0, n = 2)
J3 (m = 0, n = 3)
J4 (m = 1, n = 0)
J5 (m = 1, n = 1)
J6 (m = 1, n = 2)
J7 (m = 2, n = 0)
J8 (m = 2, n = 1)
J9 (m = 3, n = 0)

K1 (m = 0, n = 1)
K2 (m = 0, n = 2)
K3 (m = 0, n = 3)
K4 (m = 1, n = 0)
K5 (m = 1, n = 1)

L1 (m = 0, n = 1)
L2 (m = 0, n = 2)
L3 (m = 0, n = 3)
L4 (m = 1, n = 0)
L5 (m = 1, n = 1)

TABLE 3-continued

K6 (m = 1, n = 2)
K7 (m = 2, n = 0)
K8 (m = 2, n = 1)
K9 (m = 3, n = 0)

L6 (m = 1, n = 2)
L7 (m = 2, n = 0)
L8 (m = 2, n = 1)
L9 (m = 3, n = 0)

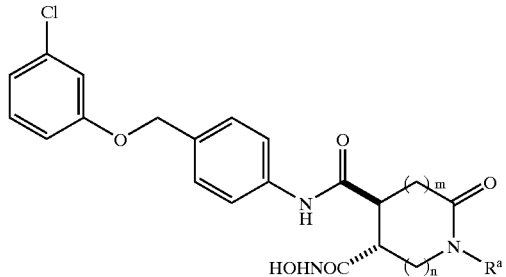

M1 (m = 0, n = 1)
M2 (m = 0, n = 2)
M3 (m = 0, n = 3)
M4 (m = 1, n = 0)
M5 (m = 1, n = 1)
M6 (m = 1, n = 2)
M7 (m = 2, n = 0)
M8 (m = 2, n = 1)
M9 (m = 3, n = 0)

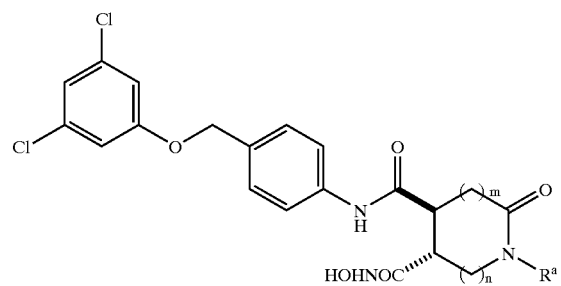

N1 (m = 0, n = 1)
N2 (m = 0, n = 2)
N3 (m = 0, n = 3)
N4 (m = 1, n = 0)
N5 (m = 1, n = 1)
N6 (m = 1, n = 2)
N7 (m = 2, n = 0)
N8 (m = 2, n = 1)
N9 (m = 3, n = 0)

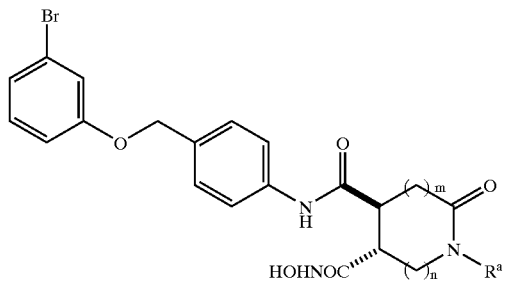

O1 (m = 0, n = 1)
O2 (m = 0, n = 2)
O3 (m = 0, n = 3)
O4 (m = 1, n = 0)
O5 (m = 1, n = 1)
O6 (m = 1, n = 2)
O7 (m = 2, n = 0)
O8 (m = 2, n = 1)
O9 (m = 3, n = 0)

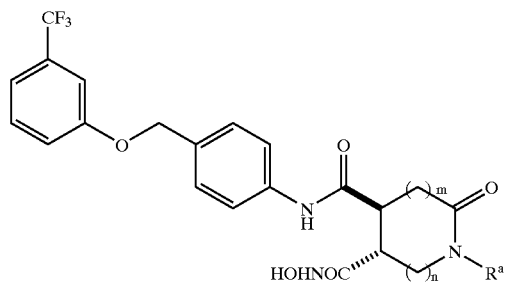

P1 (m = 0, n = 1)
P2 (m = 0, n = 2)
P3 (m = 0, n = 3)
P4 (m = 1, n = 0)
P5 (m = 1, n = 1)
P6 (m = 1, n = 2)
P7 (m = 2, n = 0)
P8 (m = 2, n = 1)
P9 (m = 3, n = 0)

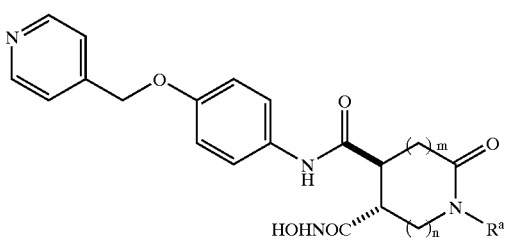

Q1 (m = 0, n = 1)
Q2 (m = 0, n = 2)
Q3 (m = 0, n = 3)
Q4 (m = 1, n = 0)
Q5 (m = 1, n = 1)
Q6 (m = 1, n = 2)
Q7 (m = 2, n = 0)
Q8 (m = 2, n = 1)
Q9 (m = 3, n = 0)

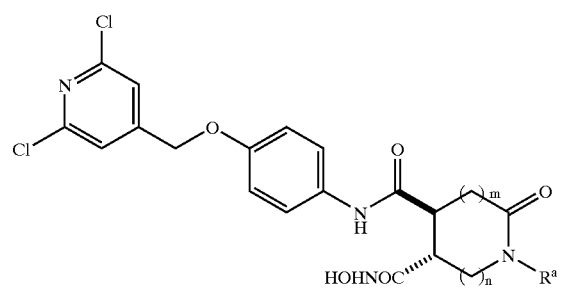

R1 (m = 0, n = 1)
R2 (m = 0, n = 2)
R3 (m = 0, n = 3)
R4 (m = 1, n = 0)
R5 (m = 1, n = 1)
R6 (m = 1, n = 2)
R7 (m = 2, n = 0)
R8 (m = 2, n = 1)
R9 (m = 3, n = 0)

TABLE 3-continued
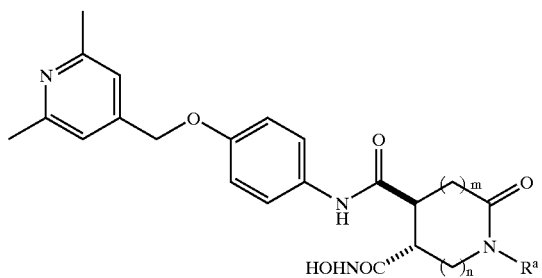
S1 (m = 0, n = 1)
S2 (m = 0, n = 2)
S3 (m = 0, n = 3)
S4 (m = 1, n = 0)
S5 (m = 1, n = 1)
S6 (m = 1, n = 2)
S7 (m = 2, n = 0)
S8 (m = 2, n = 1)
S9 (m = 3, n = 0)
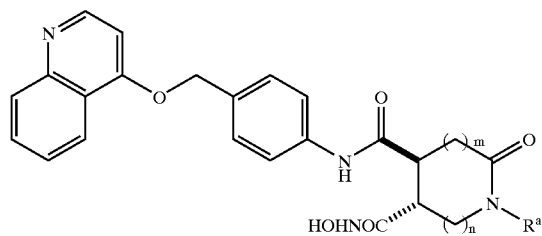
T1 (m = 0, n = 1)
T2 (m = 0, n = 2)
T3 (m = 0, n = 3)
T4 (m = 1, n = 0)
T5 (m = 1, n = 1)
T6 (m = 1, n = 2)
T7 (m = 2, n = 0)
T8 (m = 2, n = 1)
T9 (m = 3, n = 0)
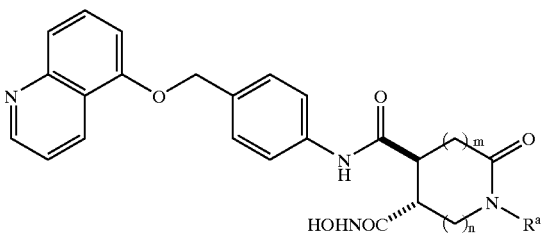
U1 (m = 0, n = 1)
U2 (m = 0, n = 2)
U3 (m = 0, n = 3)
U4 (m = 1, n = 0)
U5 (m = 1, n = 1)
U6 (m = 1, n = 2)
U7 (m = 2, n = 0)
U8 (m = 2, n = 1)
U9 (m = 3, n = 0)
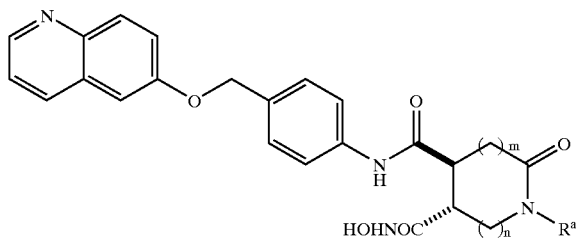
V1 (m = 0, n = 1)
V2 (m = 0, n = 2)
V3 (m = 0, n = 3)
V4 (m = 1, n = 0)
V5 (m = 1, n = 1)
V6 (m = 1, n = 2)
V7 (m = 2, n = 0)
V8 (m = 2, n = 1)
V9 (m = 3, n = 0)
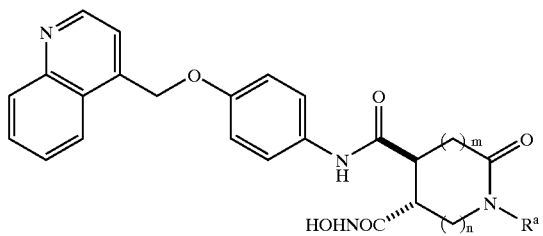
W1 (m = 0, n = 1)
W2 (m = 0, n = 2)
W3 (m = 0, n = 3)
W4 (m = 1, n = 0)
W5 (m = 1, n = 1)
W6 (m = 1, n = 2)
W7 (m = 2, n = 0)
W8 (m = 2, n = 1)
W9 (m = 3, n = 0)
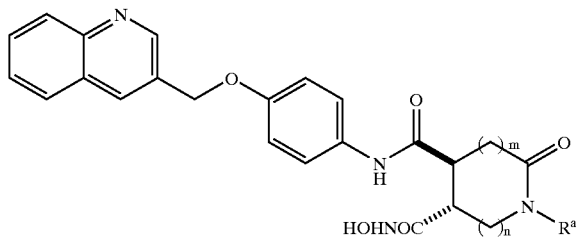
X1 (m = 0, n = 1)
X2 (m = 0, n = 2)
X3 (m = 0, n = 3)
X4 (m = 1, n = 0)
X5 (m = 1, n = 1)
X6 (m = 1, n = 2)
X7 (m = 2, n = 0)
X8 (m = 2, n = 1)
X9 (m = 3, n = 0)

TABLE 3-continued

[Structure: 2-methylquinoline-CH2-O-phenyl-NHC(=O)-piperidinone with HOHNOC substituent and N-Rᵃ]

Y1 (m = 0, n = 2)
Y2 (m = 0, n = 3)
Y3 (m = 1, n = 2)
Y4 (m = 1, n = 1)
Y5 (m = 2, n = 0)
Y6 (m = 2, n = 1)
Y7 (m = 3, n = 0)

| Ex # | Rᵃ |
|---|---|
| 1 | methyl |
| 2 | ethyl |
| 3 | propyl |
| 4 | butyl |
| 5 | pentyl |
| 6 | hexyl |
| 7 | isopropyl |
| 8 | isobutyl |
| 9 | 3-methylbutyl |
| 10 | 4-methylpentyl |
| 11 | neopentyl |
| 12 | cyclopropanemethyl |
| 13 | cyclopentanemethyl |
| 14 | cyclohexanemethyl |
| 15 | t-butylethyl |
| 16 | cyclopropaneethyl |
| 17 | benzyl |
| 18 | 2-methylbenzyl |
| 19 | 3-methylbenzyl |
| 20 | 4-methylbenzyl |
| 21 | 2-fluorobenzyl |
| 22 | 3-fluorobenzyl |
| 23 | 4-fluorobenzyl |
| 24 | 2-chlorobenzyl |
| 25 | 3-chlorobenzyl |
| 26 | 4-chlorobenzyl |
| 27 | 2-picolyl |
| 28 | 3-picolyl |
| 29 | 4-picolyl |
| 30 | 2-thiazolemethyl |
| 31 | 2-thiophenemethyl |
| 32 | 2-furfuryl |
| 33 | phenethyl |

TABLE 4

[Left structure: 4-chlorophenoxy-phenyl-NHC(=O)-piperidine with HOHNOC and N-Rᵃ]

A1 (m = 0, n = 1)
A2 (m = 0, n = 2)
A3 (m = 0, n = 3)
A4 (m = 1, n = 0)
A5 (m = 1, n = 1)
A6 (m = 1, n = 2)
A7 (m = 2, n = 0)

[Right structure: 3-chlorophenoxy-phenyl-NHC(=O)-piperidine with HOHNOC and N-Rᵃ]

B1 (m = 0, n = 1)
B2 (m = 0, n = 2)
B3 (m = 0, n = 3)
B4 (m = 1, n = 0)
B5 (m = 1, n = 1)
B6 (m = 1, n = 2)
B7 (m = 2, n = 0)

TABLE 4-continued

A8 (m = 2, n = 1)
A9 (m = 3, n = 0)

B8 (m = 2, n = 1)
B9 (m = 3, n = 0)

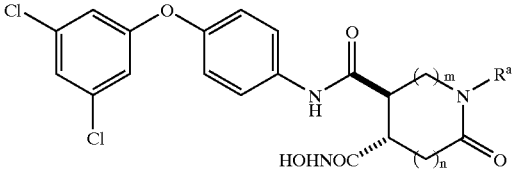

C1 (m = 0, n = 1)
C2 (m = 0, n = 2)
C3 (m = 0, n = 3)
C4 (m = 1, n = 0)
C5 (m = 1, n = 1)
C6 (m = 1, n = 2)
C7 (m = 2, n = 0)
C8 (m = 2, n = 1)
C9 (m = 3, n = 0)

D1 (m = 0, n = 1)
D2 (m = 0, n = 2)
D3 (m = 0, n = 3)
D4 (m = 1, n = 0)
D5 (m = 1, n = 1)
D6 (m = 1, n = 2)
D7 (m = 2, n = 0)
D8 (m = 2, n = 1)
D9 (m = 3, n = 0)

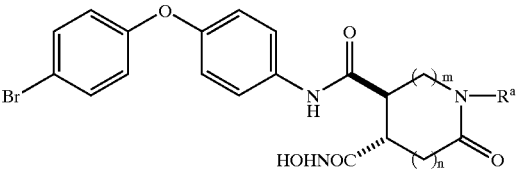

E1 (m = 0, n = 1)
E2 (m = 0, n = 2)
E3 (m = 0, n = 3)
E4 (m = 1, n = 0)
E5 (m = 1, n = 1)
E6 (m = 1, n = 2)
E7 (m = 2, n = 0)
E8 (m = 2, n = 1)
E9 (m = 3, n = 0)

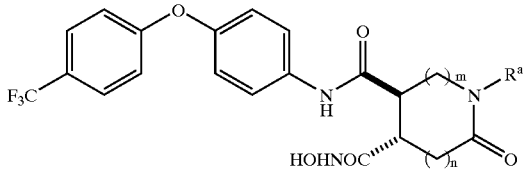

F1 (m = 0, n = 1)
F2 (m = 0, n = 2)
F3 (m = 0, n = 3)
F4 (m = 1, n = 0)
F5 (m = 1, n = 1)
F6 (m = 1, n = 2)
F7 (m = 2, n = 0)
F8 (m = 2, n = 1)
F9 (m = 3, n = 0)

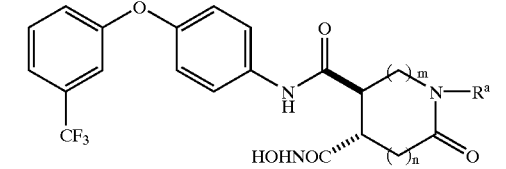

G1 (m = 0, n = 1)
G2 (m = 0, n = 2)
G3 (m = 0, n = 3)
G4 (m = 1, n = 0)
G5 (m = 1, n = 1)
G6 (m = 1, n = 2)
G7 (m = 2, n = 0)
G8 (m = 2, n = 1)
G9 (m = 3, n = 0)

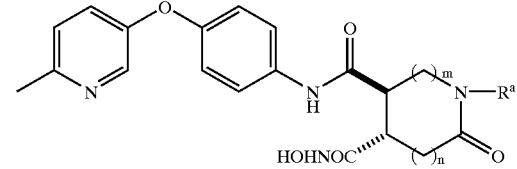

H1 (m = 0, n = 1)
H2 (m = 0, n = 2)
H3 (m = 0, n = 3)
H4 (m = 1, n = 0)
H5 (m = 1, n = 1)
H6 (m = 1, n = 2)
H7 (m = 2, n = 0)
H8 (m = 2, n = 1)
H9 (m = 3, n = 0)

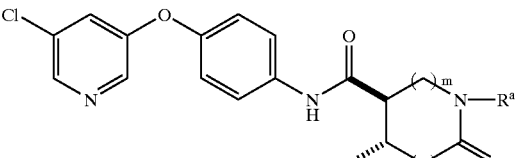

I1 (m = 0, n = 1)
I2 (m = 0, n = 2)
I3 (m = 0, n = 3)
I4 (m = 1, n = 0)
I5 (m = 1, n = 1)
I6 (m = 1, n = 2)
I7 (m = 2, n = 0)
I8 (m = 2, n = 1)
I9 (m = 3, n = 0)

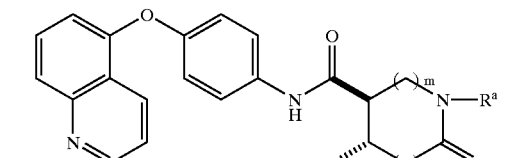

J1 (m = 0, n = 1)
J2 (m = 0, n = 2)
J3 (m = 0, n = 3)
J4 (m = 1, n = 0)
J5 (m = 1, n = 1)
J6 (m = 1, n = 2)
J7 (m = 2, n = 0)
J8 (m = 2, n = 1)
J9 (m = 3, n = 0)

TABLE 4-continued
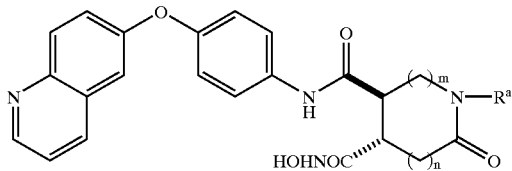
K1 (m = 0, n = 1)
K2 (m = 0, n = 2)
K3 (m = 0, n = 3)
K4 (m = 1, n = 0)
K5 (m = 1, n = 1)
K6 (m = 1, n = 2)
K7 (m = 2, n = 0)
K8 (m = 2, n = 1)
K9 (m = 3, n = 0)
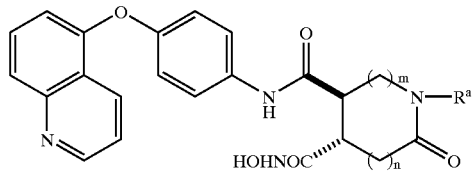
L1 (m = 0, n = 1)
L2 (m = 0, n = 2)
L3 (m = 0, n = 3)
L4 (m = 1, n = 0)
L5 (m = 1, n = 1)
L6 (m = 1, n = 2)
L7 (m = 2, n = 0)
L8 (m = 2, n = 1)
L9 (m = 3, n = 0)
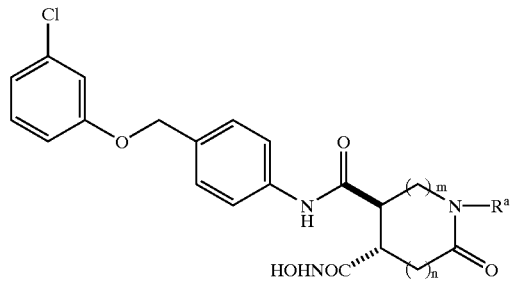
M1 (m = 0, n = 1)
M2 (m = 0, n = 2)
M3 (m = 0, n = 3)
M4 (m = 1, n = 0)
M5 (m = 1, n = 1)
M6 (m = 1, n = 2)
M7 (m = 2, n = 0)
M8 (m = 2, n = 1)
M9 (m = 3, n = 0)
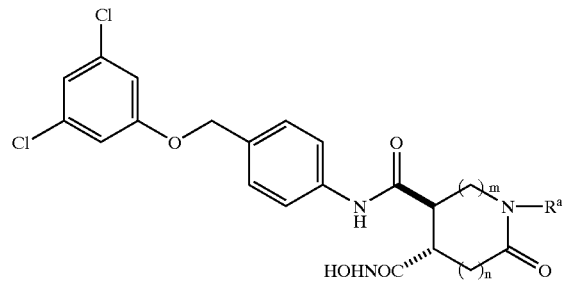
N1 (m = 0, n = 1)
N2 (m = 0, n = 2)
N3 (m = 0, n = 3)
N4 (m = 1, n = 0)
N5 (m = 1, n = 1)
N6 (m = 1, n = 2)
N7 (m = 2, n = 0)
N8 (m = 2, n = 1)
N9 (m = 3, n = 0)
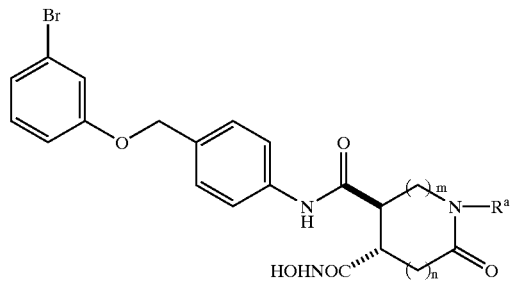
O1 (m = 0, n = 1)
O2 (m = 0, n = 2)
O3 (m = 0, n = 3)
O4 (m = 1, n = 0)
O5 (m = 1, n = 1)
O6 (m = 1, n = 2)
O7 (m = 2, n = 0)
O8 (m = 2, n = 1)
O9 (m = 3, n = 0)
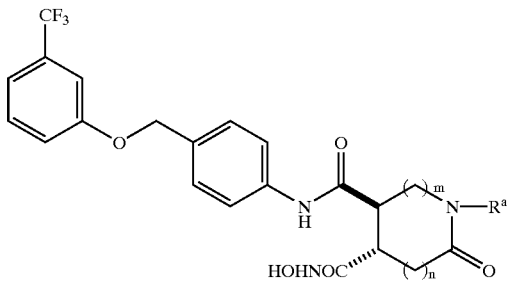
P1 (m = 0, n = 1)
P2 (m = 0, n = 2)
P3 (m = 0, n = 3)
P4 (m = 1, n = 0)
P5 (m = 1, n = 1)
P6 (m = 1, n = 2)
P7 (m = 2, n = 0)
P8 (m = 2, n = 1)
P9 (m = 3, n = 0)

TABLE 4-continued
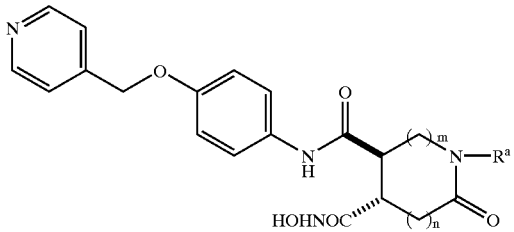
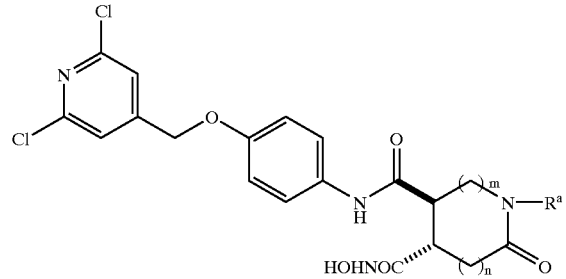
Q1 (m = 0, n = 1)
Q2 (m = 0, n = 2)
Q3 (m = 0, n = 3)
Q4 (m = 1, n = 0)
Q5 (m = 1, n = 1)
Q6 (m = 1, n = 2)
Q7 (m = 2, n = 0)
Q8 (m = 2, n = 1)
Q9 (m = 3, n = 0)
R1 (m = 0, n = 1)
R2 (m = 0, n = 2)
R3 (m = 0, n = 3)
R4 (m = 1, n = 0)
R5 (m = 1, n = 1)
R6 (m = 1, n = 2)
R7 (m = 2, n = 0)
R8 (m = 2, n = 1)
R9 (m = 3, n = 0)
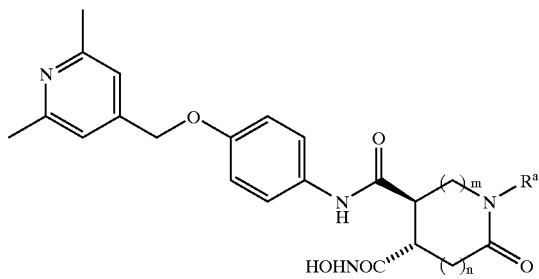
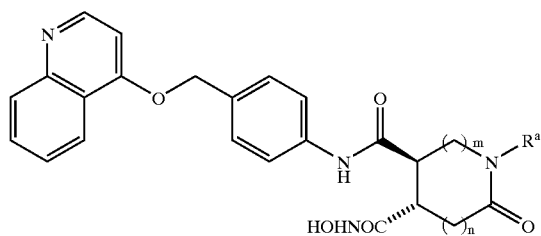
S1 (m = 0, n = 1)
S2 (m = 0, n = 2)
S3 (m = 0, n = 3)
S4 (m = 1, n = 0)
S5 (m = 1, n = 1)
S6 (m = 1, n = 2)
S7 (m = 2, n = 0)
S8 (m = 2, n = 1)
S9 (m = 3, n = 0)
T1 (m = 0, n = 1)
T2 (m = 0, n = 2)
T3 (m = 0, n = 3)
T4 (m = 1, n = 0)
T5 (m = 1, n = 1)
T6 (m = 1, n = 2)
T7 (m = 2, n = 0)
T8 (m = 2, n = 1)
T9 (m = 3, n = 0)
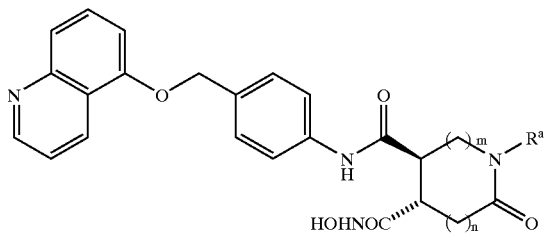
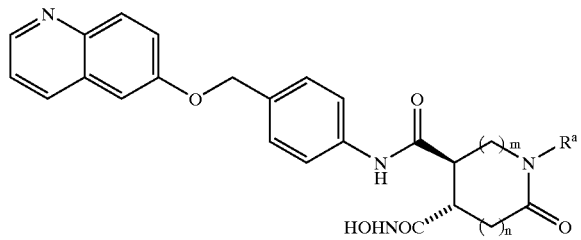
U1 (m = 0, n = 1)
U2 (m = 0, n = 2)
U3 (m = 0, n = 3)
U4 (m = 1, n = 0)
U5 (m = 1, n = 1)
U6 (m = 1, n = 2)
U7 (m = 2, n = 0)
U8 (m = 2, n = 1)
U9 (m = 3, n = 0)
V1 (m = 0, n = 1)
V2 (m = 0, n = 2)
V3 (m = 0, n = 3)
V4 (m = 1, n = 0)
V5 (m = 1, n = 1)
V6 (m = 1, n = 2)
V7 (m = 2, n = 0)
V8 (m = 2, n = 1)
V9 (m = 3, n = 0)

TABLE 4-continued

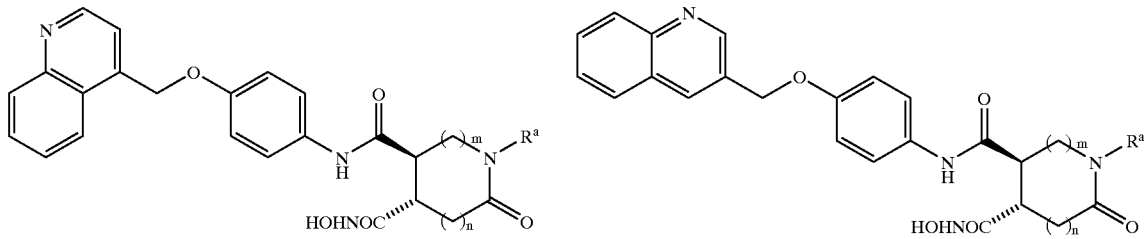

W1 (m = 0, n = 1)
W2 (m = 0, n = 2)
W3 (m = 0, n = 3)
W4 (m = 1, n = 0)
W5 (m = 1, n = 1)
W6 (m = 1, n = 2)
W7 (m = 2, n = 0)
W8 (m = 2, n = 1)
W9 (m = 3, n = 0)

X1 (m = 0, n = 1)
X2 (m = 0, n = 2)
X3 (m = 0, n = 3)
X4 (m = 1, n = 0)
X5 (m = 1, n = 1)
X6 (m = 1, n = 2)
X7 (m = 2, n = 0)
X8 (m = 2, n = 1)
X9 (m = 3, n = 0)

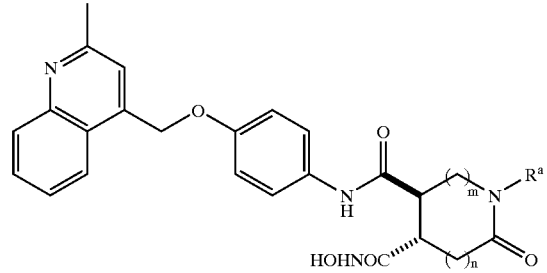

Y1 (m = 0, n = 2)
Y2 (m = 0, n = 3)
Y3 (m = 1, n = 2)
Y4 (m = 1, n = 1)
Y5 (m = 2, n = 0)
Y6 (m = 2, n = 1)
Y7 (m = 3, n = 0)

| Ex # | $R^a$ |
| --- | --- |
| 1 | methyl |
| 2 | ethyl |
| 3 | propyl |
| 4 | butyl |
| 5 | pentyl |
| 6 | hexyl |
| 7 | isopropyl |
| 8 | isobutyl |
| 9 | 3-methylbutyl |
| 10 | 4-methylpentyl |
| 11 | neopentyl |
| 12 | cyclopropanemethyl |
| 13 | cyclopentanemethyl |
| 14 | cyclohexanemethyl |
| 15 | t-butylethyl |
| 16 | cyclopropaneethyl |
| 17 | benzyl |
| 18 | 2-methylbenzyl |
| 19 | 3-methylbenzyl |
| 20 | 4-methylbenzyl |
| 21 | 2-fluorobenzyl |
| 22 | 3-fluorobenzyl |
| 23 | 4-fluorobenzyl |
| 24 | 2-chlorobenzyl |
| 25 | 3-chlorobenzyl |
| 26 | 4-chlorobenzyl |
| 27 | 2-picolyl |
| 28 | 3-picolyl |
| 29 | 4-picolyl |
| 30 | 2-thiazolemethyl |

TABLE 4-continued

| | |
|---|---|
| 31 | 2-thiophenemethyl |
| 32 | 2-furyl |
| 33 | phenethyl |

TABLE 5

A1 (m = 0, n = 2)
A2 (m = 0, n = 3)
A3 (m = 1, n = 2)
A4 (m = 1, n = 1)
A5 (m = 2, n = 0)
A6 (m = 2, n = 1)
A7 (m = 3, n = 0)

B1 (m = 0, n = 2)
B2 (m = 0, n = 3)
B3 (m = 1, n = 2)
B4 (m = 1, n = 1)
B5 (m = 2, n = 0)
B6 (m = 2, n = 1)
B7 (m = 3, n = 0)

C1 (m = 0, n = 2)
C2 (m = 0, n = 3)
C3 (m = 1, n = 2)
C4 (m = 1, n = 1)
C5 (m = 2, n = 0)
C6 (m = 2, n = 1)
C7 (m = 3, n = 0)

D1 (m = 0, n = 2)
D2 (m = 0, n = 3)
D3 (m = 1, n = 2)
D4 (m = 1, n = 1)
D5 (m = 2, n = 0)
D6 (m = 2, n = 1)
D7 (m = 3, n = 0)

E1 (m = 0, n = 2)
E2 (m = 0, n = 3)
E3 (m = 1, n = 2)
E4 (m = 1, n = 1)
E5 (m = 2, n = 0)
E6 (m = 2, n = 1)
E7 (m = 3, n = 0)

F1 (m = 0, n = 2)
F2 (m = 0, n = 3)
F3 (m = 1, n = 2)
F4 (m = 1, n = 1)
F5 (m = 2, n = 0)
F6 (m = 2, n = 1)
F7 (m = 3, n = 0)

G1 (m = 0, n = 2)
G2 (m = 0, n = 3)
G3 (m = 1, n = 2)
G4 (m = 1, n = 1)
G5 (m = 2, n = 0)
G6 (m = 2, n = 1)
G7 (m = 3, n = 0)

H1 (m = 0, n = 2)
H2 (m = 0, n = 3)
H3 (m = 1, n = 2)
H4 (m = 1, n = 1)
H5 (m = 2, n = 0)
H6 (m = 2, n = 1)
H7 (m = 3, n = 0)

TABLE 5-continued
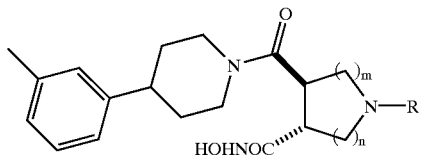
I1 (m = 0, n = 2)
I2 (m = 0, n = 3)
I3 (m = 1, n = 2)
I4 (m = 1, n = 1)
I5 (m = 2, n = 0)
I6 (m = 2, n = 1)
I7 (m = 3, n = 0)
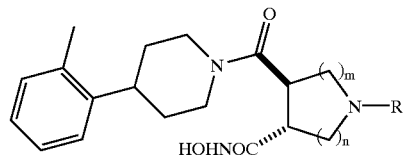
J1 (m = 0, n = 2)
J2 (m = 0, n = 3)
J3 (m = 1, n = 2)
J4 (m = 1, n = 1)
J5 (m = 2, n = 0)
J6 (m = 2, n = 1)
J7 (m = 3, n = 0)
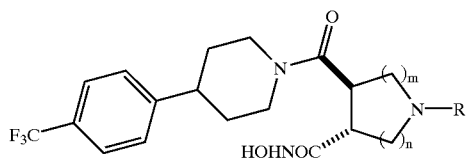
K1 (m = 0, n = 2)
K2 (m = 0, n = 3)
K3 (m = 1, n = 2)
K4 (m = 1, n = 1)
K5 (m = 2, n = 0)
K6 (m = 2, n = 1)
K7 (m = 3, n = 0)
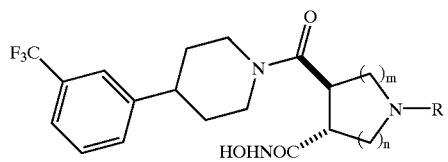
L1 (m = 0, n = 2)
L2 (m = 0, n = 3)
L3 (m = 1, n = 2)
L4 (m = 1, n = 1)
L5 (m = 2, n = 0)
L6 (m = 2, n = 1)
L7 (m = 3, n = 0)
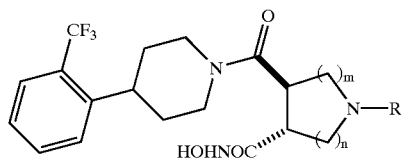
M1 (m = 0, n = 2)
M2 (m = 0, n = 3)
M3 (m = 1, n = 2)
M4 (m = 1, n = 1)
M5 (m = 2, n = 0)
M6 (m = 2, n = 1)
M7 (m = 3, n = 0)
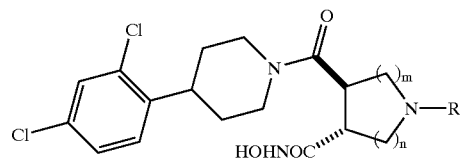
N1 (m = 0, n = 2)
N2 (m = 0, n = 3)
N3 (m = 1, n = 2)
N4 (m = 1, n = 1)
N5 (m = 2, n = 0)
N6 (m = 2, n = 1)
N7 (m = 3, n = 0)
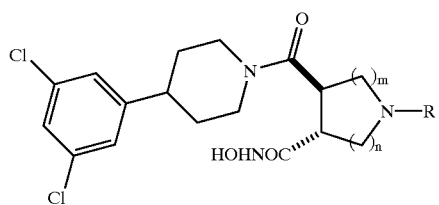
O1 (m = 0, n = 2)
O2 (m = 0, n = 3)
O3 (m = 1, n = 2)
O4 (m = 1, n = 1)
O5 (m = 2, n = 0)
O6 (m = 2, n = 1)
O7 (m = 3, n = 0)
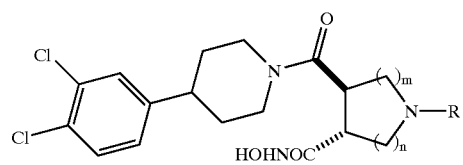
P1 (m = 0, n = 2)
P2 (m = 0, n = 3)
P3 (m = 1, n = 2)
P4 (m = 1, n = 1)
P5 (m = 2, n = 0)
P6 (m = 2, n = 1)
P7 (m = 3, n = 0)
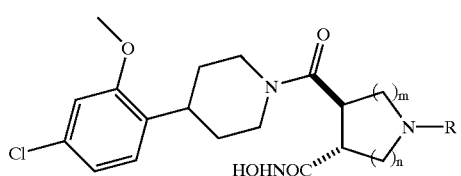

TABLE 5-continued

Q1 (m = 0, n = 2)
Q2 (m = 0, n = 3)
Q3 (m = 1, n = 2)
Q4 (m = 1, n = 1)
Q5 (m = 2, n = 0)
Q6 (m = 2, n = 1)
Q7 (m = 3, n = 0)

R1 (m = 0, n = 2)
R2 (m = 0, n = 3)
R3 (m = 1, n = 2)
R4 (m = 1, n = 1)
R5 (m = 2, n = 0)
R6 (m = 2, n = 1)
R7 (m = 3, n = 0)

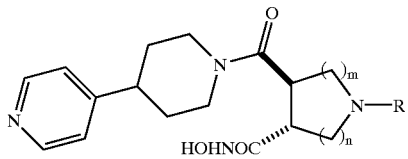

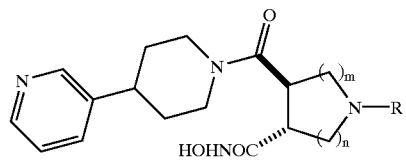

S1 (m = 0, n = 2)
S2 (m = 0, n = 3)
S3 (m = 1, n = 2)
S4 (m = 1, n = 1)
S5 (m = 2, n = 0)
S6 (m = 2, n = 1)
S7 (m = 3, n = 0)

T1 (m = 0, n = 2)
T2 (m = 0, n = 3)
T3 (m = 1, n = 2)
T4 (m = 1, n = 1)
T5 (m = 2, n = 0)
T6 (m = 2, n = 1)
T7 (m = 3, n = 0)

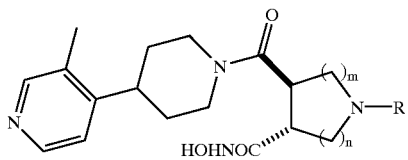

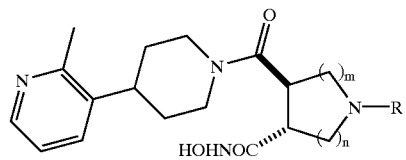

U1 (m = 0, n = 2)
U2 (m = 0, n = 3)
U3 (m = 1, n = 2)
U4 (m = 1, n = 1)
U5 (m = 2, n = 0)
U6 (m = 2, n = 1)
U7 (m = 3, n = 0)

V1 (m = 0, n = 2)
V2 (m = 0, n = 3)
V3 (m = 1, n = 2)
V4 (m = 1, n = 1)
V5 (m = 2, n = 0)
V6 (m = 2, n = 1)
V7 (m = 3, n = 0)

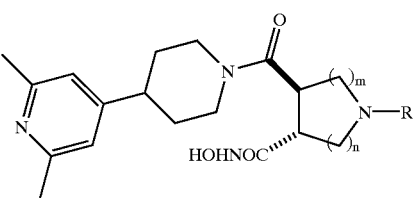

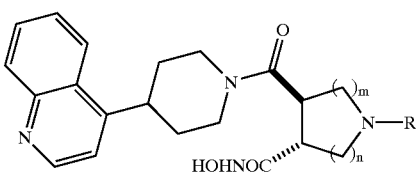

W1 (m = 0, n = 2)
W2 (m = 0, n = 3)
W3 (m = 1, n = 2)
W4 (m = 1, n = 1)
W5 (m = 2, n = 0)
W6 (m = 2, n = 1)
W7 (m = 3, n = 0)

X1 (m = 0, n = 2)
X2 (m = 0, n = 3)
X3 (m = 1, n = 2)
X4 (m = 1, n = 1)
X5 (m = 2, n = 0)
X6 (m = 2, n = 1)
X7 (m = 3, n = 0)

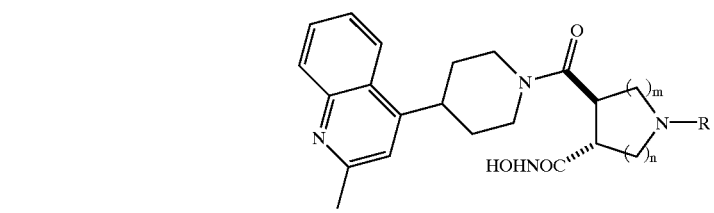

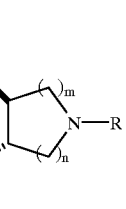

Y1 (m = 0, n = 2)
Y2 (m = 0, n = 3)
Y3 (m = 1, n = 2)
Y4 (m = 1, n = 1)
Y5 (m = 2, n = 0)
Y6 (m = 2, n = 1)
Y7 (m = 3, n = 0)

TABLE 5-continued

| Ex # | R$^a$ |
|---|---|
| 1 | methyl |
| 2 | ethyl |
| 3 | propyl |
| 4 | butyl |
| 5 | pentyl |
| 6 | hexyl |
| 7 | isopropyl |
| 8 | isobutyl |
| 9 | 3-methylbutyl |
| 10 | 4-methylpentyl |
| 11 | neopentyl |
| 12 | cyclopropanemethyl |
| 13 | cyclopentanemethyl |
| 14 | cyclohexanemethyl |
| 15 | t-butylethyl |
| 16 | cyclopropaneethyl |
| 17 | benzyl |
| 18 | 2-methylbenzyl |
| 19 | 3-methylbenzyl |
| 20 | 4-methylbenzyl |
| 21 | 2-fluorobenzyl |
| 22 | 3-fluorobenzyl |
| 23 | 4-fluorobenzyl |
| 24 | 2-chlorobenzyl |
| 25 | 3-chlorobenzyl |
| 26 | 4-chlorobenzyl |
| 27 | 2-picolyl |
| 28 | 3-picolyl |
| 29 | 4-picolyl |
| 30 | 2-thiazolemethyl |
| 31 | 2-thiophenemethyl |
| 32 | 2-furfuryl |
| 33 | phenethyl |

TABLE 6

A1 (m = 0, n = 1)
A2 (m = 0, n = 2)
A3 (m = 0, n = 3)
A4 (m = 1, n = 0)
A5 (m = 1, n = 1)
A6 (m = 1, n = 2)
A7 (m = 2, n = 0)
A8 (m = 2, n = 1)
A9 (m = 3, n = 0)

B1 (m = 0, n = 1)
B2 (m = 0, n = 2)
B3 (m = 0, n = 3)
B4 (m = 1, n = 0)
B5 (m = 1, n = 1)
B6 (m = 1, n = 2)
B7 (m = 2, n = 0)
B8 (m = 2, n = 1)
B9 (m = 3, n = 0)

C1 (m = 0, n = 1)
C2 (m = 0, n = 2)
C3 (m = 0, n = 3)
C4 (m = 1, n = 0)
C5 (m = 1, n = 1)
C6 (m = 1, n = 2)
C7 (m = 2, n = 0)
C8 (m = 2, n = 1)
C9 (m = 3, n = 0)

D1 (m = 0, n = 1)
D2 (m = 0, n = 2)
D3 (m = 0, n = 3)
D4 (m = 1, n = 0)
D5 (m = 1, n = 1)
D6 (m = 1, n = 2)
D7 (m = 2, n = 0)
D8 (m = 2, n = 1)
D9 (m = 3, n = 0)

TABLE 6-continued

E1 (m = 0, n = 1)
E2 (m = 0, n = 2)
E3 (m = 0, n = 3)
E4 (m = 1, n = 0)
E5 (m = 1, n = 1)
E6 (m = 1, n = 2)
E7 (m = 2, n = 0)
E8 (m = 2, n = 1)
E9 (m = 3, n = 0)

F1 (m = 0, n = 1)
F2 (m = 0, n = 2)
F3 (m = 0, n = 3)
F4 (m = 1, n = 0)
F5 (m = 1, n = 1)
F6 (m = 1, n = 2)
F7 (m = 2, n = 0)
F8 (m = 2, n = 1)
F9 (m = 3, n = 0)

G1 (m = 0, n = 1)
G2 (m = 0, n = 2)
G3 (m = 0, n = 3)
G4 (m = 1, n = 0)
G5 (m = 1, n = 1)
G6 (m = 1, n = 2)
G7 (m = 2, n = 0)
G8 (m = 2, n = 1)
G9 (m = 3, n = 0)

H1 (m = 0, n = 1)
H2 (m = 0, n = 2)
H3 (m = 0, n = 3)
H4 (m = 1, n = 0)
H5 (m = 1, n = 1)
H6 (m = 1, n = 2)
H7 (m = 2, n = 0)
H8 (m = 2, n = 1)
H9 (m = 3, n = 0)

I1 (m = 0, n = 1)
I2 (m = 0, n = 2)
I3 (m = 0, n = 3)
I4 (m = 1, n = 0)
I5 (m = 1, n = 1)
I6 (m = 1, n = 2)
I7 (m = 2, n = 0)
I8 (m = 2, n = 1)
I9 (m = 3, n = 0)

J1 (m = 0, n = 1)
J2 (m = 0, n = 2)
J3 (m = 0, n = 3)
J4 (m = 1, n = 0)
J5 (m = 1, n = 1)
J6 (m = 1, n = 2)
J7 (m = 2, n = 0)
J8 (m = 2, n = 1)
J9 (m = 3, n = 0)

K1 (m = 0, n = 1)
K2 (m = 0, n = 2)
K3 (m = 0, n = 3)
K4 (m = 1, n = 0)
K5 (m = 1, n = 1)
K6 (m = 1, n = 2)
K7 (m = 2, n = 0)
K8 (m = 2, n = 1)
K9 (m = 3, n = 0)

L1 (m = 0, n = 1)
L2 (m = 0, n = 2)
L3 (m = 0, n = 3)
L4 (m = 1, n = 0)
L5 (m = 1, n = 1)
L6 (m = 1, n = 2)
L7 (m = 2, n = 0)
L8 (m = 2, n = 1)
L9 (m = 3, n = 0)

TABLE 6-continued

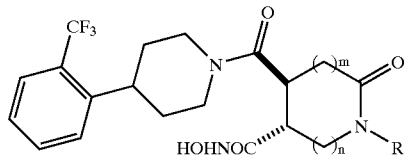

M1 (m = 0, n = 1)
M2 (m = 0, n = 2)
M3 (m = 0, n = 3)
M4 (m = 1, n = 0)
M5 (m = 1, n = 1)
M6 (m = 1, n = 2)
M7 (m = 2, n = 0)
M8 (m = 2, n = 1)
M9 (m = 3, n = 0)

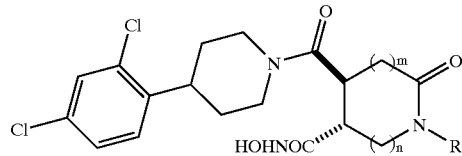

N1 (m = 0, n = 1)
N2 (m = 0, n = 2)
N3 (m = 0, n = 3)
N4 (m = 1, n = 0)
N5 (m = 1, n = 1)
N6 (m = 1, n = 2)
N7 (m = 2, n = 0)
N8 (m = 2, n = 1)
N9 (m = 3, n = 0)

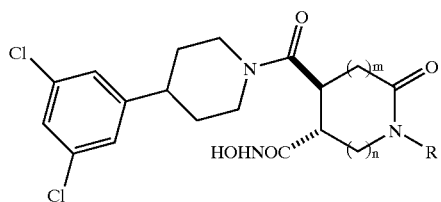

O1 (m = 0, n = 1)
O2 (m = 0, n = 2)
O3 (m = 0, n = 3)
O4 (m = 1, n = 0)
O5 (m = 1, n = 1)
O6 (m = 1, n = 2)
O7 (m = 2, n = 0)
O8 (m = 2, n = 1)
O9 (m = 3, n = 0)

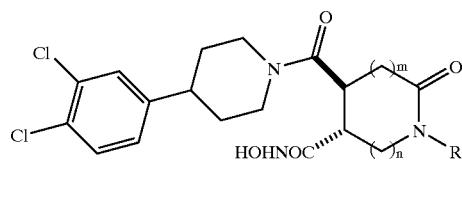

P1 (m = 0, n = 1)
P2 (m = 0, n = 2)
P3 (m = 0, n = 3)
P4 (m = 1, n = 0)
P5 (m = 1, n = 1)
P6 (m = 1, n = 2)
P7 (m = 2, n = 0)
P8 (m = 2, n = 1)
P9 (m = 3, n = 0)

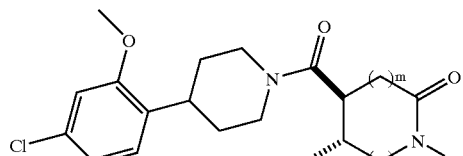

Q1 (m = 0, n = 1)
Q2 (m = 0, n = 2)
Q3 (m = 0, n = 3)
Q4 (m = 1, n = 0)
Q5 (m = 1, n = 1)
Q6 (m = 1, n = 2)
Q7 (m = 2, n = 0)
Q8 (m = 2, n = 1)
Q9 (m = 3, n = 0)

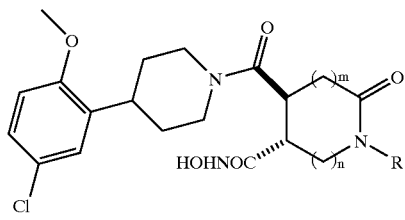

R1 (m = 0, n = 1)
R2 (m = 0, n = 2)
R3 (m = 0, n = 3)
R4 (m = 1, n = 0)
R5 (m = 1, n = 1)
R6 (m = 1, n = 2)
R7 (m = 2, n = 0)
R8 (m = 2, n = 1)
R9 (m = 3, n = 0)

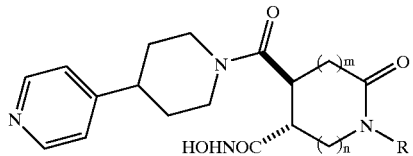

S1 (m = 0, n = 1)
S2 (m = 0, n = 2)
S3 (m = 0, n = 3)
S4 (m = 1, n = 0)
S5 (m = 1, n = 1)
S6 (m = 1, n = 2)
S7 (m = 2, n = 0)
S8 (m = 2, n = 1)
S9 (m = 3, n = 0)

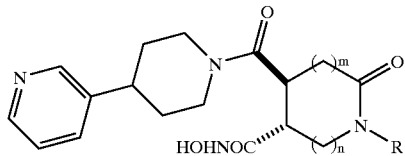

T1 (m = 0, n = 1)
T2 (m = 0, n = 2)
T3 (m = 0, n = 3)
T4 (m = 1, n = 0)
T5 (m = 1, n = 1)
T6 (m = 1, n = 2)
T7 (m = 2, n = 0)
T8 (m = 2, n = 1)
T9 (m = 3, n = 0)

TABLE 6-continued

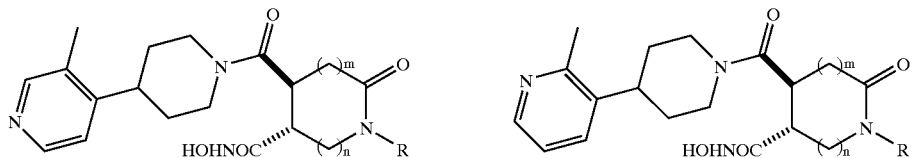

U1 (m = 0, n = 1)
U2 (m = 0, n = 2)
U3 (m = 0, n = 3)
U4 (m = 1, n = 0)
U5 (m = 1, n = 1)
U6 (m = 1, n = 2)
U7 (m = 2, n = 0)
U8 (m = 2, n = 1)
U9 (m = 3, n = 0)

V1 (m = 0, n = 1)
V2 (m = 0, n = 2)
V3 (m = 0, n = 3)
V4 (m = 1, n = 0)
V5 (m = 1, n = 1)
V6 (m = 1, n = 2)
V7 (m = 2, n = 0)
V8 (m = 2, n = 1)
V9 (m = 3, n = 0)

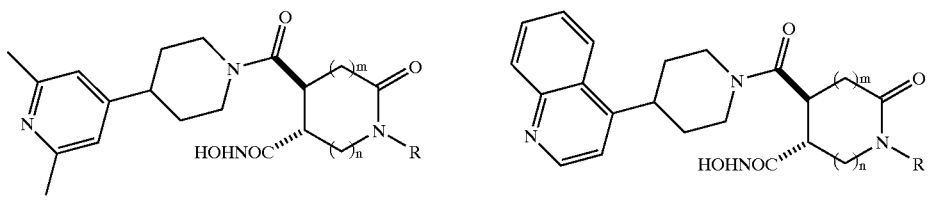

W1 (m = 0, n = 1)
W2 (m = 0, n = 2)
W3 (m = 0, n = 3)
W4 (m = 1, n = 0)
W5 (m = 1, n = 1)
W6 (m = 1, n = 2)
W7 (m = 2, n = 0)
W8 (m = 2, n = 1)
W9 (m = 3, n = 0)

X1 (m = 0, n = 1)
X2 (m = 0, n = 2)
X3 (m = 0, n = 3)
X4 (m = 1, n = 0)
X5 (m = 1, n = 1)
X6 (m = 1, n = 2)
X7 (m = 2, n = 0)
X8 (m = 2, n = 1)
X9 (m = 3, n = 0)

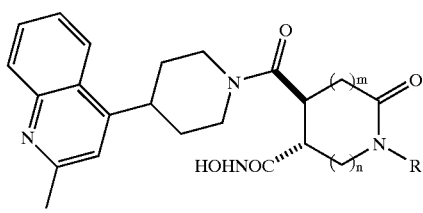

Y1 (m = 0, n = 2)
Y2 (m = 0, n = 3)
Y3 (m = 1, n = 2)
Y4 (m = 1, n = 1)
Y5 (m = 2, n = 0)
Y6 (m = 2, n = 1)
Y7 (m = 3, n = 0)

| Ex # | R$^a$ |
|---|---|
| 1 | methyl |
| 2 | ethyl |
| 3 | propyl |
| 4 | butyl |
| 5 | pentyl |
| 6 | hexyl |
| 7 | isopropyl |
| 8 | isobutyl |
| 9 | 3-methylbutyl |
| 10 | 4-methylpentyl |
| 11 | neopentyl |
| 12 | cyclopropanemethyl |
| 13 | cyclopentanemethyl |
| 14 | cyclohexanemethyl |
| 15 | t-butylethyl |
| 16 | cyclopropaneethyl |
| 17 | benzyl |
| 18 | 2-methylbenzyl |
| 19 | 3-methylbenzyl |

TABLE 6-continued

| | |
|---|---|
| 20 | 4-methylbenzyl |
| 21 | 2-fluorobenzyl |
| 22 | 3-fluorobenzyl |
| 23 | 4-fluorobenzyl |
| 24 | 2-chlorobenzyl |
| 25 | 3-chlorobenzyl |
| 26 | 4-chlorobenzyl |
| 27 | 2-picolyl |
| 28 | 3-picolyl |
| 29 | 4-picolyl |
| 30 | 2-thiazolemethyl |
| 31 | 2-thiophenemethyl |
| 32 | 2-furfuryl |
| 33 | phenethyl |

TABLE 7

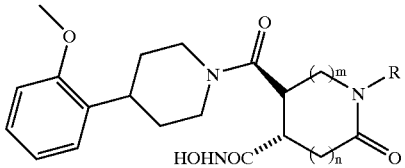

G1 (m = 0, n = 1)
G2 (m = 0, n = 2)
G3 (m = 0, n = 3)
G4 (m = 1, n = 0)
G5 (m = 1, n = 1)
G6 (m = 1, n = 2)
G7 (m = 2, n = 0)
G8 (m = 2, n = 1)
G9 (m = 3, n = 0)

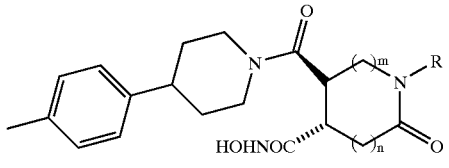

H1 (m = 0, n = 1)
H2 (m = 0, n = 2)
H3 (m = 0, n = 3)
H4 (m = 1, n = 0)
H5 (m = 1, n = 1)
H6 (m = 1, n = 2)
H7 (m = 2, n = 0)
H8 (m = 2, n = 1)
H9 (m = 3, n = 0)

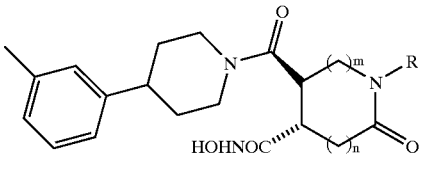

I1 (m = 0, n = 1)
I2 (m = 0, n = 2)
I3 (m = 0, n = 3)
I4 (m = 1, n = 0)
I5 (m = 1, n = 1)
I6 (m = 1, n = 2)
I7 (m = 2, n = 0)
I8 (m = 2, n = 1)
I9 (m = 3, n = 0)

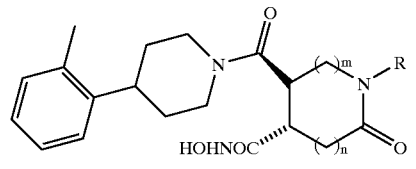

J1 (m = 0, n = 1)
J2 (m = 0, n = 2)
J3 (m = 0, n = 3)
J4 (m = 1, n = 0)
J5 (m = 1, n = 1)
J6 (m = 1, n = 2)
J7 (m = 2, n = 0)
J8 (m = 2, n = 1)
J9 (m = 3, n = 0)

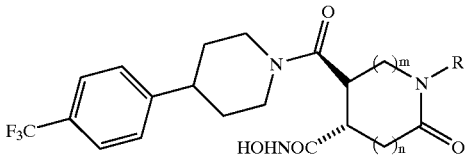

K1 (m = 0, n = 1)
K2 (m = 0, n = 2)
K3 (m = 0, n = 3)
K4 (m = 1, n = 0)
K5 (m = 1, n = 1)
K6 (m = 1, n = 2)
K7 (m = 2, n = 0)
K8 (m = 2, n = 1)
K9 (m = 3, n = 0)

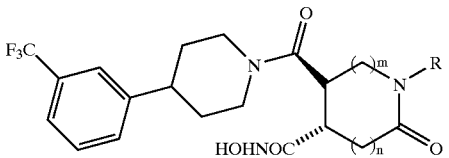

L1 (m = 0, n = 1)
L2 (m = 0, n = 2)
L3 (m = 0, n = 3)
L4 (m = 1, n = 0)
L5 (m = 1, n = 1)
L6 (m = 1, n = 2)
L7 (m = 2, n = 0)
L8 (m = 2, n = 1)
L9 (m = 3, n = 0)

TABLE 7-continued

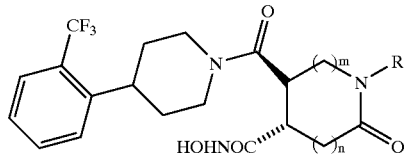 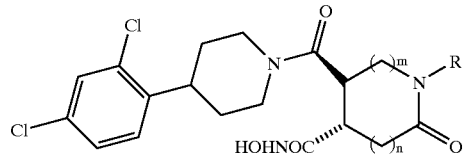

M1 (m = 0, n = 1)  N1 (m = 0, n = 1)
M2 (m = 0, n = 2)  N2 (m = 0, n = 2)
M3 (m = 0, n = 3)  N3 (m = 0, n = 3)
M4 (m = 1, n = 0)  N4 (m = 1, n = 0)
M5 (m = 1, n = 1)  N5 (m = 1, n = 1)
M6 (m = 1, n = 2)  N6 (m = 1, n = 2)
M7 (m = 2, n = 0)  N7 (m = 2, n = 0)
M8 (m = 2, n = 1)  N8 (m = 2, n = 1)
M9 (m = 3, n = 0)  N9 (m = 3, n = 0)

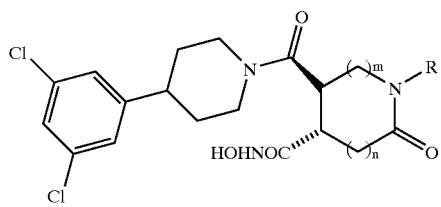 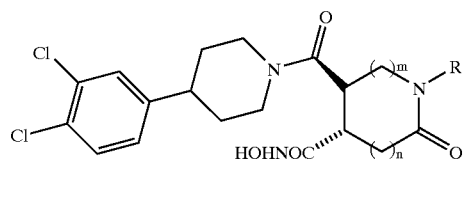

O1 (m = 0, n = 1)  P1 (m = 0, n = 1)
O2 (m = 0, n = 2)  P2 (m = 0, n = 2)
O3 (m = 0, n = 3)  P3 (m = 0, n = 3)
O4 (m = 1, n = 0)  P4 (m = 1, n = 0)
O5 (m = 1, n = 1)  P5 (m = 1, n = 1)
O6 (m = 1, n = 2)  P6 (m = 1, n = 2)
O7 (m = 2, n = 0)  P7 (m = 2, n = 0)
O8 (m = 2, n = 1)  P8 (m = 2, n = 1)
O9 (m = 3, n = 0)  P9 (m = 3, n = 0)

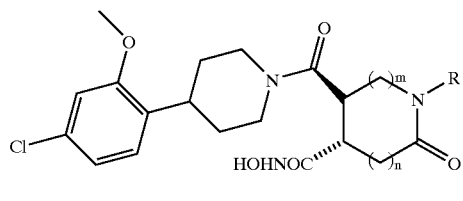 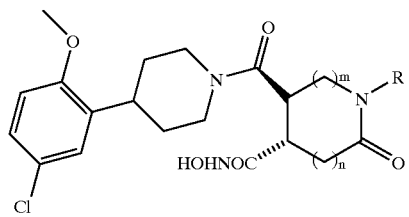

Q1 (m = 0, n = 1)  R1 (m = 0, n = 1)
Q2 (m = 0, n = 2)  R2 (m = 0, n = 2)
Q3 (m = 0, n = 3)  R3 (m = 0, n = 3)
Q4 (m = 1, n = 0)  R4 (m = 1, n = 0)
Q5 (m = 1, n = 1)  R5 (m = 1, n = 1)
Q6 (m = 1, n = 2)  R6 (m = 1, n = 2)
Q7 (m = 2, n = 0)  R7 (m = 2, n = 0)
Q8 (m = 2, n = 1)  R8 (m = 2, n = 1)
Q9 (m = 3, n = 0)  R9 (m = 3, n = 0)

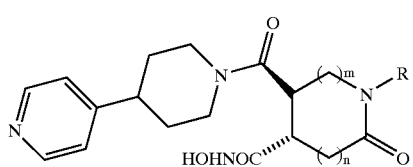 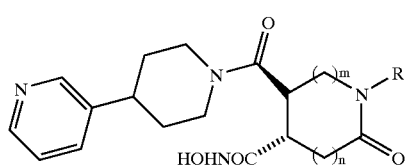

S1 (m = 0, n = 1)  T1 (m = 0, n = 1)
S2 (m = 0, n = 2)  T2 (m = 0, n = 2)
S3 (m = 0, n = 3)  T3 (m = 0, n = 3)
S4 (m = 1, n = 0)  T4 (m = 1, n = 0)
S5 (m = 1, n = 1)  T5 (m = 1, n = 1)
S6 (m = 1, n = 2)  T6 (m = 1, n = 2)
S7 (m = 2, n = 0)  T7 (m = 2, n = 0)
S8 (m = 2, n = 1)  T8 (m = 2, n = 1)
S9 (m = 3, n = 0)  T9 (m = 3, n = 0)

TABLE 7-continued

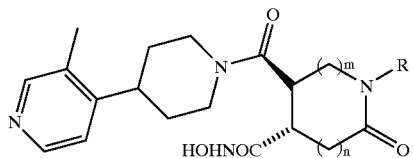

U1 (m = 0, n = 1)
U2 (m = 0, n = 2)
U3 (m = 0, n = 3)
U4 (m = 1, n = 0)
U5 (m = 1, n = 1)
U6 (m = 1, n = 2)
U7 (m = 2, n = 0)
U8 (m = 2, n = 1)
U9 (m = 3, n = 0)

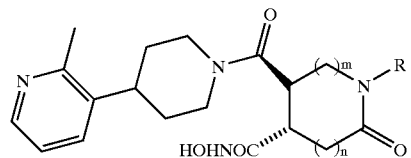

V1 (m = 0, n = 1)
V2 (m = 0, n = 2)
V3 (m = 0, n = 3)
V4 (m = 1, n = 0)
V5 (m = 1, n = 1)
V6 (m = 1, n = 2)
V7 (m = 2, n = 0)
V8 (m = 2, n = 1)
V9 (m = 3, n = 0)

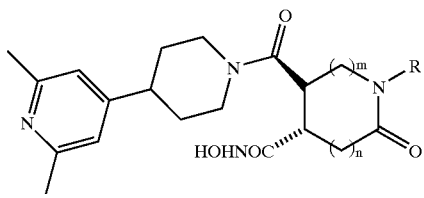

W1 (m = 0, n = 1)
W2 (m = 0, n = 2)
W3 (m = 0, n = 3)
W4 (m = 1, n = 0)
W5 (m = 1, n = 1)
W6 (m = 1, n = 2)
W7 (m = 2, n = 0)
W8 (m = 2, n = 1)
W9 (m = 3, n = 0)

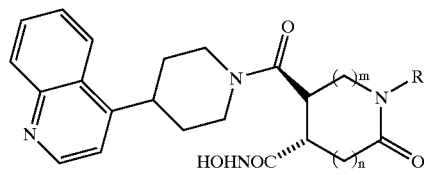

X1 (m = 0, n = 1)
X2 (m = 0, n = 2)
X3 (m = 0, n = 3)
X4 (m = 1, n = 0)
X5 (m = 1, n = 1)
X6 (m = 1, n = 2)
X7 (m = 2, n = 0)
X8 (m = 2, n = 1)
X9 (m = 3, n = 0)

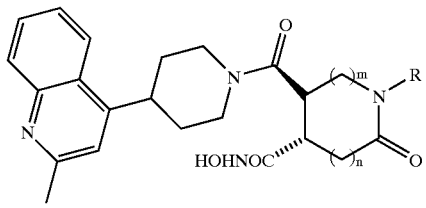

Y1 (m = 0, n = 2)
Y2 (m = 0, n = 3)
Y3 (m = 1, n = 2)
Y4 (m = 1, n = 1)
Y5 (m = 2, n = 0)
Y6 (m = 2, n = 1)
Y7 (m = 3, n = 0)

| Ex # | R[a] |
|---|---|
| 1 | methyl |
| 2 | ethyl |
| 3 | propyl |
| 4 | butyl |
| 5 | pentyl |
| 6 | hexyl |
| 7 | isopropyl |
| 8 | isobutyl |
| 9 | 3-methylbutyl |
| 10 | 4-methylpentyl |
| 11 | neopentyl |
| 12 | cyclopropanemethyl |
| 13 | cyclopentanemethyl |
| 14 | cyclohexanemethyl |
| 15 | t-butylethyl |
| 16 | cyclopropaneethyl |
| 17 | benzyl |
| 18 | 2-methylbenzyl |
| 19 | 3-methylbenzyl |

TABLE 7-continued

| | |
|---|---|
| 20 | 4-methylbenzyl |
| 21 | 2-fluorobenzyl |
| 22 | 3-fluorobenzyl |
| 23 | 4-fluorobenzyl |
| 24 | 2-chlorobenzyl |
| 25 | 3-chlorobenzyl |
| 26 | 4-chlorobenzyl |
| 27 | 2-picolyl |
| 28 | 3-picolyl |
| 29 | 4-picolyl |
| 30 | 2-thiazolemethyl |
| 31 | 2-thiophenemethyl |
| 32 | 2-furfuryl |
| 33 | phenethyl |

TABLE 8

A1 (m = 0, n = 2)
A2 (m = 0, n = 3)
A3 (m = 1, n = 2)
A4 (m = 1, n = 1)
A5 (m = 2, n = 0)
A6 (m = 2, n = 1)
A7 (m = 3, n = 0)

B1 (m = 0, n = 2)
B2 (m = 0, n = 3)
B3 (m = 1, n = 2)
B4 (m = 1, n = 1)
B5 (m = 2, n = 0)
B6 (m = 2, n = 1)
B7 (m = 3, n = 0)

C1 (m = 0, n = 2)
C2 (m = 0, n = 3)
C3 (m = 1, n = 2)
C4 (m = 1, n = 1)
C5 (m = 2, n = 0)
C6 (m = 2, n = 1)
C7 (m = 3, n = 0)

D1 (m = 0, n = 2)
D2 (m = 0, n = 3)
D3 (m = 1, n = 2)
D4 (m = 1, n = 1)
D5 (m = 2, n = 0)
D6 (m = 2, n = 1)
D7 (m = 3, n = 0)

E1 (m = 0, n = 2)
E2 (m = 0, n = 3)
E3 (m = 1, n = 2)
E4 (m = 1, n = 1)
E5 (m = 2, n = 0)
E6 (m = 2, n = 1)
E7 (m = 3, n = 0)

F1 (m = 0, n = 2)
F2 (m = 0, n = 3)
F3 (m = 1, n = 2)
F4 (m = 1, n = 1)
F5 (m = 2, n = 0)
F6 (m = 2, n = 1)
F7 (m = 3, n = 0)

TABLE 8-continued
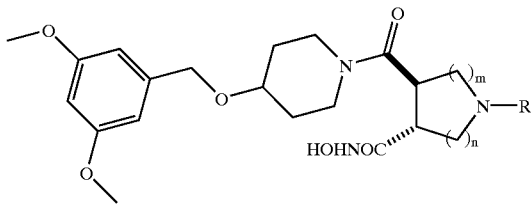
G1 (m = 0, n = 2)
G2 (m = 0, n = 3)
G3 (m = 1, n = 2)
G4 (m = 1, n = 1)
G5 (m = 2, n = 0)
G6 (m = 2, n = 1)
G7 (m = 3, n = 0)
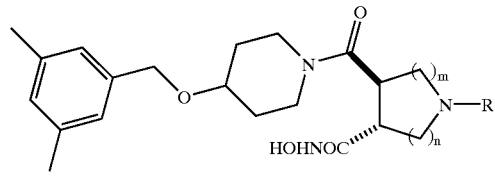
H1 (m = 0, n = 2)
H2 (m = 0, n = 3)
H3 (m = 1, n = 2)
H4 (m = 1, n = 1)
H5 (m = 2, n = 0)
H6 (m = 2, n = 1)
H7 (m = 3, n = 0)
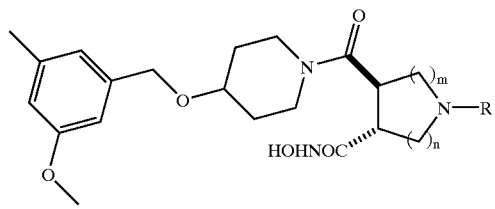
I1 (m = 0, n = 2)
I2 (m = 0, n = 3)
I3 (m = 1, n = 2)
I4 (m = 1, n = 1)
I5 (m = 2, n = 0)
I6 (m = 2, n = 1)
I7 (m = 3, n = 0)
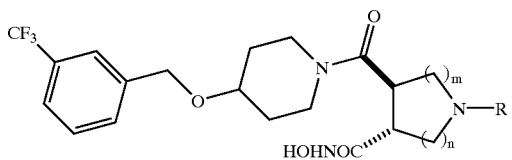
J1 (m = 0, n = 2)
J2 (m = 0, n = 3)
J3 (m = 1, n = 2)
J4 (m = 1, n = 1)
J5 (m = 2, n = 0)
J6 (m = 2, n = 1)
J7 (m = 3, n = 0)
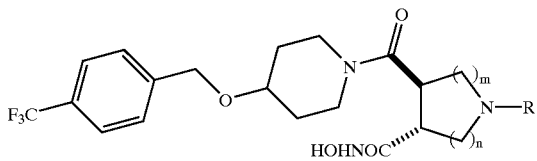
K1 (m = 0, n = 2)
K2 (m = 0, n = 3)
K3 (m = 1, n = 2)
K4 (m = 1, n = 1)
K5 (m = 2, n = 0)
K6 (m = 2, n = 1)
K7 (m = 3, n = 0)
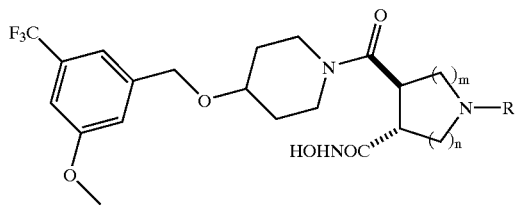
L1 (m = 0, n = 2)
L2 (m = 0, n = 3)
L3 (m = 1, n = 2)
L4 (m = 1, n = 1)
L5 (m = 2, n = 0)
L6 (m = 2, n = 1)
L7 (m = 3, n = 0)
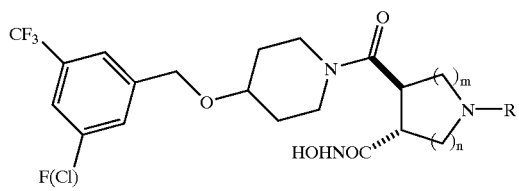
M1 (m = 0, n = 2)
M2 (m = 0, n = 3)
M3 (m = 1, n = 2)
M4 (m = 1, n = 1)
M5 (m = 2, n = 0)
M6 (m = 2, n = 1)
M7 (m = 3, n = 0)
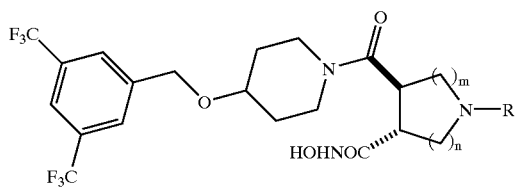
N1 (m = 0, n = 2)
N2 (m = 0, n = 3)
N3 (m = 1, n = 2)
N4 (m = 1, n = 1)
N5 (m = 2, n = 0)
N6 (m = 2, n = 1)
N7 (m = 3, n = 0)

TABLE 8-continued

[Structures for O and P series: O has 2,6-dimethylpyridin-4-ylmethoxy group; P has 2,6-dichloropyridin-4-ylmethoxy group, both attached to piperidine-carbonyl-pyrrolidine with HOHNOC and N-R substituents]

O1 (m = 0, n = 2)
O2 (m = 0, n = 3)
O3 (m = 1, n = 2)
O4 (m = 1, n = 1)
O5 (m = 2, n = 0)
O6 (m = 2, n = 1)
O7 (m = 3, n = 0)

P1 (m = 0, n = 2)
P2 (m = 0, n = 3)
P3 (m = 1, n = 2)
P4 (m = 1, n = 1)
P5 (m = 2, n = 0)
P6 (m = 2, n = 1)
P7 (m = 3, n = 0)

[Structures for Q and R series: Q has quinolin-4-ylmethoxy; R has 2-methylquinolin-4-ylmethoxy]

Q1 (m = 0, n = 2)
Q2 (m = 0, n = 3)
Q3 (m = 1, n = 2)
Q4 (m = 1, n = 1)
Q5 (m = 2, n = 0)
Q6 (m = 2, n = 1)
Q7 (m = 3, n = 0)

R1 (m = 0, n = 2)
R2 (m = 0, n = 3)
R3 (m = 1, n = 2)
R4 (m = 1, n = 1)
R5 (m = 2, n = 0)
R6 (m = 2, n = 1)
R7 (m = 3, n = 0)

[Structures for S and T series: S has 2-aminoquinolin-4-ylmethoxy; T has 2-trifluoromethylquinolin-4-ylmethoxy]

S1 (m = 0, n = 2)
S2 (m = 0, n = 3)
S3 (m = 1, n = 2)
S4 (m = 1, n = 1)
S5 (m = 2, n = 0)
S6 (m = 2, n = 1)
S7 (m = 3, n = 0)

T1 (m = 0, n = 2)
T2 (m = 0, n = 3)
T3 (m = 1, n = 2)
T4 (m = 1, n = 1)
T5 (m = 2, n = 0)
T6 (m = 2, n = 1)
T7 (m = 3, n = 0)

| Ex # | R[a] |
|---|---|
| 1 | methyl |
| 2 | ethyl |
| 3 | propyl |
| 4 | butyl |
| 5 | pentyl |
| 6 | hexyl |
| 7 | isopropyl |
| 8 | isobutyl |
| 9 | 3-methylbutyl |
| 10 | 4-methylpentyl |
| 11 | neopentyl |
| 12 | cyclopropanemethyl |
| 13 | cyclopentanemethyl |
| 14 | cyclohexanemethyl |
| 15 | t-butylethyl |
| 16 | cyclopropaneethyl |
| 17 | benzyl |
| 18 | 2-methylbenzyl |
| 19 | 3-methylbenzyl |
| 20 | 4-methylbenzyl |
| 21 | 2-fluorobenzyl |

TABLE 8-continued

| | |
|---|---|
| 22 | 3-fluorobenzyl |
| 23 | 4-fluorobenzyl |
| 24 | 2-chlorobenzyl |
| 25 | 3-chlorobenzyl |
| 26 | 4-chlorobenzyl |
| 27 | 2-picolyl |
| 28 | 3-picolyl |
| 29 | 4-picolyl |
| 30 | 2-thiazolemethyl |
| 31 | 2-thiophenemethyl |
| 32 | 2-furfuryl |
| 33 | phenethyl |

TABLE 9

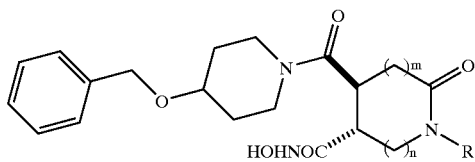

A1 (m = 0, n = 1)
A2 (m = 0, n = 2)
A3 (m = 0, n = 3)
A4 (m = 1, n = 0)
A5 (m = 1, n = 1)
A6 (m = 1, n = 2)
A7 (m = 2, n = 0)
A8 (m = 2, n = 1)
A9 (m = 3, n = 0)

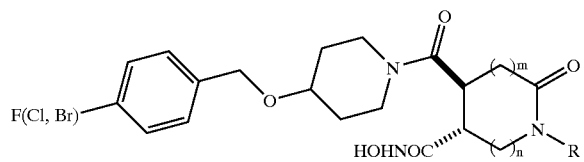

B1 (m = 0, n = 1)
B2 (m = 0, n = 2)
B3 (m = 0, n = 3)
B4 (m = 1, n = 0)
B5 (m = 1, n = 1)
B6 (m = 1, n = 2)
B7 (m = 2, n = 0)
B8 (m = 2, n = 1)
B9 (m = 3, n = 0)

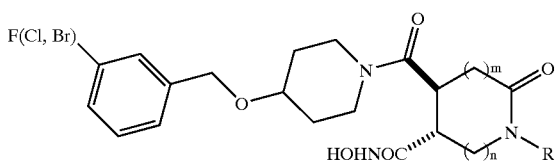

C1 (m = 0, n = 1)
C2 (m = 0, n = 2)
C3 (m = 0, n = 3)
C4 (m = 1, n = 0)
C5 (m = 1, n = 1)
C6 (m = 1, n = 2)
C7 (m = 2, n = 0)
C8 (m = 2, n = 1)
C9 (m = 3, n = 0)

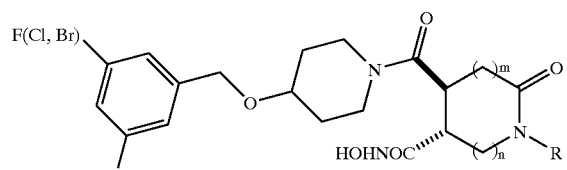

D1 (m = 0, n = 1)
D2 (m = 0, n = 2)
D3 (m = 0, n = 3)
D4 (m = 1, n = 0)
D5 (m = 1, n = 1)
D6 (m = 1, n = 2)
D7 (m = 2, n = 0)
D8 (m = 2, n = 1)
D9 (m = 3, n = 0)

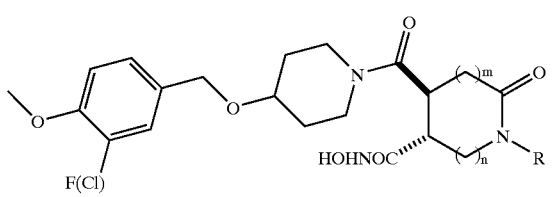

E1 (m = 0, n = 1)
E2 (m = 0, n = 2)
E3 (m = 0, n = 3)
E4 (m = 1, n = 0)
E5 (m = 1, n = 1)
E6 (m = 1, n = 2)
E7 (m = 2, n = 0)
E8 (m = 2, n = 1)
E9 (m = 3, n = 0)

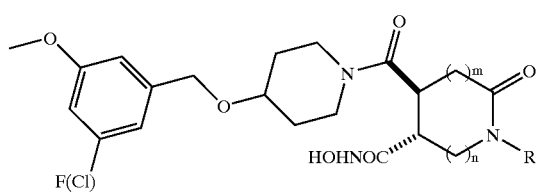

F1 (m = 0, n = 1)
F2 (m = 0, n = 2)
F3 (m = 0, n = 3)
F4 (m = 1, n = 0)
F5 (m = 1, n = 1)
F6 (m = 1, n = 2)
F7 (m = 2, n = 0)
F8 (m = 2, n = 1)
F9 (m = 3, n = 0)

TABLE 9-continued

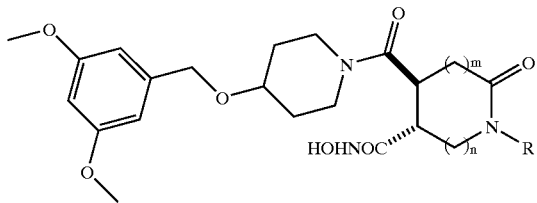

G1 (m = 0, n = 1)
G2 (m = 0, n = 2)
G3 (m = 0, n = 3)
G4 (m = 1, n = 0)
G5 (m = 1, n = 1)
G6 (m = 1, n = 2)
G7 (m = 2, n = 0)
G8 (m = 2, n = 1)
G9 (m = 3, n = 0)

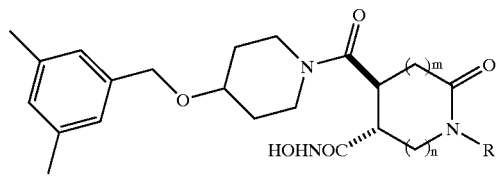

H1 (m = 0, n = 1)
H2 (m = 0, n = 2)
H3 (m = 0, n = 3)
H4 (m = 1, n = 0)
H5 (m = 1, n = 1)
H6 (m = 1, n = 2)
H7 (m = 2, n = 0)
H8 (m = 2, n = 1)
H9 (m = 3, n = 0)

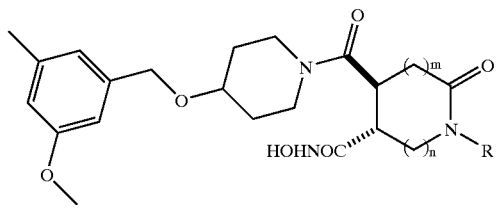

I1 (m = 0, n = 1)
I2 (m = 0, n = 2)
I3 (m = 0, n = 3)
I4 (m = 1, n = 0)
I5 (m = 1, n = 1)
I6 (m = 1, n = 2)
I7 (m = 2, n = 0)
I8 (m = 2, n = 1)
I9 (m = 3, n = 0)

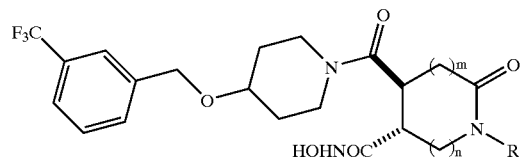

J1 (m = 0, n = 1)
J2 (m = 0, n = 2)
J3 (m = 0, n = 3)
J4 (m = 1, n = 0)
J5 (m = 1, n = 1)
J6 (m = 1, n = 2)
J7 (m = 2, n = 0)
J8 (m = 2, n = 1)
J9 (m = 3, n = 0)

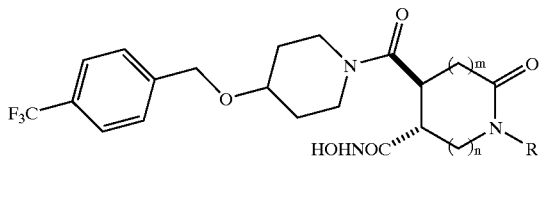

K1 (m = 0, n = 1)
K2 (m = 0, n = 2)
K3 (m = 0, n = 3)
K4 (m = 1, n = 0)
K5 (m = 1, n = 1)
K6 (m = 1, n = 2)
K7 (m = 2, n = 0)
K8 (m = 2, n = 1)
K9 (m = 3, n = 0)

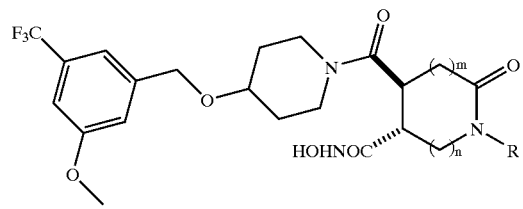

L1 (m = 0, n = 1)
L2 (m = 0, n = 2)
L3 (m = 0, n = 3)
L4 (m = 1, n = 0)
L5 (m = 1, n = 1)
L6 (m = 1, n = 2)
L7 (m = 2, n = 0)
L8 (m = 2, n = 1)
L9 (m = 3, n = 0)

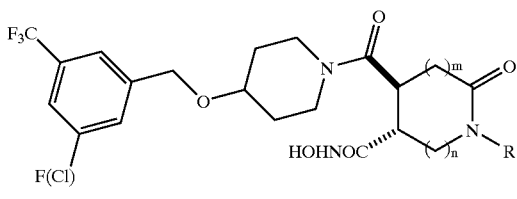

M1 (m = 0, n = 1)
M2 (m = 0, n = 2)
M3 (m = 0, n = 3)
M4 (m = 1, n = 0)
M5 (m = 1, n = 1)
M6 (m = 1, n = 2)
M7 (m = 2, n = 0)

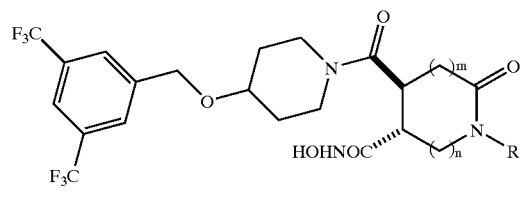

N1 (m = 0, n = 1)
N2 (m = 0, n = 2)
N3 (m = 0, n = 3)
N4 (m = 1, n = 0)
N5 (m = 1, n = 1)
N6 (m = 1, n = 2)
N7 (m = 2, n = 0)

TABLE 9-continued

M8 (m = 2, n = 1)
M9 (m = 3, n = 0)

N8 (m = 2, n = 1)
N9 (m = 3, n = 0)

O1 (m = 0, n = 1)
O2 (m = 0, n = 2)
O3 (m = 0, n = 3)
O4 (m = 1, n = 0)
O5 (m = 1, n = 1)
O6 (m = 1, n = 2)
O7 (m = 2, n = 0)
O8 (m = 2, n = 1)
O9 (m = 3, n = 0)

P1 (m = 0, n = 1)
P2 (m = 0, n = 2)
P3 (m = 0, n = 3)
P4 (m = 1, n = 0)
P5 (m = 1, n = 1)
P6 (m = 1, n = 2)
P7 (m = 2, n = 0)
P8 (m = 2, n = 1)
P9 (m = 3, n = 0)

Q1 (m = 0, n = 1)
Q2 (m = 0, n = 2)
Q3 (m = 0, n = 3)
Q4 (m = 1, n = 0)
Q5 (m = 1, n = 1)
Q6 (m = 1, n = 2)
Q7 (m = 2, n = 0)
Q8 (m = 2, n = 1)
Q9 (m = 3, n = 0)

R1 (m = 0, n = 1)
R2 (m = 0, n = 2)
R3 (m = 0, n = 3)
R4 (m = 1, n = 0)
R5 (m = 1, n = 1)
R6 (m = 1, n = 2)
R7 (m = 2, n = 0)
R8 (m = 2, n = 1)
R9 (m = 3, n = 0)

S1 (m = 0, n = 1)
S2 (m = 0, n = 2)
S3 (m = 0, n = 3)
S4 (m = 1, n = 0)
S5 (m = 1, n = 1)
S6 (m = 1, n = 2)
S7 (m = 2, n = 0)
S8 (m = 2, n = 1)
S9 (m = 3, n = 0)

T1 (m = 0, n = 1)
T2 (m = 0, n = 2)
T3 (m = 0, n = 3)
T4 (m = 1, n = 0)
T5 (m = 1, n = 1)
T6 (m = 1, n = 2)
T7 (m = 2, n = 0)
T8 (m = 2, n = 1)
T9 (m = 3, n = 0)

| Ex # | R[a] |
|---|---|
| 1 | methyl |
| 2 | ethyl |
| 3 | propyl |
| 4 | butyl |
| 5 | pentyl |
| 6 | hexyl |
| 7 | isopropyl |
| 8 | isobutyl |
| 9 | 3-methylbutyl |
| 10 | 4-methylpentyl |
| 11 | neopentyl |
| 12 | cyclopropanemethyl |

TABLE 9-continued

| | |
|---|---|
| 13 | cyclopentanemethyl |
| 14 | cyclohexanemethyl |
| 15 | t-butylethyl |
| 16 | cyclopropaneethyl |
| 17 | benzyl |
| 18 | 2-methylbenzyl |
| 19 | 3-methylbenzyl |
| 20 | 4-methylbenzyl |
| 21 | 2-fluorobenzyl |
| 22 | 3-fluorobenzyl |
| 23 | 4-fluorobenzyl |
| 24 | 2-chlorobenzyl |
| 25 | 3-chlorobenzyl |
| 26 | 4-chlorobenzyl |
| 27 | 2-picolyl |
| 28 | 3-picolyl |
| 29 | 4-picolyl |
| 30 | 2-thiazolemethyl |
| 31 | 2-thiophenemethyl |
| 32 | 2-furfuryl |
| 33 | phenethyl |

TABLE 10

A1 (m = 0, n = 1)
A2 (m = 0, n = 2)
A3 (m = 0, n = 3)
A4 (m = 1, n = 0)
A5 (m = 1, n = 1)
A6 (m = 1, n = 2)
A7 (m = 2, n = 0)
A8 (m = 2, n = 1)
A9 (m = 3, n = 0)

B1 (m = 0, n = 1)
B2 (m = 0, n = 2)
B3 (m = 0, n = 3)
B4 (m = 1, n = 0)
B5 (m = 1, n = 1)
B6 (m = 1, n = 2)
B7 (m = 2, n = 0)
B8 (m = 2, n = 1)
B9 (m = 3, n = 0)

C1 (m = 0, n = 1)
C2 (m = 0, n = 2)
C3 (m = 0, n = 3)
C4 (m = 1, n = 0)
C5 (m = 1, n = 1)
C6 (m = 1, n = 2)
C7 (m = 2, n = 0)
C8 (m = 2, n = 1)
C9 (m = 3, n = 0)

D1 (m = 0, n = 1)
D2 (m = 0, n = 2)
D3 (m = 0, n = 3)
D4 (m = 1, n = 0)
D5 (m = 1, n = 1)
D6 (m = 1, n = 2)
D7 (m = 2, n = 0)
D8 (m = 2, n = 1)
D9 (m = 3, n = 0)

E1 (m = 0, n = 1)
E2 (m = 0, n = 2)
E3 (m = 0, n = 3)
E4 (m = 1, n = 0)

F1 (m = 0, n = 1)
F2 (m = 0, n = 2)
F3 (m = 0, n = 3)
F4 (m = 1, n = 0)

TABLE 10-continued

| E5 (m = 1, n = 1) | F5 (m = 1, n = 1) |
| E6 (m = 1, n = 2) | F6 (m = 1, n = 2) |
| E7 (m = 2, n = 0) | F7 (m = 2, n = 0) |
| E8 (m = 2, n = 1) | F8 (m = 2, n = 1) |
| E9 (m = 3, n = 0) | F9 (m = 3, n = 0) |

| G1 (m = 0, n = 1) | H1 (m = 0, n = 1) |
| G2 (m = 0, n = 2) | H2 (m = 0, n = 2) |
| G3 (m = 0, n = 3) | H3 (m = 0, n = 3) |
| G4 (m = 1, n = 0) | H4 (m = 1, n = 0) |
| G5 (m = 1, n = 1) | H5 (m = 1, n = 1) |
| G6 (m = 1, n = 2) | H6 (m = 1, n = 2) |
| G7 (m = 2, n = 0) | H7 (m = 2, n = 0) |
| G8 (m = 2, n = 1) | H8 (m = 2, n = 1) |
| G9 (m = 3, n = 0) | H9 (m = 3, n = 0) |

| I1 (m = 0, n = 1) | J1 (m = 0, n = 1) |
| I2 (m = 0, n = 2) | J2 (m = 0, n = 2) |
| I3 (m = 0, n = 3) | J3 (m = 0, n = 3) |
| I4 (m = 1, n = 0) | J4 (m = 1, n = 0) |
| I5 (m = 1, n = 1) | J5 (m = 1, n = 1) |
| I6 (m = 1, n = 2) | J6 (m = 1, n = 2) |
| I7 (m = 2, n = 0) | J7 (m = 2, n = 0) |
| I8 (m = 2, n = 1) | J8 (m = 2, n = 1) |
| I9 (m = 3, n = 0) | J9 (m = 3, n = 0) |

| K1 (m = 0, n = 1) | L1 (m = 0, n = 1) |
| K2 (m = 0, n = 2) | L2 (m = 0, n = 2) |
| K3 (m = 0, n = 3) | L3 (m = 0, n = 3) |
| K4 (m = 1, n = 0) | L4 (m = 1, n = 0) |
| K5 (m = 1, n = 1) | L5 (m = 1, n = 1) |
| K6 (m = 1, n = 2) | L6 (m = 1, n = 2) |
| K7 (m = 2, n = 0) | L7 (m = 2, n = 0) |
| K8 (m = 2, n = 1) | L8 (m = 2, n = 1) |
| K9 (m = 3, n = 0) | L9 (m = 3, n = 0) |

| M1 (m = 0, n = 1) | N1 (m = 0, n = 1) |

TABLE 10-continued

M2 (m = 0, n = 2)  
M3 (m = 0, n = 3)  
M4 (m = 1, n = 0)  
M5 (m = 1, n = 1)  
M6 (m = 1, n = 2)  
M7 (m = 2, n = 0)  
M8 (m = 2, n = 1)  
M9 (m = 3, n = 0)

N2 (m = 0, n = 2)  
N3 (m = 0, n = 3)  
N4 (m = 1, n = 0)  
N5 (m = 1, n = 1)  
N6 (m = 1, n = 2)  
N7 (m = 2, n = 0)  
N8 (m = 2, n = 1)  
N9 (m = 3, n = 0)

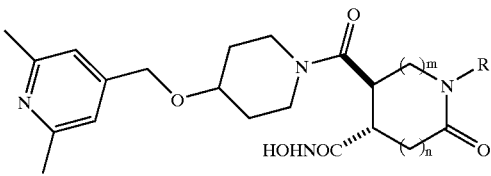

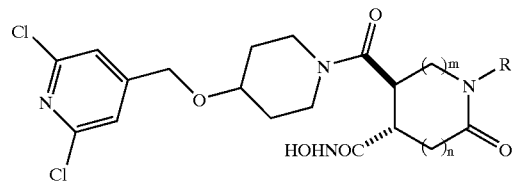

O1 (m = 0, n = 1)  
O2 (m = 0, n = 2)  
O3 (m = 0, n = 3)  
O4 (m = 1, n = 0)  
O5 (m = 1, n = 1)  
O6 (m = 1, n = 2)  
O7 (m = 2, n = 0)  
O8 (m = 2, n = 1)  
O9 (m = 3, n = 0)

P1 (m = 0, n = 1)  
P2 (m = 0, n = 2)  
P3 (m = 0, n = 3)  
P4 (m = 1, n = 0)  
P5 (m = 1, n = 1)  
P6 (m = 1, n = 2)  
P7 (m = 2, n = 0)  
P8 (m = 2, n = 1)  
P9 (m = 3, n = 0)

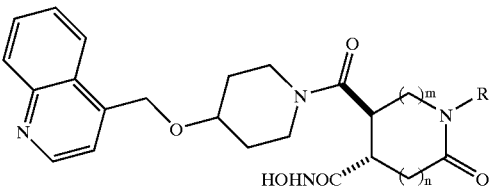

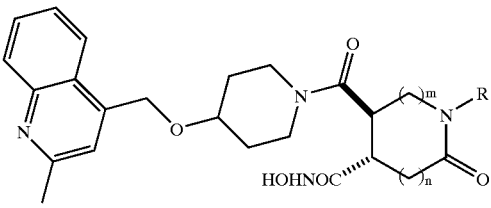

Q1 (m = 0, n = 1)  
Q2 (m = 0, n = 2)  
Q3 (m = 0, n = 3)  
Q4 (m = 1, n = 0)  
Q5 (m = 1, n = 1)  
Q6 (m = 1, n = 2)  
Q7 (m = 2, n = 0)  
Q8 (m = 2, n = 1)  
Q9 (m = 3, n = 0)

R1 (m = 0, n = 1)  
R2 (m = 0, n = 2)  
R3 (m = 0, n = 3)  
R4 (m = 1, n = 0)  
R5 (m = 1, n = 1)  
R6 (m = 1, n = 2)  
R7 (m = 2, n = 0)  
R8 (m = 2, n = 1)  
R9 (m = 3, n = 0)

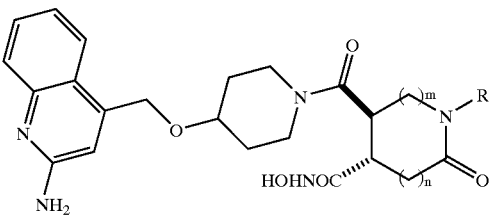

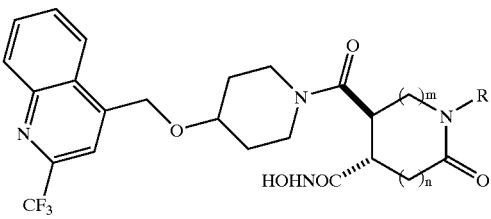

S1 (m = 0, n = 1)  
S2 (m = 0, n = 2)  
S3 (m = 0, n = 3)  
S4 (m = 1, n = 0)  
S5 (m = 1, n = 1)  
S6 (m = 1, n = 2)  
S7 (m = 2, n = 0)  
S8 (m = 2, n = 1)  
S9 (m = 3, n = 0)

T1 (m = 0, n = 1)  
T2 (m = 0, n = 2)  
T3 (m = 0, n = 3)  
T4 (m = 1, n = 0)  
T5 (m = 1, n = 1)  
T6 (m = 1, n = 2)  
T7 (m = 2, n = 0)  
T8 (m = 2, n = 1)  
T9 (m = 3, n = 0)

| Ex # | R[a] |
|---|---|
| 1 | methyl |
| 2 | ethyl |
| 3 | propyl |
| 4 | butyl |
| 5 | pentyl |
| 6 | hexyl |

TABLE 10-continued

| | |
|---|---|
| 7 | isopropyl |
| 8 | isobutyl |
| 9 | 3-methylbutyl |
| 10 | 4-methylpentyl |
| 11 | neopentyl |
| 12 | cyclopropanemethyl |
| 13 | cyclopentanemethyl |
| 14 | cyclohexanemethyl |
| 15 | t-butylethyl |
| 16 | cyclopropaneethyl |
| 17 | benzyl |
| 18 | 2-methylbenzyl |
| 19 | 3-methylbenzyl |
| 20 | 4-methylbenzyl |
| 21 | 2-fluorobenzyl |
| 22 | 3-fluorobenzyl |
| 23 | 4-fluorobenzyl |
| 24 | 2-chlorobenzyl |
| 25 | 3-chlorobenzyl |
| 26 | 4-chlorobenzyl |
| 27 | 2-picolyl |
| 28 | 3-picolyl |
| 29 | 4-picolyl |
| 30 | 2-thiazolemethyl |
| 31 | 2-thiophenemethyl |
| 32 | 2-furfuryl |
| 33 | phenethyl |

TABLE 11

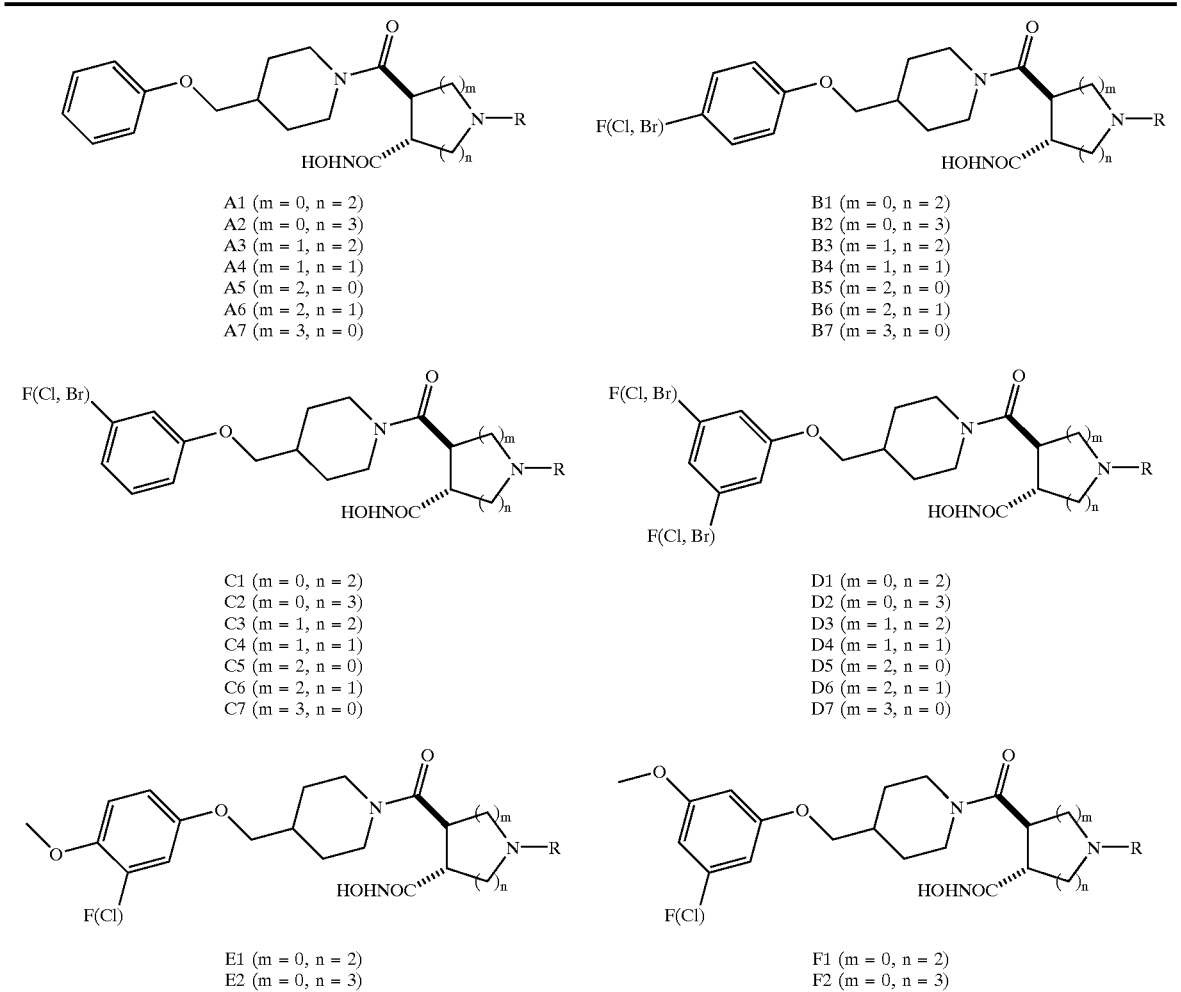

A1 (m = 0, n = 2)
A2 (m = 0, n = 3)
A3 (m = 1, n = 2)
A4 (m = 1, n = 1)
A5 (m = 2, n = 0)
A6 (m = 2, n = 1)
A7 (m = 3, n = 0)

B1 (m = 0, n = 2)
B2 (m = 0, n = 3)
B3 (m = 1, n = 2)
B4 (m = 1, n = 1)
B5 (m = 2, n = 0)
B6 (m = 2, n = 1)
B7 (m = 3, n = 0)

C1 (m = 0, n = 2)
C2 (m = 0, n = 3)
C3 (m = 1, n = 2)
C4 (m = 1, n = 1)
C5 (m = 2, n = 0)
C6 (m = 2, n = 1)
C7 (m = 3, n = 0)

D1 (m = 0, n = 2)
D2 (m = 0, n = 3)
D3 (m = 1, n = 2)
D4 (m = 1, n = 1)
D5 (m = 2, n = 0)
D6 (m = 2, n = 1)
D7 (m = 3, n = 0)

E1 (m = 0, n = 2)
E2 (m = 0, n = 3)

F1 (m = 0, n = 2)
F2 (m = 0, n = 3)

TABLE 11-continued

| | |
|---|---|
| E3 (m = 1, n = 2) | F3 (m = 1, n = 2) |
| E4 (m = 1, n = 1) | F4 (m = 1, n = 1) |
| E5 (m = 2, n = 0) | F5 (m = 2, n = 0) |
| E6 (m = 2, n = 1) | F6 (m = 2, n = 1) |
| E7 (m = 3, n = 0) | F7 (m = 3, n = 0) |

| | |
|---|---|
| G1 (m = 0, n = 2) | H1 (m = 0, n = 2) |
| G2 (m = 0, n = 3) | H2 (m = 0, n = 3) |
| G3 (m = 1, n = 2) | H3 (m = 1, n = 2) |
| G4 (m = 1, n = 1) | H4 (m = 1, n = 1) |
| G5 (m = 2, n = 0) | H5 (m = 2, n = 0) |
| G6 (m = 2, n = 1) | H6 (m = 2, n = 1) |
| G7 (m = 3, n = 0) | H7 (m = 3, n = 0) |

| | |
|---|---|
| I1 (m = 0, n = 2) | J1 (m = 0, n = 2) |
| I2 (m = 0, n = 3) | J2 (m = 0, n = 3) |
| I3 (m = 1, n = 2) | J3 (m = 1, n = 2) |
| I4 (m = 1, n = 1) | J4 (m = 1, n = 1) |
| I5 (m = 2, n = 0) | J5 (m = 2, n = 0) |
| I6 (m = 2, n = 1) | J6 (m = 2, n = 1) |
| I7 (m = 3, n = 0) | J7 (m = 3, n = 0) |

| | |
|---|---|
| K1 (m = 0, n = 2) | L1 (m = 0, n = 2) |
| K2 (m = 0, n = 3) | L2 (m = 0, n = 3) |
| K3 (m = 1, n = 2) | L3 (m = 1, n = 2) |
| K4 (m = 1, n = 1) | L4 (m = 1, n = 1) |
| K5 (m = 2, n = 0) | L5 (m = 2, n = 0) |
| K6 (m = 2, n = 1) | L6 (m = 2, n = 1) |
| K7 (m = 3, n = 0) | L7 (m = 3, n = 0) |

| | |
|---|---|
| M1 (m = 0, n = 2) | N1 (m = 0, n = 2) |
| M2 (m = 0, n = 3) | N2 (m = 0, n = 3) |
| M3 (m = 1, n = 2) | N3 (m = 1, n = 2) |
| M4 (m = 1, n = 1) | N4 (m = 1, n = 1) |
| M5 (m = 2, n = 0) | N5 (m = 2, n = 0) |
| M6 (m = 2, n = 1) | N6 (m = 2, n = 1) |

TABLE 11-continued

M7 (m = 3, n = 0)

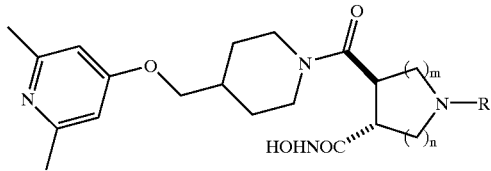

O1 (m = 0, n = 2)
O2 (m = 0, n = 3)
O3 (m = 1, n = 2)
O4 (m = 1, n = 1)
O5 (m = 2, n = 0)
O6 (m = 2, n = 1)
O7 (m = 3, n = 0)

N7 (m = 3, n = 0)

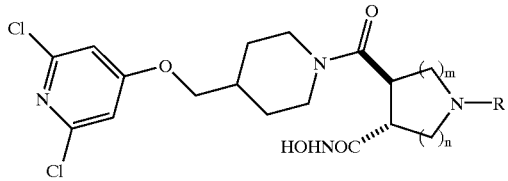

P1 (m = 0, n = 2)
P2 (m = 0, n = 3)
P3 (m = 1, n = 2)
P4 (m = 1, n = 1)
P5 (m = 2, n = 0)
P6 (m = 2, n = 1)
P7 (m = 3, n = 0)

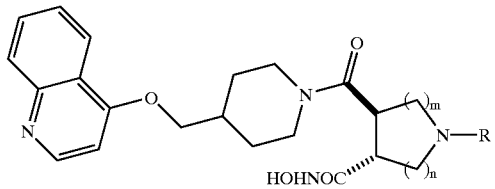

Q1 (m = 0, n = 2)
Q2 (m = 0, n = 3)
Q3 (m = 1, n = 2)
Q4 (m = 1, n = 1)
Q5 (m = 2, n = 0)
Q6 (m = 2, n = 1)
Q7 (m = 3, n = 0)

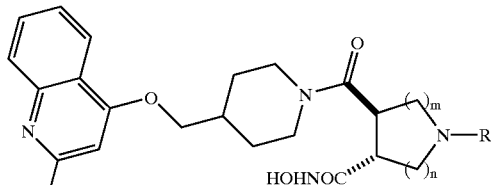

R1 (m = 0, n = 2)
R2 (m = 0, n = 3)
R3 (m = 1, n = 2)
R4 (m = 1, n = 1)
R5 (m = 2, n = 0)
R6 (m = 2, n = 1)
R7 (m = 3, n = 0)

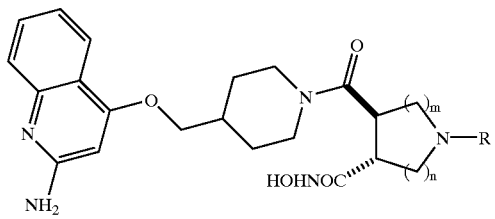

S1 (m = 0, n = 2)
S2 (m = 0, n = 3)
S3 (m = 1, n = 2)
S4 (m = 1, n = 1)
S5 (m = 2, n = 0)
S6 (m = 2, n = 1)
S7 (m = 3, n = 0)

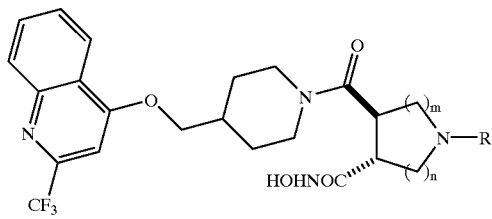

T1 (m = 0, n = 2)
T2 (m = 0, n = 3)
T3 (m = 1, n = 2)
T4 (m = 1, n = 1)
T5 (m = 2, n = 0)
T6 (m = 2, n = 1)
T7 (m = 3, n = 0)

| Ex # | R[a] |
|---|---|
| 1 | methyl |
| 2 | ethyl |
| 3 | propyl |
| 4 | butyl |
| 5 | pentyl |
| 6 | hexyl |
| 7 | isopropyl |
| 8 | isobutyl |
| 9 | 3-methylbutyl |
| 10 | 4-methylpentyl |
| 11 | neopentyl |
| 12 | cyclopropanemethyl |
| 13 | cyclopentanemethyl |
| 14 | cyclohexanemethyl |
| 15 | t-butylethyl |
| 16 | cyclopropaneethyl |
| 17 | benzyl |
| 18 | 2-methylbenzyl |
| 19 | 3-methylbenzyl |

TABLE 11-continued

| | |
|---|---|
| 20 | 4-methylbenzyl |
| 21 | 2-fluorobenzyl |
| 22 | 3-fluorobenzyl |
| 23 | 4-fluorobenzyl |
| 24 | 2-chlorobenzyl |
| 25 | 3-chlorobenzyl |
| 26 | 4-chlorobenzyl |
| 27 | 2-picolyl |
| 28 | 3-picolyl |
| 29 | 4-picolyl |
| 30 | 2-thiazolemethyl |
| 31 | 2-thiophenemethyl |
| 32 | 2-furfuryl |
| 33 | phenethyl |

TABLE 12

A1 (m = 0, n = 1)
A2 (m = 0, n = 2)
A3 (m = 0, n = 3)
A4 (m = 1, n = 0)
A5 (m = 1, n = 1)
A6 (m = 1, n = 2)
A7 (m = 2, n = 0)
A8 (m = 2, n = 1)
A9 (m = 3, n = 0)

B1 (m = 0, n = 1)
B2 (m = 0, n = 2)
B3 (m = 0, n = 3)
B4 (m = 1, n = 0)
B5 (m = 1, n = 1)
B6 (m = 1, n = 2)
B7 (m = 2, n = 0)
B8 (m = 2, n = 1)
B9 (m = 3, n = 0)

C1 (m = 0, n = 1)
C2 (m = 0, n = 2)
C3 (m = 0, n = 3)
C4 (m = 1, n = 0)
C5 (m = 1, n = 1)
C6 (m = 1, n = 2)
C7 (m = 2, n = 0)
C8 (m = 2, n = 1)
C9 (m = 3, n = 0)

D1 (m = 0, n = 1)
D2 (m = 0, n = 2)
D3 (m = 0, n = 3)
D4 (m = 1, n = 0)
D5 (m = 1, n = 1)
D6 (m = 1, n = 2)
D7 (m = 2, n = 0)
D8 (m = 2, n = 1)
D9 (m = 3, n = 0)

E1 (m = 0, n = 1)
E2 (m = 0, n = 2)
E3 (m = 0, n = 3)
E4 (m = 1, n = 0)
E5 (m = 1, n = 1)
E6 (m = 1, n = 2)
E7 (m = 2, n = 0)
E8 (m = 2, n = 1)
E9 (m = 3, n = 0)

F1 (m = 0, n = 1)
F2 (m = 0, n = 2)
F3 (m = 0, n = 3)
F4 (m = 1, n = 0)
F5 (m = 1, n = 1)
F6 (m = 1, n = 2)
F7 (m = 2, n = 0)
F8 (m = 2, n = 1)
F9 (m = 3, n = 0)

TABLE 12-continued

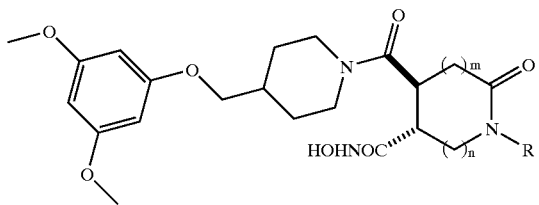 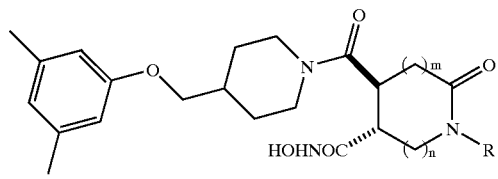

G1 (m = 0, n = 1)
G2 (m = 0, n = 2)
G3 (m = 0, n = 3)
G4 (m = 1, n = 0)
G5 (m = 1, n = 1)
G6 (m = 1, n = 2)
G7 (m = 2, n = 0)
G8 (m = 2, n = 1)
G9 (m = 3, n = 0)

H1 (m = 0, n = 1)
H2 (m = 0, n = 2)
H3 (m = 0, n = 3)
H4 (m = 1, n = 0)
H5 (m = 1, n = 1)
H6 (m = 1, n = 2)
H7 (m = 2, n = 0)
H8 (m = 2, n = 1)
H9 (m = 3, n = 0)

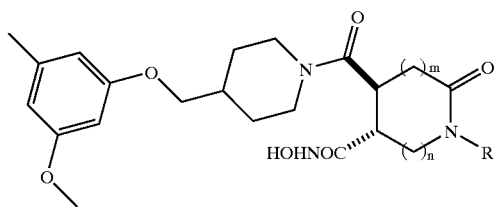 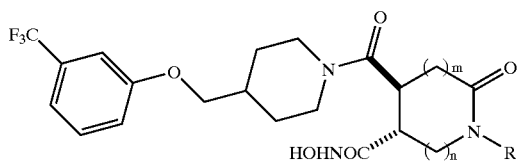

I1 (m = 0, n = 1)
I2 (m = 0, n = 2)
I3 (m = 0, n = 3)
I4 (m = 1, n = 0)
I5 (m = 1, n = 1)
I6 (m = 1, n = 2)
I7 (m = 2, n = 0)
I8 (m = 2, n = 1)
I9 (m = 3, n = 0)

J1 (m = 0, n = 1)
J2 (m = 0, n = 2)
J3 (m = 0, n = 3)
J4 (m = 1, n = 0)
J5 (m = 1, n = 1)
J6 (m = 1, n = 2)
J7 (m = 2, n = 0)
J8 (m = 2, n = 1)
J9 (m = 3, n = 0)

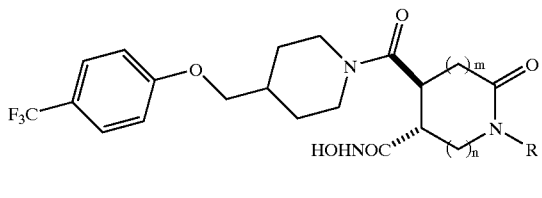 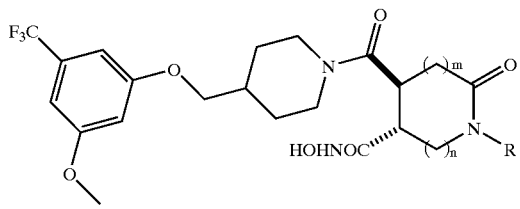

K1 (m = 0, n = 1)
K2 (m = 0, n = 2)
K3 (m = 0, n = 3)
K4 (m = 1, n = 0)
K5 (m = 1, n = 1)
K6 (m = 1, n = 2)
K7 (m = 2, n = 0)
K8 (m = 2, n = 1)
K9 (m = 3, n = 0)

L1 (m = 0, n = 1)
L2 (m = 0, n = 2)
L3 (m = 0, n = 3)
L4 (m = 1, n = 0)
L5 (m = 1, n = 1)
L6 (m = 1, n = 2)
L7 (m = 2, n = 0)
L8 (m = 2, n = 1)
L9 (m = 3, n = 0)

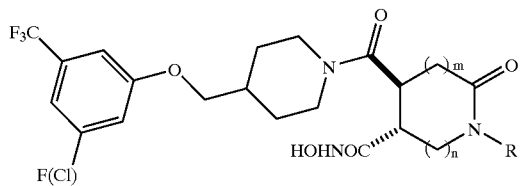 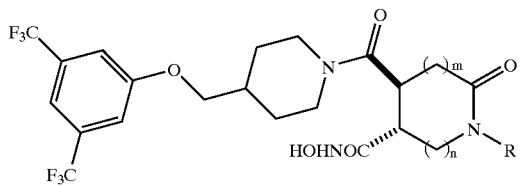

M1 (m = 0, n = 1)
M2 (m = 0, n = 2)
M3 (m = 0, n = 3)
M4 (m = 1, n = 0)
M5 (m = 1, n = 1)
M6 (m = 1, n = 2)
M7 (m = 2, n = 0)

N1 (m = 0, n = 1)
N2 (m = 0, n = 2)
N3 (m = 0, n = 3)
N4 (m = 1, n = 0)
N5 (m = 1, n = 1)
N6 (m = 1, n = 2)
N7 (m = 2, n = 0)

TABLE 12-continued

M8 (m = 2, n = 1)
M9 (m = 3, n = 0)

N8 (m = 2, n = 1)
N9 (m = 3, n = 0)

O1 (m = 0, n = 1)
O2 (m = 0, n = 2)
O3 (m = 0, n = 3)
O4 (m = 1, n = 0)
O5 (m = 1, n = 1)
O6 (m = 1, n = 2)
O7 (m = 2, n = 0)
O8 (m = 2, n = 1)
O9 (m = 3, n = 0)

P1 (m = 0, n = 1)
P2 (m = 0, n = 2)
P3 (m = 0, n = 3)
P4 (m = 1, n = 0)
P5 (m = 1, n = 1)
P6 (m = 1, n = 2)
P7 (m = 2, n = 0)
P8 (m = 2, n = 1)
P9 (m = 3, n = 0)

Q1 (m = 0, n = 1)
Q2 (m = 0, n = 2)
Q3 (m = 0, n = 3)
Q4 (m = 1, n = 0)
Q5 (m = 1, n = 1)
Q6 (m = 1, n = 2)
Q7 (m = 2, n = 0)
Q8 (m = 2, n = 1)
Q9 (m = 3, n = 0)

R1 (m = 0, n = 1)
R2 (m = 0, n = 2)
R3 (m = 0, n = 3)
R4 (m = 1, n = 0)
R5 (m = 1, n = 1)
R6 (m = 1, n = 2)
R7 (m = 2, n = 0)
R8 (m = 2, n = 1)
R9 (m = 3, n = 0)

S1 (m = 0, n = 1)
S2 (m = 0, n = 2)
S3 (m = 0, n = 3)
S4 (m = 1, n = 0)
S5 (m = 1, n = 1)
S6 (m = 1, n = 2)
S7 (m = 2, n = 0)
S8 (m = 2, n = 1)
S9 (m = 3, n = 0)

T1 (m = 0, n = 1)
T2 (m = 0, n = 2)
T3 (m = 0, n = 3)
T4 (m = 1, n = 0)
T5 (m = 1, n = 1)
T6 (m = 1, n = 2)
T7 (m = 2, n = 0)
T8 (m = 2, n = 1)
T9 (m = 3, n = 0)

| Ex # | R[a] |
|---|---|
| 1 | methyl |
| 2 | ethyl |
| 3 | propyl |
| 4 | butyl |
| 5 | pentyl |
| 6 | hexyl |
| 7 | isopropyl |
| 8 | isobutyl |
| 9 | 3-methylbutyl |
| 10 | 4-methylpentyl |
| 11 | neopentyl |
| 12 | cyclopropanemethyl |

TABLE 12-continued

| | |
|---|---|
| 13 | cyclopentanemethyl |
| 14 | cyclohexanemethyl |
| 15 | t-butylethyl |
| 16 | cyclopropaneethyl |
| 17 | benzyl |
| 18 | 2-methylbenzyl |
| 19 | 3-methylbenzyl |
| 20 | 4-methylbenzyl |
| 21 | 2-fluorobenzyl |
| 22 | 3-fluorobenzyl |
| 23 | 4-fluorobenzyl |
| 24 | 2-chlorobenzyl |
| 25 | 3-chlorobenzyl |
| 26 | 4-chlorobenzyl |
| 27 | 2-picolyl |
| 28 | 3-picolyl |
| 29 | 4-picolyl |
| 30 | 2-thiazolemethyl |
| 31 | 2-thiophenemethyl |
| 32 | 2-furfuryl |
| 33 | phenethyl |

TABLE 13

A1 (m = 0, n = 1)
A2 (m = 0, n = 2)
A3 (m = 0, n = 3)
A4 (m = 1, n = 0)
A5 (m = 1, n = 1)
A6 (m = 1, n = 2)
A7 (m = 2, n = 0)
A8 (m = 2, n = 1)
A9 (m = 3, n = 0)

B1 (m = 0, n = 1)
B2 (m = 0, n = 2)
B3 (m = 0, n = 3)
B4 (m = 1, n = 0)
B5 (m = 1, n = 1)
B6 (m = 1, n = 2)
B7 (m = 2, n = 0)
B8 (m = 2, n = 1)
B9 (m = 3, n = 0)

C1 (m = 0, n = 1)
C2 (m = 0, n = 2)
C3 (m = 0, n = 3)
C4 (m = 1, n = 0)
C5 (m = 1, n = 1)
C6 (m = 1, n = 2)
C7 (m = 2, n = 0)
C8 (m = 2, n = 1)
C9 (m = 3, n = 0)

D1 (m = 0, n = 1)
D2 (m = 0, n = 2)
D3 (m = 0, n = 3)
D4 (m = 1, n = 0)
D5 (m = 1, n = 1)
D6 (m = 1, n = 2)
D7 (m = 2, n = 0)
D8 (m = 2, n = 1)
D9 (m = 3, n = 0)

E1 (m = 0, n = 1)
E2 (m = 0, n = 2)
E3 (m = 0, n = 3)
E4 (m = 1, n = 0)

F1 (m = 0, n = 1)
F2 (m = 0, n = 2)
F3 (m = 0, n = 3)
F4 (m = 1, n = 0)

TABLE 13-continued

| | |
|---|---|
| E5 (m = 1, n = 1) | F5 (m = 1, n = 1) |
| E6 (m = 1, n = 2) | F6 (m = 1, n = 2) |
| E7 (m = 2, n = 0) | F7 (m = 2, n = 0) |
| E8 (m = 2, n = 1) | F8 (m = 2, n = 1) |
| E9 (m = 3, n = 0) | F9 (m = 3, n = 0) |

[Structure: 3,5-dimethoxyphenyl-O-CH2-piperidine-C(O)-piperidinone with HOHNOC substituent, (m, n) variable]

| | |
|---|---|
| G1 (m = 0, n = 1) | H1 (m = 0, n = 1) |
| G2 (m = 0, n = 2) | H2 (m = 0, n = 2) |
| G3 (m = 0, n = 3) | H3 (m = 0, n = 3) |
| G4 (m = 1, n = 0) | H4 (m = 1, n = 0) |
| G5 (m = 1, n = 1) | H5 (m = 1, n = 1) |
| G6 (m = 1, n = 2) | H6 (m = 1, n = 2) |
| G7 (m = 2, n = 0) | H7 (m = 2, n = 0) |
| G8 (m = 2, n = 1) | H8 (m = 2, n = 1) |
| G9 (m = 3, n = 0) | H9 (m = 3, n = 0) |

[Left structure: 3-methyl-5-methoxyphenyl variant. Right structure: 3-(trifluoromethyl)phenyl variant]

| | |
|---|---|
| I1 (m = 0, n = 1) | J1 (m = 0, n = 1) |
| I2 (m = 0, n = 2) | J2 (m = 0, n = 2) |
| I3 (m = 0, n = 3) | J3 (m = 0, n = 3) |
| I4 (m = 1, n = 0) | J4 (m = 1, n = 0) |
| I5 (m = 1, n = 1) | J5 (m = 1, n = 1) |
| I6 (m = 1, n = 2) | J6 (m = 1, n = 2) |
| I7 (m = 2, n = 0) | J7 (m = 2, n = 0) |
| I8 (m = 2, n = 1) | J8 (m = 2, n = 1) |
| I9 (m = 3, n = 0) | J9 (m = 3, n = 0) |

[Left structure: 4-(trifluoromethyl)phenyl variant. Right structure: 3-(trifluoromethyl)-5-methoxyphenyl variant]

| | |
|---|---|
| K1 (m = 0, n = 1) | L1 (m = 0, n = 1) |
| K2 (m = 0, n = 2) | L2 (m = 0, n = 2) |
| K3 (m = 0, n = 3) | L3 (m = 0, n = 3) |
| K4 (m = 1, n = 0) | L4 (m = 1, n = 0) |
| K5 (m = 1, n = 1) | L5 (m = 1, n = 1) |
| K6 (m = 1, n = 2) | L6 (m = 1, n = 2) |
| K7 (m = 2, n = 0) | L7 (m = 2, n = 0) |
| K8 (m = 2, n = 1) | L8 (m = 2, n = 1) |
| K9 (m = 3, n = 0) | L9 (m = 3, n = 0) |

[Left structure: 3-(trifluoromethyl)-5-F(Cl)-phenyl variant. Right structure: 3,5-bis(trifluoromethyl)phenyl variant]

| | |
|---|---|
| M1 (m = 0, n = 1) | N1 (m = 0, n = 1) |

TABLE 13-continued

M2 (m = 0, n = 2)
M3 (m = 0, n = 3)
M4 (m = 1, n = 0)
M5 (m = 1, n = 1)
M6 (m = 1, n = 2)
M7 (m = 2, n = 0)
M8 (m = 2, n = 1)
M9 (m = 3, n = 0)

N2 (m = 0, n = 2)
N3 (m = 0, n = 3)
N4 (m = 1, n = 0)
N5 (m = 1, n = 1)
N6 (m = 1, n = 2)
N7 (m = 2, n = 0)
N8 (m = 2, n = 1)
N9 (m = 3, n = 0)

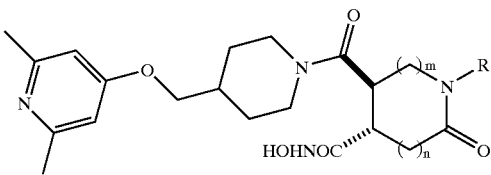

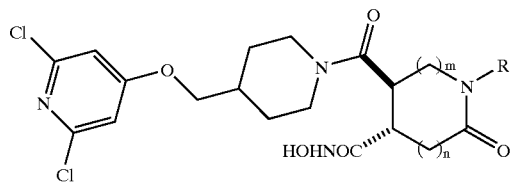

O1 (m = 0, n = 1)
O2 (m = 0, n = 2)
O3 (m = 0, n = 3)
O4 (m = 1, n = 0)
O5 (m = 1, n = 1)
O6 (m = 1, n = 2)
O7 (m = 2, n = 0)
O8 (m = 2, n = 1)
O9 (m = 3, n = 0)

P1 (m = 0, n = 1)
P2 (m = 0, n = 2)
P3 (m = 0, n = 3)
P4 (m = 1, n = 0)
P5 (m = 1, n = 1)
P6 (m = 1, n = 2)
P7 (m = 2, n = 0)
P8 (m = 2, n = 1)
P9 (m = 3, n = 0)

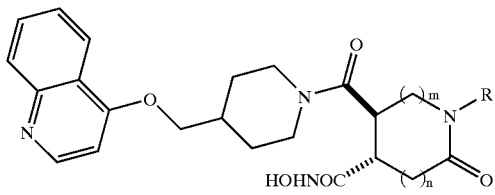

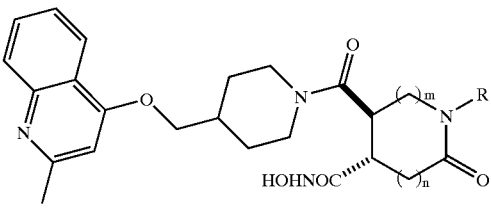

Q1 (m = 0, n = 1)
Q2 (m = 0, n = 2)
Q3 (m = 0, n = 3)
Q4 (m = 1, n = 0)
Q5 (m = 1, n = 1)
Q6 (m = 1, n = 2)
Q7 (m = 2, n = 0)
Q8 (m = 2, n = 1)
Q9 (m = 3, n = 0)

R1 (m = 0, n = 1)
R2 (m = 0, n = 2)
R3 (m = 0, n = 3)
R4 (m = 1, n = 0)
R5 (m = 1, n = 1)
R6 (m = 1, n = 2)
R7 (m = 2, n = 0)
R8 (m = 2, n = 1)
R9 (m = 3, n = 0)

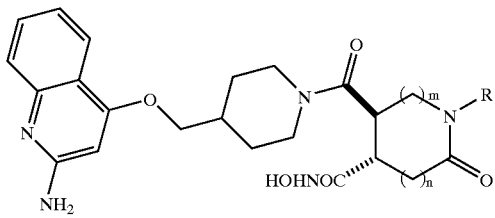

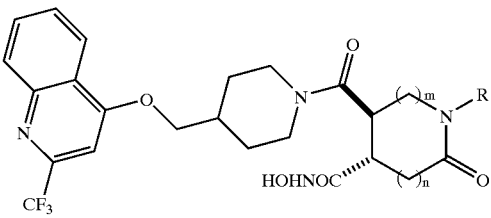

S1 (m = 0, n = 1)
S2 (m = 0, n = 2)
S3 (m = 0, n = 3)
S4 (m = 1, n = 0)
S5 (m = 1, n = 1)
S6 (m = 1, n = 2)
S7 (m = 2, n = 0)
S8 (m = 2, n = 1)
S9 (m = 3, n = 0)

T1 (m = 0, n = 1)
T2 (m = 0, n = 2)
T3 (m = 0, n = 3)
T4 (m = 1, n = 0)
T5 (m = 1, n = 1)
T6 (m = 1, n = 2)
T7 (m = 2, n = 0)
T8 (m = 2, n = 1)
T9 (m = 3, n = 0)

| Ex # | R[a] |
|---|---|
| 1 | methyl |
| 2 | ethyl |
| 3 | propyl |
| 4 | butyl |
| 5 | pentyl |
| 6 | hexyl |

TABLE 13-continued

| | |
|---|---|
| 7 | isopropyl |
| 8 | isobutyl |
| 9 | 3-methylbutyl |
| 10 | 4-methylpentyl |
| 11 | neopentyl |
| 12 | cyclopropanemethyl |
| 13 | cyclopentanemethyl |
| 14 | cyclohexanemethyl |
| 15 | t-butylethyl |
| 16 | cyclopropaneethyl |
| 17 | benzyl |
| 18 | 2-methylbenzyl |
| 19 | 3-methylbenzyl |
| 20 | 4-methylbenzyl |
| 21 | 2-fluorobenzyl |
| 22 | 3-fluorobenzyl |
| 23 | 4-fluorobenzyl |
| 24 | 2-chlorobenzyl |
| 25 | 3-chlorobenzyl |
| 26 | 4-chlorobenzyl |
| 27 | 2-picolyl |
| 28 | 3-picolyl |
| 29 | 4-picolyl |
| 30 | 2-thiazolemethyl |
| 31 | 2-thiophenemethyl |
| 32 | 2-furfuryl |
| 33 | phenethyl |

Utility

The compounds of formula I are expected to possess metalloproteinase and aggrecanase and TNF inhibitory activity. The MMP inhibitory actvity of the compounds of the present invention is demonstrated using assays of MMP activity, for example, using the assay described below for assaying inhibitors of MMP activity. The compounds of the present invention are expected to be bioavailable in vivo as demonstrated, for example, using the ex vivo assay described below. The compounds of formula I are expected to have the ability to suppress/inhibit cartilage degradation in vivo, for example, as demonstrated using the animal model of acute cartilage degradation described below.

The compounds provided by this invention should also be useful as standards and reagents in determining the ability of a potential pharmaceutical to inhibit MPs. These would be provided in commercial kits comprising a compound of this invention.

Metalloproteinases have also been implicated in the degradation of basement membranes to allow infiltration of cancer cells into the circulation and subsequent penetration into other tissues leading to tumor metastasis. (Stetler-Stevenson, Cancer and Metastasis Reviews, 9, 289–303, 1990.) The compounds of the present invention should be useful for the prevention and treatment of invasive tumors by inhibition of this aspect of metastasis.

The compounds of the present invention should also have utility for the prevention and treatment of osteopenia associated with matrixmetalloproteinase-mediated breakdown of cartilage and bone which occurs in osteoporosis patients.

Compounds which inhibit the production or action of TNF and/or Aggrecanase and/or MP's are potentially useful for the treatment or prophylaxis of various inflammatory, infectious, immunological or malignant diseases. These include, but are not limited to inflammation, fever, cardiovascular effects, hemorrhage, coagulation and acute phase response, an acute infection, septic shock, haemodynamic shock and sepsis syndrome, post ischaemic reperfusion injury, malaria, Crohn's disease, mycobacterial infection, meningitis, psoriasis, periodontits, gingivitis, congestive heart failure, fibrotic disease, cachexia, and aneroxia, graft rejection, cancer, corneal ulceration or tumor invasion by secondary metastases, autoimmune disease, skin inflammatory diseases, multiple osteo and rheumatoid arthritis, multiple sclerosis, radiation damage, HIV, and hyperoxic alveolar injury.

Some compounds of the present invention have been shown to inhibit TNF production in lipopolysacharride stimulated mice, for example, using the assay for TNF Induction in Mice and in human whole blood asdescribed below.

Some compounds of the present invention have been shown to inhibit aggrecanase a key enzyme in cartilage breakdown as determined by the aggrecanase assay described below.

As used herein "$\mu$g" denotes microgram, "mg" denotes milligram, "g" denotes gram, "$\mu$L" denotes microliter, "mL" denotes milliliter, "L" denotes liter, "nM" denotes nanomolar, "$\mu$M" denotes micromolar, "mM" denotes millimolar, "M" denotes molar and "nm" denotes nanometer. "Sigma" stands for the Sigma-Aldrich Corp. of St. Louis, Mo.

A compound is considered to be active if it has an $IC_{50}$ or $K_i$ value of less than about 10 $\mu$M for the inhibition of a desired MMP. Preferred compounds of the present invention have $K_i$'s or $IC_{50}$'s of $\leq 1$ $\mu$M. More preferred compounds of the present invention have $K_i$'s or $IC_{50}$'s of $\leq 0.1$ $\mu$M. Even more preferred compounds of the present invention have $K_i$'s or $IC_{50}$'s of $\leq 0.01$ $\mu$M. Still more preferred compounds of the present invention have $K_i$'s or $IC_{50}$'s of $\leq 0.001$ $\mu$M.

Aggrecanase Enzymatic Assay

A novel enzymatic assay was developed to detect potential inhibitors of aggrecanase. The assay uses active aggrecanase accumulated in media from stimulated bovine nasal cartilage (BNC) or related cartilage sources and purified cartilage aggrecan monomer or a fragment thereof as a substrate.

The substrate concentration, amount of aggrecanase time of incubation and amount of product loaded for Western analysis were optimized for use of this assay in screening putative aggrecanase inhibitors. Aggrecanase is generated by stimulation of cartilage slices with interleukin-1 (IL-1), tumor necrosis factor alpha (TNFα) or other stimuli. Matrix metalloproteinases (MMPs) are secreted from cartilage in an inactive, zymogen form following stimulation, although active \enzymes are present within the matrix. We have shown that following depletion of the extracellular aggrecan matrix, active MMPs are released into the culture media. (Tortorella, M. D. et. al. Trans. Ortho. Res. Soc. 20, 341, 1995). Therefore, in order to accumulate BNC aggrecanase in culture media, cartilage is first depleted of endogenous aggrecan by stimulation with 500 ng/ml human recombinant IL-β for 6 days with media changes every 2 days. Cartilage is then stimulated for an additional 8 days without media change to allow accumulation of soluble, active aggrecanase in the culture media. In order to decrease the amounts of other matrix metalloproteinases released into the media during aggrecanase accumulation, agents which inhibit MMP-1, -2, -3, and -9 biosynthesis are included during stimulation. This BNC conditioned media, containing aggrecanase activity is then used as the source of aggrecanase for the assay. Aggrecanase enzymatic activity is detected by monitoring production of aggrecan fragments produced exclusively by cleavage at the Glu373-Ala374 bond within the aggrecan core protein by Western analysis using the monoclonal antibody, BC-3 (Hughes, C E, et al., Biochem J 306:799–804, 1995). This antibody recognizes aggrecan fragments with the N-terminus, 374ARGSVIL, generated upon cleavage by aggrecanase. The BC-3 antibody recognizes this neoepitope only when it is at the N-terminus and not when it is present internally within aggrecan fragments or within the aggrecan protein core. Other proteases produced by cartilage in response to IL-1 do not cleave aggrecan at the Glu373-Ala374 aggrecanase site; therefore, only products produced upon cleavage by aggrecanase are detected. Kinetic studies using this assay yield a Km of 1.5+/−0.35 uM for aggrecanase.

To evaluate inhibition of aggrecanase, compounds are prepared as 10 mM stocks in DMSO, water or other solvents and diluted to appropriate concentrations in water. Drug (50 ul) is added to 50 ul of aggrecanase-containing media and 50 ul of 2 mg/ml aggrecan substrate and brought to a final volume of 200 ul in 0.2 M Tris, pH 7.6, containing 0.4 M NaCl and 40 mM $CaCl_2$. The assay is run for 4 hr at 37° C., quenched with 20 mM EDTA and analyzed for aggrecanase-generated products. A sample containing enzyme and substrate without drug is included as a positive control and enzyme incubated in the absence of substrate serves as a measure of background.

Removal of the glycosaminoglycan side chains from aggrecan is necessary for the BC-3 antibody to recognize the ARGSVIL epitope on the core protein. Therefore, for analysis of aggrecan fragments generated by cleavage at the Glu373-Ala374 site, proteoglycans and proteoglycan fragments are enzymatically deglycosylated with chondroitinase ABC (0.1 units/10 ug GAG) for 2 hr at 37° C. and then with keratanase (0.1 units/10 ug GAG) and keratanase II (0.002 units/10 ug GAG) for 2 hr at 37° C. in buffer containing 50 mM sodium acetate, 0.1 M Tris/HCl, pH 6.5. After digestion, aggrecan in the samples is precipitated with 5 volumes of acetone and resuspended in 30 ul of Tris glycine SDS sample buffer (Novex) containing 2.5% beta mercaptoethanol. Samples are loaded and then separated by SDS-PAGE under reducing conditions with 4–12% gradient gels, transferred to nitrocellulose and immunolocated with 1:500 dilution of antibody BC3. Subsequently, membranes are incubated with a 1:5000 dilution of goat anti-mouse IgG alkaline phosphatase second antibody and aggrecan catabolites visualized by incubation with appropriate substrate for 10–30 minutes to achieve optimal color development. Blots are quantitated by scanning densitometry and inhibition of aggrecanase determined by comparing the amount of product produced in the presence versus absence of compound.

PBMC Assay

Human peripheral blood mononuclear cells (PBMC) were obtained from normal donor blood by leukophoresis and isolated by Ficoll-Paque density separation. PBMCs were suspended in 0.5 ml RPMI 1640 with no serum at 2×10 6 cells/ml in 96 well polystyrene plates. Cells were pro incubated 10 minutes with compound, then stimulated with 1 μg/ml LPS (Lipopolysaccharide, *Salmonella typhimurium*) to induce TNF production. After an incubation of 5 hours at 37° C. in 95% air, 5% $CO_2$ environment, culture supernatants were removed and tested by standard sandwich ELISA for TNF production.

TNF Human Whole Blood Assay

Blood is drawn from normal donors into tubes containing 143 USP units of heparin/10 ml. 225 ul of blood is plated directly into sterile polypropylene tubes. Compounds are diluted in DMSO/serum free media and added to the blood samples so the final concentration of compounds are 50, 10, 5, 1, 0.5, 0.1, and 0.01 μM. The final concentration of DMSO does not exceed 0.5%. Compounds are preincubated for 15 minutes before the addition of 100 ng/ml LPS. Plates are incubated for 5 hours in an atmosphere of 5% $CO_2$ in air. At the end of 5 hours, 750 ul of serum free media is added to each tube and the samples are spun at 1200 RPM for 10 minutes. The supernatant is collected off the top and assayed for TNF-alpha production by a standard sandwich ELISA. The ability of compounds to inhibit TNF-alpha production by 50% compared to DMSO treated cultures is given by the IC50 value.

TNF Induction In Mice

Test compounds are administered to mice either I.P. or P.O. at time zero. Immediately following compound administration, mice receive an I.P. injection of 20 m of D-galactosamine plus 10 μg of lipopolysaccharide. One hour later, animals are anesthetized and bled by cardiac puncture. Blood plasma is evaluated for TNF levels by an ELISA specific for mouse TNF. Administration of representative compounds of the present invention to mice results in a dose-dependent suppression of plasma TNF levels at one hour in the above assay.

MMP Counterscreens

The enzymatic activities of recombinant MMP-1, 3 and 9 were measured at 25° C. with a fluorometric assay (Copeland, R. A.; Lombardo, D.; Giannaras, J. and Decicco, C. P. *Bioorganic Med. Chem. Lett.* 1995, 5 , 1947–1952). Final enzyme concentrations in the assay were between 0.05 and 10 nM depending on the enzyme and the potency of the inhibitor tested. The permisive peptide substrate, MCA-Pro-Leu-Gly-Leu-DPA-Ala-Arg-$NH_2$, was present at a final concentration of 10 uM in all assays. Initial velocities, in the presence or absence of inhibitor, were measured as slopes of the linear portion of the product progress curves. IC50 values were determined by plotting the inhibitor concentration dependence of the fractional velocity for each enzyme, and fitting the data by non-linear least squares methods to the standard isotherm equation (Copeland, R. A. *Enzymes: A practical Introduction to Structure, Mechanism and Data Analysis,* Wiley-VHC, New York, 1996, pp 187–223). All of the hydroxamic acids studied here were assumed to act as competitive inhibitors of the enzyme, binding to the active site Zn atom as previously demonstrated by crystallographic studies of MMP-3 complexed with related hydroxamic acids (Rockwell, A.; Melden, M.; Copeland, R. A.; Hardman, K.; Decicco, C. P. and DeGrado, W. F. *J. Am. Chem. Soc.* 1996, 118, 10337–10338). Based on the assumption of competitive inhibiton, the IC50 values were converted to Ki values as previously described.

Compounds tested in the above assay are considered to be active if they exhibit a $K_i$ of $\leq 10$ μM. Preferred compounds of the present invention have $K_i$'s of $\leq 1$ μM. More preferred compounds of the present invention have $K_i$'s of $\leq 0.1$ μM. Even more preferred compounds of the present invention have $K_i$'s of $\leq 0.01$ μM. Still more preferred compounds of the present invention have $K_i$'s of $\leq 0.001$ μM.

Using the methodology described above, a number of compounds of the present invention were found to exhibit $K_i$'s of $\leq 10$ μM, thereby confirming the utility of the compounds of the present invention.

Dosage and Formulation

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed as an antiinflammatory and antiarthritic agent.

The compounds of this invention can be administered by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. For a normal male adult human of approximately 70 kg of body weight, this translates into a dosage of 70 to 1400 mg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition. The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field. Useful pharmaceutical dosage-forms for administration of the compounds of this invention can be illustrated as follows:

Capsules

Capsules are prepared by conventional procedures so that the dosage unit is 500 milligrams of active ingredient, 100 milligrams of cellulose and 10 milligrams of magnesium stearate.

A large number of unit capsules may also prepared by filling standard two-piece hard gelatin capsules each with 100 milligrams of powdered active ingredient, 150 milligrams of lactose, 50 milligrams of cellulose, and 6 milligrams magnesium stearate.

| Syrup | |
|---|---|
| | Wt. % |
| Active Ingredient | 10 |
| Liquid Sugar | 50 |
| Sorbitol | 20 |
| Glycerine | 5 |
| Flavor, Colorant and Preservative | as required |
| Water | as required |

The final volume is brought up to 100% by the addition of distilled water.

| Aqueous Suspension | |
|---|---|
| | Wt. % |
| Active Ingredient | 10 |
| Sodium Saccharin | 0.01 |
| Keltrol ® (Food Grade Xanthan Gum) | 0.2 |
| Liquid Sugar | 5 |
| Flavor, Colorant and Preservative | as required |
| Water | as required |

Xanthan gum is slowly added into distilled water before adding the active ingredient and the rest of the formulation ingredients. The final suspension is passed through a homogenizer to assure the elegance of the final products.

| Resuspendable Powder | |
|---|---|
| | Wt. % |
| Active Ingredient | 50.0 |
| Lactose | 35.0 |
| Sugar | 10.0 |
| Acacia | 4.7 |
| Sodium Carboxylmethylcellulose | 0.3 |

Each ingredient is finely pulverized and then uniformly mixed together. Alternatively, the powder can be prepared as a suspension and then spray dried.

| Semi-Solid Gel | |
|---|---|
| | Wt. % |
| Active Ingredient | 10 |
| Sodium Saccharin | 0.02 |
| Gelatin | 2 |
| Flavor, Colorant and Preservative | as required |
| Water | as required |

Gelatin is prepared in hot water. The finely pulverized active ingredient is suspended in the gelatin solution and then the rest of the ingredients are mixed in. The suspension is filled into a suitable packaging container and cooled down to form the gel.

| Semi-Solid Paste | |
|---|---|
| | Wt. % |
| Active Ingredient | 10 |
| Gelcarin ® (Carrageenin gum) | 1 |
| Sodium Saccharin | 0.01 |
| Gelatin | 2 |
| Flavor, Colorant and Preservative | as required |
| Water | as required |

Gelcarin® is dissolved in hot water (around 80° C.) and then the fine-powder active ingredient is suspended in this solution. Sodium saccharin and the rest of the formulation ingredients are added to the suspension while it is still warm. The suspension is homogenized and then filled into suitable containers.

| Emulsifiable Paste | |
|---|---|
| | Wt. % |
| Active Ingredient | 30 |
| Tween ® 80 and Span ® 80 | 6 |
| Keltrol ® | 0.5 |
| Mineral Oil | 63.5 |

All the ingredients are carefully mixed together to make a homogenous paste.

Soft Gelatin Capsules

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

Tablets may be prepared by conventional procedures so that the dosage unit is 500 milligrams of active ingredient, 150 milligrams of lactose, 50 milligrams of cellulose and 10 milligrams of magnesium stearate.

A large number of tablets may also be prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

The compounds of the present invention may be administered in combination with a second therapeutic agent, especially non-steroidal anti-inflammatory drugs (NSAID's). The compound of Formula I and such second therapeutic agent can be administered separately or as a physical combination in a single dosage unit, in any dosage form and by various routes of administration, as described above.

The compound of Formula I may be formulated together with the second therapeutic agent in a single dosage unit (that is, combined together in one capsule, tablet, powder, or liquid, etc.). When the compound of Formula I and the second therapeutic agent are not formulated together in a single dosage unit, the compound of Formula I and the second therapeutic agent may be administered essentially at the same time, or in any order; for example the compound of Formula I may be administered first, followed by administration of the second agent. When not administered at the same time, preferably the administration of the compound of Formula I and the second therapeutic agent occurs less than about one hour apart, more preferably less than about 5 to 30 minutes apart.

Preferably the route of administration of the compound of Formula I is oral. Although it is preferable that the compound of Formula I and the second therapeutic agent are both administered by the same route that is, for example, both orally), if desired, they may each be administered by different routes and in different dosage forms (that is, for example, one component of the combination product may be administered orally, and another component may be administered intravenously).

The dosage of the compound of Formula I when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above. Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The present invention also includes pharmaceutical kits useful, for example, in the treatment or prevention of osteoarthritis or rheumatoid arthritis, which comprise one or more containers containing a pharmaceutical composition comprising a therapeutically effective amount of a compound of Formula I. Such kits may further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, may also be included in the kit.

In the present disclosure it should be understood that the specified materials and conditions are important in practicing the invention but that unspecified materials and conditions are not excluded so long as they do not prevent the benefits of the invention from being realized.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound of formula I:

$$\text{(structure I): ring B with substituents } R^3, H, R^1, A, H, R^2$$

or a stereoisomer or pharmaceutically acceptable salt form thereof, wherein;

A is selected from —COR$^5$, —CO$_2$H, CH$_2$CO$_2$H, —CO$_2$R$^6$, —CONHOH, —CONHOR$^5$, CONHOR$^6$, —NHR$^a$, —N(OH)COR$^5$, —SH, —CH$_2$SH, —SONHR$^a$, and —SN$_2$H$_2$R$^a$;

ring B is a 5–6 membered non-aromatic ring with 0–1 carbonyl groups;

R$^1$ is —U—X—Y—Z—U$^a$—X$^a$—Y$^a$—Z$^a$;

U is selected from: C(O) and C(O)NR$^{a'}$;

X is absent or selected from C$_{1-10}$ alkylene, C$_{2-10}$ alkenylene, and C$_{2-10}$ alkynylene;

Y is absent;

Z is selected from a C$_{3-13}$ carbocyclic residue substituted with 0–5 R$^b$, piperidinyl substituted with 0–5 R$^b$, and pyridyl substituted with 0–5 R$^b$;

U$^a$ is absent or is O;

X$^a$ is absent or is selected from C$_{1-10}$ alkylene, C$_{2-10}$ alkenylene, and C$_{2-10}$ alkynylene;

Y$^a$ is absent or is O;

Z$^a$ is selected from a C$_{3-13}$ carbocyclic residue substituted with 0–5 R$^c$, pyridyl substituted with 0–5 R$^c$, and quinolinyl substituted with 0–5 R$^c$;

provided that U, Z, U$^a$, Y$^a$, and Z$^a$ do not combine to form an N—N—N—O, O—N, or O—O group;

R$^2$ is selected from H, C$_{1-6}$ alkylene-Q, C$_{2-6}$ alkenylene-Q, C$_{2-6}$ alkynylene-Q, (CR$^a$R$^{a'}$)$_r$O(CR$^a$R$^{a'}$)$_r$—Q, (CR$^a$R$^{a'}$)$_r$NR$^a$(CR$^a$R$^{a'}$)$_r$—Q, (CR$^a$R$^{a'}$)$_r$C(O)(CR$^a$R$^{a'}$)$_r$—Q, (CR$^a$R$^{a'}$)$_r$C(O)O(CR$^a$R$^{a'}$)$_r$—Q, (CR$^a$R$^{a'}$)$_r$OC(O)(CR$^a$R$^{a'}$)$_r$—Q, (CR$^a$R$^{a'}$)$_r$C(O)NR$^a$(CR$^a$R$^{a'}$)$_r$—Q, (CR$^a$R$^{a'}$)$_r$NR$^a$C(O)(CR$^a$R$^{a'}$)$_r$—Q, (CR$^a$R$^{a'}$)$_r$OC(O)O (CR$^a$R$^{a'}$)$_r$—Q, (CR$^a$R$^{a'}$)$_r$OC(O)NR$^a$(CR$^a$R$^{a'}$)$_r$—Q, (CR$^a$R$^{a'}$)$_r$NR$^a$C(O)O(CR$^a$R$^{a'}$)$_r$—Q, (CR$^a$R$^{a'}$)$_r$NR$^a$C(O)NR$^a$(CR$^a$R$^{a'}$)$_r$—Q, (CR$^a$R$^{a'}$)$_r$S(O)$_p$(CR$^a$R$^{a'}$)$_r$—Q, (CR$^a$R$^{a'}$)$_r$SO$_2$NR$^a$(CR$^a$R$^{a'}$)$_r$—Q, (CR$^a$R$^{a'}$)$_r$NR$^a$SO$_2$(CR$^a$R$^{a'}$)$_r$—Q, and (CR$^a$R$^{a'}$)$_r$NR$^a$SO$_2$NR$^a$(CR$^a$R$^{a'}$)$_r$—Q;

Q is selected from H, a C$_{3-13}$ carbocyclic residue substituted with 0–5 R$^d$ and a 5–14 membered heteroaryl system containing from 1–4 heteroatoms selected from the group consisting of N, O, and S and substituted with 0–5 R$^d$.

R$^3$ is selected from H, C$_{1-6}$ alkylene-Q', C$_{2-6}$ alkenylene-Q', C$_{2-6}$ alkynylene-Q', (CR$^a$R$^{a'}$)$_r$O(CH$_2$)$_r$—Q', (CR$^a$R$^{a'}$)$_r$NR$^a$(CR$^a$R$^{a'}$)$_r$—Q', (CR$^a$R$^{a'}$)$_r$NR$^a$C(O)(CR$^a$R$^{a'}$)$_r$—Q', (CR$^a$R$^{a'}$)$_r$C(O)NR$^a$(CR$^a$R$^{a'}$)$_r$—Q', (CR$^a$R$^{a'}$)$_r$C(O)(CR$^a$R$^{a'}$)$_r$—Q', (CR$^a$R$^{a'}$)$_r$C(O)O(CR$^a$R$^{a'}$)$_r$—Q', (CR$^a$R$^{a'}$$_2$)$_r$S(O)$_p$(CR$^a$R$^{a'}$)$_r$—Q', and (CR$^a$R$^{a'}$)$_r$SO$_2$NR$^a$(CR$^a$R$^{a'}$)$_r$—Q';

Q' is selected from H, phenyl substituted with 0–3 R$^d$, naphthyl substituted with 0–3 R$^d$ and a 5–10 membered heteroaryl system containing from 1–4 heteroatoms selected from the group consisting of N, O, and S and substituted with 0–3 R$^d$.

alternatively, R$^2$ and R$^3$ combine to form a fused benzo ring substituted with R$^{3'}$;

R$^{3'}$ is selected from H, (CR$^a$R$^{a'}$)$_r$—Q', C$_{2-6}$ alkenylene-Q', C$_{2-6}$ alkynylene-Q', (CR$^a$R$^{a'}$)$_r$O(CH$_2$)$_r$—Q', (CR$^a$R$^{a'}$)$_r$NR$^a$(CR$^a$R$^{a'}$)$_r$—Q', (CR$^a$R$^{a'}$)$_r$NR$^a$C(O)(CR$^a$R$^{a'}$)$_r$—Q', (CR$^a$R$^{a'}$)$_r$C(O)NR$^a$(CR$^a$R$^{a'}$)$_r$—Q', (CR$^a$R$^{a'}$)$_r$C(O)(CR$^a$R$^{a'}$)$_r$—Q', (CR$^a$R$^{a'}$)$_r$C(O)O (CR$^a$R$^{a'}$)$_r$—Q', (CR$^a$R$^{a'}$)$_r$S(O)$_p$(CR$^a$R$^{a'}$)$_r$—Q', and (CR$^a$R$^{a'}$)$_r$SO$_2$NR$^a$(CR$^a$R$^{a'}$)$_r$—Q';

R$^a$, at each occurrence, is independently selected from H, C$_{1-4}$ alkyl, phenyl and benzyl;

R$^{a'}$, at each occurrence, is independently selected from H and C$_{1-4}$ alkyl;

alternatively, R$^a$ and R$^{a'}$ taken together with the nitrogen to which they are attached form a 5 or 6 membered ring containing from 0–1 additional heteroatoms selected from the group consisting of N, O, and S;

R$^{a''}$, at each occurrence, is independently selected from C$_{1-4}$ alkyl, phenyl and benzyl;

R$^b$, at each occurrence, is independently selected from C$_{1-6}$ alkyl, OR$^a$, Cl, F, Br, I, =O, —CN, NO$_2$, NR$^a$R$^{a'}$, C(O)R$^a$, C(O)OR$^a$, C(O)NR$^a$R$^{a'}$, R$^a$NC(O)NR$^a$R$^a$, OC(O)NR$^a$R$^{a'}$, R$^a$NC(O)O, S(O)$_2$NR$^a$R$^{a'}$, NR$^a$S(O)$_2$R$^{a''}$, NR$^a$S(O)$_2$NR$^a$R$^{a'}$, OS(O)$_2$NR$^a$R$^{a'}$, NR$^a$S(O)$_2$R$^{a''}$, S(O)$_p$R$^{a''}$, CF$_3$, and CF$_2$CF$_3$;

R$^c$, at each occurrence, is independently selected from C$_{1-6}$ alkyl, OR$^a$, Cl, F, Br, I, =O, —CN, NO$_2$, NR$^a$R$^{a'}$, C(O)R$^a$, C(O)OR$^a$, C(O)NR$^a$R$^{a'}$, R$^a$NC(O)NR$^a$R$^{a'}$, OC(O)NR$^a$R$^{a'}$, R$^a$NC(O)O, S(O)$_2$NR$^a$R$^{a'}$, NR$^a$S(O)$_2$R$^{a''}$, NR$^a$S(O)$_2$NR$^a$R$^{a'}$, OS(O)$_2$NR$^a$R$^{a'}$, NR$^a$S(O)$_2$R$^{a''}$, S(O)$_p$R$^{a''}$, CF$_3$, CF$_2$CF$_3$, C$_{3-10}$ carbocyclic residue and a 5–14 membered heterocyclic system containing from 1–4 heteroatoms selected from the group consisting of N, O, and S;

R$^d$, at each occurrence, is independently selected from C$_{1-6}$ alkyl, OR$^a$, Cl, F, Br, I, =O, —CN, NO$_2$, NR$^a$R$^{a'}$, C(O)R$^a$, C(O)OR$^a$, C(O)NR$^a$R$^{a'}$, R$^a$NC(O)NR$^a$R$^{a'}$, OC(O)NR$^a$R$^{a'}$, R$^a$NC(O)O, S(O)$_2$NR$^a$R$^{a'}$, NR$^a$S(O)$_2$R$^{a''}$, NR$^a$S(O)$_2$NR$^a$R$^{a'}$, OS(O)$_2$NR$^a$R$^{a'}$, NR$^a$S(O)$_2$R$^{a''}$, S(O)$_p$R$^{a''}$, CF$_3$, CF$_2$CF$_3$, C$_{3-10}$ carbocyclic residue and a 5–14 membered heterocyclic system containing from 1–4 heteroatoms selected from the group consisting of N, O, and S;

R$_5$, at each occurrence, is selected from C$_{1-10}$ alkyl substituted with 0–2 R$^b$, and C$_{1-8}$ alkyl substituted with 0–2 R$^e$;

R$^e$, at each occurrence, is selected from phenyl substituted with 0–2 R$^b$ and biphenyl substituted with 0–2 R$^b$;

R$^6$, at each occurrence, is selected from phenyl, naphthyl, C$_{1-10}$ alkyl-phenyl-C$_{1-6}$ alkyl-, C$_{3-11}$ cycloalkyl, C$_{1-6}$ alkylcarbonyloxy-C$_{1-3}$ alkyl-, C$_{1-6}$ alkoxycarbonyloxy-C$_{1-3}$ alkyl-, C$_{2-10}$ alkoxycarbonyl, C$_{3-6}$ cycloalkylcarbonyloxy-C$_{1-3}$ alkyl-, C$_{3-6}$ cycloalkoxycarbonyloxy-C$_{1-3}$ alkyl-, C$_{3-6}$ cycloalkoxycarbonyl, phenoxycarbonyl, phenyloxycarbonyloxy-$C_{1-3}$ alkyl-, phenylcarbonyloxy-$C_{1-3}$ alkyl-, $C_{1-6}$ alkoxy-$C_{1-6}$ alkylcarbonyloxy-$C_{1-3}$ alkyl-, [5-($C_1$–$C_5$ alkyl)-1,3-dioxa-cyclopenten-2-one-yl]methyl, [5-($R^a$)-1,3-dioxa-cyclopenten-2-one-yl]methyl, (5-aryl-1,3-dioxa-cyclopenten-2-one-yl)methyl, —$C_{1-10}$ alkyl-$NR^7R^{7a}$, —CH($R^8$)OC(=O)$R^9$, and —CH($R^8$)OC(=O)O$R^9$;

$R^7$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^{7a}$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^8$ is selected from H and $C_{1-4}$ linear alkyl;

$R^9$ is selected from H, $C_{1-8}$ alkyl substituted with 1–2 $R^f$, $C_{3-8}$ cycloalkyl substituted with 1–2 $R^f$, and phenyl substituted with 0–2 $R^b$;

$R^f$, at each occurrence, is selected from $C_{1-4}$ alkyl, $C_{3-8}$ cycloalkyl, $C_{1-5}$ alkoxy, phenyl substituted with 0–2 $R^b$;

p, at each occurrence, is selected from 0, 1, and 2;

r, at each occurrence, is selected from 0, 1, 2, 3, and 4; and, r', at each occurrence, is selected from 1, 2, 3, and 4;

provided that the moiety in ring B adjacent to CH—A is other than substituted or unsubstituted N—$SO_2$-phenyl-O—Ar and N—$SO_2$-phenyl-S—Ar, wherein Ar is aryl or heteroaryl; and, provided that when ring B is cyclopentyl or cyclohexyl, then $R^1$ is other than a substituted or unsubstituted phenyl-$S(O)_p$— group.

2. A compound according to claim 1, wherein the compound is of formula II:

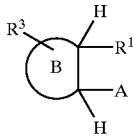

II or a stereoisomer or pharmaceutically acceptable salt form thereof, wherein;

A is selected from $COR^5$, —$CO_2H$, $CH_2CO_2H$, —CONHOH, —$CONHOR^5$, —$CONHOR^6$, —N(OH)$COR^5$, —SH, and —$CH_2SH$;

ring B is a 5–6 membered non-aromatic ring with 0–1 carbonyl groups;

$R^1$ is —U—X—Y—Z—$U^a$—$X^a$—$Y^a$—$Z^a$;

U is selected from: C(O) and C(O)$NR^{a'}$;

X is absent;

Y is absent;

Z is selected from a $C_{3-6}$ carbocyclic residue substituted with 0–5 $R^b$, piperidinyl substituted with 0–5 $R^b$, and pyridyl substituted with 0–5 $R^b$;

$U^a$ is absent or is O;

$X^a$ is absent or selected from $C_{1-4}$ alkylene;

$Y^a$ is absent or is O;

$Z^a$ is selected from a $C_{3-6}$ carbocyclic residue substituted with 0–5 $R^c$, pyridyl substituted with 0–5 $R^c$, and quinolinyl substituted with 0–5 $R^c$;

provided that U, Z, $U^a$, $Y^a$, and $Z^a$ do not combine to form an N—N N—O, O—N, or O—O group;

$R^2$ is selected from H, $C_{1-6}$ alkylene-Q, $(CR^aR^{a'})_rO$$(CR^aR^{a'})_r$—Q, $(CR^aR^{a'})_rNR^a(CR^aR^{a'})_r$—Q, $(CR^aR^{a'})_r$C(O)$(CR^aR^{a'})_r$—Q, $(CR^aR^{a'})_r$C(O)O$(CR^aR^{a'})_r$—Q, $(CR^aR^{a'})_r$C(O)$NR^a(CR^aR^{a'})_r$—Q, $(CR^aR^{a'})_r$S(O)$_p$$(CR^aR^{a'})_r$—Q, and $(CR^aR^{a'})_r$$SO_2NR^a(CR^aR^{a'})_r$—Q;

Q is selected from H, a $C_{3-6}$ carbocyclic residue substituted with 0–5 $R^d$, and a 5–10 membered heteroaryl system containing from 1–4 heteroatoms selected from the group consisting of N, O, and S and substituted with 0–5 $R^d$;

$R^3$ is selected from H, $C_{1-6}$ alkylene-Q', $(CR^aR^{a'})_rO$$(CR^aR^{a'})_r$—Q', $(CR^aR^{a'})_r$$NR^a(CR^aR^{a'})_r$—Q', $(CR^aR^{a'})_r$ C(O)$NR^a(CR^aR^{a'})_r$—Q', $(CR^aR^{a'})_r$C(O)$(CR^aR^{a'})_r$—Q', $(CR^aR^{a'})_r$C(O)O$(CR^aR^{a'})_r$—Q', $(CR^aR^{a'})_r$S(O)$_p(CR^aR^{a'})_r$—Q', and $(CR^aR^{a'})_r$$SO_2NR^a$ $(CR^aR^{a'})_r$—Q';

Q' is selected from H, phenyl substituted with 0–3 $R^d$, naphthyl substituted with 0–3 $R^d$ and a 5–6 membered heteroaryl system containing from 1–4 heteroatoms selected from the group consisting of N, O, and S and substituted with 0–3 $R^d$;

$R^a$, at each occurrence, is independently selected from H, $C_{1-4}$ alkyl, phenyl and benzyl;

$R^{a'}$, at each occurrence, is independently selected from H and $C_{1-4}$ alkyl;

alternatively, $R^a$ and $R^{a'}$ taken together with the nitrogen to which they are attached form a 5 or 6 membered ring containing from 0–1 additional heteroatoms selected from the group consisting of N, O, and S;

$R^{a''}$, at each occurrence, is independently selected from $C_{1-4}$ alkyl, phenyl and benzyl;

$R^b$, at each occurrence, is independently selected from $C_{1-6}$ alkyl, $OR^a$, Cl, F, Br, =O, —CN, $NR^aR^{a'}$, C(O)$R^a$, C(O)$OR^a$, C(O)$NR^aR^{a'}$, $S(O)_2NR^aR^{a'}$, $S(O)_pR^{a''}$, and $CF_3$;

$R^c$, at each occurrence, is independently selected from $C_{1-6}$ alkyl, $OR^a$, Cl, F, Br, =O, —CN, $NR^aR^{a'}$, C(O)$R^a$, C(O)$OR^a$, C(O)$NR^aR^{a'}$, $S(O)_2NR^aR^{a'}$, $S(O)_pR^{a''}$, $CF_3$, $C_{3-6}$ carbocyclic residue and a 5–6 membered heterocyclic system containing from 1–4 heteroatoms selected from the group consisting of N, O, and S;

$R^d$, at each occurrence, is independently selected from $C_{1-6}$ alkyl, $OR^a$, Cl, F, Br, =O, —CN, $NR^aR^{a'}$, C(O)$R^a$, C(O)$OR^a$, C(O)$NR^aR^{a'}$, $S(O)_2NR^aR^{a'}$, $S(O)_pR^{a''}$, $CF_3$, $C_{3-6}$ carbocyclic residue and a 5–6 membered heterocyclic system containing from 1–4 heteroatoms selected from the group consisting of N, O, and S;

$R^5$, at each occurrence, is selected from $C_{1-6}$ alkyl substituted with 0–2 $R^b$, and $C_{1-4}$ alkyl substituted with 0–2 $R^e$;

$R^e$, at each occurrence, is selected from phenyl substituted with 0–2 $R^b$ and biphenyl substituted with 0–2 $R^b$;

$R^6$, at each occurrence, is selected from phenyl, naphthyl, $C_{1-10}$ alkyl-phenyl-$C_{1-6}$ alkyl-, $C_{3-11}$ cycloalkyl, $C_{1-6}$ alkylcarbonyloxy-$C_{1-3}$ alkyl-, $C_{1-6}$ alkoxycarbonyloxy-$C_{1-3}$ alkyl-, $C_{2-10}$ alkoxycarbonyl, $C_{3-6}$ cycloalkylcarbonyloxy-$C_{1-3}$ alkyl-, $C_{3-6}$ cycloalkoxycarbonyloxy-$C_{1-3}$ alkyl-, $C_{3-6}$ cycloalkoxycarbonyl, phenoxycarbonyl, phenyloxycarbonyloxy-$C_{1-3}$ alkyl-, phenylcarbonyloxy-$C_{1-3}$ alkyl-, $C_{1-6}$ alkoxy-$C_{1-6}$ alkylcarbonyloxy-$C_{1-3}$ alkyl-, [5-($C_1$–$C_5$ alkyl)-1,3-dioxa-cyclopenten-2-one-yl]methyl, [5-($R^a$)-1,3-dioxa-cyclopenten-2-one-yl]methyl, (5-aryl-1,3-dioxa-cyclopenten-2-one-yl)methyl, —$C_{1-10}$ alkyl-$NR^7R^{7a}$, —CH($R^8$)OC(=O)$R^9$, and —CH($R^8$)OC(=O)O$R^9$;

$R^7$ is selected from H and $C_{1-6}$ alkyl, $C_{2-6}$ alkenyl, $C_{3-6}$ cycloalkyl-$C_{1-3}$ alkyl-, and phenyl-$C_{1-6}$ alkyl-;

$R^{7a}$ is selected from H and $C_{1-6}$ alkyl, $C_{2-6}$ alkenyl, $C_{3-6}$ cycloalkyl-$C_{1-3}$ alkyl-, and phenyl-$C_{1-6}$ alkyl-;

$R^8$ is selected from H and $C_{1-4}$ linear alkyl;

$R^9$ is selected from H, $C_{1-6}$ alkyl substituted with 1–2 $R^f$, $C_{3-6}$ cycloalkyl substituted with 1–2 $R^f$, and phenyl substituted with 0–2 $R^b$;

$R^f$, at each occurrence, is selected from $C_{1-4}$ alkyl, $C_{3-6}$ cycloalkyl, $C_{1-5}$ alkoxy, phenyl substituted with 0–2 $R^b$;

p, at each occurrence, is selected from 0, 1, and 2;

r, at each occurrence, is selected from 0, 1, 2, 3, and 4; and, r', at each occurrence, is selected from 1, 2, 3, and 4;

provided that the moiety in ring B adjacent to CH—A is other than substituted or unsubstituted N—SO$_2$-phenyl-O—Ar and N—SO$_2$-phenyl-S—Ar, wherein Ar is aryl or heteroaryl; and, provided that when ring B is cyclopentyl or cyclohexyl, then $R^1$ is other than a substituted or unsubstituted phenyl-S(Q)p— group.

3. A compound according to claim 2, wherein:

A is selected from 13 CO$_2$H, CH$_2$CO$_2$H, —CONHOH, —CONHOR$^5$, and —N(OH)COR$^5$;

$R^1$ is —U—X—Y—Z—U$^a$—X$^a$—Y$^a$—Z$^a$;

U is selected from: C(O) and C(O)NR$^{a'}$;

X is absent;

Y is absent;

Z is selected from a $C_{5-6}$ carbocyclic residue substituted with 0–3 $R^b$ and pyridyl substituted with 0–5 $R^b$;

$U^a$ is absent or is O;

$X^a$ is absent or is selected from $C_{1-2}$ alkylene;

$Y^a$ is absent or is O;

$Z^a$ is selected from a $C_{5-6}$ carbocyclic residue substituted with 0–3 $R^c$, pyridyl substituted with 0–5 $R^c$, and quinolinyl substituted with 0–5 $R^c$;

provided that U, Z, $U^a$, $Y^a$, and $Z^a$ do not combine to form an N—N N—O, O—N or O—O group;

$R^2$ is selected from H, $C_{1-6}$ alkylene-Q, (CR$^a$R$^{a'}$)$_r$C(O)(CR$^a$R$^{a'}$)$_r$—Q, (CR$^a$R$^{a'}$)$_r$C(O)O(CR$^a$R$^{a'}$)$_r$—Q, (CR$^a$R$^{a''}$)$_r$C(O)NR$^a$(CR$^a$R$^{a'}$)$_r$—Q, and (CR$^a$R$^{a'}$)$_r$S(O)$_p$(CR$^a$R$^{a'}$)$_r$—Q;

Q is selected from H, a $C_{3-6}$ carbocyclic residue substituted with 0–3 $R^d$ and a 5–10 membered heteroaryl system containing from 1–4 heteroatoms selected from the group consisting of N, O, and S and substituted with 0–3 $R^d$;

$R^3$ is selected from H, $C_{1-6}$ alkylene-Q', (CHR$^a$)$_r$O(CHR$^a$)$_r$—Q', (CHR$^a$)$_r$NR$^a$(CHR$^a$)$_r$—Q', (CHR$^a$)$_r$C(O)NR$^a$(CHR$^a$)$_r$—Q', (CHR$^a$)$_r$C(O)(CHR$^a$)$_r$—Q', and (CHR$^a$)$_r$S(O)$_p$(CHR$^a$)$_r$—Q';

Q' is selected from H, phenyl substituted with 0–3 $R^d$, and a 5–6 membered heteroaryl system containing from 1–4 heteroatoms selected from the group consisting of N, O, and S and substituted with 0–3 $R^d$;

$R^a$, at each occurrence, is independently selected from H, $C_{1-4}$ alkyl, phenyl and benzyl;

$R^{a'}$, at each occurrence, is independently selected from H and $C_{1-4}$ alkyl;

$R^{a''}$, at each occurrence, is independently selected from $C_{1-4}$ alkyl, phenyl and benzyl;

$R^b$, at each occurrence, is independently selected from $C_{1-4}$ alkyl, OR$^a$, Cl, F, =O, NR$^a$R$^{a'}$, C(O)R$^a$, C(O)OR$^a$, C(O)NR$^a$R$^{a'}$, S(O)$_2$NR$^a$R$^{a'}$, S(O)$_p$R$^{a''}$, and CF$_3$;

$R^c$, at each occurrence, is independently selected from $C_{1-6}$ alkyl, OR$^a$, Cl, F, Br, =O, NR$^a$R$^{a'}$, C(O)R$^a$, C(O)NR$^a$R$^{a'}$, S(O)$_2$NR$^a$R$^{a'}$, S(O)$_p$R$^{a''}$, and CF$_3$;

$R^d$, at each occurrence, is independently selected from $C_{1-6}$ alkyl, OR$^a$, Cl, F, Br, =O, NR$^a$R$^{a'}$, C(O)R$^a$, C(O)NR$^a$R$^{a'}$, S(O)$_2$NR$^a$R$^{a'}$, S(O)$_p$R$^{a''}$, CF$_3$ and phenyl;

$R^5$, at each occurrence, is selected from $C_{1-4}$ alkyl substituted with 0–2 $R^b$, and $C_{1-4}$ alkyl substituted with 0–2 $R^e$;

$R^e$, at each occurrence, is selected from phenyl substituted with 0–2 $R^b$ and biphenyl substituted with 0–2 $R^b$;

p, at each occurrence, is selected from 0, 1, and 2;

r, at each occurrence, is selected from 0, 1, 2, 3, and 4; and, r', at each occurrence, is selected from 1, 2, 3, and 4;

provided that the moiety in ring B adjacent to CH—A is other than substituted or unsubstituted N—SO$_2$-phenyl-O—Ar and N—SO$_2$-phenyl-S—Ar, wherein Ar is aryl or heteroaryl; and, provided that when ring B is cyclopentyl or cyclohexyl, then $R^1$ is other than a substituted or unsubstituted phenyl-S(O)$_p$— group.

4. A compound according to claim 3, wherein the compound is of formula III:

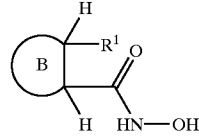

III ring B is a 5–6 membered non-aromatic ring with 0–1 carbonyl groups;

$R^1$ is —U—Z—U$^a$—X$^a$—Y$^a$—Z$^a$;

U is selected from C(O) and C(O)NR$^{a'}$;

Z is selected from phenyl substituted with 0–3 $R^b$ and pyridyl substituted with 0–3 $R^b$;

$U^a$ is absent or is O;

$X^a$ is absent or is CH$_2$ or CH$_2$CH$_2$;

$Y^a$ is absent or is O;

$Z^a$ is selected from phenyl substituted with 0–3 $R^c$, pyridyl substituted with 0–3 $R^c$, and quinolinyl substituted with 0–3 $R^c$;

provided that U, Z, $U^a$, $Y^a$, and $Z^a$ do not combine to form a N—N, N—O, O—N, or O—O group;

$R^2$ is selected from H, $C_{1-6}$ alkylene-Q, C(O)(CR$^a$R$^{a'}$)$_r$—Q, C(O)O(CR$^a$R$^{a'}$)$_r$—Q, C(O)NR$^a$(CR$^a$R$^{a'}$)$_r$—Q, and S(O)$_p$(CR$^a$R$^{a'}$)$_r$—Q;

Q is selected from H, cyclopropyl substituted with 0–1 $R^d$, cyclopentyl substituted with 0–1 $R^d$, cyclohexyl substituted with 0–1 $R^d$, phenyl substituted with 0–2 $R^d$ and a heteroaryl substituted with 0–3 $R^d$, wherein the heteroaryl is selected from pyridyl, quinolinyl, thiazolyl, furanyl, imidazolyl, and isoxazolyl;

$R^a$, at each occurrence, is independently selected from H and CH$_3$, and CH$_2$CH$_3$;

$R^{a'}$, at each occurrence, is independently selected from H and CH$_3$, and CH$_2$CH$_3$;

$R^{a''}$, at each occurrence, is independently selected from H and CH$_3$, and CH$_2$CH$_3$;

$R^b$, at each occurrence, is independently selected from $C_{1-4}$ alkyl, OR$^a$, Cl, F, =O, NR$^a$R$^{a'}$, C(O)R$^a$, C(O)OR$^a$, C(O)NR$^a$R$^{a'}$, S(O)$_2$NR$^a$R$^{a'}$, S(O)$_p$R$^{a''}$, and CF$_3$;

$R^c$, at each occurrence, is independently selected from $C_{1-6}$ alkyl, $OR_a$, Cl, F, Br, =O, $NR^aR^{a'}$, $C(O)R^a$, $C(O)NR^aR^{a'}$, $S(O)_2NR^aR^{a'}$, $S(O)_pR^{a''}$, and $CF_3$;

$R^d$, at each occurrence, is independently selected from $C_{1-6}$ alkyl, $OR^a$, Cl, F, Br, =O, $NR^aR^{a'}$, $C(O)R^a$, $C(O)NR^aR^{a'}$, $S(O)_2NR^aR^{a'}$, $S(O)_pR^{a''}$, $CF_3$ and phenyl;

p, at each occurrence, is selected from 0, 1, and 2;

r, at each occurrence, is selected from 0, 1, 2, and 3; and, r', at each occurrence, is selected from 1, 2, and 3;

provided that the moiety in ring B adjacent to CH—A is other than substituted or unsubstituted N—SO$_2$-phenyl-O—Ar and N—SO$_2$-phenyl-S—Ar, wherein Ar is aryl or heteroaryl; and, provided that when ring B is cyclopentyl or cyclohexyl, then $R^1$ is other than a substituted or unsubstituted phenyl-$S(O)_p$— group.

5. A compound according to claim 1, wherein the compound is selected from the group:

trans-N-Hydroxy-2-[(4-phenyl-1piperidinyl)carbonyl]cyclopentanecarboxamide;

trans-N-Hydroxy-2-{[4-[(4-methylphenoxy)methyl]-1-piperidinyl]carbonyl}cyclopentanecarboxamide;

trans-N-Hydroxy-2-[[4-(2-phenoxyethyl)-1-piperidinyl]carbonyl]cyclopentanecarboxamide;

trans-N-Hydroxy-N'-[4-(phenylmethoxy)phenyl]-1,2-cyclopentanedicarboxamide;

trans-N-Hydroxy-N'-[4-(4-pyridinylmethoxy)phenyl]-1,2-cyclopentanedicarboxamide;

trans-N-[4-[(3,5-Dichlorophenyl)methoxy]phenyl]-N'-hydroxy-1,2-cyclopentanedicarboxamide;

trans-N-Hydroxy-N'-[4-[4-quinolinyloxy)methyl]phenyl]-1,2-cyclopentanedicarboxamide;

trans-N-Hydroxy-N'-[4-(4-pyridinylmethyl)phenyl]-1,2-cyclopentanedicarboxamide;

trans-N-Hydroxy-N'-[4-(phenylmethoxy)phenyl]-1,2-cyclohexanedicarboxamide;

trans-N-Hydroxy-N'-[4-[(4-quinolinyloxy)methyl]phenyl]-1,2-cyclohexanedicarboxamide;

trans-N-Hydroxy-N'[4-[(5-quinolinyloxy)methyl]phenyl]-1,2-cyclohexanedicarboxamide; and, trans-N-Hydroxy-N'-[4-[(6-quinolinyloxy)methyl]phenyl]-1,2-cyclohexanedicarboxamide;

or a pharmaceutically acceptable salt form thereof.

6. A pharmaceutical composition, comprising: a pharmaceutically acceptable carrier and a therapeutically effective amount of a compound of claim 1 or a pharmaceutically acceptable salt form thereof.

7. A method for treating an inflammatory disorder, comprising: administering to a patient in need thereof a therapeutically effective amount of a compound of claim 1 or a pharmaceutically acceptable salt form thereof.

8. A method of treating a condition or disease wherein the disease or condition is referred to as rheumatoid arthritis, osteoarthritis, periodontitis, gingivitis, corneal ulceration, or psoriasis in a mammal, comprising: administering to the mammal in need of such treatment a therapeutically effective amount of a compound of claim 1 or a pharmaceutically acceptable salt form thereof.

9. A pharmaceutical composition, comprising: a pharmaceutically acceptable carrier and a therapeutically effective amount of a compound of claim 2 or a pharmaceutically acceptable salt form thereof.

10. A pharmaceutical composition, comprising: a pharmaceutically acceptable carrier and a therapeutically effective amount of a compound of claim 3 or a pharmaceutically acceptable salt form thereof.

11. A pharmaceutical composition, comprising: a pharmaceutically acceptable carrier and a therapeutically effective amount of a compound of claim 4 or a pharmaceutically acceptable salt form thereof.

12. A pharmaceutical composition, comprising: a pharmaceutically acceptable carrier and a therapeutically effective amount of a compound of claim 5 or a pharmaceutically acceptable salt form thereof.

13. A method for treating an inflammatory disorder, comprising: administering to a patient in need thereof a therapeutically effective amount of a compound of claim 2 or a pharmaceutically acceptable salt form thereof.

14. A method of treating a condition or disease wherein the disease or condition is referred to as rheumatoid arthritis, osteoarthritis, periodontitis, gingivitis, corneal ulceration, or psoriasis in a mammal, comprising: administering to the mammal in need of such treatment a therapeutically effective amount of a compound of claim 2 or a pharmaceutically acceptable salt form thereof.

15. A method for treating an inflammatory disorder, comprising: administering to a patient in need thereof a therapeutically effective amount of a compound of claim 3 or a pharmaceutically acceptable salt form thereof.

16. A method of treating a condition or disease wherein the disease or condition is referred to as rheumatoid arthritis, osteoarthritis, periodontitis, gingivitis, corneal ulceration, or psoriasis in a mammal, comprising: administering to the mammal in need of such treatment a therapeutically effective amount of a compound of claim 3 or a pharmaceutically acceptable salt form thereof.

17. A method for treating an inflammatory disorder, comprising: administering to a patient in need thereof a therapeutically effective amount of a compound of claim 4 or a pharmaceutically acceptable salt form thereof.

18. A method of treating a condition or disease wherein the disease or condition is referred to as rheumatoid arthritis, osteoarthritis, periodontitis, gingivitis, corneal ulceration, or psoriasis in a mammal, comprising: administering to the mammal in need of such treatment a therapeutically effective amount of a compound of claim 4 or a pharmaceutically acceptable salt form thereof.

19. A method for treating an inflammatory disorder, comprising: administering to a patient in need thereof a therapeutically effective amount of a compound of claim 5 or a pharmaceutically acceptable salt form thereof.

20. A method of treating a condition or disease wherein the disease or condition is referred to as rheumatoid arthritis, osteoarthritis, periodontitis, gingivitis, corneal ulceration, or psoriasis in a mammal, comprising: administering to the mammal in need of such treatment a therapeutically effective amount of a compound of claim 5 or a pharmaceutically acceptable salt form thereof.

* * * * *